United States Patent
Yan et al.

(10) Patent No.: US 12,338,459 B2
(45) Date of Patent: Jun. 24, 2025

(54) DNA-CHIMERIC ANTIGEN RECEPTOR T CELLS FOR IMMUNOTHERAPY

(71) Applicant: ARIZONA BOARD OF REGENTS ON BEHALF OF ARIZONA STATE UNIVERSITY, Scottsdale, AZ (US)

(72) Inventors: Hao Yan, Chandler, AZ (US); Bo Ning, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1241 days.

(21) Appl. No.: 16/966,264

(22) PCT Filed: Feb. 4, 2019

(86) PCT No.: PCT/US2019/016560
§ 371 (c)(1),
(2) Date: Jul. 30, 2020

(87) PCT Pub. No.: WO2019/152957
PCT Pub. Date: Aug. 8, 2019

(65) Prior Publication Data
US 2020/0390814 A1    Dec. 17, 2020

Related U.S. Application Data

(60) Provisional application No. 62/625,964, filed on Feb. 2, 2018.

(51) Int. Cl.
| | |
|---|---|
| C12N 5/00 | (2006.01) |
| A61K 40/11 | (2025.01) |
| A61K 40/31 | (2025.01) |
| A61K 40/42 | (2025.01) |
| C07K 14/705 | (2006.01) |
| C12N 5/0783 | (2010.01) |
| C12N 15/115 | (2010.01) |
| B82Y 5/00 | (2011.01) |

(52) U.S. Cl.
CPC ............ *C12N 5/0636* (2013.01); *A61K 40/11* (2025.01); *A61K 40/31* (2025.01); *A61K 40/4204* (2025.01); *A61K 40/4205* (2025.01); *A61K 40/421* (2025.01); *A61K 40/4211* (2025.01); *A61K 40/4255* (2025.01); *A61K 40/4257* (2025.01); *A61K 40/4258* (2025.01); *C07K 14/70517* (2013.01); *C12N 15/115* (2013.01); *A61K 2239/31* (2023.05); *A61K 2239/38* (2023.05); *A61K 2239/48* (2023.05); *A61K 2239/49* (2023.05); *A61K 2239/55* (2023.05); *B82Y 5/00* (2013.01); *C07K 2317/70* (2013.01); *C07K 2319/03* (2013.01); *C07K 2319/50* (2013.01); *C12N 2310/16* (2013.01); *C12N 2310/3513* (2013.01); *C12N 2510/00* (2013.01)

(58) Field of Classification Search
CPC .......................... C12N 2510/00; C12N 5/0636
See application file for complete search history.

(56) References Cited

U.S. PATENT DOCUMENTS

| | | | |
|---|---|---|---|
| 5,278,056 A | 1/1994 | Bank | |
| 5,728,388 A | 3/1998 | Terman | |
| 8,440,811 B2 * | 5/2013 | Chang et al. ......... | C07H 21/04 536/24.5 |
| 8,552,167 B2 | 10/2013 | Chang | |
| 2002/0006409 A1 | 1/2002 | Wood | |
| 2013/0287748 A1 | 10/2013 | June | |
| 2014/0154228 A1 | 6/2014 | Volk | |
| 2014/0322212 A1 * | 10/2014 | Brogdon et al. ... | C07K 16/2866 424/134.1 |
| 2019/0240248 A1 | 8/2019 | Yan | |

FOREIGN PATENT DOCUMENTS

| | | | |
|---|---|---|---|
| CN | 106350533 A | 1/2017 | |
| WO | WO94/17810 | 8/1994 | |
| WO | WO94/23744 | 10/1994 | |
| WO | WO2008/081035 A1 | 7/2008 | |
| WO | WO2015/095895 A1 | 6/2015 | |
| WO | WO2016/030414 A1 | 3/2016 | |
| WO | WO2017091546 A1 * | 6/2017 | ............ C12N 5/071 |
| WO | WO2019/140140 | 7/2019 | |
| WO | WO2019/147308 A2 | 8/2019 | |
| WO | WO2019/147309 A2 | 8/2019 | |
| WO | WO2020072764 A1 * | 4/2020 | ............ C07K 16/22 |

OTHER PUBLICATIONS

Rothemund, Paul W. K. (2006) "Folding DNA to create nanoscale shapes and patterns", Nature, 440(7082), 297-302. (Year: 2006).*
Taylor et al. (2017) "A DNA-based T cell receptor reveals a role for receptor clustering in ligand discrimination" Cell, 169(1), 108-119. (Year: 2017).*
Johnsson, Kai "SNAP-tag® Technologies: Novel Tools to Study Protein Function" New England Biolabs, web publication, accessed: Nov. 20, 2024, . . . [continued in Box V] (Year: 2024).*
[continued from Box U] . . . retrieved from: www.neb.com/en-us/tools-and-resources/feature-articles/snap-tag-technologies-novel-tools-to-study-protein-function?srsltid=AfmBOorVle7ZQItpzGJeMMQZZF2ucEiMoitqcfPUJhvmzCTzK_hWLWW. (Year: 2024).*

(Continued)

*Primary Examiner* — Teresa E Knight
*Assistant Examiner* — James Joseph Graber
(74) *Attorney, Agent, or Firm* — DUANE MORRIS LLP

(57) ABSTRACT

In certain embodiments, this disclosure provides methods to generate DNA, RNA and/or DNA-peptide nanostructures based chimeric antigen receptor (CAR) T cell (engineered T cell) for cancer immunotherapy, and compositions made by these methods.

16 Claims, 58 Drawing Sheets
(43 of 58 Drawing Sheet(s) Filed in Color)
Specification includes a Sequence Listing.

(56) References Cited

OTHER PUBLICATIONS

Liss et al. (2015) "Self-labelling enzymes as universal tags for fluorescence microscopy, super-resolution microscopy and electron microscopy" Scientific reports, 5(1), 17740, 13 pages. (Year: 2015).*
Ahmad KM, Xiao Y, Soh HT. Selection is more intelligent than design: improving the affinity of a bivalent ligand through directed evolution. Nucleic acids research. 2012;40(22):11777-83. doi: 10.1093/nar/gks899. PubMed PMID: WOS:000313414800059.
Aldaye FA, Palmer AL, Sleiman HF. Assembling materials with DNA as the guide. Science. 2008;321(5897):1795-9. doi: DOI 10.1126/science.1154533. PubMed PMID: ISI:000259501300027.
Alderton GK. Immunotherapy: Skipping out epitopes. Nature reviews Cancer. 2015;15(12):699-. doi: 10.1038/nrc4053.
Alderton GK. Tumour immunology: Suppressing tumorigenic inflammation. Nature reviews Cancer. 2012;12(4):228-. doi: 10.1038/nrc3252.
Andersen ES, Dong MD, Nielsen MM, Jahn K, Lind-Thomsen A, Mamdouh W, Gothelf KV, Besenbacher F, Kjems J. DNA origami design of dolphin-shaped structures with flexible tails. Acs Nano. 2008;2(6):1213-8. doi: Doi 10.1021/Nn800215j. PubMed PMID: ISI:000257120800018.
Beatty GL, Haas AR, Maus MV, Torigian DA, Soulen MC, Plesa G, Chew A, Zhao Y, Levine BL, Albelda SM, Kalos M, June CH. Mesothelin-Specific Chimeric Antigen Receptor mRNA-Engineered T Cells Induce Antitumor Activity in Solid Malignancies. Cancer Immunology Research. 2014;2(2):112-20. doi: 10.1158/2326-6066.CIR-13-0170. PubMed PMID: 10.1158/2326-6066.CIR-13-0170.
Beaucage SL, Caruthers MH. Deoxynucleoside Phosphoramidites—a New Class of Key Intermediates for Deoxypolynucleotide Synthesis. Tetrahedron Lett. 1981;22(20):1859-62. doi: Doi 10.1016/S0040-4039(01)90461-7. PubMed PMID: WOS:A1981LM19100003.
Bonnans C, Chou J, Werb Z. Remodelling the extracellular matrix in development and disease. Nat Rev Mol Cell Biol. 2014;15(12):786-801. Epub 2014/11/22. doi: 10.1038/nrm3904. PubMed PMID: 25415508; PMCID: PMC4316204.
Boyman O, Sprent J. The role of interleukin-2 during homeostasis and activation of the immune system. Nature Reviews Immunology. 2012;12:180. doi: 10.1038/nri3156.
Brentjens RJ, Latouche JB, Santos E, Marti F, Gong MC, Lyddane C, King PD, Larson S, Weiss M, Riviere I, Sadelain M. Eradication of systemic B-cell tumors by genetically targeted human T lymphocytes co-stimulated by CD80 and interleukin-15. Nat Med. 2003;9(3):279-86. Epub Feb. 13, 2003. doi: 10.1038/nm827. PubMed PMID: 12579196.
Buranachai C, Thavarungkul P, Kanatharana P. A Novel Reconfigurable Optical Biosensor Based on DNA Aptamers and a DNA Molecular Beacon. J Fluoresc. 2012;22(6):1617-25. doi: 10.1007/s10895-012-1105-6. PubMed Pmid: WOS:000310193200026.
Burke DH, Willis JH. Recombination, RNA evolution, and bifunctional RNA molecules isolated through Chimeric SELEX. RNA. 1998;4(9):1165-75. doi: Doi 10.1017/S1355838298980542. PubMed PMID: WOS:000075793000012.
Caruana I, Savoldo B, Hoyos V, Weber G, Liu H, Kim ES, Ittmann MM, Marchetti D, Dotti G. Heparanase promotes tumor infiltration and antitumor activity of CAR-redirected T lymphocytes. Nature medicine. 2015;21(5):524-9. doi: 10.1038/nm.3833. PubMed PMID: 10.1038/nm.3833.
Cepko, Constance, and Warren Pear. "Overview of the retrovirus transduction system." Current Protocols in Molecular Biology 36.1 (1996): 9-9; p. 9.9.1-9.9.16.
Cerchia L, de Franciscis V. Targeting cancer cells with nucleic acid aptamers. Trends Biotechnol. 2010;28(10):517-25. PubMed PMID: WOS:000282860200004.
Charo J, Finkelstein SE, Grewal N, Restifo NP, Robbins PF, Rosenberg SA. Bcl-2 Overexpression Enhances Tumor-Specific T-Cell Survival. Cancer Research. 2005;65(5):2001-8. doi: 10.1158/0008-5472.CAN-04-2006. PubMed PMID: 10.1158/0008-5472.CAN-04-2006.

Chhabra R, Sharma J, Ke YG, Liu Y, Rinker S, Lindsay S, Yan H. Spatially addressable multiprotein nanoarrays templated by aptamer-tagged DNA nanoarchitectures. Journal of the American Chemical Society. 2007;129(34):10304-5. doi: Doi 10.1021/Ja072410u. PubMed PMID: ISI:000249035200003.
Cho JH, Collins JJ, Wong WW. Universal Chimeric Antigen Receptors for Multiplexed and Logical Control of T Cell Responses. Cell. 2018. Epub May 1, 2018. doi: 10.1016/j.cell.2018.03.038. PubMed PMID: 29706540.
Chow MT, Luster AD. Chemokines in Cancer. Cancer Immunology Research. 2014;2:1125-31.
Christian S, Pilch J, Akerman ME, Porkka K, Laakkonen P, Ruoslahti E. Nucleolin expressed at the cell surface is a marker of endothelial cells in angiogenic blood vessels. The Journal of Cell Biology. 2003; 163(4):871-8. Epub Nov. 26, 2003. doi: 10.1083/jcb.200304132. PubMed PMID: 14638862; PMCID: 2173679.
Collins BE, Paulson JC. Cell surface biology mediated by low affinity multivalent protein-glycan interactions. Curr Opin Chem Biol. 2004;8(6):617-25. doi: 10.1016/j.cbpa.2004.10.004. PubMed PMID: WOS:000225782300008.
Compte M, Blanco B, Serrano F, Cuesta ÁM, Sanz L, Bernad A, Holliger P, Álvarez-Vallina L. Inhibition of tumor growth in vivo by in situ secretion of bispecific anti-CEA × anti-CD3 diabodies from lentivirally transduced human lymphocytes. Cancer Gene Therapy. 2007;14(4):380-8. doi: 10.1038/sj.cgt.7701021. PubMed PMID: 10.1038/sj.cgt.7701021.
Copolovici, Langel, Eriste, and Langel (2014) ACS Nano 2014 8 (3), 1972-1994; DOI: 10.1021/nn4057269.
Corrigan-Curay J, et al. T-cell immunotherapy: looking forward. Molecular Therapy. 2014;22(9):1564-74. Epub Sep. 5, 2014. doi: 10.1038/mt.2014.148. PubMed PMID: 25186558; PMCID: PMC4435492.
Coughlan AM, et al. Myeloid Engraftment in Humanized Mice: Impact of Granulocyte-Colony Stimulating Factor Treatment and Transgenic Mouse Strain. Stem Cells Dev. 2016;25(7):530-41. Epub Feb. 18, 2016. doi: 10.1089/scd.2015.0289. PubMed PMID: 26879149.
Craddock JA, Lu A, Bear A, Pule M, Brenner MK, Rooney CM, Foster AE. Enhanced Tumor Trafficking of GD2 Chimeric Antigen Receptor T Cells by Expression of the Chemokine Receptor CCR2b. Journal of Immunotherapy. 2010;33(8):780-8. doi: 10.1097/CJI.0b013e3181ee6675. PubMed PMID: 10.1097/CJI.0b013e3181ee6675.
Cranage et al., 1986, EMBO J. 5:3057-3063.
Danos, Olivier, and Richard C. Mulligan. "Safe and efficient generation of recombinant retroviruses with amphotropic and ecotropic host ranges." Proceedings of the National Academy of Sciences 85.17 (1988): 6460-6464.
Dapra J, Lauridsen LH, Nielsen AT, Rozlosnik N. Comparative study on aptamers as recognition elements for antibiotics in a label-free all-polymer biosensor. Biosens Bioelectron. 2013;43:315-20. doi: 10.1016/j.bios.2012.12.058. PubMed PMID: WOS:000316525300053.
Delebecque CJ, Lindner AB, Silver PA, Aldaye FA. Organization of Intracellular Reactions with Rationally Designed RNA Assemblies. Science. 2011;333(6041):470-4. doi: DOI 10.1126/science.1206938. PubMed PMID: ISI:000292959600051.
Derr ND, Goodman BS, Jungmann R, Leschziner AE, Shih WM, Reck-Peterson SL. Tug-of-War in Motor Protein Ensembles Revealed with a Programmable DNA Origami Scaffold. Science. 2012;338(6107):662-5. doi: DOI 10.1126/science.1226734. PubMed PMID: ISI:000310516000052.
Deyle, David R., and David W. Russell. "Adeno-associated virus vector integration." Current Opinion in Molecular Therapeutics 11.4 (2009): 442-447.
Diehnelt CW, Shah M, Gupta N, Belcher PE, Greving MP, Stafford P, Johnston SA. Discovery of High-Affinity Protein Binding Ligands—Backwards. PLoS One. 2010;5(5):e10728.
Domenyuk V, Loskutov A, Johnston SA, Diehnelt CW. A Technology for Developing Synbodies with Antibacterial Activity. PLoS One. 2013;8(1):e54162. doi: 10.1371/journal.pone.0054162.

(56) References Cited

OTHER PUBLICATIONS

Douglas SM, Bachelet I, Church GM. A Logic-Gated Nanorobot for Targeted Transport of Molecular Payloads. Science. 2012;335(6070):831-4. doi: DOI 10.1126/science.1214081. PubMed PMID: ISI:000300356400038.

Douglas SM, Dietz H, Liedl T, Hogberg B, Graf F, Shih WM. Self-assembly of DNA into nanoscale three-dimensional shapes. Nature. 2009;459(7245):414-8. doi: Doi 10.1038/Nature08016.

Douglas SM, Marblestone AH, Teerapittayanon S, Vazquez A, Church GM, Shih WM. Rapid prototyping of 3D DNA-origami shapes with caDNAno. Nucleic Acids Res. 2009;37(15):5001-6. doi: Doi 10.1093/Nar/Gkp436. PubMed PMID: ISI:000270016400010.

Duan N, Wu SJ, Chen XJ, Huang YK, Xia Y, Ma XY, Wang ZP. Selection and Characterization of Aptamers against *Salmonella typhimurium* Using Whole-Bacterium Systemic Evolution of Ligands by Exponential Enrichment (SELEX). J Agr Food Chem. 2013;61(13):3229-34. doi: 10.1021/jf400767d. PubMed PMID: WOS:000317259100008.

Ellington AD, Szostak JW. Invitro Selection of Rna Molecules That Bind Specific Ligands. Nature. 1990;346(6287):818-22. doi: DOI 10.1038/346818a0. PubMed PMID: WOS:A1990DW48800045.

Fadel et al., J. Virol. 88(17):9704-9717 (2014).

Fankhauser M, Broggi MAS, Potin L, Bordry N, Jeanbart L, Lund AW, Da Costa E, Hauert S, Rincon-Restrepo M, Tremblay C, Cabello E, Homicsko K, Michielin O, Hanahan D, Speiser DE, Swartz MA. Tumor lymphangiogenesis promotes T cell infiltration and potentiates immunotherapy in melanoma. Sci Transl Med. 2017;9(407). Epub Sep. 15, 2017. doi: 10.1126/scitranslmed.aal4712. PubMed PMID: 28904226.

Ferreira CSM, Cheung MC, Missailidis S, Bisland S, Gariepy J. Phototoxic aptamers selectively enter and kill epithelial cancer cells. Nucleic acids research. 2009;37(3):866-76. doi: 10.1093/nar/gkn967. PubMed PMID: WOS:000263831400030.

Fukaya T, Abe K, Savory N, Tsukakoshi K, Yoshida W, Ferri S, Sode K, Ikebukuro K. Improvement of the VEGF binding ability of DNA aptamers through in silico maturation and multimerization strategy. J Biotechnol. 2015;212:99-105. doi: 10.1016/j.jbiotec.2015.08.011. PubMed PMID: WOS:000362284400017.

Fukuhara et al. Biochemistry 1(4): 563-568, 1962.

Gautier A, Juillerat A, Heinis C, Correa IR, Kindermann M, Beaufils F, Johnsson K. An Engineered Protein Tag for Multiprotein Labeling in Living Cells. Chemistry & Biology. 2008;15(2):128-36. doi: https://doi.org/10.1016/j.chembiol.2008.01.007.

Geary C, Rothemund PWK, Andersen Es. A single-stranded architecture for cotranscriptional folding of RNA nanostructures. Science. 2014;345(6198):799-804. doi: DOI 10.1126/science. 1253920. PubMed PMID: WOS:000340593100041.

Gorman, et al. Proc. Natl. Acad. Sci. 79.22 (1982): 6777-6781.

Greving MP, Belcher PE, Cox CD, Daniel D, Diehnelt CW, Woodbury NW. High-throughput screening in two dimensions: Binding intensity and off-rate on a peptide microarray. Analytical Biochemistry. 2010;402:93-5.

Greving MP, Belcher PE, Diehnelt CW, Gonzalez-Moa MJ, Emery J, Fu J, Johnston SA, Woodbury NW. Thermodynamic Additivity of Sequence Variations: An Algorithm for Creating High Affinity Peptides Without Large Libraries or Structural Information. PLoS One. 2010;5(11):e15432.

Guo PX, Zhang CL, Chen CP, Garver K, Trottier M. Inter-RNA interaction of phage phi 29 pRNA to form a hexameric complex for viral DNA transportation. Mol Cell. 1998;2(1):149-55. doi: Doi 10.1016/S1097-2765(00)80124-0. PubMed PMID: ISI:000075174500017.

Guo PX. The emerging field of RNA nanotechnology. Nature Nanotechnology. 2010;5(12):833-42. doi: Doi 10.1038/Nnano.2010.231. PubMed PMID: ISI:000285047100008.

Gupta N, Belcher PE, Johnston SA, Diehnelt CW. Engineering a synthetic ligand for tumor necrosis factor-alpha. Bioconjug Chem. 2011;22(8):1473-8. Epub Jul. 20, 2011. doi: 10.1021/bc200091c. PubMed PMID: 21766818.

Gupta N, Lainson J, Domenyuk V, Zhao Z-G, Johnston SA, Diehnelt CW. Whole-Virus Screening to Develop Synbodies for the Influenza Virus. Bioconjugate Chemistry. 2016;27(10):2505-12. doi: 10.1021/acs.bioconjchem.6b00447.

Gupta NL, John; Belcher, Paul. E.; Shen, Luhui; Mason, Hugh S.; Johnston, Stephen Albert; Diehnelt, Chris W. Cross-Reactive Synbody Affinity Ligands Capture Diverse Noroviruses. Analytical Chemistry. 2017;89(13):7174-81.

Han DR, Pal S, Liu Y, Yan H. Folding and cutting DNA into reconfigurable topological nanostructures. Nature Nanotechnology. 2010;5(10):712-7. doi: DOI 10.1038/nnano.2010.193. PubMed PMID: ISI:000282578000008.

Han DR, Pal S, Nangreave J, Deng ZT, Liu Y, Yan H. DNA Origami with Complex Curvatures in Three-Dimensional Space. Science. 2011;332(6027):342-6. doi: DOI 10.1126/science.1202998.

Han DR, Pal S, Yang Y, Jiang SX, Nangreave J, Liu Y, Yan H. DNA Gridiron Nanostructures Based on Four-Arm Junctions. Science. 2013;339(6126): 1412-5. doi: DOI 10.1126/science.1232252.

Hao CH, Li X, Tian C, Jiang W, Wang GS, Mao CD. Construction of RNA nanocages by re-engineering the packaging RNA of Phi29 bacteriophage. Nature Communications. 2014;5. doi: Artn 389010.1038/Ncomms4890. PubMed PMID: WOS:000337503800034.

Harlin H, Meng Y, Peterson AC, Zha Y, Tretiakova M, Slingluff C, McKee M, Gajewski TF. Chemokine Expression in Melanoma Metastases Associated with CD8+ T-Cell Recruitment. Cancer Research. 2009;69(7):3077-85. doi: 10.1158/0008-5472.CAN-08-2281. PubMed PMID: 10.1158/0008-5472.CAN-08-2281.

Hasita H, Ma C, Yano H, Pan C, Ohnishi K, Fujiwara Y, Endo S, Kikukawa Y, Okuno Y, Matsuoka M, Takeya M, Komohara Y. An IL-27/Stat3 axis induces expression of programmed cell death 1 ligands (PD-L1/2) on infiltrating macrophages in lymphoma. Cancer science. 2016. Epub Aug 27, 2016. doi: 10.1111/cas.13065. PubMed PMID: 27564404.

Hawley-Nelson, Pamela, and Valentina Ciccarone. "Transfection of cultured eukaryotic cells using cationic lipid reagents." Current Protocols in Neuroscience 10.1 (2000): A-1F.

He Y, Chen Y, Liu HP, Ribbe AE, Mao CD. Self-assembly of hexagonal DNA two-dimensional (2D) arrays. Journal of the American Chemical Society. 2005;127(35):12202-12203.

He Y, Tian Y, Ribbe AE, Mao CD. Highly connected two-dimensional crystals of DNA six-point-stars. Journal of the American Chemical Society. 2006;128(50):15978-15979. doi: Doi 10.1021/Ja0665141.

Huang Y, Shi H, Zhou H, Song X, Yuan S, Luo Y. The angiogenic function of nucleolin is mediated by vascular endothelial growth factor and nonmuscle myosin. Blood. 2006;107(9):3564-71. Epub Jan. 13, 2016. doi: 10.1182/blood-2005-07-2961. PubMed PMID: 16403913.

Hwang-Verslues WW, Kuo W-H, Chang P-H, Pan C-C, Wang H-H, Tsai S-T, Jeng Y-M, Shew J-Y, Kung JT, Chen C-H, Lee EYHP, Chang K-J, Lee W-H. Multiple Lineages of Human Breast Cancer Stem/Progenitor Cells Identified by Profiling with Stem Cell Markers. PLoS ONE. 2009;4(12):e8377. doi: 10.1371/journal.pone.0008377. PubMed PMID: PMC2793431.

Iida J, Clancy R, Dorchak J, Somiari RI, Somiari S, Cutler ML, Mural RJ, Shriver CD. DNA Aptamers against Exon v10 of CD44 Inhibit Breast Cancer Cell Migration. Plos One. 2014;9(2). doi: ARTN e8871210.1371/journal.pone.0088712. PubMed PMID: WOS:000331711900041.

International Search Report/Written Opinion in International Patent Application No. PCT/US19/16560, dated May 20, 2019, in 22 pages.

Iwahori K, Kakarla S, Velasquez MP, Yu F, Yi Z, Gerken C, Song X-T, Gottschalk S. Engager T Cells: A New Class of Antigen-specific T Cells That Redirect Bystander T Cells. Molecular Therapy. 2015;23(1):171-8. doi: 10.1038/mt.2014.156. PubMed PMID: 10.1038/mt.2014.156.

Jackson HJ, Rafiq S, Brentjens RJ. Driving CAR T-cells forward. Nature reviews Clinical Oncology. 2016. doi: 10.1038/nrclinonc.2016.36.

Jayasena SD. Aptamers: An emerging class of molecules that rival antibodies in diagnostics. Clin Chem. 1999;45(9):1628-50. PubMed PMID: WOS:000082382100044.

(56) References Cited

OTHER PUBLICATIONS

Jencks WP. On the attribution and additivity of binding energies. Proc Natl Acad Sci U S A. 1981;78(7):4046-50. PubMed PMID: 16593049.

Jicha DL, Mule JJ, Rosenberg SA. Interleukin 7 generates antitumor cytotoxic T lymphocytes against murine sarcomas with efficacy in cellular adoptive immunotherapy. J Exp Med. 1991; 174(6):1511-5. Epub Dec. 1, 1991. PubMed PMID: 1744582; PMCID: PMC2119035.

John LB, Devaud C, Duong CPM, Yong CS, Beavis PA, Haynes NM, Chow MT, Smyth MJ, Kershaw MH, Darcy PK. Anti-PD-1 Antibody Therapy Potently Enhances the Eradication of Established Tumors By Gene-Modified T Cells. Clinical Cancer Research. 2013;19(20):5636-46. doi: 10.1158/1078-0432.CCR-13-0458. PubMed PMID: 10.1158/1078-0432.CCR-13-0458.

Johnson LA, Scholler J, Ohkuri T, Kosaka A, Patel PR, McGettigan SE, Nace AK, Dentchev T, Thekkat P, Loew A, Boesteanu AC, Cogdill AP, Chen T, Fraietta JA, Kloss CC, Posey AD, Engels B, Singh R, Ezell T, Idamakanti N, Ramones MH, Li N, Zhou L, Plesa G, Seykora JT, Okada H, June CH, Brogdon JL, Maus MV. Rational development and characterization of humanized anti-EGFR variant III chimeric antigen receptor T cells for glioblastoma. Science Translational Medicine. 2015;7(275):275ra22-ra22. doi: 10.1126/scitranslmed.aaa4963. PubMed PMID: 10.1126/scitranslmed.aaa4963.

Johnston SA, Domenyuk V, Gupta N, Batista MT, Lainson JC, Zhao Z-G, Lusk JF, Loskutov A, Cichacz Z, Stafford P, Legutki JB, Diehnelt CW. A Simple Platform for the Rapid Development of Antimicrobials. Scientific Reports. 2017;7(1):17610. doi: 10.1038/s41598-017-17941-7.

June, C. H., ed., 2001, Adoptive Cellular Therapy, Chapter 31, In: Cancer Chemotherapy and Biotherapy: Principles and Practice, Lippincott Williams & Wilkins, Baltimore, 29 pages.

Kebriaei, Partow, et al. "Gene therapy with the sleeping beauty transposon system." Trends in Genetics 33.11 (2017): 852-870.

Keefe AD, Pai S, Ellington A. Aptamers as therapeutics. Nature Reviews Drug Discovery. 2010;9(7):537-50. doi: 10.1038/nrd3141. PubMed PMID: WOS:000280143900024.

Keefe AD, Schaub RG. Aptamers as candidate therapeutics for cardiovascular indications. Curr Opin Pharmacol. 2008;8(2):147-52. doi: 10.1016/j.coph.2007.12.005. PubMed PMID: WOS:000254931800007.

Keppler A, Gendreizig S, Gronemeyer T, Pick H, Vogel H, Johnsson K. A general method for the covalent labeling of fusion proteins with small molecules in vivo. Nat Biotechnol. 2003;21(1):86-9. Epub Dec. 7, 2002. doi: 10.1038/nbt765. PubMed PMID: 12469133.

Keppler A, Kindermann M, Gendreizig S, Pick H, Vogel H, Johnsson K. Labeling of fusion proteins of O6-alkylguanine-DNA alkyltransferase with small molecules in vivo and in vitro. Methods. 2004;32(4):437-44. Epub Mar. 9, 2004. doi: 10.1016/j.ymeth.2003.10.007. PubMed PMID: 15003606.

Keppler A, Pick H, Arrivoli C, Vogel H, Johnsson K. Labeling of fusion proteins with synthetic fluorophores in live cells. Proc Natl Acad Sci U S A. 2004;101(27):9955-9. Epub Jul. 1, 2004. doi: 10.1073/pnas.0401923101. PubMed PMID: 15226507; PMCID: PMC454197.

Kershaw MH, Westwood JA, Darcy PK. Gene-engineered T cells for cancer therapy. Nature Reviews Cancer. 2013;13(8):525-41. doi: 10.1038/nrc3565.

Kessenbrock K, Plaks V, Werb Z. Matrix metalloproteinases: regulators of the tumor microenvironment. Cell. 2010;141(1):52-67. Epub Apr. 8, 2010. doi: 10.1016/j.cell.2010.03.015. PubMed PMID: 20371345; PMCID: PMC2862057.

Kim DN, Kilchherr F, Dietz H, Bathe M. Quantitative prediction of 3D solution shape and flexibility of nucleic acid nanostructures. Nucleic Acids Research. 2012;40(7):2862-8. doi: Doi 10.1093/Nar/Gkr1173. PubMed PMID: ISI:000303164400012.

Kim et al (2014) Genome Research, Cold Spring Harbor Laboratory Press, 24, 1012-1019.

Kim M, Bae H, Kim E, Kim S. Biosensor using newly selected aptamers for detection ofdopamine and cortisol hormones. Mol Cell Toxicol. 2010;6(3):57-. PubMed PMID: WOS:000283834700095.

Kim YS, Chung J, Song MY, Jurng J, Kim BC. Aptamer cocktails: Enhancement of sensing signals compared to single use of aptamers for detection of bacteria. Biosens Bioelectron. 2014;54:195-8. doi: 10.1016/j.bios.2013.11.003. PubMed PMID: WOS:000333071500030.

Kim, Ji-wook, et al. "Single-cell mechanogenetics using monovalent magnetoplasmonic nanoparticles." Nature Protocols 12.9 (2017): 1871-1889.

Kimoto M, Yamashige R, Matsunaga K, Yokoyama S, Hirao I. Generation of high-affinity DNA aptamers using an expanded genetic alphabet. Nature Biotechnology. 2013;31(5):453-+. doi: 10.1038/nbt.2556. PubMed PMID: WOS:000318589600026.

King NP, Sheffler W, Sawaya MR, Vollmar BS, Sumida JP, Andre I, Gonen T, Yeates TO, Baker D. Computational Design of Self-Assembling Protein Nanomaterials with Atomic Level Accuracy. Science. 2012;336(6085):1171-4. doi: DOI 10.1126/science.1219364. PubMed PMID: ISI:000304647900053.

Kingston, Chen and Okayama (2001) Current Protocols in Molecular Biology Appendix 1C, 8 pages; DOI: 10.1002/0471142301.nsa01cs01.

Klebanoff CA, Finkelstein SE, Surman DR, Lichtman MK, Gattinoni L, Theoret MR, Grewal N, Spiess PJ, Antony PA, Palmer DC, Tagaya Y, Rosenberg SA, Waldmann TA, Restifo NP. IL-15 enhances the in vivo antitumor activity of tumor-reactive CD8+ T cells. Proc Natl Acad Sci U S A. 2004;101(7):1969-74. Epub Feb. 6, 2004. doi: 10.1073/pnas.0307298101. PubMed PMID: 14762166; PMCID: PMC357036.

Klebanoff CA, Rosenberg SA, Restifo NP. Prospects for gene-engineered T cell immunotherapy for solid cancers. Nature Medicine. 2016;22(1):26-36. doi: 10.1038/nm.4015.

Kobold S, Grassmann S, Chaloupka M, Lampert C, Wenk S, Kraus F, Rapp M, Düwell P, Zeng Y, Schmollinger JC, Schnurr M, Endres S, Rothenfusser S. Impact of a New Fusion Receptor on PD-1-Mediated Immunosuppression in Adoptive T Cell Therapy. JNCI: Journal of the National Cancer Institute. 2015;107(8). doi: 10.1093/jnci/djv146. PubMed PMID: 10.1093/jnci/djv146.

Kortylewski M, Kuo YH. Push and release: TLR9 activation plus STAT3 blockade for systemic antitumor immunity. Oncoimmunology. 2014;3(1):e27441. Epub May 7, 2014. doi: 10.4161/onci.27441. PubMed PMID: 24800162; PMCID: 4006856.

Lai YT, Cascio D, Yeates TO. Structure of a 16-nm Cage Designed by Using Protein Oligomers. Science. 2012;336(6085): p. 1129. doi: DOI 10.1126/science.1219351. PubMed PMID: ISI:000304647900040.

Lai WY, Huang BT, Wang JW, Lin PY, Yang PC. A Novel PD-L1-targeting Antagonistic DNA Aptamer With Antitumor Effects. Mol Ther Nucleic Acids. 2016;5(12):e397. Epub Dec. 14, 2016. doi: 10.1038/mtna.2016.102. PubMed PMID: 27959341.

Lainson JC, Daly SM, Triplett K, Johnston SA, Hall PR, Diehnelt CW. Synthetic Antibacterial Peptide Exhibits Synergy with Oxacillin against MRSA. ACS Medicinal Chemistry Letters. 2017;8(8):853-7. doi: 10.1021/acsmedchemlett.7b00200.

Lainson JC, Fuenmayor MF, Johnston SA, Diehnelt CW. Conjugation Approach To Produce a *Staphylococcus aureus* Synbody with Activity in Serum. Bioconjugate Chemistry. 2015;26:2125-32. doi: 10.1021/acs.bioconjchem.5b00420.

Lee H, et al. Molecularly self-assembled nucleic acid nanoparticles for targeted in vivo siRNA delivery. Nature Nanotechnology. 2012;7(6):389-93. doi: Doi 10.1038/Nnano.2012.73. PubMed PMID: ISI:000305008200013.

Legutki JB, Zhao Z-G, Greving M, Woodbury N, Johnston SA, Stafford P. Scalable high-density peptide arrays for comprehensive health monitoring. Nat Commun. 2014;5. doi: 10.1038/ncomms5785.

Li et al., J. Neurosci. Methods vol. 189, pp. 56-64 (2010).

Li S, Song C, Jiang Q, Tian Y, Wang J, Zhang Y, Liu S, Zou Y, Anderson GJ, Han J-Y, Chang Y, Nie G, Ding B, Zhao Y, Yan H. A Cancer Killing Nanorobot With On-target Tumor Infarction Manuscript in preparation. 2015.

(56) References Cited

OTHER PUBLICATIONS

Li Y, Tseng YD, Kwon SY, D'Espaux L, Bunch JS, McEuen PL, Luo D. Controlled assembly of dendrimer-like DNA. Nat Mater. 2004;3(1):38-42. Epub Jan. 6, 2004. doi: 10.1038/nmat1045. PubMed PMID: 14704783.

Li, Mingyue, et al. "A matrix metalloproteinase inhibitor enhances anti-cytotoxic T lymphocyte antigen-4 antibody immunotherapy in breast cancer by reprogramming the tumor microenvironment." Oncology Reports 35.3 (2016): 1329-1339.

Lim WA, June CH. The Principles of Engineering Immune Cells to Treat Cancer. Cell. 2017;168(4):724-40. doi: 10.1016/j.cell.2017. 01.016.

Lisby, Michael, and Rodney Rothstein. "Cell biology of mitotic recombination." Cold Spring Harbor Perspectives in Biology 7.3 (2015): a016535.

Liu F, Walters KJ. Multitasking with ubiquitin through multivalent interactions. Trends Biochem Sci. 2010;35(6):352-60. doi: 10.1016/j.tibs.2010.01.002. PubMed PMID: WOS:000278946700007.

Liu TJ, Sun BC, Zhao XL, Zhao XM, Sun T, Gu Q, Yao Z, Dong XY, Zhao N, Liu N. CD133+ cells with cancer stem cell characteristics associates with vasculogenic mimicry in triple-negative breast cancer. Oncogene. 2013;32(5):544-53. Epub Apr. 4, 2012. doi: 10.1038/onc.2012.85. PubMed PMID: 22469978.

Liu XW, Xu Y, Yu T, Clifford C, Liu Y, Yan H, Chang Y. a DNA Nanostructure Platform for Directed Assembly of Synthetic Vaccines. Nano Letters. 2012;12(8):4254-9. doi: Doi 10.1021/N1301877k. PubMed PMID: ISI:000307211000060.

Liu Y, et al. Inhibition of p300 impairs Foxp3+ T regulatory cell function and promotes antitumor immunity. Nature Medicine. 2013;19(9):1173-7. doi: 10.1038/nm.3286. PubMed PMID: 10.1038/nm.3286.

Lu P, Takai K, Weaver VM, Werb Z. Extracellular matrix degradation and remodeling in development and disease. Cold Spring Harb Perspect Biol. 2011;3(12). Epub Sep. 16, 2011. doi: 10.1101/cshperspect.a005058. PubMed PMID: 21917992; PMCID: PMC3225943.

Ma et al. 1997, Proc. Natl. Acad. Sci. U.S.A. 94: 12744-12746.

Mahvi DA, Meyers JV, Tatar AJ, Contreras A, Suresh M, Leverson GE, Sen S, Cho CS. CTLA-4 Blockade Plus Adoptive T-Cell Transfer Promotes Optimal Melanoma Immunity in Mice. Journal of Immunotherapy. 2015;38(2):54-61. doi: 10.1097/CJI.0000000000000064. PubMed PMID: 10.1097/CJI.0000000000000064.

Malo J, Mitchell JC, Venien-Bryan C, Harris JR, Wille H, Sherratt DJ, Turberfield AJ. Engineering a 2D protein-DNA crystal. Angew Chem Int Edit. 2005;44(20):3057-61. doi: DOI 10.1002/anie.200463027. PubMed PMID: ISI:000229342600010.

Mandelkern M, Elias JG, Eden D, Crothers DM. The Dimensions of DNA in Solution. J Mol Biol. 1981;152(1):153-61. doi: Doi 10.1016/0022-2836(81)90099-1. PubMed PMID: WOS:A1981ML33900008.

Mardomi, Alireza, and Saeid Abediankenari. "Matrix metalloproteinase 8: could it benefit the CAR-T cell therapy of solid tumors ?-a-Commentary on therapeutic potential." Cancer Microenvironment 11.1 (2018): 93-96.

Markley JC, Sadelain M. IL-7 and IL-21 are superior to IL-2 and IL-15 in promoting human T cell-mediated rejection of systemic lymphoma in immunodeficient mice. Blood. 2010;115(17):3508-19. doi: 10.1182/blood-2009-09-241398. PubMed PMID: 10.1182/blood-2009-09-241398.

Massagué J. TGFβ in Cancer. Cell. 2008;134(2):215-30. doi: 10.1016/j.cell.2008.07.001. PubMed PMID: 10.1016/j.cell.2008.07.001.

McNeil, Paul L. "Direct introduction of molecules into cells." Current protocols in Cell Biology 18.1 (2003): 20-1.

Mei QA, Wei XX, Su FY, Liu Y, Youngbull C, Johnson R, Lindsay S, Yan H, Meldrum D. Stability of DNA Origami Nanoarrays in Cell Lysate. Nano letters. 2011;11(4):1477-82. doi: 10.1021/nl1040836. PubMed PMID: WOS:000289341500015.

Milone et al., Mol. Ther. 17(8): 1453-1464 (2009).

Moon EK, Carpenito C, Sun J, Wang LCS, Kapoor V, Predina J, Powell DJ, Riley JL, June CH, Albelda SM. Expression of a Functional CCR2 Receptor Enhances Tumor Localization and Tumor Eradication by Retargeted Human T cells Expressing a Mesothelin-Specific Chimeric Antibody Receptor. Clinical Cancer Research. 2011;17(14):4719-30. doi: 10.1158/1078-0432.CCR-11-0351. PubMed PMID: 10.1158/1078-0432.CCR-11-0351.

Moroz A, Eppolito C, Li Q, Tao J, Clegg CH, Shrikant PA. IL-21 enhances and sustains CD8+ T cell responses to achieve durable tumor immunity: comparative evaluation of IL-2, IL-15, and IL-21. J Immunol. 2004;173(2):900-9. Epub Jul. 9 2004. PubMed PMID: 15240677.

Mor-Vaknin N, Saha AK, Legendre M, Carmona-Rivera C, Amin MA, Rabquer BJ, Gonzalez-Hernandez MJ, Jorns JM, Yalavarthi S, Mohan S, Pai D, Angevine K, Adams B, Knight JS, Koch AE, Fox D, Engelke D, Kaplan MJ, Markovitz D. DEK-Targeting DNA Aptamers As Novel Therapeutics for Inflammatory Arthritis. Abstract 933, Arthritis Rheumatol. 2015;67 (suppl 10). PubMed PMID: WOS:000370860202197.

Mor-Vaknin, Nirit, et al. "DEK-targeting DNA aptamers as therapeutics for inflammatory arthritis." Nature Communications 8.1 (2017): 1-13.

Muller J, Wulffen B, Potzsch B, Mayer G. Multidomain targeting generates a high-affinity thrombin-inhibiting bivalent aptamer. Chembiochem. 2007;8(18):2223-6. doi: 10.1002/cbic.200700535. PubMed PMID: WOS:000251850900009.

Neumann T, Junker HD, Schmidt K, Sekul R. SPR-based fragment screening: Advantages and applications. Current Topics in Medicinal Chemistry. 2007;7(16):1630-42. PubMed PMID: WOS:000251582500007.

Newick K, O'Brien S, Moon E, Albelda Sm. Car T Cell Therapy for Solid Tumors. Annual Review of Medicine. 2017;68(1):139-52. doi: 10.1146/annurev-med-062315-120245.

Niemeyer CM. Semisynthetic DNA-Protein Conjugates for Biosensing and Nanofabrication. Angew Chem Int Edit. 2010;49(7):1200-16. doi: DOI 10.1002/anie.200904930. PubMed PMID: ISI:000274910100003.

Nishio N, Diaconu I, Liu H, Cerullo V, Caruana I, Hoyos V, Bouchier-Hayes L, Savoldo B, Dotti G. Armed Oncolytic Virus Enhances Immune Functions of Chimeric Antigen Receptor-Modified T Cells in Solid Tumors. Cancer Research. 2014;74(18):5195.

Ogata et al. Journal of Organic Chemistry 74:2585-2588, 2009.

Oh SA, Li MO. TGF-: Guardian of T Cell Function. The Journal of Immunology. 2013;191(8):3973-9. doi: 10.4049/jimmunol.1301843. PubMed PMID: 10.4049/jimmunol.1301843.

Pegram et al, CD28z CARs and armored CARs, 2014, Cancer J. 20(2):127-133.

Perna SK, Pagliara D, Mahendravada A, Liu H, Brenner MK, Savoldo B, Dotti G. Interleukin-7 Mediates Selective Expansion of Tumor-redirected Cytotoxic T Lymphocytes (CTLs) without Enhancement of Regulatory T-cell Inhibition. Clinical Cancer Research. 2014;20(1):131-9. doi: 10.1158/1078-0432.CCR-13-1016. PubMed PMID: 10.1158/1078-0432.CCR-13-1016.

Pinheiro AV, Han DR, Shih WM, Yan H. Challenges and opportunities for structural DNA nanotechnology. Nature nanotechnology. 2011;6(12):763-72. doi: Doi 10.1038/Nnano.2011.187. PubMed PMID: WOS:000298248300007.

Ponnuswamy N, Bastings MMC, Nathwani B, Ryu JH, Chou LYT, Vinther M, Li WA, Anastassacos FM, Mooney DJ, Shih WM. Oligolysine-based coating protects DNA nanostructures from low-salt denaturation and nuclease degradation. Nat Commun. 2017;8:15654. Epub Jun. 1, 2017. doi: 10.1038/ncomms15654. PubMed PMID: 28561045; PMCID: PMC5460023.

Potter (2001) Current Protocols in Molecular Biology unit 10.15, 3 pages; DOI: 10.1002/0471142735.im1015s03.

Potter, Huntington, and Richard Heller. "Transfection by electroporation." Current Protocols in Immunology 117.1 (2017): 10-15.

Praetorius F, Kick B, Behler KL, Honemann MN, Weuster-Botz D, Dietz H. Biotechnological mass production of DNA origami. Nature. 2017;552(7683):84-+. doi: 10.1038/nature24650.

Purmal et al. Nucleic Acids Research 22(1): 72-78, 1994.

Qian Y, Qiu M, Wu Q, Tian Y, Zhang Y, Gu N, Li S, Xu L, Yin R. Enhanced cytotoxic activity of cetuximab in EGFR-positive lung cancer by conjugating with gold nanoparticles. Scientific Reports. 2014;4:7490. doi: 10.1038/srep07490.

(56) References Cited

OTHER PUBLICATIONS

Rabinowitz JA, Lainson JC, Johnston SA, Diehnelt CW. Non-natural amino acid peptide microarrays to discover Ebola virus glycoprotein ligands. Chemical Communications. 2018. doi: 10.1039/C7CC08242H.

Rinker S, Ke YG, Liu Y, Chhabra R, Yan H. Self-assembled DNA nanostructures for distance-dependent multivalent ligand-protein binding. Nature Nanotechnology. 2008;3(7):418-22. doi: 10.1038/nnano.2008.164. PubMed PMID: WOS:000257984700014.

Rochman Y, Spolski R, Leonard WJ. New insights into the regulation of T cells by gamma(c) family cytokines. Nat Rev Immunol. 2009;9(7):480-90. Epub Jun. 23, 2009. doi: 10.1038/nri2580. PubMed PMID: 19543225; PMCID: PMC2814538.

Rodriguez D, Morrison CJ, Overall CM. Matrix metalloproteinases: what do they not do? New substrates and biological roles identified by murine models and proteomics. Biochim Biophys Acta. 2010;1803(1):39-54. Epub Oct. 6, 2009. doi: 10.1016/j.bbamcr.2009.09.015. PubMed PMID: 19800373.

Rothemund PWK. Folding DNA to create nanoscale shapes and patterns. Nature. 2006;440(7082):297-302. doi: Doi 10.1038/Nature04586.

Ruscito A, DeRosa MC. Small-Molecule Binding Aptamers: Selection Strategies, Characterization, and Applications. Front Chem. 2016;4. doi: ARTN 1410.3389/fchem.2016.00014. PubMed PMID: WOS:000375407400001.

Sacca B, Meyer R, Erkelenz M, Kiko K, Arndt A, Schroeder H, Rabe KS, Niemeyer CM. Orthogonal Protein Decoration of DNA Origami. Angew Chem Int Edit. 2010;49(49):9378-83. doi: DOI 10.1002/anie.201005931. PubMed PMID: ISI:000285210300010.

Sadelain et al., Nature Rev. 12:51-58 (2012);.

Sakaguchi S, Miyara M, Costantino CM, Hafler DA. FOXP3+ regulatory T cells in the human immune system. Nature Reviews Immunology. 2010;10(7):490-500. doi: 10.1038/nri2785. PubMed PMID: 10.1038/nri2785.

Seeman NC. De NovoDesign of Sequences for Nucleic Acid Structural Engineering. Journal of Biomolecular Structure and Dynamics. 1990;8(3):573-81. doi: 10.1080/07391102.1990.10507829.

Seeman NC. Nanomaterials Based on DNA. Annual Review of Biochemistry. 2010;79(1):65-87. doi: 10.1146/annurev-biochem-060308-102244.

Sefah K, Meng L, Lopez-Colon D, Jimenez E, Liu C, Tan WH. DNA Aptamers as Molecular Probes for Colorectal Cancer Study. Plos One. 2010;5(12). doi: ARTN e14269 10.1371/journal.pone.0014269. PubMed PMID: WOS:000285181400003.

Sefah K, Shangguan D, Xiong XL, O'Donoghue MB, Tan WH. Development of DNA aptamers using Cell-SELEX. Nat Protoc. 2010;5(6):1169-85. doi: 10.1038/nprot.2010.66. PubMed PMID: WOS:000278354700019.

Selmi DN, Adamson RJ, Attrill H, Goddard AD, Gilbert RJC, Watts A, Turberfield AJ. DNA-Templated Protein Arrays for Single-Molecule Imaging. Nano letters. 2011;11(2):657-60. doi: Doi 10.1021/N11037769. PubMed PMID: ISI:000287049100059.

Service RF. DNA Nanotechnology Grows Up. Science. 2011;332(6034):1140-2. PubMed PMID: ISI:000291205200015.

Sharei, Armon, et al. "A vector-free microfluidic platform for intracellular delivery." Proceedings of the National Academy of Sciences 110.6 (2013): 2082-2087.

Sharon et al. (2013) Proc. Natl. Acad. Sci., 110(6).

Shibaguchi, Hirotomo, et al. "Enhancement of antitumor activity by using a fully human gene encoding a single-chain fragmented antibody specific for carcinoembryonic antigen." OncoTargets and Therapy 10 (2017): 3979-3990.

Shuker SB, Hajduk PJ, Meadows RP, Fesik SW. Discovering High-Affinity Ligands for Proteins: SAR by NMR. Science. 1996;274(5292):1531-4. doi: 10.1126/science.274.5292.1531.

Shukla GC, Haque F, Tor Y, Wilhelmsson LM, Toulme J-J, Isambert H, Guo P, Rossi JJ, Tenenbaum SA, Shapiro BA. A Boost for the Emerging Field of RNA Nanotechnology. Acs Nano. 2011;5(5):3405-18. doi: 10.1021/nn200989r.

Shultz LD, Lyons BL, Burzenski LM, Gott B, Chen X, Chaleff S, Kotb M, Gillies SD, King M, Mangada J, Greiner DL, Handgretinger R. Human lymphoid and myeloid cell development in NOD/LtSz-scid IL2R gamma null mice engrafted with mobilized human hemopoietic stem cells. J Immunol. 2005;174(10):6477-89. Epub May 10, 2005. PubMed PMID: 15879151.

Simmons SC, Jamsa H, Silva D, Cortez CM, Mckenzie EA, Bitu CC, Salo S, Nurmenniemi S, Nyberg P, Risteli J, deAlmeida CEB, Brenchley PEC, Salo T, Missailidisi S. Anti-Heparanase Aptamers as Potential Diagnostic and Therapeutic Agents for Oral Cancer. Plos One. 2014;9(10). doi: ARTN e96846 10.1371/journal.pone.0096846. PubMed PMID: WOS:000345204000001.

Sonpavde G, Wang M, Peterson LE, Wang HY, Joe T, Mims MP, Kadmon D, Ittmann MM, Wheeler TM, Gee AP, Wang R-F, Hayes TG. HLA-restricted NY-ESO-1 peptide immunotherapy for metastatic castration resistant prostate cancer. Investigational New Drugs. 2014;32(2):235-42. doi: 10.1007/s10637-013-9960-9.

Soundararajan S, Wang L, Sridharan V, Chen W, Courtenay-Luck N, Jones D, Spicer EK, Fernandes DJ. Plasma membrane nucleolin is a receptor for the anticancer aptamer AS1411 in MV4-11 leukemia cells. Molecular Pharmacology. 2009;76(5):984-91. Epub Aug. 7, 2009. doi: 10.1124/mol.109.055947. PubMed PMID: 19657047; PMCID: 2774992.

Sprengel, Andreas, et al. "Tailored protein encapsulation into a DNA host using geometrically organized supramolecular interactions." Nature Communications 8.1 (2017): 1-12.

Srivastava S, Riddell SR. Engineering CAR-T cells: Design concepts. Trends in Immunology. 2015;36(8):494-502. doi: 10.1016/j.it.2015.06.004.

Stephanopoulos N, Liu MH, Tong GJ, Li Z, Liu Y, Yan H, Francis MB. Immobilization and One-Dimensional Arrangement of Virus Capsids with Nanoscale Precision Using DNA Origami. Nano letters. 2010;10(7):2714-20. doi: Doi 10.1021/N11018468. PubMed PMID: WOS:000280416200070.

Subik K, Lee J-F, Baxter L, Strzepek T, Costello D, Crowley P, Xing L, Hung M-C, Bonfiglio T, Hicks DG, Tang P. The Expression Patterns of ER, PR, HER2, CK5/6, EGFR, Ki-67 and AR by Immunohistochemical Analysis in Breast Cancer Cell Lines. Breast Cancer : Basic and Clinical Research. 2010;4:35-41. PubMed PMID: PMC2914277.

Tannenberg RK, Al Shamaileh H, Lauridsen LH, Kanwar JR, Dodd PR, Veedu RN. Nucleic Acid Aptamers as Novel Class of Therapeutics to Mitigate Alzheimer's Disease Pathology. Curr Alzheimer Res. 2013;10(4):442-8. PubMed PMID: WOS:000318345600009.

Teng Y, Girvan AC, Casson LK, Pierce WM, Jr., Qian M, Thomas SD, Bates PJ. AS1411 alters the localization of a complex containing protein arginine methyltransferase 5 and nucleolin. Cancer Res. 2007;67(21):10491-500. Epub Nov. 3, 2007. doi: 10.1158/0008-5472.CAN-06-4206. PubMed PMID: 17974993.

Tian L, Heyduk T. Bivalent Ligands with Long Nanometer-Scale Flexible Linkers. Biochemistry-Us. 2009;48(2):264-75. doi: 10.1021/bi801630b. PubMed PMID: WOS:000262430500008.

Tran E, Turcotte S, Gros A, Robbins PF, Lu Y-C, Dudley ME, Wunderlich JR, Somerville RP, Hogan K, Hinrichs CS, Parkhurst MR, Yang JC, Rosenberg SA. Cancer immunotherapy based on mutation-specific CD4+ T cells in a patient with epithelial cancer. Science (New York, NY). 2014;344(6184):641-5. doi: 10.1126/science.1251102. PubMed PMID: 24812403.

Tuerk C, Gold L. Systematic Evolution of Ligands by Exponential Enrichment—RNA Ligands to Bacteriophage-T4 DNA-Polymerase. Science. 1990;249(4968):505-10. doi: DOI 10.1126/science.2200121. PubMed PMID: WOS:A1990DR81100032.

Urbanska, Katarzyna, and Daniel J. Powell. "Development of a novel universal immune receptor for antigen targeting: To infinity and beyond." Oncoimmunology 1.5 (2012): 777-779.

Verma S, Eckstein F. Modified oligonucleotides: Synthesis and strategy for users. Annual Review of Biochemistry. 1998;67:99-134. doi: DOI 10.1146/annurev.biochem.67.1.99. PubMed PMID: WOS:000075721700006.

Vonderheide et al., 2003, Immun. Research 27:1-15.

Wallace A, Kapoor V, Sun J, Mrass P, Weninger W, Heitjan DF, June C, Kaiser LR, Ling LE, Albelda SM. Transforming Growth Factor-Receptor Blockade Augments the Effectiveness of Adoptive T-Cell

(56) References Cited

OTHER PUBLICATIONS

Therapy of Established Solid Cancers. Clinical Cancer Research. 2008;14(12):3966-74. doi: 10.1158/1078-0432.CCR-08-0356. PubMed PMID: 10.1158/1078-0432.CCR-08-0356.

Wandtke T, Wozniak J, Kopinski P. Aptamers in Diagnostics and Treatment of Viral Infections. Viruses-Basel. 2015;7(2):751-80. doi: 10.3390/v7020751. PubMed PMID: WOS:000350670800017.

Wang HY, Cheng H, Wang J, Xu LJ, Chen HX, Pei RJ. Selection and characterization of DNA aptamers for the development of light-up biosensor to detect Cd(II). Talanta. 2016;154:498-503. doi: 10.1016/j.talanta.2016.04.005. PubMed PMID: WOS:000376696400066.

Wang LCS, Lo A, Scholler J, Sun J, Majumdar RS, Kapoor V, Antzis M, Cotner CE, Johnson LA, Durham AC, Solomides CC, June CH, Pure E, Albelda SM. Targeting Fibroblast Activation Protein in Tumor Stroma with Chimeric Antigen Receptor T Cells Can Inhibit Tumor Growth and Augment Host Immunity without Severe Toxicity. Cancer Immunology Research. 2014;2(2):154-66. doi: 10.1158/2326-6066.CIR-13-0027. PubMed PMID: 10.1158/2326-6066.CIR-13-0027.

Wang P, Yang Y, Hong H, Zhang Y, Cai W, Fang D. Aptamers as Therapeutics in Cardiovascular Diseases. Curr Med Chem. 2011;18(27):4169-74. PubMed PMID: WOS:000295447500008.

Watson JD, Crick FHC. Molecular Structure of Nucleic Acids—a Structure for Deoxyribose Nucleic Acid. Nature. 1953;171(4356):737-8. doi: Doi 10.1038/171737a0. PubMed PMID: WOS:A1953UA43400007.

Wilkins MHF, Stokes AR, Wilson HR. Molecular Structure of Deoxypentose Nucleic Acids. Nature. 1953;171(4356):738-40. doi: Doi 10.1038/171738a0. PubMed PMID: WOS:A1953UA43400008.

Williams BAR, Diehnelt CW, Belcher P, Greving M, Woodbury NW, Johnston SA, Chaput JC. Creating Protein Affinity Reagents by Combining Peptide Ligands on Synthetic DNA Scaffolds. J Am Chem Soc 2009; 131(47):17233-41. doi: 10.1021/ja9051735.

Williams BAR, Lund K, Liu Y, Yan H, Chaput JC. Self-assembled peptide nanoarrays: An approach to studying protein-protein interactions. Angew Chem Int Edit. 2007;46(17):3051-4. doi: DOI 10.1002/anie.200603919. PubMed PMID: WOS:000246139400020.

Williams S, Lund K, Lin C, Wonka P, Lindsay S, Yan H. Tiamat: A Three-Dimensional Editing Tool for Complex DNA Structures International Workshop on DNA-Based Computers; 5347: pp. 90-101. doi: 10.1007/978-3-642-03076-5_8; In: Goel A., Simmel F.C., Sosík P. (eds) DNA Computing. DNA 2008. Lecture Notes in Computer Science, vol. 5347. Springer, Berlin, Heidelberg. https://doi.org/10.1007/978-3-642-03076-5_8.

Wilson R, Bourne C, Chaudhuri RR, Gregory R, Kenny J, Cossins A. Single-Step Selection of Bivalent Aptamers Validated by Comparison with SELEX Using High-Throughput Sequencing. Plos One. 2014;9(6). doi: ARTN e10057210.1371/journal.pone.0100572. PubMed PMID: WOS:000338709500064.

Winfree E, Liu FR, Wenzler LA, Seeman NC. Design and self-assembly of two-dimensional DNA crystals. Nature. 1998;394(6693):539-44. doi: Doi 10.1038/28998.

Wollman AJM, Sanchez-Cano C, Carstairs HMJ, Cross RA, Turberfield AJ. Transport and self-organization across different length scales powered by motor proteins and programmed by DNA. Nature nanotechnology. 2014;9(1):44-7. doi: Doi 10.1038/Nnano.2013.230. PubMed PMID: ISI:000329315000013.

Xu et al. Tetrahedron 48(9): 1729-1740, 1992.

Xu JH, Teng IT, Zhang LQ, Delgado S, Champanhac C, Cansiz S, Wu CC, Shan H, Tan WH. Molecular Recognition of Human Liver Cancer Cells Using DNA Aptamers Generated via Cell-SELEX. Plos One. 2015;10(5). doi: ARTN e012586310.1371/journal.pone.0125863. PubMed PMID: WOS:000353943000112.

Yakovchuk P, Protozanova E, Frank-Kamenetskii MD. Base-stacking and base-pairing contributions into thermal stability of the DNA double helix. Nucleic Acids Research. 2006;34(2):564-74. doi: Doi 10.1093/Nar/Gkj454. PubMed PMID: WOS:000235291300026.

Yan H, Park SH, Finkelstein G, Reif JH, LaBean TH. DNA-templated self-assembly of protein arrays and highly conductive nanowires. Science. 2003;301(5641):1882-1884. doi: DOI 10.1126/science.1089389.

Yao X, Ahmadzadeh M, Lu YC, Liewehr DJ, Dudley ME, Liu F, Schrump DS, Steinberg SM, Rosenberg SA, Robbins PF. Levels of peripheral CD4+FoxP3+ regulatory T cells are negatively associated with clinical response to adoptive immunotherapy of human cancer. Blood. 2012;119(24):5688-96. doi: 10.1182/blood-2011-10-386482. PubMed PMID: 10.1182/blood-2011-10-386482.

Ye et al., PNAS 111(26):9591-9596 (2014).

Yong CSM, Dardalhon V, Devaud C, Taylor N, Darcy PK, Kershaw MH. CAR T-cell therapy of solid tumors. Immunology and Cell Biology. 2017;95(4):356-63. doi: 10.1038/icb.2016.128.

Yoon, Dok Hyun, et al. "Incorporation of immune checkpoint blockade into chimeric antigen receptor T cells (CAR-Ts): combination or built-in CAR-T." International Journal of Molecular Sciences 19.2 (2018): 340, 16 pages.

Zadegan RM, Norton ML. Structural DNA Nanotechnology: From Design to Applications. Int J Mol Sci. 2012;13(6):7149-62. doi: Doi 10.3390/Ijms13067149. PubMed PMID: ISI:000306188700037.

Zadeh JN, Steenberg CD, Bois JS, Wolfe BR, Pierce MB, Khan AR, Dirks RM, Pierce NA. NUPACK: Analysis and Design of Nucleic Acid Systems. J Comput Chem. 2011;32(1):170-3. doi: Doi 10.1002/Jcc.21596. PubMed PMID: ISI:000285311200016.

Zamay GS, Zamay TN, Kolovskaya OS, Krat AV, Glazyrin YE, Dubinina AV, Zamay AS. Development of a biosensor for electrochemical detection of tumor-associated proteins in blood plasma of cancer patients by aptamers. Dokl Biochem Biophys. 2016;466(1):70-3. doi: 10.1134/S1607672916010208. PubMed PMID: WOS:000373348600018.

Zhang F, Nangreave J, Liu Y, Yan H. Structural DNA Nanotechnology: State of the Art and Future Perspective. Journal of the American Chemical Society. 2014;136(32):11198-211. doi: Doi 10.1021/Ja505101a. PubMed PMID: WOS:000340442700001.

Zhou G, Ding ZC, Fu J, Levitsky HI. Presentation of acquired peptide-MHC class II ligands by CD4+ regulatory T cells or helper cells differentially regulates antigen-specific CD4+ T cell response. Journal of immunology. 2011;186(4):2148-55. Epub Jan. 19, 2011. doi: 10.4049/jimmunol.1002917. PubMed PMID: 21242518.

\* cited by examiner

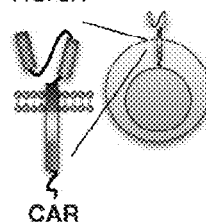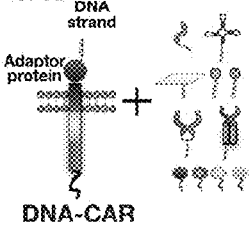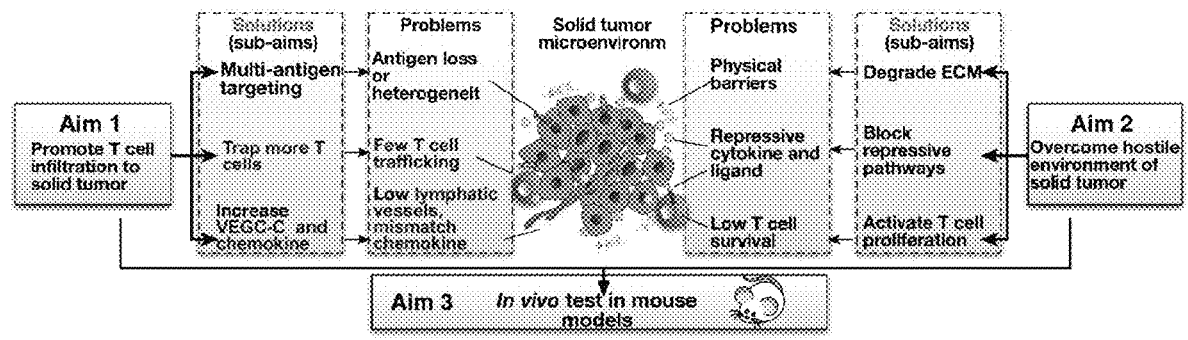

FIG. 5A
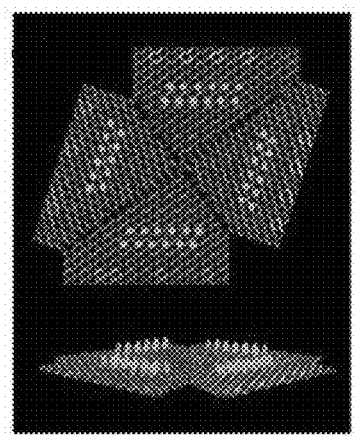
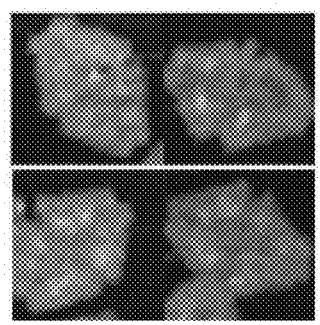
FIG. 5B
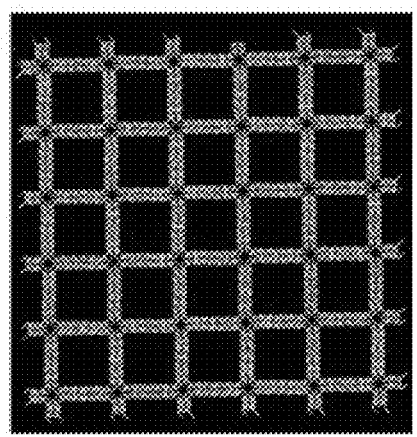
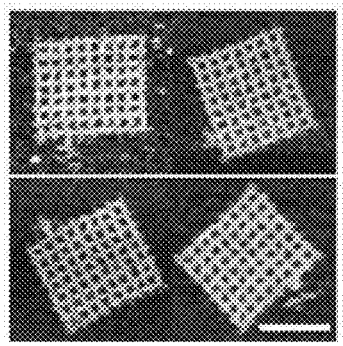

Group A
single signal 2

Group B
Leader +
single signal 2

Group C
double signal 2

Group D
Leader +
double signal 2

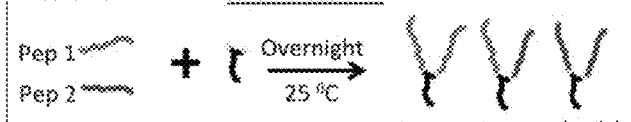
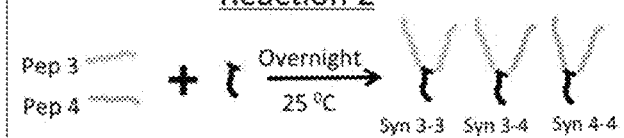
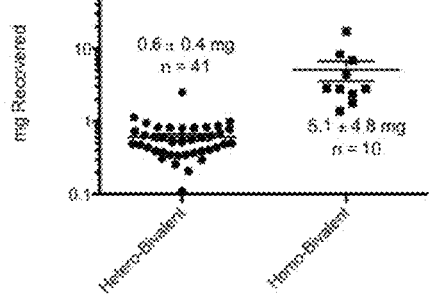

FIG. 13A
FIG. 13B
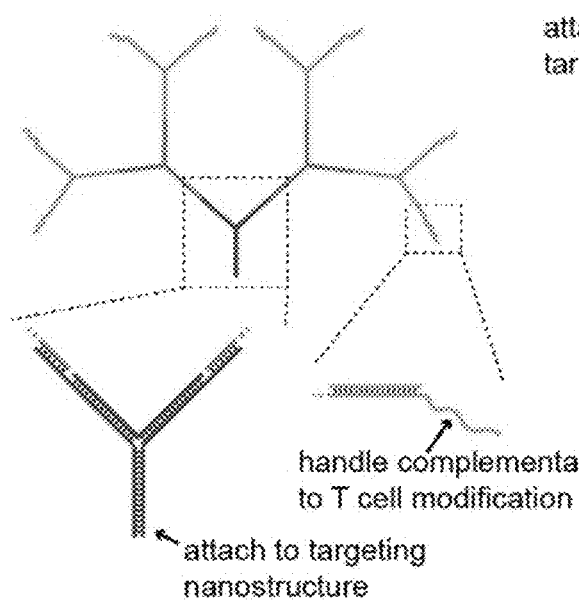
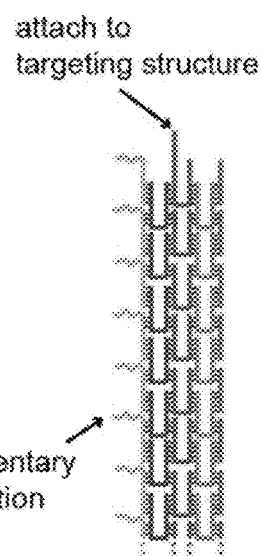

Chemokine levle: High — CCL1, CXCL3

Chemokine levle: Medium — CCL7, CXCL5, CXCL11, CCL5, CXCL1, CXCL10

Chemokine levle: Low — CCL8, CCL9

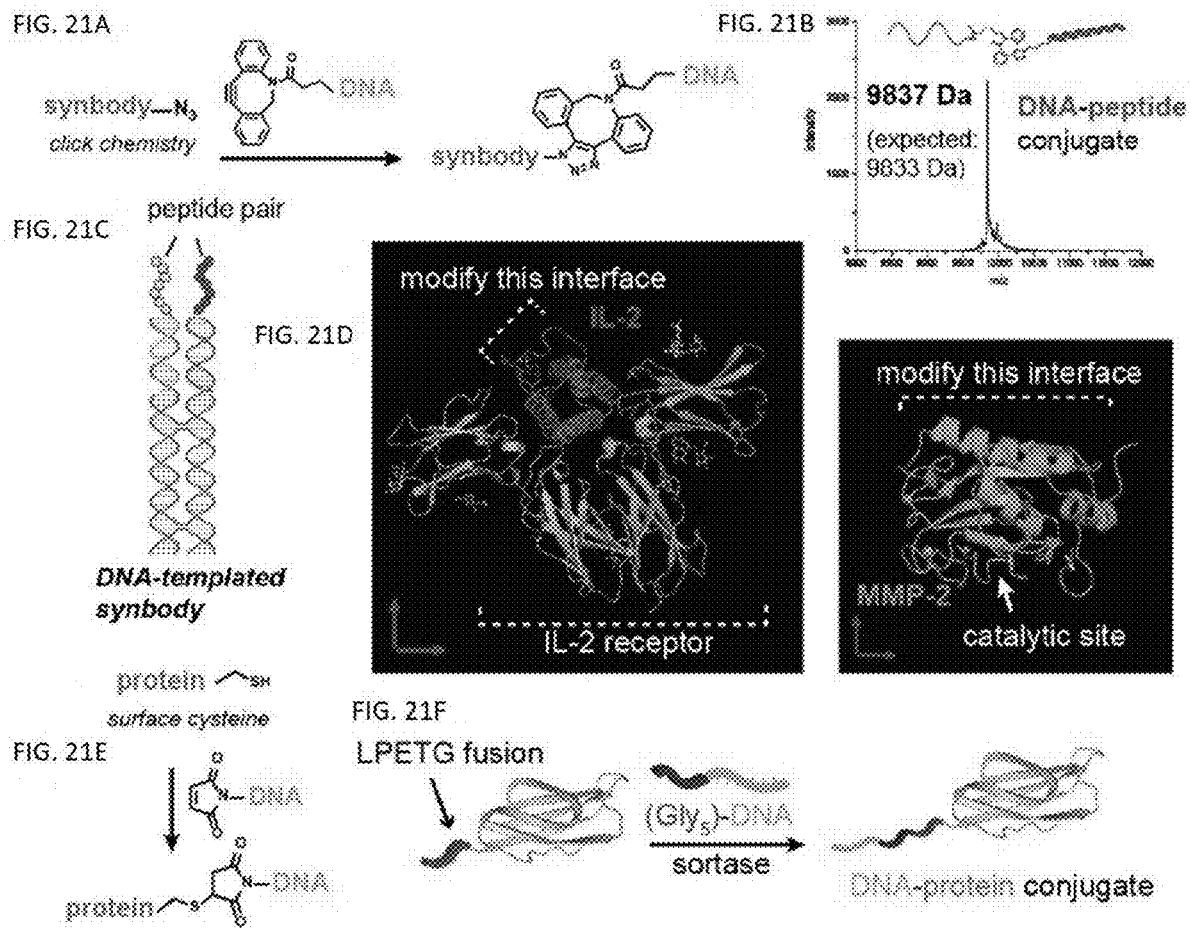

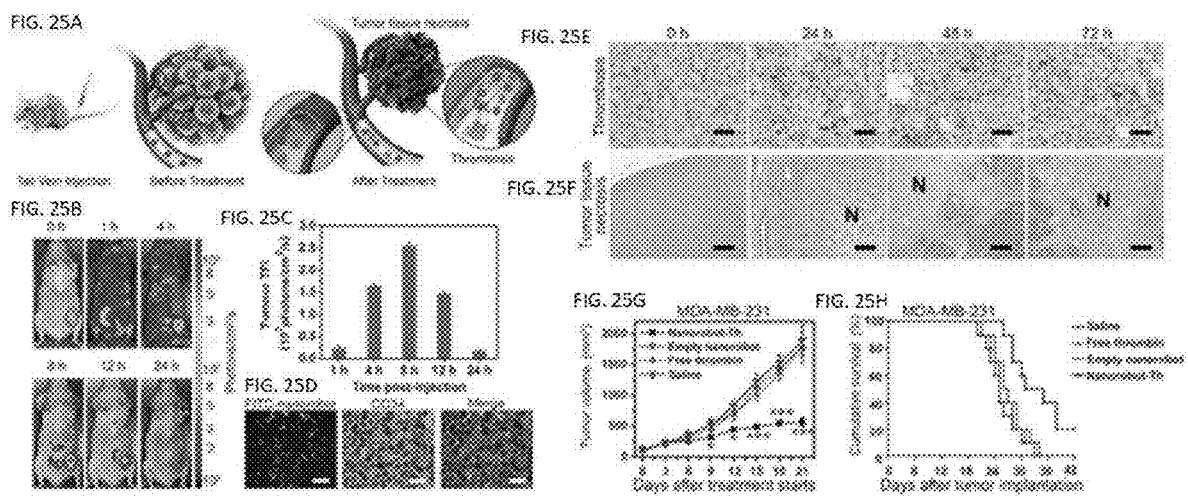

FIG. 26A    FIG. 26B    FIG. 26C
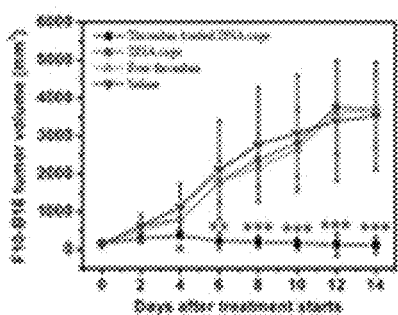 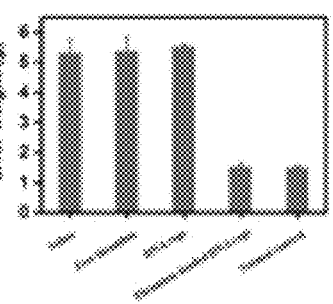 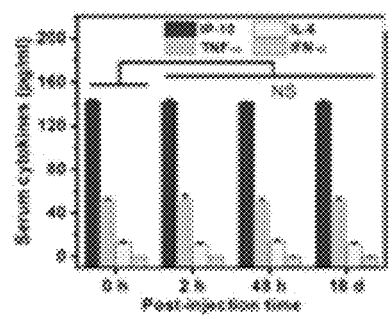
FIG. 26D
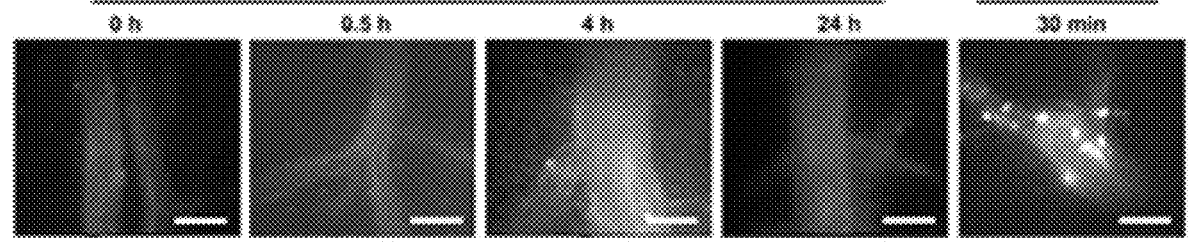

FIG. 40

| hPD-L1-apt1 | ACG GGC CAC ATC AAC TCA TTG ATA GAC AAT GCG TCC ACT GCC CGT | SEQ ID NO.: 5 |
|---|---|---|
| hMUC1-apt1 | GCA GTT GAT CCT TTG GAT ACC CTG G | SEQ ID NO.: 6 |
| hMUC1-apt2 | GCAGT TGATC CTTTG GATAC CCTGG TTTTTA AAA | SEQ ID NO.: 7 |
| hMUC1-apt3 | GGGAGACAAGAATAAACGCTCAAGCAGTTGATCCT TTGGATACCCTGGTTCGACAGGA GGC TCA CAA CAGGC | SEQ ID NO.: 8 |
| hEGFR-apt1 | TACCAGTGCGATGCTCAGTGCCGTTTCTTCTCTTTC GCTTTTTTTGCTTTTGAGC A TGCTGACGCATTCG GTT GAC | SEQ ID NO.: 9 |
| Scg8 | ATC TAA CTG CTG CGC CGC CGG GAA AAT ACT GTA CGG TTA GA | SEQ ID NO.: 10 |
| Control Apt | AAAAAAAAAAAAAAACGTGCAGTACGCCAAC CTTTCTCATGCGCTGCCC CTC TTA | SEQ ID NO.: 11 |

FIG. 41A
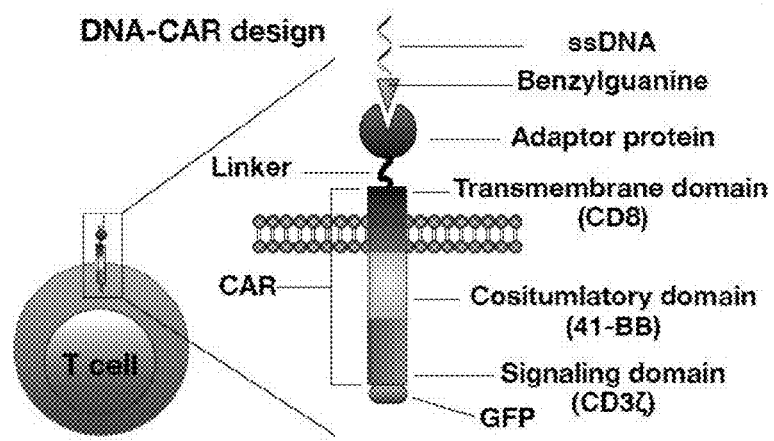
FIG. 41B
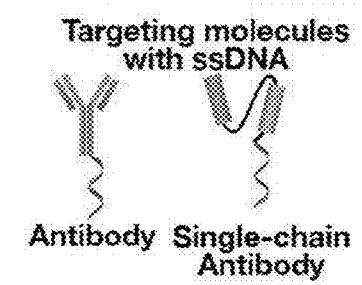
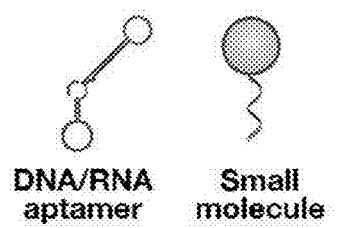
FIG. 41C
DNA-CAR T recongize and kill tumor cells
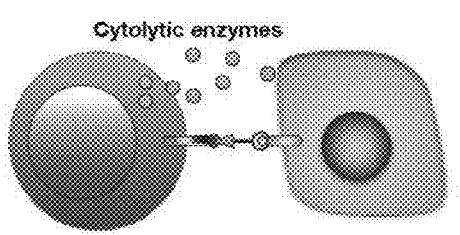
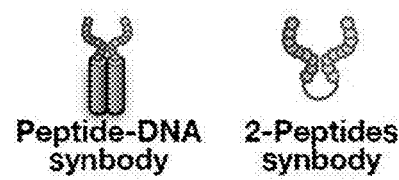

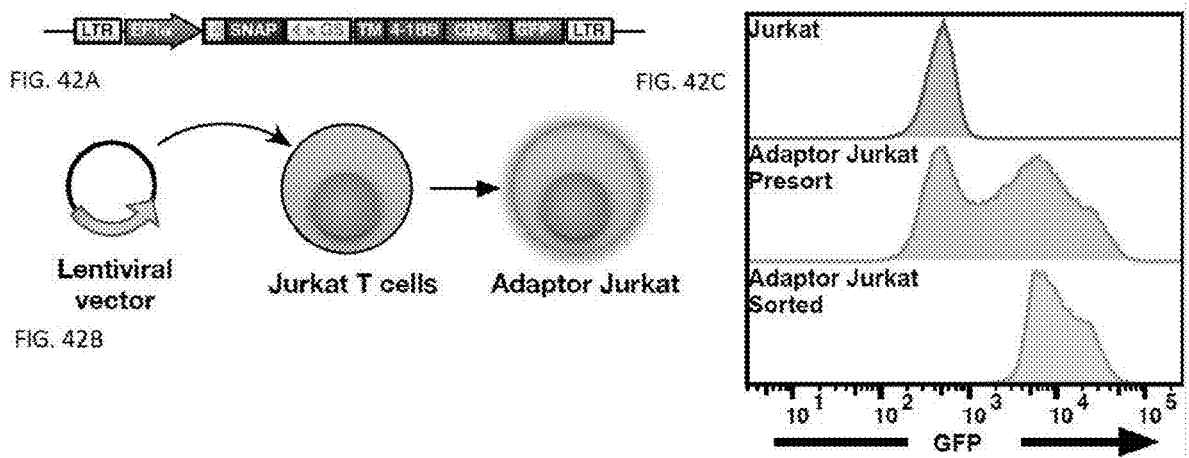

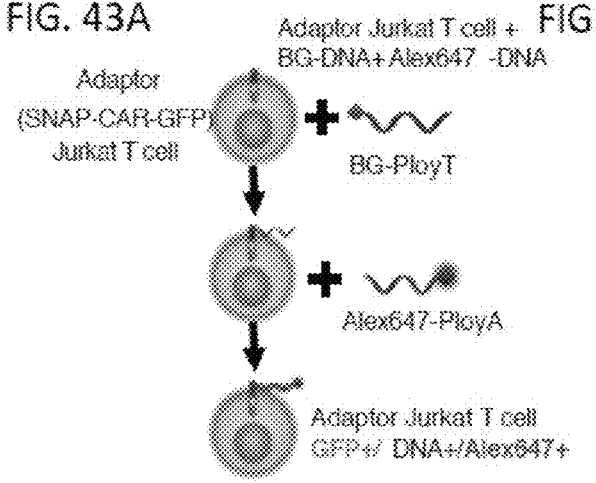
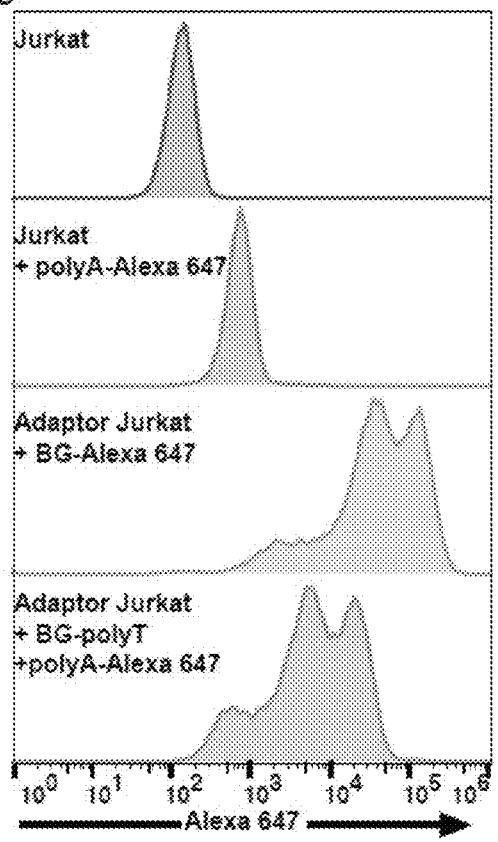
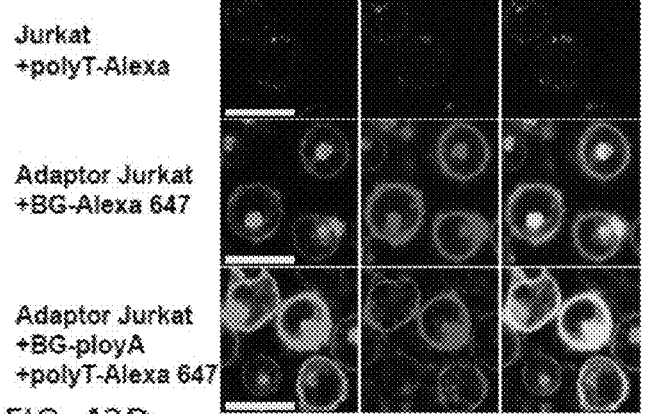
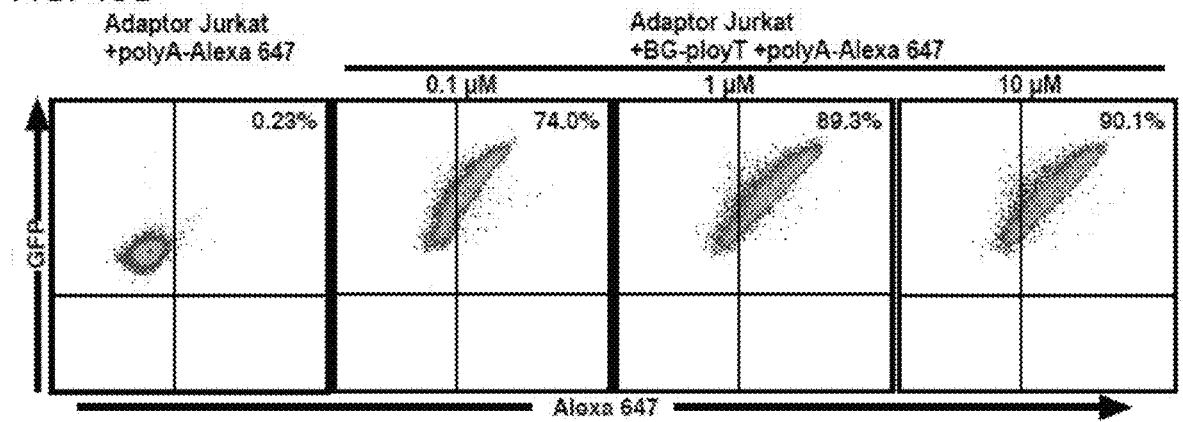

FIG. 52

Lentiviral vector sequence:

GTCGACGGATCGGGAGATCTCCCGATCCCCTATGGTGCACTCTCAGTACAATCTGCTCTGATGCCGCATA
GTTAAGCCAGTATCTGCTCCCTGCTTGTGTGTTGGAGGTCGCTGAGTAGTGCGCGAGCAAAATTTAAGC
TACAACAAGGCAAGGCTTGACCGACAATTGCATGAAGAATCTGCTTAGGGTTAGGCGTTTTGCGCTGCT
TCGCGATGTACGGGCCAGATATCGCGTTGACATTGATTATTGACTAGTTATTAATAGTAATCAATTACGG
GGTCATTAGTTCATAGCCCATATATGGAGTTCCGCGTTACATAACTTACGGTAAATGGCCCGCCTGGCTG
ACCGCCCAACGACCCCCGCCCATTGACGTCAATAATGACGTATGTTCCCATAGTAACGCCAATAGGGACT
TTCCATTGACGTCAATGGGTGGAGTATTTACGGTAAACTGCCCACTTGGCAGTACATCAAGTGTATCATA
TGCCAAGTACGCCCCCTATTGACGTCAATGACGGTAAATGGCCCGCCTGGCATTATGCCCAGTACATGAC
CTTATGGGACTTTCCTACTTGGCAGTACATCTACGTATTAGTCATCGCTATTACCATGGTGATGCGGTTTT
GGCAGTACATCAATGGGCGTGGATAGCGGTTTGACTCACGGGGATTTCCAAGTCTCCACCCCATTGACG
TCAATGGGAGTTTGTTTTGGCACCAAAATCAACGGGACTTTCCAAAATGTCGTAACAACTCCGCCCCATT
GACGCAAATGGGCGGTAGGCGTGTACGGTGGGAGGTCTATATAAGCAGCGCGTTTTGCCTGTACTGGG
TCTCTCTGGTTAGACCAGATCTGAGCCTGGGAGCTCTCTGGCTAACTAGGGAACCCACTGCTTAAGCCTC
AATAAAGCTTGCCTTGAGTGCTTCAAGTAGTGTGTGCCCGTCTGTTGTGTGACTCTGGTAACTAGAGATC
CCTCAGACCCTTTTAGTCAGTGTGGAAAATCTCTAGCAGTGGCGCCCGAACAGGGACTTGAAAGCGAAA
GGGAAACCAGAGGAGCTCTCTCGACGCAGGACTCGGCTTGCTGAAGCGCGCACGGCAAGAGGCGAGG
GGCGGCGACTGGTGAGTACGCCAAAAATTTTGACTAGCGGAGGCTAGAAGGAGAGAGATGGGTGCGA
GAGCGTCAGTATTAAGCGGGGAGAATTAGATCGCGATGGGAAAAAATTCGGTTAAGGCCAGGGGGA
AAGAAAAAATATAAATTAAAACATATAGTATGGGCAAGCAGGGAGCTAGAACGATTCGCAGTTAATCCT
GGCCTGTTAGAAACATCAGAAGGCTGTAGACAAATACTGGGACAGCTACAACCATCCCTTCAGACAGGA
TCAGAAGAACTTAGATCATTATATAATACAGTAGCAACCCTCTATTGTGTGCATCAAAGGATAGAGATAA
AAGACACCAAGGAAGCTTTAGACAAGATAGAGGAAGAGCAAAACAAAAGTAAGACCACCGCACAGCA
AGCGGCCGGCCGCTGATCTTCAGACCTGGAGGAGGAGATATGAGGGACAATTGGAGAAGTGAATTATA
TAAATATAAAGTAGTAAAAATTGAACCATTAGGAGTAGCACCCACCAAGGCAAAGAGAAGAGTGGTGC
AGAGAGAAAAAAGAGCAGTGGGAATAGGAGCTTTGTTCCTTGGGTTCTTGGGAGCAGCAGGAAGCACT
ATGGGCGCAGCGTCAATGACGCTGACGGTACAGGCCAGACAATTATTGTCTGGTATAGTGCAGCAGCA
GAACAATTTGCTGAGGGCTATTGAGGCGCAACAGCATCTGTTGCAACTCACAGTCTGGGGCATCAAGCA
GCTCCAGGCAAGAATCCTGGCTGTGGAAAGATACCTAAAGGATCAACAGCTCCTGGGGATTTGGGGTT
GCTCTGGAAAACTCATTTGCACCACTGCTGTGCCTTGGAATGCTAGTTGGAGTAATAAATCTCTGGAACA
GATTTGGAATCACACGACCTGGATGGAGTGGGACAGAGAAATTAACAATTACACAAGCTTAATACACTC
CTTAATTGAAGAATCGCAAAACCAGCAAGAAAAGAATGAACAAGAATTATTGGAATTAGATAAATGGG
CAAGTTTGTGGAATTGGTTTAACATAACAAATTGGCTGTGGTATATAAAATTATTCATAATGATAGTAGG
AGGCTTGGTAGGTTTAAGAATAGTTTTTGCTGTACTTTCTATAGTGAATAGAGTTAGGCAGGGATATTCA
CCATTATCGTTTCAGACCCACCTCCCAACCCCGAGGGGACCCGACAGGCCCGAAGGAATAGAAGAAGAA
GGTGGAGAGAGAGACAGAGACAGATCCATTCGATTAGTGAACGGATCGGCACTGCGTGCGCCAATTCT
GCAGACAAATGGCAGTATTCATCCACAATTTTAAAAGAAAAGGGGGGATTGGGGGGTACAGTGCAGGG
GAAAGAATAGTAGACATAATAGCAACAGACATACAAACTAAAGAATTACAAAAACAAATTACAAAAATT
CAAAATTTTCGGGTTTATTACAGGGACAGCAGAGATCCAGTTTGGTTAGTACCGGGCCCGCTCTAGACA
TGTCCAATATGACCGCCATGTTGCTCCGGTGCCCGTCAGTGGGCAGAGCGCACATCGCCCACAGTCCCC
GAGAAGTTGGGGGGAGGGGTCGGCAATTGAACCGGTGCCTAGAGAAGGTGGCGCGGGGTAAACTGG

FIG. 52, continued

```
GAAAGTGATGTCGTGTACTGGCTCCGCCTTTTTCCCGAGGGTGGGGGAGAACCGTATATAAGTGCAGTA
GTCGCCGTGAACGTTCTTTTTCGCAACGGGTTTGCCGCCAGAACACAGGTAAGTGCCGTGTGTGGTTCC
CGCGGGCCTGGCCTCTTTACGGGTTATGGCCCTTGCGTGCCTTGAATTACTTCCACGCCCCTGGCTGCAG
TACGTGATTCTTGATCCCGAGCTTCGGGTTGGAAGTGGGTGGGAGAGTTCGAGGCCTTGCGCTTAAGG
AGCCCCTTCGCCTCGTGCTTGAGTTGAGGCCTGGCCTGGGCGCTGGGGCCGCCGCGTGCGAATCTGGTG
GCACCTTCGCGCCTGTCTCGCTGCTTTCGATAAGTCTCTAGCCATTTAAAATTTTTGATGACCTGCTGCGA
CGCTTTTTTTCTGGCAAGATAGTCTTGTAAATGCGGGCCAAGATCTGCACACTGGTATTTCGGTTTTTGG
GGCCGCGGGCGGCGACGGGGCCCGTGCGTCCCAGCGCACATGTTCGGCGAGGCGGGGCCTGCGAGCG
CGGCCACCGAGAATCGGACGGGGGTAGTCTCAAGCTGGCCGGCCTGCTCTGGTGCCTGGCCTCGCGCC
GCCGTGTATCGCCCCGCCCTGGGCGGCAAGGCTGGCCCGGTCGGCACCAGTTGCGTGAGCGGAAAGAT
GGCCGCTTCCGGCCCTGCTGCAGGGAGCTCAAAATGGAGGACGCGGCGCTCGGGAGAGCGGGCGGG
TGAGTCACCCACACAAAGGAAAAGGGCCTTTCCGTCCTCAGCCGTCGCTTCATGTGACTCCACGGAGTA
CCGGGCGCCGTCCAGGCACCTCGATTAGTTCTCGAGCTTTTGGAGTACGTCGTCTTTAGGTTGGGGGGA
GGGGTTTTATGCGATGGAGTTTCCCCACACTGAGTGGGTGGAGACTGAAGTTAGGCCAGCTTGGCACTT
GATGTAATTCTCCTTGGAATTTGCCCTTTTTGAGTTTGGATCTTGGTTCATTCTCAAGCCTCAGACAGTGG
TTCAAAGTTTTTTTCTTCCATTTCAGGTGTCGTGAATGGCCCTGCCTGTGACAGCCCTGCTGCTGCCTCTG
GCTCTGCTGCTGCATGCCGCTAGACCCGACAAAGACTGCGAAATGAAGCGCACCACCCTGGATAGCCCT
CTGGGCAAGCTGGAACTGTCTGGGTGCGAACAGGGCCTGCACCGTATCATCTTCCTGGGCAAAGGAAC
ATCTGCCGCCGACGCCGTGGAAGTGCCTGCCCCAGCCGCCGTGCTGGGCGGACCAGAGCCACTGATGC
AGGCCACCGCCTGGCTCAACGCCTACTTTCACCAGCCTGAGGCCATCGAGGAGTTCCCTGTGCCAGCCCT
GCACCACCCAGTGTTCCAGCAGGAGAGCTTTACCCGCCAGGTGCTGTGGAAACTGCTGAAAGTGGTGA
AGTTCGGAGAGGTCATCAGCTACAGCCACCTGGCCGCCCTGGCCGGCAATCCCGCCGCCACCGCCGCCG
TGAAAACCGCCCTGAGCGGAAATCCCGTGCCCATTCTGATCCCCTGCCACCGGGTGGTGCAGGGCGACC
TGGACGTGGGGGGCTACGAGGGCGGGCTCGCCGTGAAAGAGTGGCTGCTGGCCCACGAGGGCCACAG
ACTGGGCAAGCCTGGGCTGGGTTCAGGTGGAGGCGGTTCAGGTGGAGGCGGTTCAGGTGGAGGCGGT
ATCTACATCTGGGCGCCCTTGGCCGGGACTTGTGGGTCCTTCTCCTGTCACTGGTTATCACCCTTTACTG
CAAACGGGGCAGAAAGAAACTCCTGTATATATTCAAACAACCATTTATGAGACCAGTACAAACTACTCA
AGAGGAAGATGGCTGTAGCTGCCGATTTCCAGAAGAAGAAGAAGGAGGATGTGAACTGAGAGTGAAG
TTCAGCAGGAGCGCAGACGCCCCCGCGTACAAGCAGGGCCAGAACCAGCTCTATAACGAGCTCAATCTA
GGACGAAGAGAGGAGTACGATGTTTTGGACAAGAGACGTGGCCGGGACCCTGAGATGGGGGGAAAG
CCGAGAAGGAAGAACCCTCAGGAAGGCCTGTACAATGAACTGCAGAAAGATAAGATGGCGGAGGCCT
ACAGTGAGATTGGGATGAAAGGCGAGCGCCGGAGGGGCAAGGGGCACGATGGCCTTTACCAGGGTCT
CAGTACAGCCACCAAGGACACCTACGACGCCCTTCACATGCAGGCCCTGCCCCCTCGACGCGTACGCGG
CCGCTCGAGAATGAGCGGGGCGAGGAGCTGTTCGCCGGCATCGTGCCCGTGCTGATCGAGCTGGACG
GCGACGTGCACGGCCACAAGTTCAGCGTGCGCGGCGAGGGCGAGGGCGACGCCGACTACGGCAAGCT
GGAGATCAAGTTCATCTGCACCACCGGCAAGCTGCCCGTGCCCTGGCCCACCCTGGTGACCACCCTCTGC
TACGGCATCCAGTGCTTCGCCCGCTACCCCGAGCACATGAAGATGAACGACTTCTTCAAGAGCGCCATG
CCCGAGGGCTACATCCAGGAGCGCACCATCCAGTTCCAGGACGACGGCAAGTACAAGACCCGCGGCGA
GGTGAAGTTCGAGGGCGACACCCTGGTGAACCGCATCGAGCTGAAGGGCAAGGACTTCAAGGAGGAC
GGCAACATCCTGGGCCACAAGCTGGAGTACAGCTTCAACAGCCACAACGTGTACATCCGCCCCGACAAG
GCCAACAACGGCCTGGAGGCTAACTTCAAGACCCGCCACAACATCGAGGGCGGCGGCGTGCAGCTGGC
CGACCACTACCAGACCAACGTGCCCCTGGGCGACGGCCCCGTGCTGATCCCCATCAACCACTACCTGAG
```

FIG. 52, continued

CACTCAGACCAAGATCAGCAAGGACCGCAACGAGGCCCGCGACCACATGGTGCTCCTGGAGTCCTTCAG
CGCCTGCTGCCACACCCACGGCATGGACGAGCTGTACAGGTAGTCCGGACTCAGAGTTTGGGTAGGAA
GCGGAGCTACTAACTTCAGCCTGCTGAAGCAGGCTGGAGACGTGGAGGAGAACCCTGGACCTATGACC
GAGTACAAGCCCACGGTGCGCCTCGCCACCCGCGACGACGTCCCCAGGGCCGTACGCACCCTCGCCGCC
GCGTTCGCCGACTACCCCGCCACGCGCCACACCGTCGATCCGGATCGCCACATCGAGCGGGTCACCGAG
CTGCAAGAACTCTTCCTCACGCGCGTCGGGCTCGACATCGGCAAGGTGTGGGTCGCGGACGACGGCGC
CGCGGTGGCGGTCTGGACCACGCCGGAGAGCGTCGAAGCGGGGGCGGTGTTCGCCGAGATCGGCCCG
CGCATGGCCGAGTTGAGCGGTTCCCGGCTGGCCGCGCAGCAACAGATGGAAGGCCTCCTGGCGCCGCA
CCGGCCCAAGGAGCCCGCGTGGTTCCTGGCCACCGTCGGCGTCTCGCCCGACCACCAGGGCAAGGGTC
TGGGCAGCGCCGTCGTGCTCCCCGGAGTGGAGGCGGCCGAGCGCGCCGGGGTGCCCGCCTTCCTGGA
GACCTCCGCGCCCCGCAACCTCCCCTTCTACGAGCGGCTCGGCTTCACCGTCACCGCCGACGTCGAGGTG
CCCGAAGGACCGCGCACCTGGTGCATGACCCGCAAGCCCGGTGCCTGATGTACACCCAAACGGCCGGC
CGCGGTCTGTACAAGTAGGATTCGTCGAGGGACCTAATAACTTCGTATAGCATACATTATACGAAGTTAT
ACATGTTTAAGGGTTCCGGTTCCACTAGGTACAATTCGATATCAAGCTTATCGATAATCAACCTCTGGATT
ACAAAATTTGTGAAAGATTGACTGGTATTCTTAACTATGTTGCTCCTTTTACGCTATGTGGATACGCTGCT
TTAATGCCTTTGTATCATGCTATTGCTTCCCGTATGGCTTTCATTTTCTCCTCCTTGTATAAATCCTGGTTGC
TGTCTCTTTATGAGGAGTTGTGGCCCGTTGTCAGGCAACGTGGCGTGGTGTGCACTGTGTTTGCTGACG
CAACCCCCACTGGTTGGGGCATTGCCACCACCTGTCAGCTCCTTTCCGGGACTTTCGCTTTCCCCCTCCCT
ATTGCCACGGCGGAACTCATCGCCGCCTGCCTTGCCCGCTGCTGGACAGGGGCTCGGCTGTTGGGCACT
GACAATTCCGTGGTGTTGTCGGGGAAATCATCGTCCTTTCCTTGGCTGCTCGCCTGTGTTGCCACCTGGA
TTCTGCGCGGGACGTCCTTCTGCTACGTCCCTTCGGCCCTCAATCCAGCGGACCTTCCTTCCCGCGGCCTG
CTGCCGGCTCTGCGGCCTCTTCCGCGTCTTCGCCTTCGCCCTCAGACGAGTCGGATCTCCCTTTGGGCCG
CCTCCCCGCATCGATACCGTCGACCTCGATCGAGACCTAGAAAAACATGGAGCAATCACAAGTAGCAAT
ACAGCAGCTACCAATGCTGATTGTGCCTGGCTAGAAGCACAAGAGGAGGAGGAGGTGGGTTTTCCAGT
CACACCTCAGGTACCTTTAAGACCAATGACTTACAAGGCAGCTGTAGATCTTAGCCACTTTTTAAAAGAA
AAGGGGGGACTGGAAGGGCTAATTCACTCCCAACGAAGACAAGATATCCTTGATCTGTGGATCTACCAC
ACACAAGGCTACTTCCCTGATTGGCAGAACTACACACCAGGGCCAGGGATCAGATATCCACTGACCTTT
GGATGGTGCTACAAGCTAGTACCAGTTGAGCAAGAGAAGGTAGAAGAAGCCAATGAAGGAGAGAACA
CCCGCTTGTTACACCCTGTGAGCCTGCATGGGATGGATGACCCGGAGAGAGAAGTATTAGAGTGGAGG
TTTGACAGCCGCCTAGCATTTCATCACATGGCCCGAGAGCTGCATCCGGACTGTACTGGGTCTCTCTGGT
TAGACCAGATCTGAGCCTGGGAGCTCTCTGGCTAACTAGGGAACCCACTGCTTAAGCCTCAATAAAGCT
TGCCTTGAGTGCTTCAAGTAGTGTGTGCCCGTCTGTTGTGTGACTCTGGTAACTAGAGATCCCTCAGACC
CTTTTAGTCAGTGTGGAAAATCTCTAGCAGCATGTGAGCAAAAGGCCAGCAAAGGCCAGGAACCGTA
AAAAGGCCGCGTTGCTGGCGTTTTCCATAGGCTCCGCCCCCTGACGAGCATCACAAAAATCGACGCTC
AAGTCAGAGGTGGCGAAACCCGACAGGACTATAAAGATACCAGGCGTTTCCCCCTGGAAGCTCCCTCGT
GCGCTCTCCTGTTCCGACCCTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCTCCAAGCTGGGCTGTGTGC
ACGAACCCCCCGTTCAGCCCGACCGCTGCGCCTTATCCGGTAACTATCGTCTTGAGTCCAACCCGGTAAG
ACACGACTTATCGCCACTGGCAGCAGCCACTGGTAACAGGATTAGCAGAGCGAGGTATGTAGGCGGTG
CTACAGAGTTCTTGAAGTGGTGGCCTAACTACGGCTACACTAGAAGAACAGTATTTGGTATCTGCGCTCT
GCTGAAGCCAGTTACCTTCGGAAAAAGAGTTGGTAGCTCTTGATCCGGCAAACAAACCACCGCTGGTAG
CGGTGGTTTTTTTGTTTGCAAGCAGCAGATTACGCGCAGAAAAAAGGATCTCAAGAAGATCCTTTGAT

FIG. 52, continued

CTTTTCTACGGGGTCTGACGCTCAGTGGAACGAAAACTCACGTTAAGGGATTTTGGTCATGATTACGCCC
CGCCCTGCCACTCATCGCAGTACTGTTGTAATTCATTAAGCATTCTGCCGACATGGAAGCCATCACAAAC
GGCATGATGAACCTGAATCGCCAGCGGCATCAGCACCTTGTCGCCTTGCGTATAATATTTGCCCATGGTG
AAAACGGGGGCGAAGAAGTTGTCCATATTGGCCACGTTTAAATCAAAACTGGTGAAACTCACCCAGGG
ATTGGCTGAGACGAAAAACATATTCTCAATAAACCCTTTAGGGAAATAGGCCAGGTTTTCACCGTAACAC
GCCACATCTTGCGAATATATGTGTAGAAACTGCCGGAAATCGTCGTGGTATTCACTCCAGAGCGATGAA
AACGTTTCAGTTTGCTCATGGAAAACGGTGTAACAAGGGTGAACACTATCCCATATCACCAGCTCACCGT
CTTTCATTGCCATACGGAACTCCGGATGAGCATTCATCAGGCGGGCAAGAATGTGAATAAAGGCCGGAT
AAAACTTGTGCTTATTTTTCTTTACGGTCTTTAAAAAGGCCGTAATATCCAGCTGAACGGTCTGGTTATAG
GTACATTGAGCAACTGACTGAAATGCCTCAAAATGTTCTTTACGATGCCATTGGGATATATCAACGGTGG
TATATCCAGTGATTTTTTTCTCCATACTCTTCCTTTTTCAATATTATTGAAGCATTTATCAGGGTTATTGTCT
CATGAGCGGATACATATTTGAATGTATTTAGAAAAATAAACAAATAGGGGTTCCGCGCACATTTCCCCG
AAAAGTGCCACCTGAC (SEQ ID NO: 15)

FIG. 53

GAAAATTCATAAGTAAGCGTCATACATGGCTTAGACGGGAGA (SEQ ID NO:16)
ATATTCACAAAATAAAAACAGGGAAGCGCATTTTGATGATAC (SEQ ID NO: 17)
AGGAGTGTACTAATAAACAGCCATATTATTTAATTGGCCTTG (SEQ ID NO: 18)
GCCAGTTACAAGGTAATAAGTTTTAACGGGGTGTCCTGAACA (SEQ ID NO: 19)
GCAGAACGCGCGAGGTTGAGGCAGGTCAGACGTCCCAATCCA (SEQ ID NO: 20)
AATAAGAAACGGACTTGAGCCATTTGGGAATTTTCAGCTAAT (SEQ ID NO: 21)
GAGAGAATAACCAAATAAATCCTCATTAAAGCAAAAGGGCGA (SEQ ID NO: 22)
AGCATTGACAGCTGTTTATCAACAATAGATAACAGTGCCTTG (SEQ ID NO: 23)
AGTAACAGTGCCCAGTAATAAGAGAATATAAAAGCCGCCGCC (SEQ ID NO: 24)
GCATTTTCGAGCCGTATAAACAGTTAATGCCCTATCAAAATC (SEQ ID NO: 25)
ATTAAGACGCTCGCCACCAGAACCACCACCAGGTACCGACAA (SEQ ID NO: 26)
AAGGTAAAGTAAGCACCATTACCATTAGCAAGGATAGCTTAG (SEQ ID NO: 27)
TACCGTTCCTGGTTTACCAGCGCCAAAGACCAGAATGGAAAG (SEQ ID NO: 28)
CATTCAACCGATTGACGGAAATTATTCATTAAAGCCTTTACA (SEQ ID NO: 29)
GAAAATAGCAGGTGAATTATCACCGTCACCATTTTTTGTT (SEQ ID NO: 30)
GCAAAGACACCGTAAATGAATTTTCTGTATGGTAATTGAGCG (SEQ ID NO: 31)
TAGCATTCCACACCCTGAACAAAGTCAGAGGGGATTTTGCTA (SEQ ID NO: 32)
AACAACTTTCACGCTAACGAGCGTCTTTCCAGACAACGCCTG (SEQ ID NO: 33)
AATCTTACCAAACAGTTTCAGCGGAGTGAGAAATGTAGAAAC (SEQ ID NO: 34)
AGAAAATAATGTTTCGTCACCAGTACAAACTAGCCTAATTT (SEQ ID NO: 35)
ATTAACTGAACAGACAGCCCTCATAGTTAGCGACAATCAATA (SEQ ID NO: 36)
AACAACATGAGAGCCAGCAAAATCACCAGTATTCTGTCCA (SEQ ID NO: 37)
CGTAACACTGAATCCCATCCTAATTTACGAGCTAGAAGGAA (SEQ ID NO: 38)
CAACTAAAGGATTAACAACGCCAACATGTAATACCCATGTAC (SEQ ID NO: 39)
AATCGCCATATATTGCGAATAATAATTTTTTCGCTTAGGTTG (SEQ ID NO: 40)
ATAGGTCTGAGGGGATAGCAAGCCCAATAGGATTAGGCAGAG (SEQ ID NO: 41)
CAGACGTTAACGGAATAAGTTTATTTTGTCTAACGATCTAAA (SEQ ID NO: 42)
TCGCCCACGCAGCCATTGCAACAGGAAAATGCGCCGACA (SEQ ID NO: 43)
CCTCATTTTCAAGACTACCTTTTTAACCTCCGACGTTGAAAA (SEQ ID NO: 44)
TCTCCAAAAATGAATTACCTTTTTAATGGAGAGCCACCAC (SEQ ID NO: 45)
ATATAAGTATTTGACGCTCAATCGTCTGAAGATAAGTGCC (SEQ ID NO: 46)
ACCCTCAGAGCGAGAAGAGTCAATAGTGAATTCCTGCCTATT (SEQ ID NO: 47)
TCGGAACCTATTGTGAGTGAATAACCTTGCTTCAGAGCCACC (SEQ ID NO: 48)
CGTTTGCCAATTCACCAGTCACACGACCAGTTCGGTCATA (SEQ ID NO: 49)
AAACATAGCGCCGGAAACGTCACCAATGAATAATTTTCCC (SEQ ID NO: 50)
ACAATTTCATTAAGGCTCCAAAAGGAGCCTTTTATACTTCTG (SEQ ID NO: 51)

FIG. 53, continued

GAACAAAGAATCAGTAGCGACAGAATCAAGTTGAGTAACA (SEQ ID NO: 52)
GATAATACATTTGCTTTCGAGGTGAATTTCTTAGCCCTAAAA (SEQ ID NO: 53)
ACAGAGATATAGCGCGTTTTCATCGGCATTTAATAAAAGG (SEQ ID NO: 54)
ATTTTAAAAGTTTTGCCTTTAGCGTCAGACTGGAACCCTTCT (SEQ ID NO: 55)
GACCTGAAAGCCGGAACCAGAGCCACCACCGGAACGTTATTA (SEQ ID NO: 56)
ATCAAAATCACGTAAGAATACGTGGCACAGACGGTTTTGCTC (SEQ ID NO: 57)
AGTACCAGGCGATGGATTATTTACATTGGCAGTCTTTTCATA (SEQ ID NO: 58)
AATTCGACAACGAGAAGGATTAGGATTAGCGGAATATTTTTG (SEQ ID NO: 59)
AATGGCTATTACCGTACTCAGGAGGTTTAGTACTTTACAAAC (SEQ ID NO: 60)
TAGGTGTATCAGTCTTTAATGCGCGAACTGATAAACAGCTTG (SEQ ID NO: 61)
ATACCGATAGTCGCTCATGGAAATACCTACATTAGCCCGGAA (SEQ ID NO: 62)
GTTTATCAGCTTGAGGATTTAGAAGTATTAGACCGCCACCCT (SEQ ID NO: 63)
CAGAACCGCCATATAATCCTGATTGTTTGGATAATTGTATCG (SEQ ID NO: 64)
AGACTCCTCAATCGTATTAAATCCTTTGCCCGAACCGCCTCC (SEQ ID NO: 65)
CTCAGAGCCGCTATCATCATATTCCTGATTATTAAGAGGCTG (SEQ ID NO: 66)
TCGCTATTAATACCATCGATAGCAGCACCGTAAACCACCAGA (SEQ ID NO: 67)
AGGAGCGGAATCACCCTCAGAACCGCCACCCTCTGTAAATCG (SEQ ID NO: 68)
AAATCAATATATATTCTGAAACATGAAAGTATCAGATGATGG (SEQ ID NO: 69)
CAATTCATCAACCCTCAGAACCGCCACCCTCAAACAGTACAT (SEQ ID NO: 70)
GGTTATATAACCGGCTACAGAGGCTTTGAGGACTTAATTGAG (SEQ ID NO: 71)
TAAGGCGTTCCCAATTCTGCGAACGAGTAGTGAAATACCG (SEQ ID NO: 72)
TTAATTGCTAACGCAATAATAACGGAATACAGGTCATTTTTG (SEQ ID NO: 73)
TAATTTCATCTACTTCAAATATCGCGTTTTAATCATAATTAC (SEQ ID NO: 74)
TAGAAAAGCCGTTTACCAGACGACGATAAAAATATTTTAGT (SEQ ID NO: 75)
TTGAGATTTAGACTCCTTATTACGCAGTATATTATTACAGGT (SEQ ID NO: 76)
AAGACAAAGAATAATCATTGTGAATTACCTTATACAAATTCT (SEQ ID NO: 77)
TACCAGTATAATCCATGTTACTTAGCCGGAACATCCAATCGC (SEQ ID NO: 78)
CTTTGACCCATACATAAAGGTGGCAACATAGGCAAAGAATA (SEQ ID NO: 79)
AACCGAGGAGAATATAATGCTGTAGCTCAAGCCGAACAAA (SEQ ID NO: 80)
CTAATATCAGAGCACCAACCTAAAACGAAAGATAAAGAAAC (SEQ ID NO: 81)
CCACTACGAAGGAGATAACCCACAAGAATTGAAAACAAAGTA (SEQ ID NO: 82)
CAACGGAGATTCTATTTTGCACCCAGCTACAAATACGTAATG (SEQ ID NO: 83)
TAGAAGGCTAAGTACGGTGTCTGGAAGTTTCCCAATAGCA (SEQ ID NO: 84)
CAATCAATAATAGTTTCCATTAAACGGGTAAATTTTATCCTG (SEQ ID NO: 85)
TTTCATGAGGACGGCTGTCTTTCCTTATCATTGTGTCGAAAT (SEQ ID NO: 86)
CCGCGACCTGCAGCCAACGCTCAACAGTAGGGCTAAAGACTT (SEQ ID NO: 87)

FIG. 53, continued

AAGATTAGTTGTGTATCATCGCCTGATAAATTCCAAGAACGG (SEQ ID NO: 88)
GTATTAAACCAATTATACCAGTCAGGACGTTGGCCTTAAATC (SEQ ID NO: 89)
AGAACTGGCTCAGTACCGCACTCATCGAGAACAGCAACACTA (SEQ ID NO: 90)
TCATAACCCTCTGTTTAGTATCATATGCGTTATGCGATTTTA (SEQ ID NO: 91)
AGCGAACCTCCGGAATTACGAGGCATAGTAAGAAGCAAGCCG (SEQ ID NO: 92)
TTTTTATTTTCGACCGGAAGCAAACTCCAACAGAGGCGTTTT (SEQ ID NO: 93)
AAAGCGAACCAATCGTAGGAATCATTACCGCGCATTCCATAT (SEQ ID NO: 94)
AACAGTTGATTAAATAAGAATAAACACCGGAATTCGAGCTTC (SEQ ID NO: 95)
ATATGCAACTATATCCGGTATTCTAAGAACGCGGTCAGGATT (SEQ ID NO: 96)
AGAGAGTACCTTTTAAGAAAAGTAAGCAGATACATGTTTTAA (SEQ ID NO: 97)
TAACGCCAAAACGACTTGCGGGAGGTTTTGAAGGAAGAAAAA (SEQ ID NO: 98)
TCTACGTTAATAAGAAACAATGAAATAGCAATTGCAGATACA (SEQ ID NO: 99)
GTAGAAAATACCCAGCGATTATACCAAGCGCGGTTAAGCCCA (SEQ ID NO: 100)
ATAATAAGAGCAAAACGAACTAACGGAACAACGTTAGCAAAC (SEQ ID NO: 101)
TGGCATGATTAAGGAATACCACATTCAACTAAAGCTATCTTA (SEQ ID NO: 102)
CCGAAGCCCTTTTAATTGCTCCTTTTGATAAGCCAAAAGAAC (SEQ ID NO: 103)
AAGCCCGAAAGTCTGACCTAAATTTAATGGTTATTTAGTTTG (SEQ ID NO: 104)
ACCATTAGATAGATTGCTTTGAATACCAAGTTGATTAAGAGG (SEQ ID NO: 105)
TAAACAGTTTTTGATTAGTAATAACATCACCATTGAATCC (SEQ ID NO: 106)
AATTTCAACTTCGCGAGAAAACTTTTTCAAATACCAAAATAG (SEQ ID NO: 107)
CGAGAGGCTTTTTATTCATTTCAATTACCTGAGAGATGGTTT (SEQ ID NO: 108)
ATTCATTACAACTATCGGCCTTGCTGGTAAAGTAATCTTG (SEQ ID NO: 109)
GAGGGTAGCAATATATGTAAATGCTGATGCAAGAGGCGCAGA (SEQ ID NO: 110)
CGGTCAATCATAACATCAAGAAAACAAAATTAGCATCGGAAC (SEQ ID NO: 111)
GATTCGCCTCATTTCGCAAATGGTCAATAATTACATCGGG (SEQ ID NO: 112)
AATAATGGAAGCACCCTCAGCAGCGAAAGACAATTACATTTA (SEQ ID NO: 113)
TGCGGGATCGTGGTTAGAACCTACCATATCAATTTGAAAGAG (SEQ ID NO: 114)
GACAGATGAACACTAACAACTAATAGATTAGAAGGCCGCTTT (SEQ ID NO: 115)
CTCAAATATTTGGGGCGCGAGCTGAAAAGGTCTAAAGCAT (SEQ ID NO: 116)
CATCGCCATTACTGAGGCTTGCAGGGAGTTAAGCCGTCAATA (SEQ ID NO: 117)
ATATTCGGTCGAAAATACCGAACGAACCACCAGGCTGGCTGA (SEQ ID NO: 118)
CCTTCATCAAGTATCCAGAACAATATTACCGCCATAACCGAT (SEQ ID NO: 119)
TCTTTAGGAGCGGTGTACAGACCAGGCGCATAGCAGAAGATA (SEQ ID NO: 120)
AAACAGAGGTGGCTCATTCAGTGAATAAGGCTATCTAAAATA (SEQ ID NO: 121)
GTAACAAAGCTAGGCGGTCAGTATTAACACCGTGCGGAATCG (SEQ ID NO: 122)
TCATAAATATTTTGCCTGAGTAGAAGAACTCACCAAATCAAC (SEQ ID NO: 123)

FIG. 53, continued

AAATCAACAGTAGACTGGATAGCGTCCAATACCCTGCAACAG (SEQ ID NO: 124)
TGCCACGCTGAAATCAAAAATCAGGTCTTTACGTCAGTTGGC (SEQ ID NO: 125)
GAATGACCATAGAGCCAGCAGCAAATGAAAAATGGCATCAAT (SEQ ID NO: 126)
TCTACTAATAGTAACCGTTGTAGCAATACTTCCAGAAAACGA (SEQ ID NO: 127)
TATATTTTCATCAAACCCTCAATCAATATCTGCCTGACTATT (SEQ ID NO: 128)
ATAGTCAGAAGAATATACAGTAACAGTACCTTCCTGTTTAGC (SEQ ID NO: 129)
GTAAAATGTTTTGAAAGGAATTGAGGAAGGTTTGCCCTGACG (SEQ ID NO: 130)
AGAAACACCAGAAATAAAGAAATTGCGTAGATGGGGGTAATA (SEQ ID NO: 131)
ATGATGAAACAAAGGGAACCGAACTGACCAACAATTATTTGC (SEQ ID NO: 132)
ACGTAAAACAGAACGAGTAGTAAATTGGGCTTGCAAAAGAAG (SEQ ID NO: 133)
GCAGAGGCGAATGCAAAAGAAGTTTTGCCAGATTTCAGGTTT (SEQ ID NO: 134)
AACGTCAGATGCAAAGCGGATTGCATCAAAAAACAAATCGC (SEQ ID NO: 135)
CCTCCCGACTTGCGGGAGGTTCTGCATTAATGAATCGGCCAA (SEQ ID NO: 136)
TAACTCACATTAATTGCGTTGAGAATTAACTGAACACCCTGA (SEQ ID NO: 137)
AAAATGAAAATAGCAGCCTTTTTAAATTTTTGTTAAATCAGC (SEQ ID NO: 138)
AACAGGAAGATTGTATAAGCATACAATTTTATCCTGAATCTT (SEQ ID NO: 139)
AGTTGCTATTTTGCACCCAGCAATATTTAAATTGTAAACGTT (SEQ ID NO: 140)
AATATTTTGTTAAAATTCGCAACAGAGAGAATAACATAAAAA (SEQ ID NO: 141)
CAGGGAAGCGCATTAGACGGGCGCTCACTGCCCGCTTTCCAG (SEQ ID NO: 142)
TCGGGAAACCTGTCGTGCCAGTTGAAGCCTTAAATCAAGATT (SEQ ID NO: 143)
ACCAACGCTAACGAGCGTCTTTGTCAATCATATGTACCCCGG (SEQ ID NO: 144)
GGTCATTGCCTGAGAGTCTGGACGATTTTTTGTTTAACGTCA (SEQ ID NO: 145)
TTATCCCAATCCAAATAAGAAAGCAAACAAGAGAATCGATGA (SEQ ID NO: 146)
ACGGTAATCGTAAAACTAGCATCCAGAGCCTAATTTGCCAGT (SEQ ID NO: 147)
CCGCCACCCTCAGAGCCACCATTTCATCAACATTAAATGTGA (SEQ ID NO: 148)
TCATTTTTTAACCAATAGGAAGTAGCGCGTTTTCATCGGCAT (SEQ ID NO: 149)
AACCATCGATAGCAGCACCGTTGGGGTGCCTAATGAGTGAGC (SEQ ID NO: 150)
AGCTTGCATGCCTGCAGGTCGTAGTTGCGCCGACAATGACAA (SEQ ID NO: 151)
TTTCGGTCATAGCCCCCTTATAGAGATCTACAAAGGCTATCA (SEQ ID NO: 152)
CCTCATATATTTTAAATGCAAAAAAAGGCTCCAAAAGGAGC (SEQ ID NO: 153)
TTTCACGTTGAAAATCTCCAATGCCTGAGTAATGTGTAGGTA (SEQ ID NO: 154)
AAGATTCAAAAGGGTGAGAAATGAGAATAGAAAGGAACAACT (SEQ ID NO: 155)
TCATAGTTAGCGTAACGATCTTGGTCATAGCTGTTTCCTGTG (SEQ ID NO: 156)
CCGAGCTCGAATTCGTAATCAAAAGTTTTGTCGTCTTTCCAG (SEQ ID NO: 157)
ACGTTAGTAAATGAATTTTCTTCTCCGTGGGAACAAACGGCG (SEQ ID NO: 158)
GCGAGTAACAACCCGTCGGATGTATGGGATTTTGCTAAACAA (SEQ ID NO: 159)

FIG. 53, continued

CTTTAATTGTATCGGTTTATCTCACGTTGGTGTAGATGGGCG (SEQ ID NO: 160)
GATTGACCGTAATGGGATAGGAGCTTGCTTTCGAGGTGAATT (SEQ ID NO: 161)
CTTTCAACAGTTTCAGCGGAGGGCCGGAGACAGTCAAATCAC (SEQ ID NO: 162)
CATCAATATGATATTCAACCGTCAGAGCCGCCACCCTCAGAA (SEQ ID NO: 163)
CCACCACCGGAACCGCCTCCCTTCTAGCTGATAAATTAATGC (SEQ ID NO: 164)
TGAAATTGTTATCCGCTCACAGCATTGACAGGAGGTTGAGGC (SEQ ID NO: 165)
CCACCACCAGAGCCGCCGCCAATTCCACACAACATACGAGCC (SEQ ID NO: 166)
TCTGGCCTTCCTGTAGCCAGCCCCTCAGAGCCGCCACCAGAA (SEQ ID NO: 167)
CGGAGAGGGTAGCTATTTTGTAGCGTTTGCCATCTTTTCAT (SEQ ID NO: 168)
TCTTAAACAGCTTGATACCGAACTCTAGAGGATCCCCGGGTA (SEQ ID NO: 169)
GGAAGCATAAAGTGTAAAGCCAATCAGTAGCGACAGAATCAA (SEQ ID NO: 170)
GTTTGCCTTTAGCGTCAGACTCGCCATCAAAAATAATTCGCG (SEQ ID NO: 171)
ACAGGTAGAAAGATTCATCAGACTCCAGCCAGCTTTCCGGCA (SEQ ID NO: 172)
CATCGTAACCGTGCATCTGCCTGGTTTAATTTCAACTTTAAT (SEQ ID NO: 173)
ATTCAGTGAATAAGGCTTGCCGTAAAACGACGGCCAGTGCCA (SEQ ID NO: 174)
CATTGTGAATTACCTTATGCGAAGGATAAAAATTTTTAGAAC (SEQ ID NO: 175)
TAGCAAAATTAAGCAATAAAGTCTACTAATAGTAGTAGCATT (SEQ ID NO: 176)
CGAACGAGTAGATTTAGTTTGCGCTATTACGCCAGCTGGCGA (SEQ ID NO: 177)
GGCGATCGGTGCGGGCCTCTTACCATTAGATACATTTCGCAA (SEQ ID NO: 178)
ATGGTCAATAACCTGTTTAGCAGGCAAAGCGCCATTCGCCAT (SEQ ID NO: 179)
CCGCTTCTGGTGCCGGAAACCTATATTTTCATTTGGGGCGCG (SEQ ID NO: 180)
AGCTGAAAAGGTGGCATCAATCCTCAGAGCATAAAGCTAAAT (SEQ ID NO: 181)
CGGTTGTACCAAAAACATTATAACTAACGGAACAACATTATT (SEQ ID NO: 182)
AAAATCACGTTAATAAAACGGACCCTGTAATACTTTTGCGG (SEQ ID NO: 183)
AAGGGGGATGTGCTGCAAGGCACGCCAAAAGGAATTACGAGG (SEQ ID NO: 184)
TTCAACTAATGCAGATACATAGATTAAGTTGGGTAACGCCAG (SEQ ID NO: 185)
TATCGGCCTCAGGAAGATCGCTTGAGATTTAGGAATACCACA (SEQ ID NO: 186)
GAGAAGCCTTTATTTCAACGCATTTAAGAACTGGCTCATTA (SEQ ID NO: 187)
GGTTTTCCCAGTCACGACGTTCTGACGAGAAACACCAGAACG (SEQ ID NO: 188)
AGTAGTAAATTGGGCTTGAGAAGTTTGAGGGGACGACGACAG (SEQ ID NO: 189)
TCTTTCCTTATCATTCCAAGACGTAAAACAGAAATAAAGAAA (SEQ ID NO: 190)
TTGTTTGGATTATACTTCTGAAAAGTTACCAGAAGGAAACCG (SEQ ID NO: 191)
AATGAAATAGCAATAGCTATCAATGGATTATTTACATTGGCA (SEQ ID NO: 192)
CCAGCCATTGCAACAGGAAAAGCCGTTTTTATTTTCATCGTA (SEQ ID NO: 193)
GCACTCATCGAGAACAAGCAAACGCTCATGGAAATACCTACA (SEQ ID NO: 194)
TTTTGACGCTCAATCGTCTGATTACCGAAGCCCTTTTTAAGA (SEQ ID NO: 195)

FIG. 53, continued

AAAGTAAGCAGATAGCCGAACATAATGGAAGGGTTAGAACCT (SEQ ID NO: 196)
ACCATATCAAAATTATTTGCAACGGGTATTAAACCAAGTACC (SEQ ID NO: 197)
GGAATCATTACCGCGCCCAATTCAAACTATCGGCCTTGCTGG (SEQ ID NO: 198)
AATTAACCGTTGTAGCAATACCCAATAATAAGAGCAAGAAAC (SEQ ID NO: 199)
ACAAAGTCAGAGGGTAATTGACCGCCTGGCCCTGAGAGAGTT (SEQ ID NO: 200)
TATTGGGCGCCAGGGTGGTTTAACGCGAGGCGTTTTAGCGAA (SEQ ID NO: 201)
AGGCTTATCCGGTATTCTAAGTTCTTTTCACCAGTGAGACGG (SEQ ID NO: 202)
GCAACAGCTGATTGCCCTTCAGCGCTAATATCAGAGAGATAA (SEQ ID NO: 203)
CCCACAAGAATTGAGTTAAGCTTCTTTGATTAGTAATAACAT (SEQ ID NO: 204)
CACTTGCCTGAGTAGAAGAACAGCAAGCAAATCAGATATAGA (SEQ ID NO: 205)
TTCCAGTAAGCGTCATACATGTGACCTGAAAGCGTAAGAATA (SEQ ID NO: 206)
GATTCACCAGTCACACGACCAAAGGTGAATTATCACCGTCAC (SEQ ID NO: 207)
CAAAAGGGCGACATTCAACCGAATTCATCAATATAATCCTGA (SEQ ID NO: 208)
TTTACAAACAATTCGACAACTACTTTTTCATGAGGAAGTTTC (SEQ ID NO: 209)
CAACCATCGCCCACGCATAACAAAGAACGTGGACTCCAACGT (SEQ ID NO: 210)
GCAGCAAGCGGTCCACGCTGGGGCCGGAAACGTCACCAATGA (SEQ ID NO: 211)
CGACTTGAGCCATTTGGGAATAAAGAGTCTGTCCATCACGCA (SEQ ID NO: 212)
CTTGCAGGGAGTTAAAGGCCGATAACGTGCTTTCCTCGTTAG (SEQ ID NO: 213)
AATCAGAGCGGGAGCTAAACACCGTAACACTGAGTTTCGTCA (SEQ ID NO: 214)
GGAGGTTTAGTACCGCCACCCTGAGTAACATTATCATTTTGC (SEQ ID NO: 215)
ACGTTATTAATTTTAAAAGTTTCAGAACCGCCACCCTCAGAA (SEQ ID NO: 216)
CCGCCACCCTCAGAGCCACCAGAATGGCTATTAGTCTTTAAT (SEQ ID NO: 217)
CGTGGCACAGACAATATTTTTCCCTCATTTTCAGGGATAGCA (SEQ ID NO: 218)
CAGCAGCGAAAGACAGCATCGACATCGCCATTAAAAATACCG (SEQ ID NO: 219)
GCGCGAACTGATAGCCCTAAAGAACGAGGGTAGCAACGGCTA (SEQ ID NO: 220)
AGCCCAATAGGAACCCATGTAGGAGGCCGATTAAAGGGATTT (SEQ ID NO: 221)
ATCAAAAGAATAGCCCGAGATGTAGCATTCCACAGACAGCCC (SEQ ID NO: 222)
CCAGTACAAACTACAACGCCTAGGGTTGAGTGTTGTTCCAGT (SEQ ID NO: 223)
TAGACAGGAACGGTACGCCAGGCGCAGTCTCTGAATTTACCG (SEQ ID NO: 224)
AGGTCAGACGATTGGCCTTGAAATCGGCAAAATCCCTTATAA (SEQ ID NO: 225)
CCTGTTTGATGGTGGTTCCGATATTCACAAACAAATAAATCC (SEQ ID NO: 226)
TCATTAAAGCCAGAATGGAAAAATCCTGAGAAGTGTTTTTAT (SEQ ID NO: 227)
GGAACAAAGAAACCACCAGAAGGGTCAGTGCCTTGAGTAACA (SEQ ID NO: 228)
TACTGGTAATAAGTTTTAACGGGAGCGGAATTATCATCATAT (SEQ ID NO: 229)
CCAACAGAGATAGAACCCTTCGCTTTTGATGATACAGGAGTG (SEQ ID NO: 230)
AATCAGTGAGGCCACCGAGTATAGAGCCAGCAAAATCACCAG (SEQ ID NO: 231)

FIG. 53, continued

TAGCACCATTACCATTAGCAATTTGCCCCAGCAGGCGAAAAT (SEQ ID NO: 232)
TTGGAACAAGAGTCCACTATTCGATATATTCGGTCGCTGAGG (SEQ ID NO: 233)
CAGAGGCTTTGAGGACTAAAGCGTATTAAATCCTTTGCCCGA (SEQ ID NO: 234)
TCCTGATTATCAGATGATGGCATTGAGGGAGGGAAGGTAAAT (SEQ ID NO: 235)
ATTGACGGAAATTATTCATTAGTAATAAAAGGGACATTCTGG (SEQ ID NO: 236)
TTTGCCAGAGGGGGTAATAGTGTGCCACGCTGAGAGCCAGCA (SEQ ID NO: 237)
AACGAACCACCAGCAGAAGATATGAACGGTGTACAGACCAGG (SEQ ID NO: 238)
CGGAACGAGGCGCAGACGGTCGAGGATTTAGAAGTATTAGAC (SEQ ID NO: 239)
CAAAGGGCGAAAAACCGTCTAATCAACGTAACAAAGCTGCTC (SEQ ID NO: 240)
CGCATAGGCTGGCTGACCTTCGCCGCTACAGGGCGCGTACTA (SEQ ID NO: 241)
CGTGGCGAGAAAGGAAGGGAAATATGCAACTAAAGTACGGTG (SEQ ID NO: 242)
AGGATTAGAGAGTACCTTTAAGAAAGGAATTGAGGAAGGTTA (SEQ ID NO: 243)
TCAGTTGGCAAATCAACAGTTTTGCTCCTTTTGATAAGAGGT (SEQ ID NO: 244)
CATTTTTGCGGATGGCTTAGATCACCTTGCTGAACCTCAAAT (SEQ ID NO: 245)
GCAAATGAAAAATCTAAAGCAGCTTAATTGCTGAATATAATG (SEQ ID NO: 246)
CTGTAGCTCAACATGTTTTAAGAAAGCGAAAGGAGCGGGCGC (SEQ ID NO: 247)
TAAAGCACTAAATCGGAACCCAACAGTTGATTCCCAATTCTG (SEQ ID NO: 248)
TCTGGAAGTTTCATTCCATATTAAAGGGAGCCCCCGATTTAG (SEQ ID NO: 249)
TAGGGCGCTGGCAAGTGTAGCAGAGGCTTTTGCAAAAGAAGT (SEQ ID NO: 250)
CATAGTAAGAGCAACACTATCTTTTTTGGGGTCGAGGTGCCG (SEQ ID NO: 251)
TGAACCATCACCCAAATCAAGATAACCCTCGTTTACCAGACG (SEQ ID NO: 252)
ACGATAAAAACCAAAATAGCGGGTCACGCTGCGCGTAACCAC (SEQ ID NO: 253)
TCTAAAATATCTTTAGGAGCAATAAATATTCATTGAATCCCC (SEQ ID NO: 254)
GTCCAATACTGCGGAATCGTCCTAACAACTAATAGATTAGAG (SEQ ID NO: 255)
GTATTAACACCGCCTGCAACAAAATGTTTAGACTGGATAGC (SEQ ID NO: 256)
CACACCCGCCGCGCTTAATGCATCAAGAGTAATCTTGACAAG (SEQ ID NO: 257)
AACCGGATATTCATTACCCAATCAGGGCGATGGCCCACTACG (SEQ ID NO: 258)
CCGTCAATAGATAATACATTTAATCATAAGGGAACCGAACTG (SEQ ID NO: 259)
ACCAACTTTGAAAGAGGACAGAAAACAGAGGTGAGGCGGTCA (SEQ ID NO: 260)
ATCAACAATAGATAAGTCCTGTGTCCAGACGACGACAATAAA (SEQ ID NO: 261)
GCAGAGGCATTTTCGAGCCAGGTATGTTAGCAAACGTAGAAA (SEQ ID NO: 262)
AGGAAACGCAATAATAACGGATTGCTTTGAATACCAAGTTAC (SEQ ID NO: 263)
GTCAGATGAATATACAGTAACAAACCAATCAATAATCGGCTG (SEQ ID NO: 264)
TCCTAATTTACGAGCATGTAGAGTACCTTTTACATCGGGAGA (SEQ ID NO: 265)
AACAATAACGGATTCGCCTGAATACCCAAAAGAACTGGCATG (SEQ ID NO: 266)
ATTAAGACTCCTTATTACGCATAATAAGAGAATATAAAGTAC (SEQ ID NO: 267)

FIG. 53, continued

CGACAAAAGGTAAAGTAATTCAACAAGAAAAATAATATCCCA (SEQ ID NO: 268)
CATTAAACGGGTAAAATACGTTGAGTGAATAACCTTGCTTCT (SEQ ID NO: 269)
AAAATCGCGCAGAGGCGAATTATGGTTTACCAGCGCCAAAGA (SEQ ID NO: 270)
ATAAAAGAAACGCAAAGACACCAACGCCAACATGTAATTTAG (SEQ ID NO: 271)
GTGATAAATAAGGCGTTAAATAGAATACACTAAAACACTCAT (SEQ ID NO: 272)
ACCTAAAACGAAAGAGGCAAAAAGAATAAACACCGGAATCAT (SEQ ID NO: 273)
AATTACTAGAAAAAGCCTGTTGGATAAGTGCCGTCGAGAGGG (SEQ ID NO: 274)
GGGTTTTGCTCAGTACCAGGCTAGTATCATATGCGTTATACA (SEQ ID NO: 275)
TACATTTAACAATTTCATTTGATAGGTGTATCACCGTACTCA (SEQ ID NO: 276)
TTGATATAAGTATAGCCCGGAATTACCTTTTTTAATGGAAA (SEQ ID NO: 277)
AATTCTTACCAGTATAAAGCCGTATTAAGAGGCTGAGACTCC (SEQ ID NO: 278)
GTGCCCGTATAAACAGTTAATCATCAAGAAAACAAAATTAAT (SEQ ID NO: 279)
AAAAGAAGATGATGAAACAAAGCCCCCTGCCTATTTCGGAAC (SEQ ID NO: 280)
CTATTATTCTGAAACATGAAAAACGCTCAACAGTAGGGCTTA (SEQ ID NO: 281)
ATTGAGAATCGCCATATTTAACACGGAATAAGTTTATTTTGT (SEQ ID NO: 282)
CACAATCAATAGAAAATTCATATTCATTTCAATTACCTGAGC (SEQ ID NO: 283)
CAGTACATAAATCAATATATGAATGCCACTACGAAGGCACCA (SEQ ID NO: 284)
GTAAATCGTCGCTATTAATTAACCTGCTCCATGTTACTTAGC (SEQ ID NO: 285)
AGCGCGAAACAAAGTACAACGATGGTTTGAAATACCGACCGT (SEQ ID NO: 286)
TATAACTATATGTAAATGCTGCAAATATCGCGTTTTAATTCG (SEQ ID NO: 287)
AAGAGGAAGCCCGAAAGACTTATGCAAATCCAATCGCAAGAC (SEQ ID NO: 288)
TAGTGAATTTATCAAAATCATGGAAGCAAACTCCAACAGGTC (SEQ ID NO: 289)
AGCTTCAAAGCGAACCAGACCAGGTCTGAGAGACTACCTTTT (SEQ ID NO: 290)
AAAGAACGCGAGAAAACTTTTCTGACTATTATAGTCAGAAGC (SEQ ID NO: 291)
CTCAAATGCTTTAAACAGTTCTAAGACGCTGAGAAGAGTCAA (SEQ ID NO: 292)
AAACATAGCGATAGCTTAGATAGAAAACGAGAATGACCATAA (SEQ ID NO: 293)
ATCAAAAATCAGGTCTTTACCTCAAATATATTTTAGTTAATT (SEQ ID NO: 294)
TCATCTTCTGACCTAAATTTAGAGATTTGTATCATCGCCTGA (SEQ ID NO: 295)
TAAATTGTGTCGAAATCCGCGATTTTCCCTTAGAATCCTTGA (SEQ ID NO: 296)

SEQUENCE LISTING

```
<160> NUMBER OF SEQ ID NOS: 296

<210> SEQ ID NO 1
<211> LENGTH: 40
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"
<220> FEATURE:
<221> NAME/KEY: SITE
<222> LOCATION: (1)..(40)
<223> OTHER INFORMATION: /note="This sequence may encompass 1-8 'Gly
      Gly Gly Gly Ser' repeating units"

<400> SEQUENCE: 1

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 2
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly Gly Gly Gly Ser Gly Gly Gly Gly Ser Gly Gly Gly Gly Ser Gly
1               5                   10                  15

Gly Gly Gly Ser
            20

<210> SEQ ID NO 3
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(100)
<223> OTHER INFORMATION: /note="This sequence may encompass 1-20 'Gly
      Gly Gly Gly Ser' repeating units"

<400> SEQUENCE: 3

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100

<210> SEQ ID NO 4
<211> LENGTH: 45
<212> TYPE: PRT

-continued

<213> ORGANISM: Homo sapiens

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 5
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
acgggccaca tcaactcatt gatagacaat gcgtccactg cccgt                    45

<210> SEQ ID NO 6
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
gcagttgatc ctttggatac cctgg                                          25

<210> SEQ ID NO 7
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
gcagttgatc ctttggatac cctggttttt aaaa                                34

<210> SEQ ID NO 8
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
gggagacaag aataaacgct caagcagttg atcctttgga taccctggtt cgacaggagg    60
ctcacaacag gc                                                        72

<210> SEQ ID NO 9
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 9
taccagtgcg atgctcagtg ccgtttcttc tctttcgctt ttttgctttt tgagcatgct    60
gacgcattcg gttgac    76

<210> SEQ ID NO 10
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
atctaactgc tgcgccgccg ggaaaatact gtacggttag a    41

<210> SEQ ID NO 11
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
aaaaaaaaaa aaaaacgtgc agtacgccaa cctttctcat gcgctgcccc tctta    55

<210> SEQ ID NO 12
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Leu Pro Glu Thr Gly
1               5

<210> SEQ ID NO 13
<211> LENGTH: 315
<212> TYPE: PRT
<213> ORGANISM: Rhodopseudomonas palustris

<400> SEQUENCE: 13

Ala Glu Gly Ser Val Ala Arg Gln Pro Asp Leu Leu Thr Cys Asp Asp
1               5                   10                  15

Glu Pro Ile His Ile Pro Gly Ala Ile Gln Pro His Gly Leu Leu Leu
                20                  25                  30

Ala Leu Ala Ala Asp Met Thr Ile Val Ala Gly Ser Asp Asn Leu Pro
            35                  40                  45

Glu Leu Thr Gly Leu Ala Ile Gly Ala Leu Ile Gly Arg Ser Ala Ala
        50                  55                  60

Asp Val Phe Asp Ser Glu Thr His Asn Arg Leu Thr Ile Ala Leu Ala
65                  70                  75                  80

Glu Pro Gly Ala Ala Val Gly Ala Pro Ile Thr Val Gly Phe Thr Met
                85                  90                  95

Arg Lys Asp Ala Gly Phe Ile Gly Ser Trp His Arg His Asp Gln Leu
                100                 105                 110

```
Ile Phe Leu Glu Leu Glu Pro Pro Gln Arg Asp Val Ala Glu Pro Gln
    115                 120                 125

Ala Phe Phe Arg Arg Thr Asn Ser Ala Ile Arg Arg Leu Gln Ala Ala
130                 135                 140

Glu Thr Leu Glu Ser Ala Cys Ala Ala Ala Gln Glu Val Arg Lys
145                 150                 155                 160

Ile Thr Gly Phe Asp Arg Val Met Ile Tyr Arg Phe Ala Ser Asp Phe
                165                 170                 175

Ser Gly Glu Val Ile Ala Glu Asp Arg Cys Ala Glu Val Glu Ser Lys
                180                 185                 190

Leu Gly Leu His Tyr Pro Ala Ser Thr Val Pro Ala Gln Ala Arg Arg
            195                 200                 205

Leu Tyr Thr Ile Asn Pro Val Arg Ile Ile Pro Asp Ile Asn Tyr Arg
        210                 215                 220

Pro Val Pro Val Thr Pro Asp Leu Asn Pro Val Thr Gly Arg Pro Ile
225                 230                 235                 240

Asp Leu Ser Phe Ala Ile Leu Arg Ser Val Ser Pro Val His Leu Glu
                245                 250                 255

Phe Met Arg Asn Ile Gly Met His Gly Thr Met Ser Ile Ser Ile Leu
            260                 265                 270

Arg Gly Glu Arg Leu Trp Gly Leu Ile Val Cys His His Arg Thr Pro
        275                 280                 285

Tyr Tyr Val Asp Leu Asp Gly Arg Gln Ala Cys Glu Leu Val Ala Gln
    290                 295                 300

Val Leu Ala Trp Gln Ile Gly Val Met Glu Glu
305                 310                 315

<210> SEQ ID NO 14
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Gly Gly Ser Gly Gly Gly Ser Gly Gly Gly Ser Gly Gly Gly Ser
1               5                   10                  15

<210> SEQ ID NO 15
<211> LENGTH: 9396
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat cgcgttgaca     240
ttgattattg actagttatt aatagtaatc aattacgggg tcattagttc atagcccata     300
tatggagttc cgcgttacat aacttacggt aaatggcccg cctggctgac cgcccaacga     360
```

-continued

```
cccccgccca ttgacgtcaa taatgacgta tgttcccata gtaacgccaa tagggacttt      420
ccattgacgt caatgggtgg agtatttacg gtaaactgcc cacttggcag tacatcaagt      480
gtatcatatg ccaagtacgc cccctattga cgtcaatgac ggtaaatggc ccgcctggca      540
ttatgcccag tacatgacct tatgggactt tcctacttgg cagtacatct acgtattagt      600
catcgctatt accatggtga tgcggttttg gcagtacatc aatgggcgtg gatagcggtt      660
tgactcacgg ggatttccaa gtctccaccc cattgacgtc aatgggagtt tgttttggca      720
ccaaaatcaa cgggactttc caaaatgtcg taacaactcc gccccattga cgcaaatggg      780
cggtaggcgt gtacggtggg aggtctatat aagcagcgcg ttttgcctgt actgggtctc      840
tctggttaga ccagatctga gcctgggagc tctctggcta actagggaac ccactgctta      900
agcctcaata aagcttgcct tgagtgcttc aagtagtgtg tgcccgtctg ttgtgtgact      960
ctggtaacta gagatccctc agacccttt agtcagtgtg aaaatctct agcagtggcg       1020 cccgaacagg gacttgaaag cgaaagggaa accagaggag ctctctcgac gcaggactcg     1080
gcttgctgaa gcgcgcacgg caagaggcga ggggcggcga ctggtgagta cgccaaaaat     1140
tttgactagc ggaggctaga aggagagaga tgggtgcgag agcgtcagta ttaagcgggg     1200
gagaattaga tcgcgatggg aaaaaattcg gttaaggcca gggggaaaga aaaaatataa     1260
attaaaacat atagtatggg caagcaggga gctagaacga ttcgcagtta atcctggcct     1320
gttagaaaca tcagaaggct gtagacaaat actgggacag ctacaaccat cccttcagac     1380
aggatcagaa gaacttagat cattatataa tacagtagca accctctatt gtgtgcatca     1440
aaggatagag ataaaagaca ccaaggaagc tttagacaag atagaggaag agcaaaacaa     1500
aagtaagacc accgcacagc aagcggccgg ccgctgatct tcagacctgg aggaggagat     1560
atgagggaca attggagaag tgaattatat aaatataaag tagtaaaaat tgaaccatta     1620
ggagtagcac ccaccaaggc aaagagaaga gtggtgcaga gagaaaaaag agcagtggga     1680
ataggagctt tgttccttgg gttcttggga gcagcaggaa gcactatggg cgcagcgtca     1740
atgacgctga cggtacaggc cagacaatta ttgtctggta tagtgcagca gcagaacaat     1800
ttgctgaggg ctattgaggc gcaacagcat ctgttgcaac tcacagtctg ggcatcaag     1860 cagctccagg caagaatcct ggctgtggaa agatacctaa aggatcaaca gctcctgggg     1920
atttggggtt gctctggaaa actcatttgc accactgctg tgccttggaa tgctagttgg     1980
agtaataaat ctctggaaca gatttggaat cacacgacct ggatggagtg ggacagagaa     2040
attaacaatt acacaagctt aatacactcc ttaattgaag aatcgcaaaa ccagcaagaa     2100
aagaatgaac aagaattatt ggaattagat aaatgggcaa gtttgtggaa ttggtttaac     2160
ataacaaatt ggctgtggta tataaaatta ttcataatga tagtaggagg cttggtaggt     2220
ttaagaatag ttttgctgt actttctata gtgaatagag ttaggcaggg atattcacca     2280
ttatcgtttc agacccacct cccaaccccg aggggacccg acaggcccga aggaatagaa     2340
gaagaaggtg gagagagaga cagagacaga tccattcgat tagtgaacgg atcggcactg     2400
cgtgcgccaa ttctgcagac aaatggcagt attcatccac aattttaaaa gaaaagggg     2460 gattgggggg tacagtgcag gggaaagaat agtagacata atagcaacag acatacaaac     2520
taaagaatta caaaaacaaa ttacaaaaat tcaaaatttt cgggtttatt acagggacag     2580
cagagatcca gtttggttag taccgggccc gctctagaca tgtccaatat gaccgccatg     2640
ttgctccggt gcccgtcagt gggcagagcg cacatcgccc acagtcccg agaagttggg       2700 gggaggggtc ggcaattgaa ccggtgccta gagaaggtgg cgcggggtaa actgggaaag     2760
```

```
tgatgtcgtg tactggctcc gccttttttcc cgagggtggg ggagaaccgt atataagtgc    2820
agtagtcgcc gtgaacgttc tttttcgcaa cgggtttgcc gccagaacac aggtaagtgc    2880
cgtgtgtggt tcccgcgggc ctggcctctt tacgggttat ggcccttgcg tgccttgaat    2940
tacttccacg cccctggctg cagtacgtga ttcttgatcc cgagcttcgg gttggaagtg    3000
ggtgggagag ttcgaggcct tgcgcttaag gagccccttc gcctcgtgct tgagttgagg    3060
cctggcctgg gcgctgggc cgccgcgtgc gaatctggtg gcaccttcgc gcctgtctcg    3120
ctgctttcga taagtctcta gccatttaaa attttttgatg acctgctgcg acgctttttt    3180
tctggcaaga tagtcttgta aatgcgggcc aagatctgca cactggtatt tcggttttg    3240
gggccgcggg cggcgacggg gcccgtgcgt cccagcgcac atgttcggcg aggcggggcc    3300
tgcgagcgcg gccaccgaga atcggacggg ggtagtctca agctggccgg cctgctctgg    3360
tgcctggcct cgcgccgccg tgtatcgccc cgccctgggc ggcaaggctg gcccggtcgg    3420
caccagttgc gtgagcggaa agatggccgc ttcccggccc tgctgcaggg agctcaaaat    3480
ggaggacgcg gcgctcggga gagcgggcgg gtgagtcacc cacacaaagg aaaagggcct    3540
ttccgtcctc agccgtcgct tcatgtgact ccacggagta ccgggcgccg tccaggcacc    3600
tcgattagtt ctcgagcttt tggagtacgt cgtctttagg ttgggggag gggttttatg    3660
cgatggagtt tccccacact gagtgggtgg agactgaagt taggccagct tggcacttga    3720
tgtaattctc cttggaattt gcccttttttg agtttggatc ttggttcatt ctcaagcctc    3780
agacagtggt tcaaagtttt tttcttccat ttcaggtgtc gtgaatggcc ctgcctgtga    3840
cagccctgct gctgcctctg gctctgctgc tgcatgccgc tagacccgac aaagactgcg    3900
aaatgaagcg caccaccctg gatagccctc tgggcaagct ggaactgtct gggtgcgaac    3960
agggcctgca ccgtatcatc ttcctgggca aggaacatc tgccgccgac gccgtggaag    4020
tgcctgcccc agccgccgtg ctgggcggac cagagccact gatgcaggcc accgcctggc    4080
tcaacgccta ctttcaccag cctgaggcca tcgaggagtt ccctgtgcca gccctgcacc    4140
acccagtgtt ccagcaggag agctttaccc gccaggtgct gtggaaactg ctgaaagtgg    4200
tgaagttcgg agaggtcatc agctacagcc acctggccgc cctggccggc aatcccgccg    4260
ccaccgccgc cgtgaaaacc gccctgagcg gaaatcccgt gcccattctg atcccctgcc    4320
accgggtggt gcagggcgac ctggacgtgg ggggctacga gggcgggctc gccgtgaaag    4380
agtggctgct ggcccacgag ggccacagac tgggcaagcc tgggctgggt tcaggtggag    4440
gcggttcagg tggaggcggt tcaggtggag gcggtatcta catctgggcg cccttggccg    4500
ggacttgtgg ggtccttctc ctgtcactgg ttatcaccct ttactgcaaa cggggcagaa    4560
agaaactcct gtatatattc aaacaaccat ttatgagacc agtacaaact actcaagagg    4620
aagatggctg tagctgccga tttccagaag aagaagaagg aggatgtgaa ctgagagtga    4680
agttcagcag gagcgcagac gccccgcgct acaagcaggg ccagaaccag ctctataacg    4740
agctcaatct aggacgaaga gaggagtacg atgttttgga caagagacgt ggccgggacc    4800
ctgagatggg gggaaagccg agaaggaaga accctcagga aggcctgtac aatgaactgc    4860
agaaagataa gatggcggag gcctacagtg agattgggat gaaaggcgag cgccggaggg    4920
gcaaggggca cgatggcctt taccagggtc tcagtacagc caccaaggac acctacgacg    4980
cccttcacat gcaggccctg ccccctcgac gcgtacgcgg ccgctcgaga atgagcgggg    5040
gcgaggagct gttcgccggc atcgtgcccg tgctgatcga gctggacggc gacgtgcacg    5100
```

```
gccacaagtt cagcgtgcgc ggcgagggcg agggcgacgc cgactacggc aagctggaga    5160
tcaagttcat ctgcaccacc ggcaagctgc ccgtgccctg ccccaccctg gtgaccaccc    5220
tctgctacgg catccagtgc ttcgcccgct accccgagca catgaagatg aacgacttct    5280
tcaagagcgc catgcccgag ggctacatcc aggagcgcac catccagttc caggacgacg    5340
gcaagtacaa gacccgcggc gaggtgaagt tcgagggcga caccctggtg aaccgcatcg    5400
agctgaaggg caaggacttc aaggaggacg gcaacatcct gggccacaag ctggagtaca    5460
gcttcaacag ccacaacgtg tacatccgcc ccgacaaggc caacaacggc ctggaggcta    5520
acttcaagac ccgccacaac atcgagggcg gcggcgtgca gctggccgac cactaccaga    5580
ccaacgtgcc cctgggcgac ggccccgtgc tgatccccat caaccactac ctgagcactc    5640
agaccaagat cagcaaggac cgcaacgagg cccgcgacca catggtgctc ctggagtcct    5700
tcagcgcctg ctgccacacc cacggcatgg acagctgta caggtagtcc ggactcagag    5760
tttgggtagg aagcggagct actaacttca gcctgctgaa gcaggctgga gacgtggagg    5820
agaaccctgg acctatgacc gagtacaagc ccacggtgcg cctcgccacc cgcgacgacg    5880
tccccagggc cgtacgcacc ctcgccgccg cgttcgccga ctaccccgcc acgcgccaca    5940
ccgtcgatcc ggatcgccac atcgagcggg tcaccgagct gcaagaactc ttcctcacgc    6000
gcgtcgggct cgacatcggc aaggtgtggg tcgcggacga cggcgccgcg gtggcggtct    6060
ggaccacgcc ggagagcgtc gaagcggggg cggtgttcgc cgagatcggc ccgcgcatgg    6120
ccgagttgag cggttcccgg ctggccgcgc agcaacagat ggaaggcctc ctggcgccgc    6180
accggcccaa ggagcccgcg tggttcctgg ccaccgtcgg cgtctcgccc gaccaccagg    6240
gcaagggtct gggcagcgcc gtcgtgctcc ccggagtgga ggcggccgag cgcgccgggg    6300
tgcccgcctt cctggagacc tccgcgcccc gcaacctccc cttctacgag cggctcggct    6360
tcaccgtcac cgccgacgtc gaggtgcccg aaggaccgcg cacctggtgc atgacccgca    6420
agcccggtgc tgatgtaca cccaaacggc cggccgcggt ctgtacaagt aggattcgtc    6480
gagggaccta ataacttcgt atagcataca ttatacgaag ttatacatgt ttaagggttc    6540
cggttccact aggtacaatt cgatatcaag cttatcgata atcaacctct ggattacaaa    6600
atttgtgaaa gattgactgg tattcttaac tatgttgctc cttttacgct atgtggatac    6660
gctgctttaa tgccttttgta tcatgctatt gcttcccgta tggctttcat tttctcctcc    6720
ttgtataaat cctggttgct gtctctttat gaggagttgt ggcccgttgt caggcaacgt    6780
ggcgtggtgt gcactgtgtt tgctgacgca acccccactg gttggggcat tgccaccacc    6840
tgtcagctcc tttccgggac tttcgctttc cccctcccta ttgccacggc ggaactcatc    6900
gccgcctgcc ttgcccgctg ctggacaggg gctcggctgt tgggcactga caattccgtg    6960
gtgttgtcgg ggaaatcatc gtcctttcct ggctgctcg cctgtgttgc cacctggatt    7020
ctgcgcggga cgtccttctg ctacgtccct tcggccctca atccagcgga ccttccttcc    7080
cgcggcctgc tgccggctct gcggcctctt ccgcgtcttc gccttcgccc tcagacgagt    7140
cggatctccc tttgggccgc ctccccgcat cgataccgtc gacctcgatc gagacctaga    7200
aaaacatgga gcaatcacaa gtagcaatac agcagctacc aatgctgatt gtgcctggct    7260
agaagcacaa gaggaggagg aggtgggttt tccagtcaca cctcaggtac ctttaagacc    7320
aatgacttac aaggcagctg tagatcttag ccacttttta aaagaaaagg ggggactgga    7380
agggctaatt cactcccaac gaagacaaga tatccttgat ctgtggatct accacacaca    7440
aggctacttc cctgattggc agaactacac accagggcca gggatcagat atccactgac    7500
```

```
ctttggatgg tgctacaagc tagtaccagt tgagcaagag aaggtagaag aagccaatga    7560
aggagagaac acccgcttgt tacaccctgt gagcctgcat gggatggatg acccggagag    7620
agaagtatta gagtggaggt ttgacagccg cctagcattt catcacatgg cccgagagct    7680
gcatccggac tgtactgggt ctctctggtt agaccagatc tgagcctggg agctctctgg    7740
ctaactaggg aacccactgc ttaagcctca ataaagcttg ccttgagtgc ttcaagtagt    7800
gtgtgcccgt ctgttgtgtg actctggtaa ctagagatcc ctcagaccct tttagtcagt    7860
gtggaaaatc tctagcagca tgtgagcaaa aggccagcaa aaggccagga accgtaaaaa    7920
ggccgcgttg ctggcgtttt tccataggct ccgcccccct gacgagcatc acaaaaatcg    7980
acgctcaagt cagaggtggc gaaacccgac aggactataa agataccagg cgtttccccc    8040
tggaagctcc ctcgtgcgct ctcctgttcc gaccctgccg cttaccggat acctgtccgc    8100
ctttctccct tcgggaagcg tggcgctttc tcatagctca cgctgtaggt atctcagttc    8160
ggtgtaggtc gttcgctcca agctgggctg tgtgcacgaa ccccccgttc agcccgaccg    8220
ctgcgcctta tccggtaact atcgtcttga gtccaacccg gtaagacacg acttatcgcc    8280
actggcagca gccactggta acaggattag cagagcgagg tatgtaggcg gtgctacaga    8340
gttcttgaag tggtggccta actacggcta cactagaaga acagtatttg gtatctgcgc    8400
tctgctgaag ccagttacct tcggaaaaag agttggtagc tcttgatccg gcaaacaaac    8460
caccgctggt agcggtggtt ttttttgttt gcaagcagca gattacgcgca gaaaaaaagg    8520 atctcaagaa gatcctttga tcttttctac ggggtctgac gctcagtgga acgaaaactc    8580
acgttaaggg attttggtca tgattacgcc ccgccctgcc actcatcgca gtactgttgt    8640
aattcattaa gcattctgcc gacatggaag ccatcacaaa cggcatgatg aacctgaatc    8700
gccagcggca tcagcacctt gtcgccttgc gtataatatt tgcccatggt gaaaacgggg    8760
gcgaagaagt tgtccatatt ggccacgttt aaatcaaaac tggtgaaact cacccaggga    8820
ttggctgaga cgaaaaacat attctcaata aaccctttag ggaaataggc caggttttca    8880
ccgtaacacg ccacatcttg cgaatatatg tgtagaaact gccggaaatc gtcgtggtat    8940
tcactccaga gcgatgaaaa cgtttcagtt tgctcatgga aaacggtgta acaagggtga    9000
acactatccc atatcaccag ctcaccgtct ttcattgcca tacggaactc cggatgagca    9060
ttcatcaggc gggcaagaat gtgaataaag gccggataaa acttgtgctt atttttcttt    9120
acggtcttta aaaaggccgt aatatccagc tgaacggtct ggttataggt acattgagca    9180
actgactgaa atgcctcaaa atgttcttta cgatgccatt gggatatatc aacggtggta    9240
tatccagtga tttttttctc catactcttc cttttcaat attattgaag catttatcag    9300
ggttattgtc tcatgagcgg atacatattt gaatgtattt agaaaaataa acaaataggg    9360
gttccgcgca catttccccg aaaagtgcca cctgac                              9396
```

<210> SEQ ID NO 16
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16

```
gaaaattcat aagtaagcgt catacatggc ttagacggga ga                        42
```

<210> SEQ ID NO 17
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
atattcacaa aataaaaaca gggaagcgca ttttgatgat ac            42

<210> SEQ ID NO 18
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
aggagtgtac taataaacag ccatattatt taattggcct tg            42

<210> SEQ ID NO 19
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
gccagttaca aggtaataag ttttaacggg gtgtcctgaa ca            42

<210> SEQ ID NO 20
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
gcagaacgcg cgaggttgag gcaggtcaga cgtcccaatc ca            42

<210> SEQ ID NO 21
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
aataagaaac ggacttgagc catttgggaa ttttcagcta at            42

<210> SEQ ID NO 22
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
gagagaataa ccaaataaat cctcattaaa gcaaaagggc ga                              42

<210> SEQ ID NO 23
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
agcattgaca gctgtttatc aacaatagat aacagtgcct tg                              42

<210> SEQ ID NO 24
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
agtaacagtg cccagtaata agagaatata aaagccgccg cc                              42

<210> SEQ ID NO 25
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
gcattttcga gccgtataaa cagttaatgc cctatcaaaa tc                              42

<210> SEQ ID NO 26
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
attaagacgc tcgccaccag aaccaccacc aggtaccgac aa                              42

<210> SEQ ID NO 27
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
aaggtaaagt aagcaccatt accattagca aggatagctt ag                              42

<210> SEQ ID NO 28
<211> LENGTH: 42
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
taccgttcct ggtttaccag cgccaaagac cagaatggaa ag                    42

<210> SEQ ID NO 29
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
cattcaaccg attgacggaa attattcatt aaagccttta ca                    42

<210> SEQ ID NO 30
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
gaaaatagca ggtgaattat caccgtcacc atttttttgtt                      40

<210> SEQ ID NO 31
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
gcaaagacac cgtaaatgaa ttttctgtat ggtaattgag cg                    42

<210> SEQ ID NO 32
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
tagcattcca caccctgaac aaagtcagag gggattttgc ta                    42

<210> SEQ ID NO 33
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
aacaactttc acgctaacga gcgtcttttcc agacaacgcc tg                   42
```

<210> SEQ ID NO 34
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 34
aatcttacca aacagtttca gcggagtgag aaatgtagaa ac          42

<210> SEQ ID NO 35
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 35
agaaaaataa tgtttcgtca ccagtacaaa ctagcctaat tt          42

<210> SEQ ID NO 36
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 36
attaactgaa cagacagccc tcatagttag cgacaatcaa ta          42

<210> SEQ ID NO 37
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 37
aacaacatga gagccagcaa aatcaccagt attctgtcca             40

<210> SEQ ID NO 38
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 38
cgtaacactg aatcccatcc taatttacga gctagaaagg aa          42

<210> SEQ ID NO 39
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 39
caactaaagg attaacaacg ccaacatgta atacccatgt ac                           42

<210> SEQ ID NO 40
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
aatcgccata tattgcgaat aataattttt tcgcttaggt tg                           42

<210> SEQ ID NO 41
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
ataggtctga ggggatagca agcccaatag gattaggcag ag                           42

<210> SEQ ID NO 42
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
cagacgttaa cggaataagt ttattttgtc taacgatcta aa                           42

<210> SEQ ID NO 43
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
tcgcccacgc agccattgca acaggaaaaa tgcgccgaca                              40

<210> SEQ ID NO 44
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
cctcattttc aagactacct ttttaacctc cgacgttgaa aa                           42

<210> SEQ ID NO 45
<211> LENGTH: 42

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
tctccaaaaa atgaattacc tttttttaatg gagagccacc ac                           42

<210> SEQ ID NO 46
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
atataagtat ttgacgctca atcgtctgaa gataagtgcc                              40

<210> SEQ ID NO 47
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
accctcagag cgagaagagt caatagtgaa ttcctgccta tt                           42

<210> SEQ ID NO 48
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
tcggaaccta ttgtgagtga ataaccttgc ttcagagcca cc                           42

<210> SEQ ID NO 49
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
cgtttgccaa ttcaccagtc acacgaccag ttcggtcata                              40

<210> SEQ ID NO 50
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
```
aaacatagcg ccggaaacgt caccaatgaa taatttt ccc            40

<210> SEQ ID NO 51
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
acaatttcat taaggctcca aaaggagcct tttatacttc tg            42

<210> SEQ ID NO 52
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
gaacaaagaa tcagtagcga cagaatcaag ttgagtaaca            40

<210> SEQ ID NO 53
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
gataatacat ttgctttcga ggtgaatttc ttagccctaa aa            42

<210> SEQ ID NO 54
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
acagagatat agcgcgtttt catcggcatt taataaaagg            40

<210> SEQ ID NO 55
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
attttaaaag ttttgccttt agcgtcagac tggaaccctt ct            42

<210> SEQ ID NO 56
<211> LENGTH: 42
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 56
gacctgaaag ccggaaccag agccaccacc ggaacgttat ta                         42

<210> SEQ ID NO 57
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
atcaaaatca cgtaagaata cgtggcacag acggttttgc tc                         42

<210> SEQ ID NO 58
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
agtaccaggc gatggattat ttacattggc agtcttttca ta                         42

<210> SEQ ID NO 59
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
aattcgacaa cgagaaggat taggattagc ggaatatttt tg                         42

<210> SEQ ID NO 60
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
aatggctatt accgtactca ggaggtttag tactttacaa ac                         42

<210> SEQ ID NO 61
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
taggtgtatc agtctttaat gcgcgaactg ataaacagct tg                         42

<210> SEQ ID NO 62
```

```
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
ataccgatag tcgctcatgg aaatacctac attagcccgg aa                              42

<210> SEQ ID NO 63
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
gtttatcagc ttgaggattt agaagtatta gaccgccacc ct                              42

<210> SEQ ID NO 64
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
cagaaccgcc atataatcct gattgtttgg ataattgtat cg                              42

<210> SEQ ID NO 65
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
agactcctca atcgtattaa atcctttgcc cgaaccgcct cc                              42

<210> SEQ ID NO 66
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
ctcagagccg ctatcatcat attcctgatt attaagaggc tg                              42

<210> SEQ ID NO 67
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
```

```
tcgctattaa taccatcgat agcagcaccg taaaccacca ga                42
```

<210> SEQ ID NO 68
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68

```
aggagcggaa tcaccctcag aaccgccacc ctctgtaaat cg                42
```

<210> SEQ ID NO 69
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69

```
aaatcaatat atattctgaa acatgaaagt atcagatgat gg                42
```

<210> SEQ ID NO 70
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70

```
caattcatca accctcagaa ccgccaccct caaacagtac at                42
```

<210> SEQ ID NO 71
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71

```
ggttatataa ccggctacag aggctttgag gacttaattg ag                42
```

<210> SEQ ID NO 72
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72

```
taaggcgttc ccaattctgc gaacgagtag tgaaataccg                   40
```

<210> SEQ ID NO 73
<211> LENGTH: 42
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 73
ttaattgcta acgcaataat aacggaatac aggtcatttt tg                42

<210> SEQ ID NO 74
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
taatttcatc tacttcaaat atcgcgtttt aatcataatt ac                42

<210> SEQ ID NO 75
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
tagaaaaagc cgtttaccag acgacgataa aaatatttta gt                42

<210> SEQ ID NO 76
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
ttgagattta gactccttat tacgcagtat attattacag gt                42

<210> SEQ ID NO 77
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
aagacaaaga ataatcattg tgaattacct tatacaaatt ct                42

<210> SEQ ID NO 78
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
taccagtata atccatgtta cttagccgga acatccaatc gc                42
```

<210> SEQ ID NO 79
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
ctttgaccca tacataaagg tggcaacata ggcaaaagaa ta                              42

<210> SEQ ID NO 80
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
aaccgaggag aatataatgc tgtagctcaa gccgaacaaa                                40

<210> SEQ ID NO 81
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
ctaatatcag agcaccaacc taaaacgaaa gataaaagaa ac                              42

<210> SEQ ID NO 82
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
ccactacgaa ggagataacc cacaagaatt gaaaacaaag ta                              42

<210> SEQ ID NO 83
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
caacggagat tctattttgc acccagctac aaatacgtaa tg                              42

<210> SEQ ID NO 84
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
tagaaggcta agtacggtgt ctggaagttt cccaatagca                          40

<210> SEQ ID NO 85
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
caatcaataa tagtttccat taaacgggta aattttatcc tg                       42

<210> SEQ ID NO 86
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
tttcatgagg acggctgtct ttccttatca ttgtgtcgaa at                       42

<210> SEQ ID NO 87
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
ccgcgacctg cagccaacgc tcaacagtag ggctaaagac tt                       42

<210> SEQ ID NO 88
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
aagattagtt gtgtatcatc gcctgataaa ttccaagaac gg                       42

<210> SEQ ID NO 89
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
gtattaaacc aattatacca gtcaggacgt tggccttaaa tc                       42

<210> SEQ ID NO 90
<211> LENGTH: 42
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 90
agaactggct cagtaccgca ctcatcgaga acagcaacac ta                         42

<210> SEQ ID NO 91
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
tcataaccct ctgtttagta tcatatgcgt tatgcgattt ta                         42

<210> SEQ ID NO 92
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
agcgaacctc cggaattacg aggcatagta agaagcaagc cg                         42

<210> SEQ ID NO 93
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
tttttatttt cgaccggaag caaactccaa cagaggcgtt tt                         42

<210> SEQ ID NO 94
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
aaagcgaacc aatcgtagga atcattaccg cgcattccat at                         42

<210> SEQ ID NO 95
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
aacagttgat taaataagaa taaacaccgg aattcgagct tc                         42
```

<210> SEQ ID NO 96
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
atatgcaact atatccggta ttctaagaac gcggtcagga tt                          42

<210> SEQ ID NO 97
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
agagagtacc ttttaagaaa agtaagcaga tacatgtttt aa                          42

<210> SEQ ID NO 98
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
taacgccaaa acgacttgcg ggaggttttg aaggaagaaa aa                          42

<210> SEQ ID NO 99
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
tctacgttaa taagaaacaa tgaaatagca attgcagata ca                          42

<210> SEQ ID NO 100
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
gtagaaaata cccagcgatt ataccaagcg cggttaagcc ca                          42

<210> SEQ ID NO 101
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
ataataagag caaaacgaac taacggaaca acgttagcaa ac                              42

<210> SEQ ID NO 102
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
tggcatgatt aaggaatacc acattcaact aaagctatct ta                              42

<210> SEQ ID NO 103
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
ccgaagccct tttaattgct cctttgata agccaaaaga ac                               42

<210> SEQ ID NO 104
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
aagcccgaaa gtctgaccta aatttaatgg ttatttagtt tg                              42

<210> SEQ ID NO 105
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
accattagat agattgcttt gaataccaag ttgattaaga gg                              42

<210> SEQ ID NO 106
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
taaacagttt ttgattagta ataacatcac cattgaatcc                                 40

<210> SEQ ID NO 107
<211> LENGTH: 42
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
aatttcaact tcgcgagaaa acttttttcaa ataccaaaat ag          42

<210> SEQ ID NO 108
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
cgagaggctt tttattcatt tcaattacct gagagatggt tt           42

<210> SEQ ID NO 109
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
attcattaca actatcggcc ttgctggtaa agtaatcttg              40

<210> SEQ ID NO 110
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
gagggtagca atatatgtaa atgctgatgc aagaggcgca ga           42

<210> SEQ ID NO 111
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
cggtcaatca taacatcaag aaaacaaaat tagcatcgga ac           42

<210> SEQ ID NO 112
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
gattcgcctc atttcgcaaa tggtcaataa ttacatcggg              40
```

<210> SEQ ID NO 113
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 113
aataatggaa gcaccctcag cagcgaaaga caattacatt ta                42

<210> SEQ ID NO 114
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 114
tgcgggatcg tggttagaac ctaccatatc aatttgaaag ag                42

<210> SEQ ID NO 115
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 115
gacagatgaa cactaacaac taatagatta gaaggccgct tt                42

<210> SEQ ID NO 116
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 116
ctcaaatatt tggggcgcga gctgaaaagg tctaaagcat                40

<210> SEQ ID NO 117
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 117
catcgccatt actgaggctt gcagggagtt aagccgtcaa ta                42

<210> SEQ ID NO 118
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 118
atattcggtc gaaataccg aacgaaccac caggctggct ga    42

<210> SEQ ID NO 119
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
ccttcatcaa gtatccagaa caatattacc gccataaccg at    42

<210> SEQ ID NO 120
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
tctttaggag cggtgtacag accaggcgca tagcagaaga ta    42

<210> SEQ ID NO 121
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
aaacagaggt ggctcattca gtgaataagg ctatctaaaa ta    42

<210> SEQ ID NO 122
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
gtaacaaagc taggcggtca gtattaacac cgtgcggaat cg    42

<210> SEQ ID NO 123
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
tcataaatat tttgcctgag tagaagaact caccaaatca ac    42

<210> SEQ ID NO 124
<211> LENGTH: 42

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
aaatcaacag tagactggat agcgtccaat accctgcaac ag                    42

<210> SEQ ID NO 125
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
tgccacgctg aaatcaaaaa tcaggtctttt acgtcagttg gc                   42

<210> SEQ ID NO 126
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
gaatgaccat agagccagca gcaaatgaaa aatggcatca at                    42

<210> SEQ ID NO 127
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
tctactaata gtaaccgttg tagcaatact tccagaaaac ga                    42

<210> SEQ ID NO 128
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
tatattttca tcaaaccctc aatcaatatc tgcctgacta tt                    42

<210> SEQ ID NO 129
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
```
atagtcagaa gaatatacag taacagtacc ttcctgttta gc        42

<210> SEQ ID NO 130
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
gtaaaatgtt ttgaaaggaa ttgaggaagg tttgccctga cg        42

<210> SEQ ID NO 131
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
agaaacacca gaaataaaga aattgcgtag atgggggtaa ta        42

<210> SEQ ID NO 132
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
atgatgaaac aaagggaacc gaactgacca acaattattt gc        42

<210> SEQ ID NO 133
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
acgtaaaaca gaacgagtag taaattgggc ttgcaaaaga ag        42

<210> SEQ ID NO 134
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
gcagaggcga atgcaaaaga agttttgcca gatttcaggt tt        42

<210> SEQ ID NO 135
<211> LENGTH: 42
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 135
aacgtcagat gcaaagcgga ttgcatcaaa aaacaaaatc gc                          42

<210> SEQ ID NO 136
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
cctcccgact gcgggaggt tctgcattaa tgaatcggcc aa                           42

<210> SEQ ID NO 137
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
taactcacat taattgcgtt gagaattaac tgaacaccct ga                          42

<210> SEQ ID NO 138
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
aaaatgaaaa tagcagcctt tttaaatttt tgttaaatca gc                          42

<210> SEQ ID NO 139
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
aacaggaaga ttgtataagc atacaatttt atcctgaatc tt                          42

<210> SEQ ID NO 140
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
agttgctatt ttgcacccag caatatttaa attgtaaacg tt                          42

<210> SEQ ID NO 141
```

```
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
aatattttgt taaaattcgc aacagagaga ataacataaa aa                          42

<210> SEQ ID NO 142
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
cagggaagcg cattagacgg gcgctcactg cccgctttcc ag                          42

<210> SEQ ID NO 143
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
tcgggaaacc tgtcgtgcca gttgaagcct taaatcaaga tt                          42

<210> SEQ ID NO 144
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
accaacgcta acgagcgtct ttgtcaatca tatgtacccc gg                          42

<210> SEQ ID NO 145
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
ggtcattgcc tgagagtctg gacgattttt tgtttaacgt ca                          42

<210> SEQ ID NO 146
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
```
ttatcccaat ccaaataaga aagcaaacaa gagaatcgat ga                          42

<210> SEQ ID NO 147
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
acggtaatcg taaaactagc atccagagcc taatttgcca gt                          42

<210> SEQ ID NO 148
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
ccgccaccct cagagccacc atttcatcaa cattaaatgt ga                          42

<210> SEQ ID NO 149
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
tcatttttta accaatagga agtagcgcgt tttcatcggc at                          42

<210> SEQ ID NO 150
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
aaccatcgat agcagcaccg ttggggtgcc taatgagtga gc                          42

<210> SEQ ID NO 151
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
agcttgcatg cctgcaggtc gtagttgcgc cgacaatgac aa                          42

<210> SEQ ID NO 152
<211> LENGTH: 42
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 152
tttcggtcat agccccctta tagagatcta caaaggctat ca                    42

<210> SEQ ID NO 153
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
cctcatatat tttaaatgca aaaaaaggc tccaaaagga gc                     42

<210> SEQ ID NO 154
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
tttcacgttg aaaatctcca atgcctgagt aatgtgtagg ta                    42

<210> SEQ ID NO 155
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
aagattcaaa agggtgagaa atgagaatag aaaggaacaa ct                    42

<210> SEQ ID NO 156
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
tcatagttag cgtaacgatc ttggtcatag ctgtttcctg tg                    42

<210> SEQ ID NO 157
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
ccgagctcga attcgtaatc aaaagttttg tcgtctttcc ag                    42
```

<210> SEQ ID NO 158
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
acgttagtaa atgaatttc ttctccgtgg gaacaaacgg cg                            42

<210> SEQ ID NO 159
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
gcgagtaaca acccgtcgga tgtatgggat tttgctaaac aa                           42

<210> SEQ ID NO 160
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
ctttaattgt atcggtttat ctcacgttgg tgtagatggg cg                           42

<210> SEQ ID NO 161
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
gattgaccgt aatgggatag gagcttgctt tcgaggtgaa tt                           42

<210> SEQ ID NO 162
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
ctttcaacag tttcagcgga gggccggaga cagtcaaatc ac                           42

<210> SEQ ID NO 163
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
catcaatatg atattcaacc gtcagagccg ccaccctcag aa            42

<210> SEQ ID NO 164
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
ccaccaccgg aaccgcctcc cttctagctg ataaattaat gc            42

<210> SEQ ID NO 165
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
tgaaattgtt atccgctcac agcattgaca ggaggttgag gc            42

<210> SEQ ID NO 166
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
ccaccaccag agccgccgcc aattccacac aacatacgag cc            42

<210> SEQ ID NO 167
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
tctggccttc ctgtagccag cccctcagag ccgccaccag aa            42

<210> SEQ ID NO 168
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
cggagagggt agctattttt gtagcgtttg ccatcttttc at            42

<210> SEQ ID NO 169
<211> LENGTH: 42
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic oligonucleotide"

<400> SEQUENCE: 169
tcttaaacag cttgataccg aactctagag gatccccggg ta                          42

<210> SEQ ID NO 170
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
ggaagcataa agtgtaaagc caatcagtag cgacagaatc aa                          42

<210> SEQ ID NO 171
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
gtttgccttt agcgtcagac tcgccatcaa aaataattcg cg                          42

<210> SEQ ID NO 172
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
acaggtagaa agattcatca gactccagcc agctttccgg ca                          42

<210> SEQ ID NO 173
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
catcgtaacc gtgcatctgc ctggtttaat ttcaacttta at                          42

<210> SEQ ID NO 174
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
attcagtgaa taaggcttgc cgtaaaacga cggccagtgc ca                          42
```

<210> SEQ ID NO 175
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
cattgtgaat taccttatgc gaaggataaa aattttaga ac                           42

<210> SEQ ID NO 176
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
tagcaaaatt aagcaataaa gtctactaat agtagtagca tt                          42

<210> SEQ ID NO 177
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
cgaacgagta gatttagttt gcgctattac gccagctggc ga                          42

<210> SEQ ID NO 178
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
ggcgatcggt gcgggcctct taccattaga tacatttcgc aa                          42

<210> SEQ ID NO 179
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
atggtcaata acctgtttag caggcaaagc gccattcgcc at                          42

<210> SEQ ID NO 180
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 180
ccgcttctgg tgccggaaac ctatattttc atttggggcg cg                         42

<210> SEQ ID NO 181
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
agctgaaaag gtggcatcaa tcctcagagc ataaagctaa at                         42

<210> SEQ ID NO 182
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
cggttgtacc aaaaacatta taactaacgg aacaacatta tt                         42

<210> SEQ ID NO 183
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
aaaatctacg ttaataaaac ggaccctgta atacttttgc gg                         42

<210> SEQ ID NO 184
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184 aaggggatg tgctgcaagg cacgccaaaa ggaattacga gg                          42

<210> SEQ ID NO 185
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
ttcaactaat gcagatacat agattaagtt gggtaacgcc ag                         42

<210> SEQ ID NO 186
<211> LENGTH: 42
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
tatcggcctc aggaagatcg cttgagattt aggaatacca ca                        42

<210> SEQ ID NO 187
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
gagaagcctt tatttcaacg cattttaaga actggctcat ta                        42

<210> SEQ ID NO 188
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
ggttttccca gtcacgacgt tctgacgaga aacaccagaa cg                        42

<210> SEQ ID NO 189
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
agtagtaaat tgggcttgag aagtttgagg ggacgacgac ag                        42

<210> SEQ ID NO 190
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
tctttcctta tcattccaag acgtaaaaca gaaataaaga aa                        42

<210> SEQ ID NO 191
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
ttgtttggat tatacttctg aaaagttacc agaaggaaac cg                        42
```

<210> SEQ ID NO 192
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
aatgaaatag caatagctat caatggatta tttacattgg ca                          42

<210> SEQ ID NO 193
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
ccagccattg caacaggaaa agccgttttt attttcatcg ta                          42

<210> SEQ ID NO 194
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
gcactcatcg agaacaagca aacgctcatg gaaataccta ca                          42

<210> SEQ ID NO 195
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
ttttgacgct caatcgtctg attaccgaag ccctttttaa ga                          42

<210> SEQ ID NO 196
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
aaagtaagca gatagccgaa cataatggaa gggttagaac ct                          42

<210> SEQ ID NO 197
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 197
accatatcaa aattatttgc aacgggtatt aaaccaagta cc                    42

<210> SEQ ID NO 198
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
ggaatcatta ccgcgcccaa ttcaaactat cggccttgct gg                    42

<210> SEQ ID NO 199
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
aattaaccgt tgtagcaata cccaataata agagcaagaa ac                    42

<210> SEQ ID NO 200
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
acaaagtcag agggtaattg accgcctggc cctgagagag tt                    42

<210> SEQ ID NO 201
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
tattgggcgc cagggtggtt taacgcgagg cgttttagcg aa                    42

<210> SEQ ID NO 202
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
aggcttatcc ggtattctaa gttcttttca ccagtgagac gg                    42

<210> SEQ ID NO 203
<211> LENGTH: 42

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
gcaacagctg attgcccttc agcgctaata tcagagagat aa         42

<210> SEQ ID NO 204
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
cccacaagaa ttgagttaag cttctttgat tagtaataac at         42

<210> SEQ ID NO 205
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
cacttgcctg agtagaagaa cagcaagcaa atcagatata ga         42

<210> SEQ ID NO 206
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
ttccagtaag cgtcatacat gtgacctgaa agcgtaagaa ta         42

<210> SEQ ID NO 207
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
gattcaccag tcacacgacc aaaggtgaat tatcaccgtc ac         42

<210> SEQ ID NO 208
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
caaaagggcg acattcaacc gaattcatca atataatcct ga        42

<210> SEQ ID NO 209
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
tttacaaaca attcgacaac tacttttca tgaggaagtt tc         42

<210> SEQ ID NO 210
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
caaccatcgc ccacgcataa caaagaacgt ggactccaac gt        42

<210> SEQ ID NO 211
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
gcagcaagcg gtccacgctg gggccggaaa cgtcaccaat ga        42

<210> SEQ ID NO 212
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
cgacttgagc catttgggaa taaagagtct gtccatcacg ca        42

<210> SEQ ID NO 213
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
cttgcaggga gttaaaggcc gataacgtgc tttcctcgtt ag        42

<210> SEQ ID NO 214
<211> LENGTH: 42
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 214
aatcagagcg ggagctaaac accgtaacac tgagtttcgt ca                          42

<210> SEQ ID NO 215
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
ggaggtttag taccgccacc ctgagtaaca ttatcatttt gc                          42

<210> SEQ ID NO 216
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
acgttattaa ttttaaaagt ttcagaaccg ccaccctcag aa                          42

<210> SEQ ID NO 217
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
ccgccaccct cagagccacc agaatggcta ttagtcttta at                          42

<210> SEQ ID NO 218
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
cgtggcacag acaatatttt tccctcattt tcagggatag ca                          42

<210> SEQ ID NO 219
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
cagcagcgaa agacagcatc gacatcgcca ttaaaaatac cg                          42

<210> SEQ ID NO 220
```

```
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
gcgcgaactg atagccctaa agaacgaggg tagcaacggc ta                        42

<210> SEQ ID NO 221
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
agcccaatag gaacccatgt aggaggccga ttaaagggat tt                        42

<210> SEQ ID NO 222
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
atcaaaagaa tagcccgaga tgtagcattc cacagacagc cc                        42

<210> SEQ ID NO 223
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
ccagtacaaa ctacaacgcc tagggttgag tgttgttcca gt                        42

<210> SEQ ID NO 224
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
tagacaggaa cggtacgcca ggcgcagtct ctgaatttac cg                        42

<210> SEQ ID NO 225
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
```
aggtcagacg attggccttg aaatcggcaa aatcccttat aa                    42

<210> SEQ ID NO 226
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
cctgtttgat ggtggttccg atattcacaa acaaataaat cc                    42

<210> SEQ ID NO 227
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
tcattaaagc cagaatggaa aaatcctgag aagtgttttt at                    42

<210> SEQ ID NO 228
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
ggaacaaaga aaccaccaga agggtcagtg ccttgagtaa ca                    42

<210> SEQ ID NO 229
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
tactggtaat aagttttaac gggagcggaa ttatcatcat at                    42

<210> SEQ ID NO 230
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
ccaacagaga tagaacccctt cgcttttgat gatacaggag tg                    42

<210> SEQ ID NO 231
<211> LENGTH: 42
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 231
aatcagtgag gccaccgagt atagagccag caaaatcacc ag                          42

<210> SEQ ID NO 232
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
tagcaccatt accattagca atttgcccca gcaggcgaaa at                          42

<210> SEQ ID NO 233
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
ttggaacaag agtccactat tcgatatatt cggtcgctga gg                          42

<210> SEQ ID NO 234
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
cagaggcttt gaggactaaa gcgtattaaa tcctttgccc ga                          42

<210> SEQ ID NO 235
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
tcctgattat cagatgatgg cattgaggga gggaaggtaa at                          42

<210> SEQ ID NO 236
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
attgacggaa attattcatt agtaataaaa gggacattct gg                          42
```

```
<210> SEQ ID NO 237
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
tttgccagag ggggtaatag tgtgccacgc tgagagccag ca                           42

<210> SEQ ID NO 238
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
aacgaaccac cagcagaaga tatgaacggt gtacagacca gg                           42

<210> SEQ ID NO 239
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
cggaacgagg cgcagacggt cgaggattta gaagtattag ac                           42

<210> SEQ ID NO 240
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
caaagggcga aaaccgtct aatcaacgta acaaagctgc tc                            42

<210> SEQ ID NO 241
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
cgcataggct ggctgacctt cgccgctaca gggcgcgtac ta                           42

<210> SEQ ID NO 242
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 242
cgtggcgaga aaggaaggga aatatgcaac taaagtacgg tg                              42

<210> SEQ ID NO 243
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
aggattagag agtaccttta agaaaggaat tgaggaaggt ta                              42

<210> SEQ ID NO 244
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
tcagttggca aatcaacagt tttgctcctt ttgataagag gt                              42

<210> SEQ ID NO 245
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
catttttgcg gatggcttag atcaccttgc tgaacctcaa at                              42

<210> SEQ ID NO 246
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
gcaaatgaaa aatctaaagc agcttaattg ctgaatataa tg                              42

<210> SEQ ID NO 247
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
ctgtagctca acatgtttta agaaagcgaa aggagcgggc gc                              42

<210> SEQ ID NO 248
<211> LENGTH: 42
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 248
taaagcacta aatcggaacc caacagttga ttcccaattc tg                    42

<210> SEQ ID NO 249
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
tctggaagtt tcattccata ttaaagggag cccccgattt ag                    42

<210> SEQ ID NO 250
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
tagggcgctg gcaagtgtag cagaggcttt tgcaaaagaa gt                    42

<210> SEQ ID NO 251
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
catagtaaga gcaacactat cttttttggg gtcgaggtgc cg                    42

<210> SEQ ID NO 252
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
tgaaccatca cccaaatcaa gataaccctc gtttaccaga cg                    42

<210> SEQ ID NO 253
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
acgataaaaa ccaaaatagc gggtcacgct gcgcgtaacc ac                    42
```

<210> SEQ ID NO 254
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
tctaaaatat ctttaggagc aataaatatt cattgaatcc cc                         42

<210> SEQ ID NO 255
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
gtccaatact gcggaatcgt cctaacaact aatagattag ag                         42

<210> SEQ ID NO 256
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
gtattaacac cgcctgcaac aaaaatgttt agactggata gc                         42

<210> SEQ ID NO 257
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
cacacccgcc gcgcttaatg catcaagagt aatcttgaca ag                         42

<210> SEQ ID NO 258
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
aaccggatat tcattaccca atcagggcga tggcccacta cg                         42

<210> SEQ ID NO 259
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
ccgtcaatag ataatacatt taatcataag ggaaccgaac tg					42

<210> SEQ ID NO 260
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
accaactttg aaagaggaca gaaaacagag gtgaggcggt ca					42

<210> SEQ ID NO 261
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
atcaacaata gataagtcct gtgtccagac gacgacaata aa					42

<210> SEQ ID NO 262
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
gcagaggcat tttcgagcca ggtatgttag caaacgtaga aa					42

<210> SEQ ID NO 263
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
aggaaacgca ataataacgg attgctttga ataccaagtt ac					42

<210> SEQ ID NO 264
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
gtcagatgaa tatacagtaa caaaccaatc aataatcggc tg					42

<210> SEQ ID NO 265
<211> LENGTH: 42
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
tcctaattta cgagcatgta gagtaccttt tacatcggga ga                              42

<210> SEQ ID NO 266
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
aacaataacg gattcgcctg aatacccaaa agaactggca tg                              42

<210> SEQ ID NO 267
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
attaagactc cttattacgc ataataagag aatataaagt ac                              42

<210> SEQ ID NO 268
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
cgacaaaagg taaagtaatt caacaagaaa ataatatcc ca                              42

<210> SEQ ID NO 269
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
cattaaacgg gtaaaatacg ttgagtgaat aaccttgctt ct                              42

<210> SEQ ID NO 270
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
aaaatcgcgc agaggcgaat tatggtttac cagcgccaaa ga                              42
```

<210> SEQ ID NO 271
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
ataaaagaaa cgcaaagaca ccaacgccaa catgtaattt ag                              42

<210> SEQ ID NO 272
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
gtgataaata aggcgttaaa tagaatacac taaaacactc at                              42

<210> SEQ ID NO 273
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
acctaaaacg aaagaggcaa aaagaataaa caccggaatc at                              42

<210> SEQ ID NO 274
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
aattactaga aaaagcctgt tggataagtg ccgtcgagag gg                              42

<210> SEQ ID NO 275
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
gggttttgct cagtaccagg ctagtatcat atgcgttata ca                              42

<210> SEQ ID NO 276
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 276
tacatttaac aatttcattt gataggtgta tcaccgtact ca        42

<210> SEQ ID NO 277
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
ttgatataag tatagcccgg aaattacctt ttttaatgga aa        42

<210> SEQ ID NO 278
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
aattcttacc agtataaagc cgtattaaga ggctgagact cc        42

<210> SEQ ID NO 279
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
gtgcccgtat aaacagttaa tcatcaagaa aacaaaatta at        42

<210> SEQ ID NO 280
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
aaaagaagat gatgaaacaa agcccctgc ctatttcgga ac        42

<210> SEQ ID NO 281
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
ctattattct gaaacatgaa aaacgctcaa cagtagggct ta        42

<210> SEQ ID NO 282
<211> LENGTH: 42

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
attgagaatc gccatattta acacggaata agtttatttt gt                          42

<210> SEQ ID NO 283
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
cacaatcaat agaaaattca tattcatttc aattacctga gc                          42

<210> SEQ ID NO 284
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
cagtacataa atcaatatat gaatgccact acgaaggcac ca                          42

<210> SEQ ID NO 285
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
gtaaatcgtc gctattaatt aacctgctcc atgttactta gc                          42

<210> SEQ ID NO 286
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
agcgcgaaac aaagtacaac gatggtttga aataccgacc gt                          42

<210> SEQ ID NO 287
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
```

```
tataactata tgtaaatgct gcaaatatcg cgttttaatt cg          42
```

<210> SEQ ID NO 288
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288

```
aagaggaagc ccgaaagact tatgcaaatc caatcgcaag ac          42
```

<210> SEQ ID NO 289
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289

```
tagtgaattt atcaaaatca tggaagcaaa ctccaacagg tc          42
```

<210> SEQ ID NO 290
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290

```
agcttcaaag cgaaccagac caggtctgag agactacctt tt          42
```

<210> SEQ ID NO 291
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291

```
aaagaacgcg agaaaacttt tctgactatt atagtcagaa gc          42
```

<210> SEQ ID NO 292
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292

```
ctcaaatgct ttaaacagtt ctaagacgct gagaagagtc aa          42
```

<210> SEQ ID NO 293
<211> LENGTH: 42
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 293
aaacatagcg atagcttaga tagaaaacga gaatgaccat aa                      42

<210> SEQ ID NO 294
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
atcaaaaatc aggtctttac ctcaaatata ttttagttaa tt                      42

<210> SEQ ID NO 295
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
tcatcttctg acctaaattt agagatttgt atcatcgcct ga                      42

<210> SEQ ID NO 296
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
taaattgtgt cgaaatccgc gattttccct tagaatcctt ga                      42
```

DNA-CHIMERIC ANTIGEN RECEPTOR T CELLS FOR IMMUNOTHERAPY

RELATED APPLICATIONS

This application claims the benefit of U.S. Provisional Application No. 62/625,964, filed on Feb. 2, 2018, the entire disclosure of which is incorporated herein by reference.

SEQUENCE LISTING

The instant application contains a Sequence Listing which has been submitted electronically in ASCII format and is hereby incorporated by reference in its entirety. Said ASCII copy, created on Apr. 12, 2019, is named G8118-01201_SL.txt and is 93,208 bytes in size.

BACKGROUND

Cancer immunotherapy is an emerging field that has demonstrated significant promise in recent years. Perhaps the most exciting of these approaches has been the use of peripheral blood T cells genetically modified to express chimeric antigen receptor (CAR) genes for use in hematological "liquid cancers". However, in the much more common case of solid tumor cancers, CAR T cells meet obstacles including physical barriers, loss of antigen and immunosuppressive environments. Accordingly, cancer therapies that overcome these obstacles are needed.

Adoptive cell transfer denotes the transfer of immunocompetent cells for the treatment of cancer or infectious diseases (June, C. H., ed., 2001, In: Cancer Chemotherapy and Biotherapy: Principles and Practice, Lippincott Williams & Wilkins, Baltimore; Vonderheide et al., 2003, Immun. Research 27:1-15). Adoptive cell therapy is a strategy aimed at replacing, repairing, or enhancing the biological function of a damaged tissue or system by means of autologous or allogeneic cells, and thus can be used in cancer immunotherapy.

SUMMARY

In certain aspects, this disclosure provides a method to generate an engineered T cell for cancer immunotherapy. In some aspects, the engineered T cell comprises a DNA, RNA and/or DNA-peptide nanostructure-based chimeric antigen receptor (CAR) domain.

In certain aspects, this disclosure provides an engineered T cell comprising: an expressed engineered chimeric antigen receptor which comprises an extracellular adaptor protein; a protein tag bound to said adaptor protein; a first oligonucleotide connected to said protein tag; a second oligonucleotide wherein a portion of the second oligonucleotide sequence is complementary to a portion of the first oligonucleotide sequence; and a targeting agent connected to the second oligonucleotide, where the targeting agent comprises one or a plurality of targeting molecules. In certain aspects, the targeting agent comprises a DNA origami nanostructure comprising a central polynucleotide strand and a first staple strand which comprises the second oligonucleotide sequence and a plurality of second staple strands which comprises one or a plurality of third distinct oligonucleotide sequences; and one or more targeting molecules connected to one or a plurality of fourth distinct oligonucleotide sequence(s). In certain aspects, a portion of the third distinct oligonucleotide sequence is complementary to a portion of the fourth oligonucleotide sequence.

In certain aspects, the expressed engineered chimeric antigen receptor comprises: a signaling polypeptide domain; a transmembrane polypeptide domain; a spacer polypeptide domain; a costimulatory polypeptide domain; and an adaptor protein tag domain. In certain aspects, the expressed engineered chimeric antigen receptor further comprises a fluorescent protein domain. The fluorescent protein domain is selected from green fluorescent protein (GFP), blue fluorescent proteins (EBFP, EBFP2, Azurite, mKalama1), cyan fluorescent proteins (ECFP, Cerulean, CyPet, mTurquoise2), yellow fluorescent proteins (YFP, Citrine, Venus, YPet), and bilirubin-inducible fluorescent proteins (UnaG, dsRed, eqFP611, Dronpa, TagRFPs, KFP, EosFP, Dendra, and IrisFP). In certain embodiments, the fluorescent protein domain is a fluorescent protein having a major excitation peak of about 488 nm, and an emission of about 509 nm.

In certain aspects, the polynucleotide sequence encoding the expressed engineered chimeric antigen receptor comprises an antibiotic resistant gene. The purpose of the antibiotic resistant gene is to identify the transfected cells in cell culture. In some embodiments, the antibiotic resistant gene is a puromycin gene. In some embodiments, the antibiotic resistant gene is selected from puro, pac, pUNO1-pac, or pEGFP-puro.

In certain aspects, the signaling polypeptide domain is CD3ζ.

In certain aspects, the transmembrane polypeptide domain is CD8.

In certain aspects, the costimulatory domain is selected from: CD28, 4-1BB, OX-40, and combinations thereof.

In certain aspects, the spacer polypeptide domain is a repeat of the sequence (Gly-Gly-Gly-Gly-Ser)$_n$, where n is an integer selected from 1 to 8 (SEQ ID NO: 1).

In certain aspects, the adaptor protein tag domain is selected from the SNAP-Tag™, CLIP-Tag™, or HALO-Tag™ adaptor proteins.

In certain aspects, the signaling polypeptide domain is CD3ζ, the transmembrane polypeptide domain is CD8, the costimulatory domain is 4-1BB, the spacer polypeptide domain is (Gly-Gly-Gly-Gly-Ser)$_4$ (SEQ ID NO: 2), and the adaptor protein tag domain is SNAP-Tag™ adaptor protein.

In certain aspects, the targeting molecule is selected from: an aptamer, a synbody, and an antibody or fragment thereof. In certain aspects, the antibody fragment is a scFv. In certain aspects. The aptamer is scg8 having SEQ ID NO: 10.

In certain aspects, the targeting molecule comprises a matrix metalloproteinase.

In certain aspects, the targeting molecule comprises a cytokine, chemokine, or a combination thereof.

In certain aspects, the targeting molecule comprises an inhibitory pathway overcoming agent. In certain aspects, the inhibitory pathway overcoming agent is selected from an anti-PD-1L antibody, an anti-PD-1L aptamer, an anti-CTLA4 antibody, or an anti-CTLA4 aptamer.

In certain aspects, the T cell is selected from a natural killer T cell, a regulatory T cell, a helper T cell, a cytotoxic T cell, a memory T cell, a gamma delta T cell and a mucosal invariant T cell.

In certain aspects, this disclosure relates to a vector encoding a chimeric antigen receptor described herein.

In certain aspects, this disclosure relates to a method of preparing an engineered T cell comprising the steps of: inserting a DNA sequence which encodes for the CAR polypeptide into a virus; contacting the virus with a T cell to form or produce a viral-infused T cell; growing the viral-infused T cells to produce an adaptor T cell expressing the CAR comprising the extracellular adaptor protein; isolating the adaptor T cell; contacting the extracellular adaptor protein of the isolated adaptor T cells with a first oligonucleotide functionalized with a cognate protein tag; forming a complex between the extracellular adaptor protein of the adaptor T cells with the cognate protein tag to form a first oligonucleotide-functionalized adaptor T cell; contacting the first oligonucleotide-functionalized adaptor T cell with a second oligonucleotide comprising a targeting agent under appropriate conditions to form a hybridization complex between a portion of the first linker oligonucleotide and a portion of the second linker oligonucleotide.

In certain aspects, this disclosure relates to a method of preparing the engineered T cell comprising the steps of: inserting the DNA sequence which encodes for the CAR polypeptide into a virus; contacting the virus with a T cell to form or produce a viral-infused T cell; growing the viral-infused T cells to produce an adaptor T cell expressing the CAR comprising the extracellular adaptor protein; isolating the adaptor T cell; contacting the extracellular adaptor protein of the isolated adaptor T cells with a first oligonucleotide functionalized with a cognate protein tag of the adaptor T cells with the cognate protein tag to form a first oligonucleotide-functionalized adaptor T cell; contacting the first oligonucleotide-functionalized adaptor T cell with a first staple strand of a DNA origami nanostructure comprising a central polynucleotide sequence, a first staple strand, and one or a plurality of third distinct oligonucleotide sequences to form a hybridization complex between a portion of the first oligonucleotide and a portion of the one or a plurality of third distinct oligonucleotide sequences; contacting said DNA origami nanostructure with one or a plurality of targeting molecules comprising a second oligonucleotide sequence under appropriate conditions to form a hybridization complex between a portion of the sequences of the one or a plurality of third distinct oligonucleotide sequences and a portion of the second oligonucleotide sequence. In certain aspects, the virus is selected from a lentivirus, retrovirus or adeno-associated virus.

In certain aspects, this disclosure relates to a method of activating an engineered T cell comprising contacting a cancer cell with an engineered T cell described herein. In certain aspects, the cancer cell is selected from a hematological cancer or a tumor cell. In some aspects, the cancer cell is a T lymphoid blastoma. In some aspects, the T lymphoid plastoma is a CCRF-CEM cell. In some aspects, the cancer cell is a breast cancer cell or a lung cancer cell.

In certain aspects, this disclosure relates to a method of killing a cancer cell comprising contacting a cancer cell with an engineered T cell described herein. In certain aspects, the cancer cell is selected from a hematological cancer or a tumor cell. In some aspects, the cancer cell is a T lymphoid blastoma. In some aspects, the T lymphoid plastoma is a CCRF-CEM cell. In some aspects, the cancer cell is a breast cancer cell or a lung cancer cell.

In certain aspects, this disclosure relates to a method of killing a cancer cell comprising the steps of contacting a cancer cell with a DNA nanostructure comprising a plurality of staple strands where a first staple strand is unhybridized and a second staple strand is hybridized to a fourth oligonucleotide which is chemically conjugated to a targeting molecule, and said targeting molecule binds to said cancer cell; then contacting the DNA nanostructure with an engineered T cell comprising a first oligonucleotide which is complementary to the first staple strand on the DNA nanostructure to form a hybridization complex between the first oligonucleotide and the first staple strand to bring the engineered T cell in local proximity to the cancer cell and begin a cytolytic mechanism.

In certain aspects, this disclosure relates to a composition comprising the engineered T cell as described herein with a pharmaceutically acceptable excipient. In some aspects, this disclosure relates to a method for activating engineered T cells and/or killing cancer cells in a subject having or suspected of having cancer by administering to said subject said composition.

In certain aspects, this disclosure provides a single- or multiple-target antigen-specific CAR T cells.

In certain aspects, this disclosure provides a single- or multiple-target antigen-specific ECM degrading CAR T cell.

In certain aspects, this disclosure provides a single- or multiple-target antigen-specific cytokine expressing CAR T cell.

In certain aspects, this disclosure provides a single- or multiple-target antigen-specific inhibitory pathway overcoming CAR T cell.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 3A-3B. Advantages of engineered T cells for cancer immunotherapy. FIG. 3A. Current CAR T structures and issues have resulted in failure of CAR T therapy in solid tumors. Hostile microenvironments decreased therapy effects of CAR T cells. FIG. 3B: Novel T cell toolkit using DNA nanotechnology ("engineered T cell"). DNA origami carrying targeting and functional molecules helps engineered T cells overcome obstacles in solid tumor. This strategy bypasses the difficulties of genetic engineering and allow for rapid, modular generation of targeting engineered T cells using a wider range of targeting ligands than previously possible.

FIG. 4. Approach overview of engineered T cell in solid tumor therapy. Using engineered T cells can solve specific problems by assembly different functional molecules. DNA nanotechnology promotes T cell infiltration overcomes the hostile environment in solid tumor.

FIG. 5A-FIG. 5B. Design models (top row) and corresponding AFM images of two representative DNA nanostructures. (FIG. 5A) DNA nanostructures with close-packed helices and (FIG. 5B) DNA nanostructures with wireframe patterns.

(FIG. 7A) Second generation engineered T cell comprising an engineered CAR comprising: a SNAP-Tag™ protein following with CD8 transmembrane Domain™, CD3ζ activation domain and different signaling domains: CD28, 4-1BB or OX-40; (FIG. 7B) Second generation engineered T cell with a CD8 leader sequence (L). (FIG. 7C) Third generation engineered T cell comprising an engineered CAR comprising: a SNAP-Tag™ tag following with TM, CD3 activation domain and two signaling domains: CD28 with 4-1BB or OX-40; (FIG. 7D) Third generation T cell comprising an engineered CAR with CD8 leader sequence.

FIG. 11A: Layout of peptide libraries on slide. The 125K peptide library is synthesized as individually addressable arrays, A1 through A24. FIG. 11B TNFA (x-axis) and TNFA+TNFR1 complex (y-axis) binding to 125 k peptide microarray. Each spot represents the signal from a single peptide. FIG. 11C: TNFR1 binding site peptides illustrated by decrease in binding intensity when the TNFA/TNFR1 complex.

FIGS. 12A-12C. Synbody library production. FIG. 12A: Reaction scheme to produce synbody library. FIG. 12B: Pairwise combinations of peptides to produce 55 synbodies from 45 reactions. FIG. 12C: Average amount of hetero-bivalent and homo-bivalent synbody recovered from synbody library production for a protein target.

FIGS. 13A-13B. Multivalent structures for trapping engineered T cells. FIG. 13A: Branched DNA dendrimers (4). FIG. 13B: repeating DNA ribbons attached to a targeting nanostructure allows for a single recognition event to coat a tumor with multiple copies of a ssDNA handle. Engineered T cells modified with similarly multivalent structures are trapped at the tumor site upon circulation.

FIG. 14A: a tubular DNA nanocage of this disclosure. FIG. 14B: A tetrahedral DNA nanocage. FIG. 14C: A pyramidal DNA nanocage.

FIG. 15A: high level chemokines, FIG. 15B: Low level chemokines FIG. 15C: Medium level chemokines FIGS. 16A-16B. Nucleolin aptamer-functionalized DNA nanocage.

(FIG. 20A) Chemokine receptor mRNA expression levels in antigen-specific T cells. (FIG. 20C) Cytokine increased T cell proliferation in antigen-specific T cells.

FIGS. 21A-21F. Depiction of bioconjugation strategies. (FIG. 21A) Copper-free click chemistry for attaching a synbody to a DNA handle. (FIG. 21B) MALDI-TOF MS of a purified peptide-DNA conjugate. (FIG. 21C) Using DNA to template the two peptides of a synbody pair. (FIG. 21D) Structure of IL-2 bound with its receptor (left) and MMP-2 indicating the catalytic site (right). The indicated interfaces are modified to avoid compromising protein function. (FIG. 21E) Cysteine alkylation using maleimide-DNA to modify the protein surface. (FIG. 21F) Sortase-mediated conjugation of oligonucleotide handles using a peptide-DNA conjugate. FIG. 21F discloses SEQ ID NO: 12.

FIGS. 25A-25H. Thrombin comprising DNA nanocage for on-target tumor infection in vivo. (FIG. 25A) Schematic representation of the therapeutic mechanism of nanocage within tumor vessels. DNA nanocages were administrated to breast tumor xenografted mice intravenously and were targeted to the tumor-associated vessels. The nanocages binds to the vascular endothelium by recognizing nucleolin and opens to expose the encapsulated thrombin, which induces a localized thrombosis, tumor infarction and cell necrosis. (FIG. 25B) Optical imaging of a MDA-MB-231 human breast tumor-comprising mouse before and after intravenous injection of Cy5.5-labeled nanocages. A high-intensity fluorescence signal was detected only in the tumor region of mice 8 h post-injection. (0 h=before injection.) (FIG. 25C) In vivo fluorescence intensity at the tumor sites was quantified as Total Fluorescence Intensity (TFI) at several time points after administration of the nanorobots; n=3. (FIG. 25D) FITC-labeled nanocages were injected intravenously into mice comprising MDA-MB-231 tumors. Tumors were harvested 8 h later, and tumor sections were stained with antibodies and examined by confocal microscopy. The nanocages (green) appear in the blood vessel-rich regions (anti-CD34; brown). Nuclei were stained with DAPI (blue). Scale bars, 20 µm. (FIG. 25E) Immunostaining to detect thrombosis (brown) in MDA-MB-231 tumors before and 24, 48 or 72 h post-administration of nanorobot-Th. (FIG. 25F) Haematoxylin and eosin (H&E) staining of the corresponding sections reveals a widespread necrosis (N). Scale bars, 50 µm. Data are representative of at least three separate experiments. (G&H) MDA-MB-231 tumor-comprising mice were treated on day 0 with saline, free thrombin (~1.5 U/mouse), empty nanocages or nanocage-Th. Tumor volumes up to day 21 (FIG. 25G) and cumulative survival of mice (FIG. 25H) were shown. *p<0.05, p<0.01 and *p<0.001, compared with the other groups.

FIGS. 26A-26D. Anti-tumor activity and safety of DNA nanocage. (FIG. 26A) Inhibition of tumor growth by thrombin-loaded DNA nanocage; (FIG. 26B) Reduction of tumor loads in the liver of the mice treated with thrombin-loaded DNA nanocage; (FIG. 26C) Serum cytokine levels and (FIG. 26D) Microthrombi in cerebral venous vessels were detected at various time points post treatment.

FIG. 30A shows the present clinical outcomes of other attempts at published CAR T cell therapy for hematological malignancies, indicating that T cells targeted to CD19 have the highest rate of complete response or positive response for hematological malignancies. FIG. 30B shows the present clinical outcomes of other attempts at published CAR T therapy for solid tumor therapies, indicating that T cells targeting GD2 have the highest complete response or positive response for solid tumor malignancies.

FIG. 32 depicts a CAR comprising an adaptor protein which is connected to a first oligonucleotide, but where the first oligonucleotide is connected to a CLIP-Tag™ protein which is tethered to a Langmuir-Blodgett film for downstream T cell signaling analysis. The CAR in FIG. 32 also lacks a spacer domain. In some embodiments, the engineered CAR does not include the CAR depicted in FIG. 32.

FIG. 33A depicts a "Third generation CAR T cell" (e.g., CD19 scFv-comprising T cell), and its disadvantages in T cell therapy which include only targeting a single target is limited to addressing only one challenge category of solid tumor cell targeting, and reliance on genetic engineering to optimize binding affinity. FIG. 33B shows the strategy for designing some embodiments of engineered T cells of this disclosure by including a targeting agent which comprises a DNA nanostructure which, in some embodiments, further comprises a plurality of targeting molecules. The advantages of an engineered T cell include the ability to address multiple targets, the ability to address multiple challenges in targeting solid tumors, and the ease of assembly to modulate different targets. Also depicted is an AFM image of a DNA nanostructure with selectively positioned targeting molecules demonstrating that the targeting molecules are precisely positioned relative to each other to enhance both binding affinity and binding avidity.

FIG. 40: Representative aptamers of the present disclosure.

FIG. 41A: Engineered CAR design. FIG. 41B: Targeting molecules of this disclosure which are chemically conjugated to an oligonucleotide. FIG. 41C: Mechanism by which engineered T cells ("DNA-CAR T cell") interact with tumor cell and release cytolytic enzymes.

FIG. 42A: Lentivirus transfer plasmid encoding an engineered CAR. FIG. 42B: Procedure of transferring lentiviral vector into Jurkat T cells. FIG. 42C: GFP fluorescence intensity of flow cytometry sorted cells shows that the adaptor-infected Jurkat T cells encode the engineered CAR.

FIG. 43A: Adaptor Jurkat T cells (engineered T cells) conjugate BG ss DNA (polyT) and hybridize with a complement oligonucleotide (Alexa647-polyA). FIG. 43B: Fluorescence microscopy image of adaptor Jurkat T cells linked to a molecule through DNA hybridization. FIG. 43C: Fluorescence intensity of Alexa647 on engineered T cells shows that the cells with adaptor protein is higher than cells without adaptor structures.

FIG. 43D: The ratio of Alexa 647 positive engineered T cells to all cells (GFP cells) shows a dose-dependent signal as the BG-polyT concentration added to the cells is increased.

FIG. 46A: Adaptor Jurkat T cells conjugate with BG-polyT to generate polyT comprising engineered T cells. FIG. 46B: Luciferase assay measurements showing that engineered T cells are activated by target cancer cells.

FIG. 52 The DNA sequence inserted into a lentivirus encoding one embodiment of an engineered CAR of this disclosure.

FIG. 53 lists representative staple strands of this disclosure.

DETAILED DESCRIPTION

Figure 1:
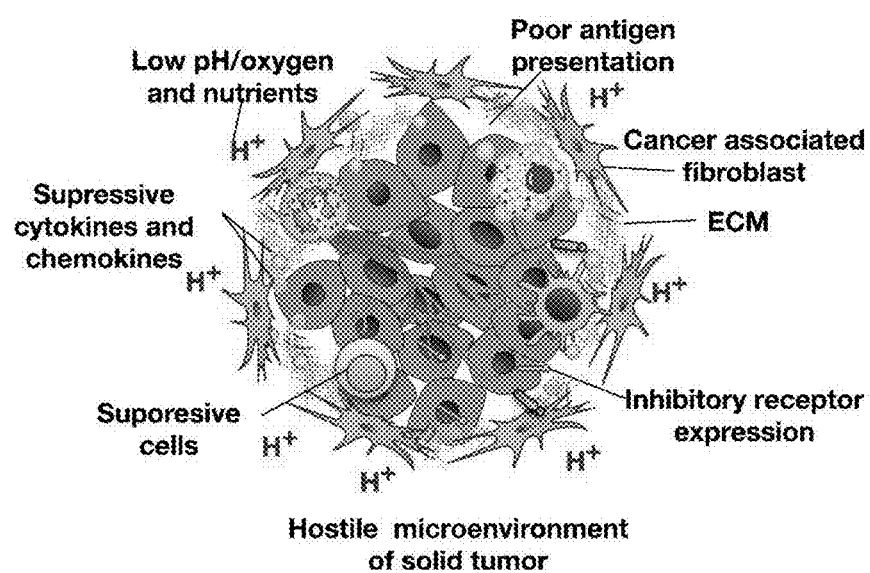
FIG. 1. The immunosuppressive tumor microenvironment presents multiple challenges for chimeric antigen receptor (CAR) T cells. In addition to proper trafficking and successful infiltration, there are additional hurdles presented upon their arrival in a solid tumor microenvironment. Including low pH, hypoxia, suppressive immune cells or cytokines and co-inhibitory molecules including PD-1 or CTLA4. Failure to overcome the presence of these negative elements results in inhibition of the T cell activity and unabated tumor growth.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry and Molecular Biology, Revised, 2000, Oxford University Press, provide one of skill with a general dictionary of many of the terms used in this disclosure.

Units, prefixes, and symbols are denoted in their System International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

To overcome obstacles including physical barriers, loss of antigen and immunosuppressive environments, different strategies have been developed for CAR T cells, including CAR structures targeting two antigens to overcome antigen heterogeneity, engineering CARs to co-express chemokine receptors that increase T cell traffic to tumor area, and employing CARs that deplete the fibroblast cells that surround a solid tumor. However, T cells have only been engineerable to solve one of the above problems at a time. Furthermore, the foregoing strategies require long-term molecular cloning and structure optimizations which is an extremely costly and time-consuming process that is not always successful.

The inventors have recognized that the ability to manipulate T cells according to the methods disclosed herein provides a plethora of opportunities and advantages for additional changes and improvements.

In some embodiments, targeting agents comprise targeting molecules. In some embodiments, targeting molecules can include or exclude aptamers, peptides, or small molecules. Targeting agents and/or targeting molecules are attached to the engineered T cells using a site-specific type of chemistry using protein-tag chemistry. In some embodiments of this disclosure, for this purpose, SNAP-Tag™ or CLIP-Tag™ proteins are incorporated into the CARs. In some embodiments, the targeting agents and molecules, include DNA nanostructures and proteins, and are conjugated with a single strand DNA sequence complimentary to a single stranded DNA oligonucleotide sequence connected to the engineered T cell surface.

In some embodiments, this disclosure provides a method to generate DNA, RNA and/or DNA-peptide nanostructure based chimeric antigen receptor (CAR) T cell (engineered T cell) for cancer immunotherapy. This method allows rapid generation of single- or multiple-target antigen-specific T cells, ECM degrading T cells (including matrix metalloproteinase comprising targeting agents), cytokine expressing T cells and inhibitory pathway overcoming T cells without further genetic engineering.

In some embodiments, this disclosure provides a novel DNA nanotechnology-based strategy to engineer T cells to: 1) Allow for precise tumor targeting through dual/multiple-binding specificities to minimize tumor immune escape; 2) Increase cell survival and trafficking to tumor area; and 3) Generate multifunctional engineered T cells rapidly economically. An engineered CAR T cell toolkit is generated using DNA nanotechnology (engineered T cell). T cells are engineered to express signaling CAR domains and an "adaptable receptor" protein domain that allows the attachment of a targeting agent with high efficiency. In some embodiments the targeting agent is a DNA nanostructure (also referred to herein as a "DNA nano-scaffold"). These DNA scaffolds carry targeting molecules which can include or exclude peptides, synbodies, aptamers, or small molecules, and functional molecules which enhance T cell survival penetration into the solid tumor environment. This highly modular and combinatorial approach circumvents the long, expensive process of specific genetic engineering, allow for non-genetically encodable functionality, and enhances T cell activity through multivalent effects. The engineered T cell is unprecedented in its economic manufacture and broad use in cancer immunotherapy research and clinical application. The engineered T cells comprising targeting agents which comprise DNA significantly improve the success of engineered T cells against solid tumors and are therefore highly beneficial for personalized cancer immunotherapy.

Using DNA, RNA and/or peptide nanotechnologies, engineered T cells are provided that more precisely target tumor cells with remarkable specificity for different levels of expression, have increased survival resistance to the immunosuppressive solid tumor environment, and increased T cell traffic to the tumor area.

The inventors have recognized that the designed engineered T cells addresses the problems of T cell immunotherapy for solid tumor cancers of a low level or loss of tumor antigen expression, poor T cell trafficking and infiltration into the tumor, and an immune response-repressive environment.

Definitions

Abbreviations: CAR: chimeric antigen receptor; ACT: adoptive T cell transfer; TAA tumor-associated antigens; CTL: cytolytic lymphocytes; DCs: dendritic cells; scFv: single-chain variable fragment; ELISPOT: enzyme-linked immunosorbent spot; TME: tumor microenvironment; PD-1: programmed cell death protein 1; GFP: green fluorescence protein; CTLA4: cytotoxic T-lymphocyte-associated antigen 4; MDSC: myeloid derived suppressor cell; MHC-JJ: major histocompatibility complex-II; Tregs: regulatory T cells; OVA: ovalbumin; ECM: extracellular matrix; MMP: matrix metallopeptidase; RLU: relative light unit; SA: streptavidin; siRNA: small interfering RNA; Synbody: peptide-based multivalent synthetic antibodies; SELEX: systemic evolution of ligands by exponential enrichment; SPR: surface plasmon resonance; IHC: immunohistochemistry; MSLN: mesothelin, CEA: carcinoembryonic antigen; EGFR: Epidermal growth factor receptor, GPC3: Glypican-3; HER2: human epidermal growth factor receptor 2; nt: nucleotides (often used to refer to the number of nucleotides in a ssDNA strand); bp: basepairs (often used to refer to the number of nucleotides in a ssDNA strand).

As used herein, the term "activation" refers to the state of an immune cell, e.g., a T cell, that has been sufficiently stimulated to induce detectable cellular proliferation. Activation can also be associated with induced cytokine production and detectable effector functions. The term "activated T cells" refers to, among other things, T cells that are undergoing cell division.

As used herein, the term "administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

As used herein, the term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen-binding portion thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region comprises one constant domain, CL. The VH and VL regions are further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system. An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" can include or exclude both naturally occurring and non-naturally occurring Abs; monoclonal and polyclonal Abs; chimeric and humanized Abs; human or nonhuman Abs; wholly synthetic Abs; and single chain Abs. A nonhuman Ab may be humanized by recombinant methods to reduce its immunogenicity in man. The term "antibody" also includes an antigen-binding fragment or an antigen-binding portion of any of the aforementioned immunoglobulins, and includes a monovalent and a divalent fragment or portion, and a single chain Ab.

As used herein, the term "antigen binding molecule" or "antibody fragment" refers to any portion of an antibody less than the whole. An antigen binding molecule can include the antigenic complementarity determining regions (CDRs). Examples of antibody fragments can include or exclude, Fab, Fab', F(ab')2, and Fv fragments, dAb, linear antibodies, scFv, nanobodies, and multispecific antibodies formed from antigen binding molecules.

As used herein, the term "antigen" refers to any molecule that provokes an immune response or is capable of being bound by an antibody. The immune response may involve either antibody production, or the activation of specific immunologically-competent cells, or both. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, including a cancer cell, or it can be broadly expressed. In addition, fragments of larger molecules can act as antigens. In one embodiment, antigens are tumor antigens.

As used herein, the term "epitope" refers to the portion of an antigen capable of eliciting an immune response, or the portion of an antigen that binds to an antibody. Epitopes can be a protein sequence or subsequence that is recognized by an antibody.

As used herein, the term "single chain antibody" (scFv) refers to an immunoglobulin molecule with function in antigen-binding activities. An antibody in scFv (single chain fragment variable) format consists of variable regions of heavy (VH) and light (VL) chains, which are joined together by a flexible peptide linker.

As used herein, the term "synbody" refers to a synthetic molecule having a molecular weight of about 6 kDa to about 8 kDa and comprise bivalent peptides that bind their target with antibody-like affinity. The synbody mimics a synthetic antibody. The two peptides are different and bind to orthogonal sections of the target. The two peptides are conjoined either directly through a linker or indirectly. The directly conjoined peptides linked through a linker are linked using a trivalent linker as described herein. The indirectly conjoined peptides are brought in local proximity when a first peptide is connected to a first oligonucleotide, and a second peptide is connected to a second oligonucleotide, and a portion of the first oligonucleotide sequence is complementary to a portion of the second oligonucleotide sequence such that the first and second oligonucleotides form a hybridization complex.

As used herein, the term "autologous" refers to any material derived from the same individual to which it is later to be re-introduced. In some embodiments, the engineered autologous T cell therapy method described herein involves collection of lymphocytes from a patient, which are then engineered to express, e.g., an engineered CAR construct, contacted with a protein tag which is connected with ta first oligonucleotide, contacted with a targeting agent which is connected to a second oligonucleotide, wherein a portion of the first oligonucleotide and a portion of the second oligonucleotide are complementary, and then administered back to the same patient.

As used herein, the term "allogeneic" refers to any material derived from one individual which is then introduced, after T cell engineering according to the methods described herein, to another individual of the same species, e.g., allogeneic engineered T cell transplantation.

As used herein, the term "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. In some embodiments, a "cancer" or "cancer tissue" can include a tumor. The types of cancers that are treated by the methods of this disclosure can include or exclude cancers of the immune system including lymphoma, acute lymphoblastoid leukemia, leukemia, and other leukocyte malignancies. In some embodiments, the methods of this disclosure reduce the tumor size of a tumor derived from, for example, bone cancer, pancreatic cancer, breast cancer, brain cancer, lung cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, and combinations of said cancers. In some embodiments, the cancer is acute lymphoblastoid leukemia.

As used herein, the term "anti-tumor effect" refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor.

As used herein, the term "progression-free survival," or "PFS," refers to the time from the treatment date to the date of disease progression per the revised IWG Response Criteria for Malignant Lymphoma or death from any cause.

As used herein, the term "complementary" refers to the concept of subunit sequence complementarity between two nucleic acids, e.g., two DNA molecules, or two RNA molecules, or a DNA molecule with a cognate RNA molecule. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs for DNA, or A:U and G:C for RNA).

An antisense sequence refers to a DNA sequence which is complementary to the sequence of a DNA molecule encoding a protein. The antisense sequence does not need to be complementary to the coding portion of the coding strand of the DNA molecule only.

As used herein, the term "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

As used herein, the term "encoding" refers to the innate property of specific sequences of nucleotides in a polynucleotide, including a gene, a cDNA, or an mRNA, to serve as templates for the synthesis of other biopolymers having either a defined sequence of nucleotides or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and the non-coding strand, used as the template for transcription of a gene or DNA, can be referred to as encoding the protein or other product of that gene.

As used herein, the term "cytokine," refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include or exclude homeostatic cytokines, chemokines, pro-inflammatory cytokines, effectors, and acute-phase proteins. Homeostatic cytokines, including interleukin (IL) 7 and IL-15, promote immune cell survival and proliferation, and pro-inflammatory cytokines can promote an inflammatory response. Examples of homeostatic cytokines can include or exclude, IL-2, IL-4, IL-5, IL-7, IL-10, IL-12p40, IL-12p70, IL-15, and interferon (IFN) gamma. Examples of pro-inflammatory cytokines can include or exclude, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors can include or exclude, granzyme A, granzyme B, soluble Fas ligand (sFasL), and perforin. In some embodiments, acute phase-proteins can include or exclude C-reactive protein (CRP) and serum amyloid A (SAA). In some embodiments, cytokines of this disclosure can include or exclude: chemokine (C-C motif) ligand (CCL) 1, CCL5, monocyte-specific chemokine 3 (MCP3 or CCL7), monocyte chemoattractant protein 2 (MCP-2 or CCL8), CCL13, IL-1, IL-3, IL-9, IL-11, IL-12, IL-14, IL-17, IL-20, IL-21, granulocyte colony-stimulating factor (G-CSF), leukemia inhibitory factor (LIF), oncostatin M (OSM), CD154, lymphotoxin (LT) beta, 4-1BB ligand (4-1BBL), a proliferation-inducing ligand (APRIL), CD70, CD153, CD178, glucocorticoid-induced TNFR-related ligand (GITRL), tumor necrosis factor superfamily member 14 (TNFSF14), OX40L, TNF- and ApoL-related leukocyte-expressed ligand 1 (TALL-1), or TNF-related apoptosis-inducing ligand (TRAIL).

As used herein, the term "chemokines" refers to a type of cytokine that mediates cell chemotaxis, or directional movement. Examples of chemokines can include or exclude, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

As used herein, the terms "serum level" and "serum concentration" refer to the amount of an analyte in the serum of a subject. Serum levels of a given analyte are measured using any method known in the art. For example, cytokine serum levels are measured using an enzyme-linked immunosorbent assay (ELISA). In one particular embodiment, cytokine serum levels are measured using an EMDmillipore LUMINEX@xMAP® multiplex assay.

As used herein, the term "dosing interval," refers to the amount of time that elapses between multiple doses of a formulation disclosed herein being administered to a subject. Dosing interval can thus be indicated as ranges.

Doses can be presented as a "weight based dose" or as a "body surface area (BSA) based dose." A weight based dose is a dose that is administered to a patient that is calculated based on the weight of the patient, e.g., mg/kg. A BSA based dose is a dose that is administered to a patient that is calculated based on the surface area of the patient, e.g., mg/m2. The two forms of dose measurement can be converted for human dosing by multiplying the weight based dose by 37 or dividing the BSA based dose by 37. For example, a dose of 60 mg/kg to be administered to a human subject is equivalent to a 2220 mg/m2 dose of the same drug to be administered to the same subject.

As used herein, the term "dosing frequency" refers to the frequency of administering doses of a formulation disclosed herein in a given time. Dosing frequency can be indicated as the number of doses per a given time.

As used herein, the term "fragment" as applied to a polynucleotide sequence, refers to a portion of said polynucleotide sequence which consists essentially of less than the entire polynucleotide sequence. In some embodiments, the polynucleotide fragment is at least about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 200, 300, 400, or 500 nucleotides in length, or any number of nucleotides in between any of the aforementioned values.

As used herein, the term "genomic DNA" refers to a DNA strand which has a nucleotide sequence homologous with a gene as it exists in the natural host.

As used herein, the term "homologous" or "identity" refers to the subunit sequence similarity between two polymeric molecules, e.g., between two nucleic acid molecules, e.g., two DNA molecules or two RNA molecules, or between two polypeptide molecules. When the terms "homology" or "identity" are used herein to refer to the nucleic acids and proteins, it should be construed to be applied to homology or identity at both the nucleic acid and the amino acid sequence levels.

As used herein, the following abbreviations for the commonly occurring nucleic acid bases are used: "A" refers to adenosine, "C" refers to cytidine, "G" refers to guanosine, "T" refers to thymidine, and "U" refers to uridine.

As used herein, when describing two polynucleotides (also referred to as "polynucleotide sequence") as "operably linked", a single-stranded or double-stranded nucleic acid moiety comprises the two polynucleotides arranged within the nucleic acid moiety in such a manner that at least one of the two polynucleotides is able to exert a physiological effect by which it is characterized upon the other. In some embodiments, a promoter polynucleotide sequence operably linked to the coding region of a gene promotes transcription of the coding region.

As used herein, when describing an oligonucleotide as "connected" to another moiety, the oligonucleotide is covalently bound to said moiety. The covalent bond is formed using a linker molecule (e.g., sulfo-SMCC (ThermoFisher), where the oligonucleotide is 5' or 3' modified with the appropriate functional group (amino, sulfuryl, carboxyl, aldehyde, etc.—all available from Glen Research Inc.) to bind to the linker. The moiety can likewise be functionalized, or possess an innate functional group (e.g., amino group from a lysine amino acid in a protein) to react to said linker group.

When the nucleic acid encoding the desired protein further comprises a promoter/regulatory sequence, the promoter/regulatory is positioned at the 5' end of the desired protein coding sequence such that it drives expression of the desired protein in a cell.

As used herein, the term "promoter sequence" refers to a nucleic acid sequence which is required for expression of a gene product operably linked to the promoter/regulatory sequence. In some embodiments, this conjoined sequence may be the core promoter sequence. In other embodiments, this conjoined sequence may also comprise an enhancer sequence and other regulatory elements which are required for expression of the gene product. In some embodiments, the promoter/regulatory sequence may be one which expresses the gene product in a tissue specific manner.

As used herein, the term "polynucleotide" or "polynucleotide sequence" refers to a single strand or parallel and anti-parallel strands of a nucleic acid. The polynucleotide may be either a single-stranded or a double-stranded nucleic acid.

As used herein "nucleic acid," refers to any compound and/or substance that comprise a polymer of nucleotides linked via a phosphodiester bond. Exemplary nucleic acids include ribonucleic acids (RNAs), deoxyribonucleic acids (DNAs), threose nucleic acids (TNAs), glycol nucleic acids (GNAs), peptide nucleic acids (PNAs), locked nucleic acids (LNAs) or hybrids thereof. They may also include RNAi-inducing agents, RNAi agents, siRNAs, shRNAs, miRNAs, antisense RNAs, ribozymes, catalytic DNA, tRNA, RNAs that induce triple helix formation, aptamers, vectors, etc.

In some embodiments, modified nucleosides and nucleotides are prepared according to the synthetic methods described in Ogata et al. Journal of Organic Chemistry 74:2585-2588, 2009; Purmal et al. Nucleic Acids Research 22(1): 72-78, 1994; Fukuhara et al. Biochemistry 1(4): 563-568, 1962; and Xu et al. Tetrahedron 48(9): 1729-1740, 1992, each of which are incorporated by reference.

Modified nucleic acids (e.g., staple strands chemically connected or conjugated to a targeting molecule) need not be uniformly modified along the entire length of the molecule. Different nucleotide modifications and/or backbone structures may exist at various positions in the nucleic acid. The nucleotide analogs or other modification(s) may be located at any position(s) of a nucleic acid such that the function of the nucleic acid is not substantially decreased. A modification may also be a 5' or 3' terminal modification. The nucleic acids may contain at a minimum one and at maximum 100% modified nucleotides, or any intervening percentage, including at least 50% modified nucleotides, at least 80% modified nucleotides, or at least 90% modified nucleotides.

In some embodiments, a staple strand is a modified nucleic acid.

The synthetic modified oligonucleotides described herein include modifications to prevent rapid degradation by endo- and exo-nucleases and to avoid or reduce the cell's innate immune or interferon response to the oligonucleotide. Modifications can include or exclude, for example, (a) end modifications, e.g., 5' end modifications (phosphorylation dephosphorylation, conjugation, inverted linkages, etc.), 3' end modifications (conjugation, DNA nucleotides, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, as well as (d) internucleoside linkage modifications, including modification or replacement of the phosphodiester linkages.

As used herein, the term "central polynucleotide strand" refers to a polynucleotide sequence which is about 45 to about 15,000 nucleotides in length, and can form tertiary structures via Watson-Crick basepairing and/or intra-duplex interactions.

As used herein, "staple strands" are short single-stranded oligonucleotides of about 20 to about 40 nucleotides in length, including 20, 21, 22, 23, 24, 25, 26, 27, 28, 29, 30, 31, 32, 33, 34, 35, 36, 37, 38, 39, or 40 nucleotides in length, wherein one end of the staple strand hybridizes with a region of the scaffold strand, and the second end of the staple strand hybridizes with another region of the scaffold strand, thereby "stapling" the two regions of the scaffold strand. Exemplary staple strands include those described herein and in the included Sequence Listing.

As used herein, the term "adaptor protein" or "adaptor receptor" refers to a protein which can form covalent bonds to a specific predetermined small molecule which is covalently connected to an oligonucleotide. In some embodiments, the adaptor protein is selected from SNAP-Tag™, CLIP-Tag™, or HALO-Tag™.

As used herein, the term "engineered T cells" or "engineered CAR T cells" refers to T cells comprising signaling CAR domains and further comprising an "adaptor protein" that enables the attachment of a targeting agent via immobilization to a first oligonucleotide chemically conjugated to a targeting agent and/or targeting molecule. In some embodiments, the targeting agent comprises a DNA origami nano-scaffold ("DNA nanostructure").

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand".

As used herein, the term "portion" of a polynucleotide refers at least at least about twelve sequential nucleotide residues of the polynucleotide. It is understood that a portion of a polynucleotide may include every nucleotide residue of the polynucleotide.

As used herein, the term "recombinant polynucleotide" refers to a polynucleotide having sequences that are not naturally joined together. An amplified or assembled recombinant polynucleotide may be included in a suitable vector, and the vector transform a suitable host cell. In some embodiments, a recombinant polynucleotide may serve a non-coding function (e.g., promoter, origin of replication, spacer, ribosome-binding site, etc.) as well.

As used herein, the term "recombinant polypeptide" refers to a polypeptide which is produced upon expression of a recombinant polynucleotide.

As used herein, the term "polypeptide" refers to a biopolymer consisting essentially of amino acid residues, related naturally occurring structural variants, and synthetic non-naturally occurring analogs thereof linked via peptide bonds, related naturally occurring structural variants, and synthetic non-naturally occurring analogs thereof. A protein or polypeptide must contain at least two amino acids, and no limitation is placed on the maximum number of amino acids that can comprise a protein's or peptide's sequence. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

Conventional notation is used herein to portray polypeptide sequences: the left-hand end of a polypeptide sequence is the amino-terminus; the right-hand end of a polypeptide sequence is the carboxyl-terminus.

As used herein, the term "fluorescent protein domain" refers to a polypeptide, the expression of which can be detected using a known method. In some embodiments, the fluorescent protein domain is GFP.

As used herein, the term "high stringency" refers to when a first oligonucleotide anneals with a second oligonucleotide under conditions whereby only oligonucleotides which are at least about 73%, more preferably, at least about 75%, even more preferably, at least about 80%, even more preferably, at least about 85%, yet more preferably, at least about 90%, and most preferably, at least about 95%, complementary anneal with one another. The stringency of conditions used to anneal two oligonucleotides is a function of, among other factors, ionic strength of the annealing medium, temperature, the incubation period, the length of the oligonucleotides, the G-C content of the oligonucleotides, and the expected degree of non-homology between the two oligonucleotides.

As used herein when referring to polypeptides, the term "protein tag" or "polypeptide tag" refers to any chemical moiety which, when linked by a peptide bond to a protein of interest, may be used to form a covalent bond with the binding site of an adaptor protein. In some embodiments, the polypeptide tag can be selected from a SNAP-Tag™, CLIP-Tag™, or HALO-Tag™ tag. The SNAP-Tag™ is an approximately 20 kDa version of a protein O'-alkylguanine-DNA alkyltransferase which has a single reactive cysteine with a very high affinity for guanines alkylated at the O'-position. The alkyl group, including any immobilization moiety attached to the alkyl group (e.g., an oligonucleotide connected to the guanine via a linker (e.g. sulfo-SMCC) can be transferred covalently from the guanine to the cysteine in the alkyltransferase protein. A CLIP-Tag™ is a modified version of SNAP-Tag™, engineered to react with benzyl-cytosine rather than benzylguanine derivatives. SNAP-Tag™ and CLIP-Tag™ are available from New England Biolabs. The HALO-Tag™ is a 297 residue peptide (73.6 kDa) derived from a haloalkane dehalogenase and reacts with an alpha-halogenated haloalkane substituent to form a covalent bond. The HALO-Tag™ is available from Promega.

As used herein, the term "vector" refers to any plasmid or virus encoding an exogenous nucleic acid. The term should also be construed to include non-plasmid and non-viral compounds which facilitate transfer of nucleic acid into virions or cells, including, for example, polylysine compounds and the like. The vector may be a viral vector which is suitable as a delivery vehicle for delivery of a nucleic acid that encodes a CAR or the vector may be a non-viral vector which is suitable for the same purpose.

Examples of viral and non-viral vectors for delivery of DNA which encodes a CAR to cells and tissues are described in Ma et al. (1997, Proc. Natl. Acad. Sci. U.S.A. 94:12744-12746), herein incorporated by reference. Examples of viral vectors can include or exclude a lentiviral vector, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994), each of which are herein incorporated by reference.

The term "stimulation," as used herein, refers to a primary response induced by binding of a stimulatory molecule with its cognate ligand, wherein the binding mediates a signal transduction event. In some embodiments, when the first oligonucleotide connected to the protein tag is hybridized to a second oligonucleotide, stimulation of the primary T cell begins, thereby mediating a primary response by the T cell, including, but not limited to, activation, initiation of an immune response, proliferation, and the like. The targeting agent can bind to a cognate ligand, resulting in stimulation of the engineered T cell. In some embodiments, the targeting agent comprises a targeting molecule. The targeting molecule can target a stimulatory ligand which can include or exclude an MHC Class I molecule loaded with a peptide, an anti-CD3 antibody, a superagonist anti-CD28 antibody, and a superagonist anti-CD2 antibody.

As used herein, the term "stimulatory ligand," refers to a ligand that when present on an antigen presenting cell (e.g., a cancer cell) can specifically bind with a cognate binding partner on a T cell, thereby mediating a primary response by the T cell, including, but not limited to, activation, initiation of an immune response, proliferation, and the like. Stimulatory ligands can include or exclude, inter alia, an MHC Class I molecule loaded with a peptide, an anti-CD3 antibody, an anti-CD19 antibody, a superagonist anti-CD28 antibody, and a superagonist anti-CD2 antibody. In some embodiments, the stimulatory molecule is the targeting agent.

As used herein, the term "inducing an immune response" refers to the activation of an immune cell. Methods of measuring an immune response include using an assay as described in the Examples.

Certain embodiments of the invention also provide a method of treating a disease or disorder in a subject, comprising administering to the subject a therapeutically effective amount of an engineered T cell or a composition as described herein.

In certain embodiments, the therapeutic agent is a vasoconstrictor. In certain embodiments, the vasoconstrictor is selected from thrombin, prothrombin, rhThrombin, fragments thereof, and combinations thereof. In certain embodiments, the therapeutic agent is thrombin. In some embodiments, the thrombin can be human thrombin, bovine thrombin, or murine thrombin. In some embodiments, the thrombin can be thrombin alpha.

As used herein, the term "aptamer" refers to a nucleic acid sequence that interacts with a ligand under normal physiological conditions.

As used herein, the terms "chimeric antigen receptor" or "CAR" refer to a fusion protein comprising antigen recognition moieties and cell-activation elements. In some embodiments, the CAR comprises an extracellular domain, a transmembrane domain, and an intracellular domain, each of which are polypeptides encoded by a corresponding polynucleotide sequence. In certain embodiments, the CAR is designed to have two, three, four, or more costimulatory domains.

As used herein, the terms "CAR T-cell" or "CAR T-lymphocyte" refer to a T-cell containing or capable of producing a CAR polypeptide, regardless of actual expression level. A cell that is capable of expressing a CAR is a T-cell containing nucleic acid sequences for the expression of the CAR in the cell. As used herein, the term "engineered T cell" refers to a T cell expressing a CAR which comprises an extracellular protein tag and a spacer domain polypeptide.

As used herein, the terms "T-lymphocyte" or T-cell" or "T cell" refer to a hematopoietic cell that normally develops in the thymus. T-lymphocytes or T-cells can include or exclude, natural killer T cells, regulatory T cells, helper T cells, cytotoxic T cells, memory T cells, gamma delta T cells and mucosal invariant T cells. In some embodiments, the T cell is a Jurkat T cell.

As used herein, a "transmembrane sequence" refers to the polypeptide sequence between the extracellular sequence and the intracellular sequence. A portion of the transmembrane sequence exists within the cell membrane. In some embodiments, a transmembrane sequence comprises one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In some embodiments, the transmembrane sequence is associated with one of the other elements used in the engineered CAR. 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In some embodiments, the transmembrane sequence is associated with one of the other polypeptide sequences used in the engineered CAR.

In some embodiments, the transmembrane sequence is derived from a natural polypeptide, or may be artificially designed. Transmembrane sequences derived from a natural polypeptide can be obtained from any membrane-binding or transmembrane protein. In some embodiments, the transmembrane sequence of a T cell receptor α or β chain, a CD3ζ chain, CD28, CD3ε, CD45, CD4, CD5, CD8, CD9, CD16, CD22, CD33, CD37, CD64, CD80, CD86, CD134, CD137, ICOS, CD154, or a GITR can be used. An artificially designed transmembrane sequence is a polypeptide comprising hydrophobic residues including leucine and valine. In some embodiments, a triplet of phenylalanine, tryptophan and valine is found at each end of the synthetic transmembrane sequence. In some embodiments, a short oligopeptide linker or a polypeptide linker, (e.g., a linker having a length of 2 to 10 amino acids) is arranged between the transmembrane sequence and the intracellular sequence. In some embodiments, a linker sequence having a glycine-serine continuous sequence can be used.

In some embodiments, a spacer sequence can be arranged between the extracellular sequence and the transmembrane sequence, or between the intracellular element and the transmembrane element. In some embodiments, a spacer is an oligopeptide or polypeptide that serves to link the transmembrane element with the extracellular element and/or the transmembrane element with the intracellular element. In some embodiments, the spacer element comprises up to 300 amino acids, or 10 to 100 amino acids, or 25 to 50 amino acids. The spacer polypeptide sequence can be a spacer polypeptide domain. In some embodiments, the spacer polypeptide sequence can comprise glycine and serine amino acids in a repeating manner. In some embodiments, the spacer polypeptide sequence is (Gly-Gly-Gly-Gly-Ser)$_n$, where n is an integer selected from 1 to 20 (SEQ ID NO: 3). In some embodiments, n is 4. In some embodiments, the spacer can include or exclude a hinge sequence. In some embodiments, the hinge sequence can be a mammalian CD8 hinge sequence. In some embodiments, the hinge sequence can be a human CD8 hinge sequence having the sequence comprising SEQ ID NO. 4: Thr Thr Thr Pro Ala Pro Arg Pro Pro Thr Pro Ala Pro Thr Ile Ala Ser Gln Pro Leu Ser Leu Arg Pro Glu Ala Cys Arg Pro Ala Ala Gly Gly Ala Val His Thr Arg Gly Leu Asp Phe Ala Cys Asp, or an amino acid sequence that has at least 95% sequence identity or 99% sequence identity to the amino acid sequence of SEQ ID NO. 4.

The chimeric antigen receptor can further comprise a hinge region. The hinge region can be derived from the hinge region of IgG1, IgG2, IgG3, IgG4, IgA, IgD, IgE, IgM, CD28, or CD8 alpha. In one particular embodiment, the hinge region is derived from the hinge region of human CD8 alpha.

The chimeric antigen receptor can also comprise a transmembrane domain. The transmembrane domain can be a transmembrane domain of any transmembrane molecule that is a co-receptor on immune cells or a transmembrane domain of a member of the immunoglobulin superfamily. In certain embodiments, the transmembrane domain is derived from a transmembrane domain of CD28, CD8 alpha, CD4, or CD19. In one particular embodiment, the transmembrane domain comprises a domain derived from a CD28 transmembrane domain.

The chimeric antigen receptor can further comprise one or more costimulatory signaling regions. For example, the costimulatory signaling region can be a signaling region of CD28, OX-40, 41BB, CD27, inducible T cell costimulator (ICOS), CD3 gamma, CD3 delta, CD3 epsilon, CD247, Ig alpha (CD79a), or Fc gamma receptor. In one particular embodiment, the costimulatory signaling region is a CD28 signaling region.

In one embodiment, the chimeric antigen receptor further comprises a CD3 zeta signaling domain.

The terms "serum level" and "serum concentration" are used interchangeably as used herein and refer to the amount of an analyte in the serum of a subject. Serum levels of a given analyte can be measured using any method known in the art. For example, cytokine serum levels are measured using an enzyme-linked immunosorbent assay (ELISA). In one particular embodiment, cytokine serum levels are measured using an EMDmillipore LUMINEX@xMAP® multiplex assay.

A "therapeutically effective amount," "effective dose," "effective amount," or "therapeutically effective dosage" of an engineered T cell, drug or therapeutic agent is any amount of the cell or drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, including in human subjects during clinical trials, in animal model systems predictive of efficacy in humans, or by assaying the activity of the agent in in vitro assays. The term "effective amount", in referring to adoptive cell transfer therapy using the engineered T cells described herein, includes an amount of an engineered T cell described herein that induces an immune response.

The term "lymphocyte" as used herein includes natural killer (NK) cells, T cells, or B cells. In some embodiments, the T-cells can include or exclude: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory TSCM cells, like naive cells, are CD45RO−, CCR7+, CD45RA+, CD62L+(L-selectin), CD27+, CD28+ and IL-7Rα+, but they also express large amounts of CD95, IL-2Rβ, CXCR3, and LFA-1, and show numerous functional attributes distinctive of memory cells); (ii) central memory TCM cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. In some embodiments, the T-cell is a helper T-cell, a cytotoxic T-cell, a memory T-cell, a regulatory T-cell, a natural killer cell, a mucosal associated invariant T-cell, a gamma delta T cell, or a precursor or progenitor cell to the aforementioned. In some embodiments, the lymphocyte cell is a natural killer cell, or a precursor or progenitor cell to the natural killer cell.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, including, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy can include or exclude, T cell therapies. T cell therapy can include adoptive T cell therapy, tumor-infiltrating lymphocyte (TIL) immunotherapy, autologous cell therapy, engineered autologous cell therapy, and allogeneic T cell transplantation. Examples of T cell therapies for administration of T cells are described in U.S. Patent Publication Nos. 2014/0154228 and 2002/0006409, U.S. Pat. No. 5,728,388, and International Publication No. WO 2008/081035, incorporated by reference herein.

The T cells of the immunotherapy described herein can come from any source known in the art. For example, T cells are differentiated in vitro from a hematopoietic stem cell population, or T cells are obtained from a subject. In some embodiments, T cells can be obtained from peripheral blood mononuclear cells, bone marrow, lymph node tissue, cord blood, thymus tissue, tissue from a site of infection, ascites, pleural effusion, spleen tissue, and tumors. In some embodiments, the T cells are derived from one or more T cell lines available in the art. In some embodiments, T cells are obtained from a unit of blood collected from a subject using any number of techniques known to the skilled artisan, including FICOLL™ separation and/or apheresis. Methods of isolating T cells for a T cell therapy are disclosed in U.S. Patent Publication No. 2013/0287748, which is herein incorporated by reference.

The term "adoptive cell transfer," as used herein, refers to a process by which a patient's own T cells are collected and subsequently genetically altered to recognize and target one or more antigens expressed on the cell surface of one or more specific tumor cells or malignancies. T cells are engineered to express, for example, engineered chimeric antigen receptors (CAR) to express an extracellular adaptor protein with specificity for a particular protein tag which is connected to an oligonucleotide.

A "patient" as used herein includes any human who is afflicted with a cancer (e.g., a lymphoma or a leukemia). The terms "subject" and "patient" are used interchangeably herein.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission.

As described herein, any concentration range, percentage range, ratio range or integer range is to be understood to include the value of any integer within the recited range and, when appropriate, fractions thereof (including one-tenth and one-hundredth of an integer), unless otherwise indicated.

Various aspects of the invention are described in further detail in the following subsections.

Engineered DNA Car
Nucleic Acids

In some embodiments, this disclosure relates to the nucleic acids that encode, at least in part, the individual peptides, polypeptides, proteins, and RNA control devices of this disclosure. In some embodiments, the nucleic acids may be natural, synthetic or a combination thereof. The nucleic acids of the invention may be RNA, mRNA, DNA or cDNA.

In some embodiments, the nucleic acids of the invention include expression vectors, including plasmids, or viral vectors, or linear vectors, or vectors that integrate into chromosomal DNA. Expression vectors can contain a nucleic acid sequence that enables the vector to replicate in one or more selected host cells.

In some embodiments, the nucleic acids of the invention include transposons for engineering CARs. In some embodiments, the transposon is the "Sleeping Beauty" transposon system for engineering CAR as described in Trends Gen. (33), 852-870, (2017), herein incorporated by reference. The Sleeping Beauty transposon system only requires one step of plasmid transfection/electroporation, without no virus infection.

In some embodiments, the promoter which is capable of expressing an engineered CAR in a mammalian T cell is the EF1α promoter. The native EF1α promoter drives expression of the alpha subunit of the elongation factor-1 complex, which is responsible for the enzymatic delivery of aminoacyl tRNAs to the ribosome. The EF1α promoter is effective in driving CAR expression from transgenes cloned into a lentiviral vector. (Milone et al., Mol. Ther. 17(8): 1453-1464 (2009), herein incorporated by reference). In some embodiments, the promoter is the immediate early cytomegalovirus (CMV) promoter sequence. The CMV promoter sequence is a strong constitutive promoter sequence capable of driving high levels of expression of any polynucleotide sequence operatively linked thereto. In some embodiments, the promoter sequence is selected from the simian virus 40 (SV40) early promoter, mouse mammary tumor virus promoter (MMTV), human immunodeficiency virus (HIV) long terminal repeat (LTR) promoter, MoMuLV promoter, phosphoglycerate kinase (PGK) promoter, MND promoter (a synthetic promoter that contains the U3 region of a modified MoMuLV LTR with myeloproliferative sarcoma virus enhancer, (Li et al., J. Neurosci. Methods vol. 189, pp. 56-64 (2010), incorporated by reference), an avian leukemia virus promoter, an Epstein-Barr virus immediate early promoter, a Rous sarcoma virus promoter, human gene promoters (which can include or exclude: the actin promoter, the myosin promoter, the elongation factor-1a promoter, the hemoglobin promoter, and the creatine kinase promoter) and combinations thereof.

In some embodiments, expression vectors have promoter elements, (e.g., enhancers) to regulate the frequency of transcriptional initiation. In some embodiments, the promoter elements are located in the region 30-110 bp upstream of the start site, although a number of promoters have been shown to contain functional elements downstream of the start site as well. The spacing between promoter elements frequently is variable, so that promoter function is preserved when elements are inverted or moved relative to one another. Individual elements of the promoter can function either cooperatively or independently to activate transcription.

In some embodiments, the polynucleotides encoding the engineered CAR include polynucleotide sequences that are substantially equivalent to the polynucleotide sequences described herein. Polynucleotides according to the invention have at least about 80%, 90%, or 95% sequence identity to a polynucleotide sequence described herein. The invention also provides the complement of the polynucleotides including a nucleotide sequence that has at least about 80%, 90%, or 95%, sequence identity to a polynucleotide encoding a polypeptide recited above. The polynucleotide can be DNA (genomic, cDNA, amplified, or synthetic) or RNA.

The polynucleic acids of this disclosure can be linked to another polynucleic acid so as to be expressed under control of a suitable promoter. The polynucleic acid of this disclosure can be also linked to one or a plurality of regulatory elements that cooperate with a promoter or a transcription initiation site to achieve efficient transcription of the nucleic acid. In some embodiments, the one or a plurality of regulatory elements can include or exclude an enhancer sequence, a polyA site, or a terminator sequence. In some embodiments, the one or a plurality of regulatory sequence can include or exclude a P2A sequence for the co-expression of multiple genes in the vector. In some embodiments, the one or a plurality of regulatory sequence can include or exclude the IRES sequence (Internal Ribosome Entry Site). In some embodiments, the one or a plurality of regulatory sequence can include or exclude LTR sequences at the terminus of the vector sequence.

In some embodiments, the polynucleic acid encoding the engineered CAR is inserted into a vector, and the vector is introduced into a cell. In some embodiments, the polynucleic acid encoding the engineered CAR is introduced to a eukaryotic cell by transfection (e.g., Gorman, et al. Proc. Natl. Acad. Sci. 79.22 (1982): 6777-6781, herein incorporated by reference), transduction (e.g., Cepko and Pear (2001) Current Protocols in Molecular Biology unit 9.9; DOI: 10.1002/0471142727.mb0909s36, herein incorporated by reference), calcium phosphate transformation (e.g., Kingston, Chen and Okayama (2001) Current Protocols in Molecular Biology Appendix 1C; DOI: 10.1002/0471142301.nsa01cs01, herein incorporated by reference), cell-penetrating peptides (e.g., Copolovici, Langel, Eriste, and Langel (2014) ACS Nano 2014 8 (3), 1972-1994; DOI: 10.1021/nn4057269, herein incorporated by reference), electroporation (e.g Potter (2001) Current Protocols in Molecular Biology unit 10.15; DOI: 10.1002/0471142735.im1015s03 and Kim et al (2014) Genome 1012-19. doi:10.1101/gr.171322.113, Kim et al. 2014 describe the Amaza Nucleofector, an optimized electroporation system, both of which are herein incorporated by reference), microinjection (e.g., McNeil (2001) Current Protocols in Cell Biology unit 20.1; DOI: 10.1002/0471143030.cb200Is18, herein incorporated by reference), liposome or cell fusion (e.g., Hawley-Nelson and Ciccarone (2001) Current Protocols in Neuroscience Appendix 1F; DOI: 10.1002/0471142301.nsa01fs10, herein incorporated by reference), mechanical manipulation (e.g. Sharon et al. (2013) PNAS 2013 110(6); DOI: 10.1073/pnas.1218705110, herein incorporated by reference). In some embodiments, the engineered CAR polynucleic acid can be transiently expressed episomally, or can be integrated into the genome of the eukaryotic cell using recombination (e.g., Lisby and Rothstein (2015) Cold Spring Harb Perspect Biol. March 2; 7(3). pii: a016535. doi: 10.1101/cshperspect.a016535, herein incorporated by reference), or non-homologous integration (e.g., Deyle and Russell (2009) Curr Opin Mol Ther. 2009 August; 11(4):442-7, herein incorporated by reference).

In some embodiments, the nucleic acid encoding the engineered CAR is integrated into the eukaryotic cell chromosome at a genomic safe harbor site. The genomic safe harbor site can include or exclude CCR5, AAVS1, human ROSA26, or PSIP1 loci. (Sadelain et al., Nature Rev. 12:51-58 (2012); Fadel et al., J. Virol. 88(17):9704-9717 (2014); Ye et al., PNAS 111(26):9591-9596 (2014), all of which are herein incorporated by reference). In some embodiments, the integration of the polynucleic acid encoding the engineered CAR is done using a gene editing system. The gene editing system can include or exclude CRISPR, TALEN, or Zinc-Finger nuclease systems.

In some embodiments, inserting the gene encoding the engineered CAR is done via transduction. Transduction can be done with a virus vector selected from a retrovirus vector (including an oncoretrovirus vector, a lentivirus vector, or a pseudo type vector), an adenovirus vector, an adeno-associated virus (AAV) vector, a simian virus vector, a vaccinia virus vector or a sendai virus vector, an Epstein-Barr virus (EBV) vector, or adeno-associated virus and a HSV vector. In some preferred embodiments, the virus vector lacks the replicating ability so as not to self-replicate in a transfected cell. The vector comprising the gene encoding the engineered CAR can also be referred to as a "recombinant virus."

In some embodiments, when a retrovirus vector is used, the process of this disclosure can be carried out by selecting a suitable packaging cell based on a LTR sequence and a packaging signal sequence possessed by the vector and preparing a retrovirus particle using the packaging cell. The packaging cell can include or exclude: PG13 (ATCC CRL-10686), PA317 (ATCC CRL-9078), GP+E-86 and GP+en-vAm-12 (U.S. Pat. No. 5,278,056, herein incorporated by reference), and Psi-Crip (Proceedings of the National Academy of Sciences of the United States of America, vol. 85, pp. 6460-6464 (1988), herein incorporated by reference). In some embodiments, the retrovirus particle can be prepared using a 293 cell or a T cell having high transfection efficiency.

Viral based systems are used for gene transfer into mammalian cells. A selected gene can be inserted into a vector and packaged in viral particles. In some embodiments, the recombinant virus can then be isolated and delivered to cells of the subject either in vivo or ex vivo. In some embodiments, lentivirus vectors are used to deliver genes into T cells. In some embodiments, adenovirus vectors are used to deliver genes into T cells.

The modified oligonucleotides (RNA and/or DNA) described herein can be synthesized and/or modified by methods well established in the art, including those described in "Current Protocols in Nucleic Acid Chemistry," Beaucage, S. L. et al. (Edrs.), John Wiley & Sons, Inc., New York, N.Y., USA, which is hereby incorporated herein by reference in its entirety. Transcription methods are described further herein in the Examples. In one embodiment, a template for an ssDNA is synthesized using "splint-mediated ligation," which allows for the rapid synthesis of DNA constructs by controlled concatenation of long oligos and/or dsDNA PCR products and without the need to introduce restriction sites at the joining regions. In some embodiments, the foregoing process adds generic untranslated regions (UTRs) to the coding sequences of genes during T7 template generation. In some embodiments, splint mediated ligation adds nuclear localization sequences to an open reading frame, makes dominant-negative constructs with point mutations starting from a wild-type open reading frame. Briefly, single-stranded DNA ("ssDNA") and/or denatured dsDNA components are annealed to splint oligos which bring the desired ends into conjunction, the ends are ligated by a thermostable DNA ligase and the desired constructs amplified by PCR. A synthetic, modified oligonucleotide is then synthesized from the template using an RNA polymerase in vitro. After synthesis of a synthetic, modified oligonucleotide is complete, the DNA template is removed from the transcription reaction prior to use with the methods described herein. In some embodiments of these aspects, the synthetic oligonucleotides are further treated with an alkaline phosphatase.

In some embodiments, as an alternative approach to cysteine modification or sortase-mediated ligation, the non-canonical amino acid 4-azidophenylalanine is introduced into the proteins via amber codon suppression during the cell culturing to enable modification with cyclooctyne-DNA. In some embodiments, the length of the staple strand sequence is modulated to select for accessible ECM-degrading proteins immobilized to the DNA nanostructure.

Large Scale Economic Production of DNA Nanostructures

This disclosure provides for methods of large scale production of DNA nanostructures. One of the most challenging obstacles to transforming DNA nanostructures from mere curiosities into real-world solutions was the cost of synthetic DNA strands and the small production scales of DNA origami structures. In some embodiments, a phage-based biotechnology method enables the economic manufacture of the short DNA staple strands and DNA nanostructures. Bacteriophages are employed to produce single-stranded precursor DNA that contains a plurality of target strand sequences. In some embodiments, the DNA strands and oligonucleotides are prepared by the methods described in Praetorius F, Kick B, Behler K L, Honemann M N, Weuster-Botz D, Dietz H. Biotechnological mass production of DNA origami. Nature. 2017; 552(7683):84-+. doi: 10.1038/nature24650. PubMed PMID: WOS:000417560500047, herein incorporated by reference.

Figure 22:
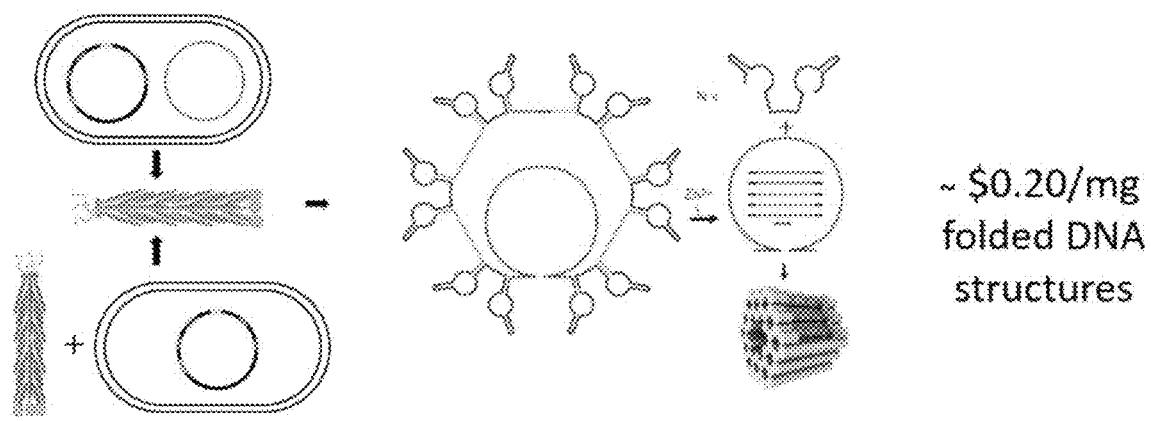
FIG. 22. The schematics show the strategy for economic production of DNA nanostructures.
Figure 23:
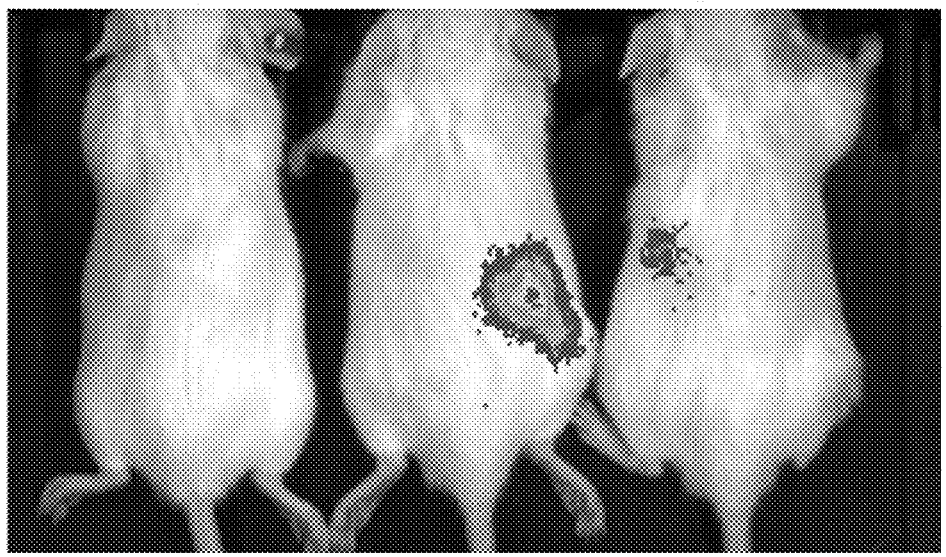
FIG. 23. Tracking adoptive transfer T cells by bioluminescence. T cells expressing luciferase were injected into mice through subcutaneous (Sub-Q, middle) or intravenous (I.V., right). Photos were taken at day 7 after T cell injections.

A piece of self-excising DNAzyme sequence was inserted between each two adjacent target strands, allowing the cleavage products to self-assemble into prescribed DNA origami structures, as shown in FIG. 22. Compared with traditional solid-phase DNA synthesis methods, the phage-based strategy reduced the costs of folded DNA origami structures from ~$200/mg to ~$0.2/mg to enable economic DNA nanotechnology production methods.

Eukaryotic Cells Expressing the Engineered CAR

The cell expressing the engineered CAR of this disclosure is a cell in which a nucleic acid encoding an engineered CAR is introduced and expressed. In one embodiment, the cell is an engineered T cell as shown in FIG. 41. In some embodiments, the engineered CAR comprises a first ssDNA oligonucleotide strand as a first oligonucleotide which can hybridize with a second oligonucleotide which is conjugated to a targeting agent and/or targeting molecule. The first ssDNA oligonucleotide is chemically conjugated to a protein tag. In some embodiments, the protein tag is a benzylguanine. The benzylguanine can react with an adaptor protein which is expressed as part of the engineered CAR on the extracellular domain. The adaptor protein can be selected from SNAP-Tag™, CLIP-Tag™, or HALO-Tag™. In some embodiments, the adaptor protein is linked via a linker to a CD8 transmembrane domain which is linked to a 41-BB costimulatory domain and a CD3-zeta signaling domain. Optionally, the engineered CAR further comprises a GFP, and optionally further comprises an antibiotic resistant gene. FIG. 41A shows one embodiment of the engineered T cell comprising an engineered CAR ("DNA CAR"). FIG. 41B shows optional embodiments where targeting molecules are conjugated to engineered T cells. Targeting molecules can include or exclude: antibodies, single chain antibodies, DNA or RNA aptamers, small molecules, peptide synthetic antibodies (synbody) which target receptors on cell surface. In some embodiments, the targeting molecules are conjugated with a BG-ssDNA strand, e.g. poly A, which hybridizes to DNA-CAR T cells. FIG. 41C depicts the mechanism by which engineered T cells recognize tumor cells and activate. Engineered T cells comprising aptamers as the targeting molecule can recognize tumor antigens on their surface, the engineered T cell is activated by tumor cells and releases cytokines (e.g. interferon γ, IFN-γ), and cytolytic enzymes (e.g. granzyme B).

Figure 18:
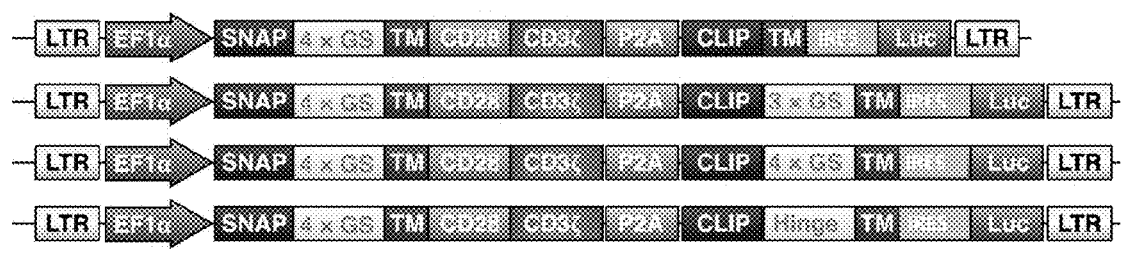
FIG. 18. Design of lentiviral vector encoding two adaptor-CAR. A SNAP-Tag™ with CAR structure following with a CLIP-Tag™, different linkers and a transmembrane Domain™ and luciferase (Luc).

In some embodiments, the engineered T cell expresses two or more adaptor proteins. The two or more adaptor proteins may, in some embodiments, be co-expressed using, for example, the CAR constructs depicted in FIG. 18. Each of the adaptor proteins can be the same or different. In some embodiments, the respective protein tag for each co-expressed adaptor protein can comprise the same or a different "first" ssDNA oligonucleotide to which targeting agents comprising second oligonucleotides of which a portion are complementary to a portion of the same or different "first" ssDNA oligonucleotide sequences.

In some embodiments, a eukaryotic cell of this disclosure binds to a specific antigen via the targeting compound to transmit a signal into the eukaryotic cell, and as a result, the eukaryotic cell is activated. The activation of the eukaryotic cell expressing the engineered CAR is varied depending on the kind of a eukaryotic cell and the intracellular element of the engineered CAR, and can be confirmed based on, for example, release of a cytokine, release of a reporter molecule (e.g., luciferin or luciferase with substrate), improvement of a cell proliferation rate, change in a cell surface molecule, or the like as an index. In some embodiments, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and/or a macrophage.

In some embodiments, eukaryotic cells expressing the engineered CAR connected to a targeting molecule or to a targeting agent comprising a targeting molecule are detected using Jurkat-Lucia™ NFAT cells (Invivogen) which encode a luciferase gene upon activation. Optical detection of luciferase activity indicates activation of the engineered T cell expressing the engineered CAR and comprising the targeting agent when the targeting agent is bound to the target ligand.

In some embodiments, the targeting molecule is associated with the engineered T cell by a means other than oligonucleotide immobilization. The adaptor tag, in some embodiments, is conjugated with a carbohydrate and the targeting agent is conjugated to a leptin. In some embodiments, the adaptor tag is conjugated with a leptin and the targeting agent is conjugated to a carbohydrate. In some embodiments, the adaptor tag/targeting agent interaction is a fluoro-fluoro interaction, where the adaptor tag is conjugated to a first perfluoroalkane molecule and the adaptor tag is conjugated to a second perfluoroalkane molecule. In some embodiments, the adaptor tag is conjugated to a lipid and the targeting agent is conjugated to a cognate lipid recognition binding agent. In some embodiments, the lipid recognition binding agent is a second lipid.

DNA Nanostructures

In some embodiments, this disclosure includes a targeting agent that comprises a DNA nanostructure and a targeting molecule. The DNA nanostructure relies on DNA self-assembly. There are several reasons for the success of DNA in nano-construction. First, Watson-Crick base-pairing between complementary DNA strands is highly predictable and stable. Second, the geometric features of the DNA double-helix is appropriate for nanoscale assembly: the helix is roughly 2 nm in diameter and 3.4 nm pitch per helical repeat. In addition, the development of several user-friendly software interfaces has facilitated the modeling of even the most intricate DNA nanostructures for experimental testing. Third, modern organic chemistry and molecular biology provide a diverse toolbox to readily synthesize, modify, and replicate DNA molecules at a relatively low cost. The biocompatibility of DNA makes it suitable for the construction of multicomponent nanostructures made from heterobiomaterials with designed functions.

Figure 2A:
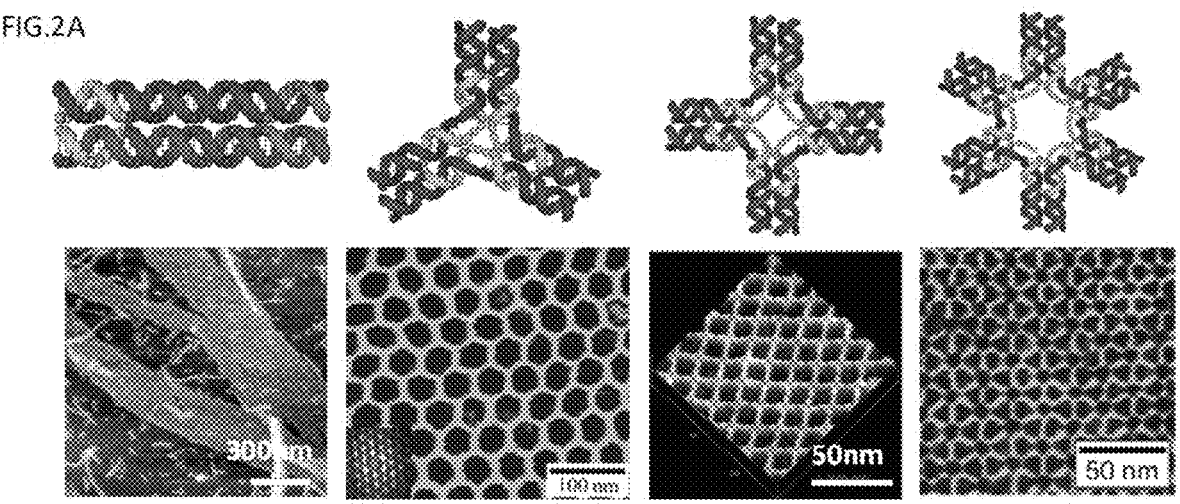
FIG. 2A. Structural DNA nanotechnology principles are used to create DNA nanostructure motifs (top) which are used to create periodic 2D arrays and corresponding AFM images (bottom): double-crossover, 3×4, 4×4, and 6×4 DNA tiles.
Figure 2B:
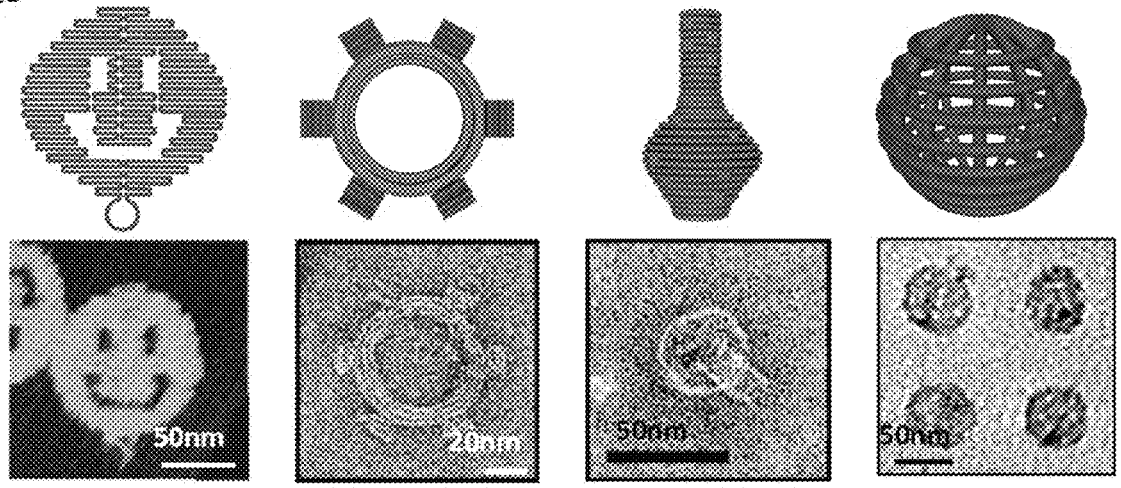
FIG. 2B: Structural DNA nanotechnology principles are used to create DNA origami nanostructures (top, schematic drawings of the structures; bottom, corresponding AFM or TEM images): 2D DNA origami smiley face, 3D DNA origami in the shape of a gear, curved single-layer 3D origami in the shape of a vase, and DNA origami gridiron.

In some embodiments, the DNA nanostructure for use with any of the embodiments described herein is based on the principle of DNA tile assembly (Winfree E, Liu F R, Wenzler L A, Seeman N C. Design and self-assembly of two-dimensional DNA crystals. Nature. 1998; 394(6693):539-44. doi: Doi 10.1038/28998. PubMed PMID: ISI:000075238700036; He Y, Chen Y, Liu H P, Ribbe A E, Mao C D. Self-assembly of hexagonal DNA two-dimensional (2D) arrays. Journal of the American Chemical Society. 2005; 127(35):12202-3. doi: Doi 10.1021/Ja0541938. PubMed PMID: ISI:000231637100027; Yan H, Park S H, Finkelstein G, Reif J H, LaBean T H. DNA-templated self-assembly of protein arrays and highly conductive nanowires. Science. 2003; 301(5641):1882-4. doi: DOI 10.1126/science.1089389. PubMed PMID: ISI:000185536700043; He Y, Tian Y, Ribbe A E, Mao C D. Highly connected two-dimensional crystals of DNA six-point-stars. Journal of the American Chemical Society. 2006; 128(50):15978-9. doi: Doi 10.1021/Ja0665141. PubMed PMID: ISI:000242825600025, each of which is incorporated by reference). DNA tile assembly is a versatile and powerful method wherein small building blocks of DNA tiles, motifs, or even single-stranded DNA-along with the interactions between the building blocks—can be pre-designed using sticky-end cohesion. The recognition between sticky ends are programed with several algorithms that guide DNA building blocks to self-assemble into large 2D arrays with diverse topological and geometric features (FIG. 2A). In some embodiments, the DNA nanostructure is based on the principle of scaffolded DNA-origami (Rothemund P W K. Folding DNA to create nanoscale shapes and patterns. Nature. 2006; 440(7082):297-302. doi: Doi 10.1038/Nature04586. PubMed PMID: WOS:000235997600044; Douglas S M, Dietz H, Liedl T, Hogberg B, Graf F, Shih W M. Self-assembly of DNA into nanoscale three-dimensional shapes. Nature. 2009; 459(7245):414-8. doi: Doi 10.1038/Nature08016. PubMed PMID: ISI:000266243700043; Han D R, Pal S, Nangreave J, Deng Z T, Liu Y, Yan H. DNA Origami with Complex Curvatures in Three-Dimensional Space. Science. 2011; 332(6027):342-6. doi: DOI 10.1126/science.1202998. PubMed PMID: ISI:000289516600042; Han D R, Pal S, Yang Y, Jiang S X, Nangreave J, Liu Y, Yan H. DNA Gridiron Nanostructures Based on Four-Arm Junctions. Science. 2013; 339(6126):1412-5. doi: DOI 10.1126/science.1232252. PubMed PMID: ISI:000316740700037, each of which is incorporated by reference). Scaffolded DNA origami is a technique which enables the folding of a long, single-stranded M13mp18 genomic DNA into a designed target shape by using a plurality of short DNA strand sequences referred to herein as "staple strands" to form a DNA origami nanostructure. In some embodiments, the folding process is programmed resulting in the formation of structures in near-quantitative yields for many designs with unpurified staple strands. The inventors have surprisingly discovered that DNA origami objects are fully addressable due to the unique sequence of long genomic DNA, where each staple strand results in possible modification positions that can be linked to other functional materials with useful biological or electronic properties. In some embodiments, a first staple strand comprises a polynucleotide with a portion of which is complementary to the first oligonucleotide, wherein the first oligonucleotide is connected to the engineered T cell. In some embodiments, the DNA origami further comprises a second staple strand which is a third oligonucleotide which comprises a portion which is complementary to a fourth oligonucleotide where the fourth oligonucleotide is conjugated to a targeting molecule. In some embodiments, the targeting molecule is selected from an aptamer, protein, cytokine, chemokine, lipid, oligonucleotide (which can include or exclude: ssDNA, dsDNA, RNA, nucleic acid-hybrids), protein, synbody, antibody or fragment thereof, or combinations thereof. In some embodiments, the long genomic strand can be RNA. In some embodiments, when the long genomic strand is DNA. In certain embodiments, the DNA origami nanostructure comprising a central polynucleotide strand and a first staple strand which comprises the second oligonucleotide sequence and a plurality of second staple strands which comprises one or a plurality of third distinct oligonucleotide sequences; and one or more targeting molecules connected to one or a plurality of fourth distinct oligonucleotide sequence(s). In certain embodiments, a portion of a third distinct oligonucleotide sequence is complementary to a portion of a distinct fourth oligonucleotide sequence. Therefore, a targeting molecule conjugated to a fourth distinct oligonucleotide sequence can be positioned at the location of the complementary third distinct oligonucleotide sequence. In some embodiments, there are a plurality of distinct targeting molecules each of which is conjugated to one of a plurality of distinct fourth oligonucleotides which comprises a portion, each of which is complementary to a portion of one of a plurality of third distinct oligonucleotides.

In certain embodiments, this disclosure includes a DNA-based nanoscale scaffold to augment T cells with additional functions for targeting solid tumors. These functions can include or exclude: 1) rapid assembly of one or more non-genetically encodable targeting molecules; 2) incorporation of multiple types of molecules, including targeting ligands and enzymes for matrix degradation; 3) precise control over stoichiometry and nanoscale presentation of said targeting molecules; and 4) dramatically reduced time for production of engineered T cells by bypassing the requirement for genetic engineering of novel CAR constructs.

This disclosure provides for methods of using DNA nanostructures as platforms to organize modular functional molecules to demonstrate the enablement of using engineered T cells to kill cancer cells and to activate engineered T cells in the presence of a cancer cell.

In some embodiments, the DNA nanostructure has a shape selected from a semi-flat or flat sheet which may be in the form of a square or rectangle, a tube, a sphere, a pyramid, a box, a rectangle, and a round flat disc. In some embodiments, the DNA origami nanostructures are selected from the structures shown in FIG. 2, 5, 13, 14, or 16. The DNA nanostructure can be designed using algorithms to generate appropriate sequences for customized DNA structures to minimize unwanted interactions between DNA strands and help achieve a high folding yield of designed structures. Design parameters including the size, shape, and helical directions of DNA nanostructures can be optimized to improve targeting molecule loading efficiency of DNA nanostructures. The assembly of such DNA structures is achieved through thermal annealing processes and the obtained structures are purified with dialysis spin columns, gel electrophoresis methods, or size-exclusion chromatography methods. Atomic force microscopy (AFM) confirms the correct formation of the designed DNA nanostructure. In some embodiments, the DNA or RNA nanostructure can include or exclude those in U.S. Pat. Nos. 8,440,811; 8,552,167; PCT App. No. PCT/US18/48973, PCT/US18/48976, U.S. application Ser. No. 16/208,103, and PCT App. No. PCT/US19/13118, all of which are herein incorporated by reference.

Figure 10:
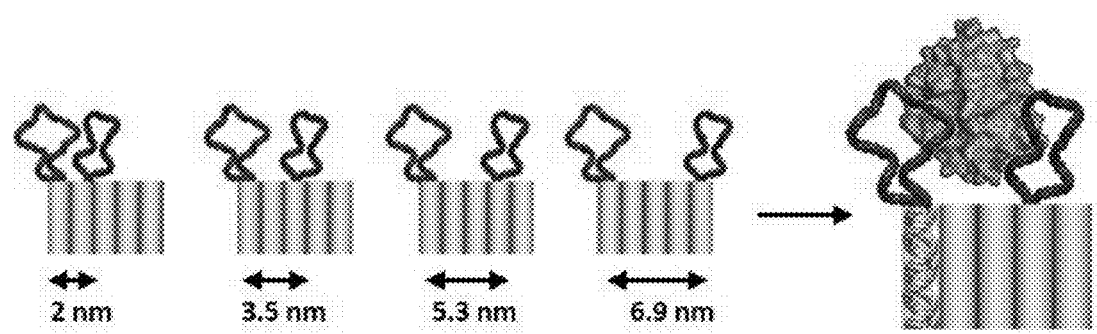
FIG. 10. The schematics show the design of bivalent aptamer of thrombin. Two different aptamers are organized together by a DNA scaffold linker with optimized distances.

In some embodiments, the DNA nanostructures comprise a plurality of unique staple strands where each unique staple strand can serve as an addressable surface location to organize modular functional targeting molecules, including MMP proteins, T cell recruiting chemokines, or T cell proliferation cytokines. As shown in FIG. 5A, different targeting molecules are attached to the DNA nanostructure with a specific DNA sequence ("second oligonucleotide") that is comprises a portion which is complementary to a portion of the sequence of staple strand sequence protruding from a DNA nanostructure ("first oligonucleotide"), whereby all the geometric parameters are precisely designed and have an addressable surface. In some embodiments, the staple strand sequences are oriented based on the conformations of the DNA nanostructure. The resulting construct enables the configuration of targeting molecules, including the distance between said molecules, their multivalency, and their relative geometry. As shown in FIG. 10, rows of different staple strands can be created to be at a precise distance apart to achieve optimal binding distance to increase the avidity of the targeting molecules to their cognate antigen.

In some embodiments, the DNA nanostructures are comprised of phosphorothioate backbones or locked nucleic acids to prevent DNA degradation by nucleases. In other embodiments, the DNA nanostructures can comprise an electrostatic coating (e.g. oligolysine-PEG conjugate), to simultaneously stabilize DNA nanostructures to low-magnesium conditions (including those encountered in the bloodstream) and help reduce degradation by endonucleases.

Design and Optimization of Adaptor Proteins for Engineered T Cells

In some embodiments, the viral vector encoding the engineered CAR comprises a plurality of orthogonal adaptor protein sequences to conjugate addition DNA strand on engineered T cell surfaces. In some embodiments, the orthogonal adaptor protein is CLIP-Tag™, which is orthogonal to SNAP-Tag™, or HALO-Tag™ which is orthogonal to both CLIP-Tag™ and SNAP-Tag™. CLIP-Tag™ is engineered from the SNAP-Tag™ protein to accept $O^2$-benzylcytosine derivatives as substrates, instead of $O^6$-benzylguanine (for SNAP-Tag™).

In some embodiments, the viral vector encoding the engineered CAR comprises a SNAP-Tag™ tag for DNA conjugation connected to a CAR structure comprising a CD8 transmembrane domain, a 41BB co-stimulatory domain, a CD3ζ signaling domain, and a CLIP-Tag™ adaptor protein as a second adaptor protein for different DNA strand conjugation, and optionally a luciferase gene for reporting the engineered CAR incorporation, as shown in FIG. 7. The orthogonal adaptor protein (e.g., CLIP-Tag™) expresses on the surface of T cells, exposing a SNAP-Tag™ adaptor protein that is used to conjugate DNA modified with an $O^6$-benzylguanine moiety and CLIP-Tag™ adaptor protein that is used to conjugate DNA modified with an $O^2$-benzylcytosine moiety.

Design and Optimization of Engineered CAR for Engineered T Cell Immunotherapy

In some embodiments, the adaptor protein is the SNAP-Tag™ protein, a protein derived from the 20 kDa DNA repair protein $O^6$-alkylguanine-DNA alkyltransferase (AGT), and which can be labeled using $O^6$-benzylguanine derivatives. SNAP-Tag™ tags are covalently labeled with $O^6$-benzylguanine (BG) derivatives comprising a chemical probe by undergoing an irreversible reaction in which the functionalized benzyl group of the BG derivative is transferred to an active site cysteine to form a covalently modified protein. Thus, by using BG-connected DNA strands as a first oligonucleotide presents a construct which can be easily functionalized by hybridizing a second oligonucleotide connected to a targeting molecule where a portion of the second oligonucleotide sequence is complementary to a portion of the first oligonucleotide sequence. The second oligonucleotide is connected to the targeting molecule using a cross-functional linker (e.g., sulfo-SMCC), which links a thio-modified oligonucleotide to an amine (e.g., lysine) on the targeting molecule. In some embodiments, the engineered CAR comprises a SNAP-Tag™ protein which is expressed on the T cell surface to attach DNA nanostructures comprising multiple ligands.

In some embodiments, the cross-functional linker is selected from: SIA, SBAP, SIAB, Sulfo-SIAB, AMAS, BMPS, GMBS, Sulfo-GMBS, MBS, Sulfo-MBS, SMCC, Sulfo-SMCC, EMCS, Sulfo-EMCS, SMPB, Sulfo-SMPB, SMPH, LC-SMCC, Sulfo-KMUS, SPDP, LC-SPDP, Sulfo-LC-SPDP, SMPT, PEG4-SPDP, PEG12-SPDP, DCC, EDC, NHS, Sulfo-NHS, BMPH, EMCH, MPBH, KMUH, PDPH, ANB-NOS, Sulfo-SANPAH, SDA, Sulfo-SDA, LC-SDA, Sulfo-LC-SDA, SDAD, Sulfo-SDAD, NHS-Azide, NHS-PEG4-Azide, and NHS-Phosphine (all of which are commercially available from ThermoFisher). In some embodiments, the cross-functional linker can be selected from Alkyne-PEG5-acid, Allyl(4-methoxyphenyl)dimethylsilane, 4-Aminobutyraldehyde diethyl acetal, (E)-N-(2-Aminoethyl)-4-{2-[4-(3-azidopropoxy)phenyl]diazenyl}benzamide hydrochloride, N-(2-Aminoethyl)maleimide trifluoroacetate salt, Amino-PEG4-alkyne, Benzyl N-(3-hydroxypropyl)carbamate, 4-(Boc-amino)butyl bromide, 2-[2-(Boc-amino)ethoxy]ethoxyacetic acid (dicyclohexylammonium) salt, 2-(Boc-amino)ethyl bromide, 6-(Boc-amino)hexyl bromide, 3-(Boc-amino)propyl bromide, N-(4-Bromobutyl)phthalimide, 4-Bromobutyryl chloride, N-(2-Bromoethyl)phthalimide, 3-(Bromomethyl)benzoic acid N-succinimidylester, 4-(Bromomethyl)phenyl isothiocyanate, N-(3-Bromopropyl)phthalimide, tert-Butyl 2-(4-{[4-(3-azidopropoxy)phenyl]azo}benzamido)ethylcarbamate, 2-[2-(tert-Butyldimethylsilyloxy)ethoxy]ethanamine, tert-Butyl 4-hydroxybutyrate, N-(2-Hydroxyethyl)maleimide, and 2-Maleimidoethyl mesylate (all of which are commercially available from Sigma Aldrich).

In some embodiments, the adaptor protein (e.g., SNAP-Tag™ protein) is used to chemically conjugate an oligonucleotide (e.g., ssDNA) to an engineered CAR structure comprising a CD8 transmembrane domain, a 41BB co-stimulatory domain, a CD3ζ signaling domain and a luciferase gene, incorporated into a viral vector. In some embodiments, the CAR can have the sequences shown in FIGS. 7 and 18. In some embodiments, the co-stimulatory domain can include or exclude CD28, OX40, and 4-1BB. The adaptor protein is expressed on the surface of the engineered T cells, to expose the adaptor protein to be used to connect ssDNA modified with an $O^6$-benzylguanine moiety. In some embodiments, the engineered CAR can include the puromycin resistance gene to allow for simple selection of effectively transduced cells by addition of puromycin. In some embodiments, the viral vector is a lentiviral vector. A control lentiviral vector encodes only a SNAP-Tag™ protein and a CD8 transmembrane domain. In some embodiments, the lentivirus vector also includes a luciferase gene ("Luc") to allow for facile T cell tracking in vivo. In some embodiments, the lentivirus vector can include a leader sequence "L" between the promoter sequence and the protein tag sequence to provide for separation between the two functional domains.

Screening Targeting Ligands for Targeting Solid Tumor Markers—Synbodies and Aptamers One of the key obstacles for CAR T cell therapy to treating solid tumors is the identification of suitable neoantigens or TAAs ("tumor-associated antigens") to serve as targets. The biological heterogeneity of solid tumor malignancies does not lend itself to a "one antigen fits all" approach. This difficulty is compounded by the frequent expression of putative target antigens on normal tissues that leads to on-target, off-tumor toxicity. Despite these limitations, acceptable antigens including CD133, EGFR variant III (EGFRIII), GD2, mucin 1 (MUC-1), mucin 16 (MUC-16), carcinoembryonic antigen, mesothelin (MSLN), and prostate-specific membrane antigen (PSMA) have been characterized and are in various stages of clinical development. However, aside from identification of a suitable TAA, trafficking administered T cells to the tumor is another key challenge to effective therapy.

Figure 9:
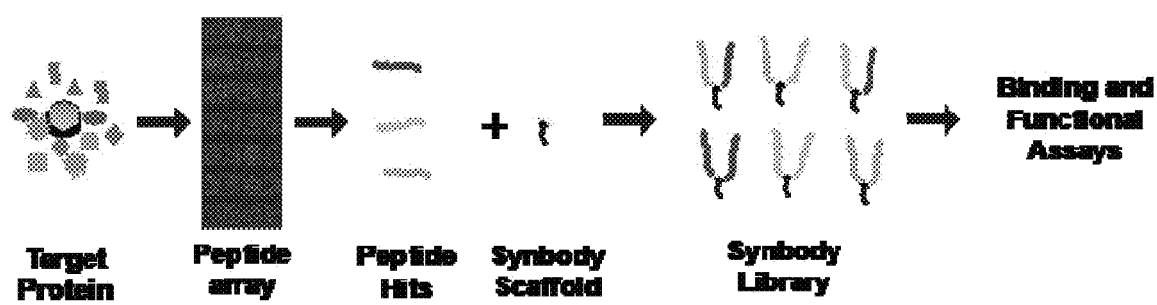
FIG. 9. Workflow to design appropriate synbodies for a target protein. The target protein is screened against a peptide array to identify low-affinity peptide hits. The hits are conjugated to a bifunctional synbody scaffold in pairwise combination to produce a library of synbodies.

In some embodiments, the targeting molecule is selected from monoclonal antibodies (mAb), single-chain variable fragments (scFv), and Synbodies. Synbodies are peptide affinity ligands. Synbodies are small (~6-8 kDa), bivalent peptides that bind their target with antibody-like affinity. Once the composition of a synbody is discovered, large (gram-scale) production is feasible. The small molecular weight of the synbody means that 10 mg of synbody contains the same molar equivalent of targeting molecules as ~200 mg of mAb (which has a molecular weight of about 200 kDa to about 600 kDa). In some embodiments, the selected synbodies used as targeting molecules are obtained from a screening assay. Synbody screening proceeds in a process by which the target protein is screened against an arrayed library of peptides (125,000 17aa peptides on 0.5 cm^2 chip) to identify low affinity binders for the target, as shown in FIG. 9). Pairs of low affinity binding peptides are then conjugated to a bivalent synbody scaffold to produce a library of synbodies that are screened for target binding. This system is based on the observation of near cooperative binding that is possible when ligands that bind separate sites on the target protein are linked in the proper orientation. Synbodies are designed with a C-terminal functional group that enables easy modification with affinity tags, fluorescent dyes, or peptides. The separation of the bivalent binding portion of the synbody from the C-terminal conjugation site enables the modification of the synbody while maintaining binding affinity for the target. The screening assay is capable of running multiple development programs in parallel.

DNA nanostructures offer a fully addressable 3D platform to accommodate controlled spatial arrangements of target molecules including protein-bound functional nucleic acids on different regions of the DNA nanostructure.

In some embodiments, the targeting molecule is an aptamer. Aptamers are single-stranded oligonucleotide molecules that mimic antibodies. They are generated from a DNA or RNA library, through an iterative in vitro selection and amplification process known as systemic evolution of ligands by exponential enrichment (SELEX). Unlike conventional nucleic acids, which carry genetic information, aptamers possess intricate tertiary structures and their intramolecular folding enables them to recognize and bind their targets with high affinity and specificity. Aptamers possess several essential advantages in their suitability for clinical application and industrialization. First, aptamers are more economical to produce in large quantities than the equivalent antibodies. Aptamers are made through chemical synthesis, a well-established automated solid-phase method with little to no variation, while antibody synthesis involves different colonies with a high amount of batch-to-batch variation. Second, aptamers are much smaller than protein-based antibodies, allowing them to diffuse through layers of cells in tissues and bind to smaller targets that antibodies cannot reach. Third, aptamers, unlike antibodies, can recover from extreme pH levels and temperatures, because aptamers are self-folded single-stranded DNA (ssDNA) or single-stranded RNA (ssRNA) that lack hydrophobic proteins domains. Fourth, antibodies are typically recognized by the immune system as foreign and often stimulates an undesired immune response, whereas aptamers possess much lower immunogenicity than antibodies and are less likely to provoke negative immune responses. Finally, chemical modifications are easily introduced to aptamers to customize tailored properties in a deterministic way.

In some embodiments, aptamers are incorporated into DNA nanostructures by the methods described herein. Aptamers can comprise a DNA or RNA strand comprising a sequence with a portion of which is complementary to one or a plurality of strand sequences on the DNA nanostructure, or is complementary to the first oligonucleotide connected to the adaptor protein of the engineered CAR. When adaptors are hybridized to DNA nanostructures, they are spatially positioned on the DNA nanostructure such that the distance and angle is identified based on the addressability of the scaffold DNA nanostructures. The inventors have previously discovered that multivalent aptamers can by connected using two aptamers against thrombin into a DNA nanostructure with various precise distances ranging from 2 to 7 nm. It was found that the optimized binding affinity was obtained at an inter-aptamer distance of 5.3 nm, with the final assembles showing a 50-fold improvement in affinity over the monovalent molecules, as shown in FIG. 10.

In some embodiments, the aptamer is an aptamer listed in Table 1.

TABLE 1

Selected aptamers of this disclosure.

| Aptamer Name | Sequence (5'→3') | SEQ ID NO. |
|---|---|---|
| hPD-L1-apt1 | ACG GGC CAC ATC AAC TCA TTG ATA GAC AAT GCG TCC ACT GCC CGT | SEQ ID NO: 5 |
| hMUC1-apt1 | GCA GTT GAT CCT TTG GAT ACC CTG G | SEQ ID NO: 6 |
| hMUC1-apt2 | GCAGT TGATC CTTTG GATAC CTGG TTT TTA AAA | SEQ ID NO: 7 |

TABLE 1-continued

Selected aptamers of this disclosure.

| Aptamer Name | Sequence (5'→3') | SEQ ID NO. |
|---|---|---|
| hMUC1-apt3 | GGGAGACAAGAATAAAC GCT CAA GCA GTT GAT CCT TTG GAT ACCCTGGTTC GAC AGG AGG CTC ACA ACA GGC | SEQ ID NO: 8 |
| hEGFR-apt1 | TACCAGTGCGATGCTCAGTGCCGTTTCT TCT CTT TCG CTT TTT TTGCTTTTGAGC ATGCTGACGCATTCG GTT GAC | SEQ ID NO: 9 |
| Scg8 | ATC TAA CTG CTG CGC CGC CGG GAA AAT ACT GTA CGG TTA GA | SEQ ID NO: 10 |
| Control Aptamer | AAAAAAAAAAAAAAACGTGCAGTACGCCA ACC TTT CTC ATG CGCTGCCCCTCTTA | SEQ ID NO: 11 |

The synbody development consists of 3 major steps: (i) peptide selection and synthesis, (ii) synbody library construction, (iii) screening and validation for synbody selection.

The synbody development process begins with purchasing the target protein (~250 μg) from commercial vendors. Upon receipt, the protein is aliquoted and stored according to specifications. The target protein is then labeled with AlexaFluor 555 and screened against an in situ synthesized peptide microarray composed of 125,000 unique 17-mer peptides of random amino acid sequence that contain both D- and L-amino acids. Peptide arrays are synthesized in the Center for Innovations in Medicine. The array format is such that the 125,000 peptide library is synthesized 24 times on a slide of standard dimensions in individually addressable arrays, as shown in FIG. 12A. This enables replicate assays to be included as well as more complex assays, as illustrated in FIG. 12B, in which TNFα was fluorescently labeled and screened on replicate arrays (x-axis). In the same assay, TNFα was complexed with TNF-receptor 1 (TNFR1) and screened on replicate arrays (y-axis). In this way, peptides that bind to TNFα in the TNFR1 binding site is blocked and their signals are lower in the TNFα/TNFR1 condition (FIG. 12C). While this assay format enables identification of peptides for use as synbody inhibitors, identification of receptor inhibiting peptides is not necessary for the proteins in Table 2, which can used for tumor targeting. Each peptide array has a number of control peptides included that provide measures of array-to-array reproducibility that are independent of the target protein. In some embodiments, the protein target is screened on peptide arrays to identify the proper peptide pairs.

In some embodiments, synbodies are constructed through the use of a conjugation rather than synthetic approach. Thiol conjugation provides a simple method to produce libraries of synbodies in a short period of time. Each binding peptide is synthesized with a terminal cysteine amino acid that is conjugated to a bi-functional peptide scaffold through a linker (e.g., sulfo-SMCC, or any of the cross-functional linkers described herein), as shown in FIG. 12A. Addition of two binding peptides produces three synbodies in a single reaction in a 1:2:1 ratio (A-A:A-B:B-B). For example, the pairwise combination of 10 peptides (as shown in FIG. 12B) produces all 55 possible synbodies from 45 reactions. For 15 peptides, a synbody library of X hetero-bivalent synbodies and Y homo-bivalent synbodies are formed. The products of each synbody reaction are purified by HPLC or solution-based extraction methods, analyzed by mass spectrometry to confirm molecular weight, and lyophilized prior to use.

In some embodiments, to identify synbodies that bind the target protein, an SPR screen is used against the immobilized target proteins. In one embodiment, the SPR system is the Biacore T200 SPR system.

In some embodiments, the targeting molecules are aptamers targeting the solid tumor biomarkers listed in Table 3. For example, CD133 is a cancer stem cell biomarker that is overexpressed in most solid tumors. Epidermal growth factor receptor (EGFR) is also an antigen over-expressed on the surface of breast, colon, lung and a range of other epithelial cancer cells and an important cancer biomarker. Both of these biomarkers are ideal antigens for clinical applications in cancer diagnosis, prognosis, imaging, and therapy. In some embodiments, high affinity bivalent aptamers against CD133 and EGFR with ssDNA library is identified through SELEX processes. The extracellular CD133 and IgV-like N domain of CD133 has a comparable size to that of thrombin. In some embodiments, the production process of recombinant proteins involves immobilized on magnetic beads either through covalent binding or His-tag trapping. In some embodiments, increasing selection pressure is applied to the selection process to enrich high affinity aptamers. The sequencing result is analyzed to identify high affinity aptamers from their percentage in the sequencing pool.

In some embodiments, the synbody screening process can include first filtering peptides based upon signal intensity for the target protein as well as intensity for other targets. This enables selection of peptides with the highest target selectivity that translates into production of high-affinity, high-selectivity synbodies. The synbody conjugation chemistry is straightforward but reaction yields are sometimes low if there is a problem with the solubility of one or more peptides. In some embodiments, small amount of organic polar aprotic solvent, including acetonitrile, is added to the reaction mixture to increase reaction yield. The synbody can be used with a variety of immobilization methods including the use of amine and carboxy conjugation to the SPR chip to immobilize the protein through different amino acids. In one embodiment, when the target protein has been expressed with an affinity tag, the use of an anti-tag antibody, including anti-His6 if the protein is His tagged is used. By changing the orientation of the protein on the surface, the synbody library can be screened against the full surface of the target protein.

In some embodiments, synbodies are synthesized with a single azide handle in the molecular structure to allow for conjugation to alkynyl-modified DNA via strain-promoted azide-alkyne cycloaddition (more commonly known as "copper-free click") with appropriately functionalized oligonucleotides as shown in FIG. 21A. In some embodiments, the alkynyl modified oligonucleotides are synthesized by incorporating into the oligonucleotide serinol alkynyl phosphoramidite or DibenzoCyclooctyl (DBCO) phosphoramidite (Glen Research, Inc.). DNA-synbody conjugate are purified by reverse phase HPLC and characterized by MALDI-TOF MS and polyacrylamide gel electrophoresis, and gel shift mobility assays are used to confirm the ability of the DNA handle (oligonucleotide) to bind its complement. In some embodiments, fluorescent dyes are incorporated into the strands to further confirm successful attachment to the DNA origami scaffold. In some embodiments, peptide-DNA conjugates are synthesized using a copper-free click method, as shown in FIG. 21B. In some embodiments, each individual peptide of a successful synbody pair is conjugated to a unique oligonucleotide sequence, the oligonucleotides sequences are complexed together in a direct hybridization or in a DNA nanostructure comprising staple strands, as shown in FIG. 21C.

Pharmaceutical Compositions

Pharmaceutical compositions of this disclosure may comprise an engineered CAR expressing cells connected to the targeting agent and/or targeting molecule, as described herein, in combination with one or more pharmaceutically or physiologically acceptable carriers, diluents or excipients. Such compositions may comprise buffers including neutral buffered saline, phosphate buffered saline and the like; carbohydrates including glucose, mannose, sucrose or dextrans, mannitol; proteins; polypeptides or amino acids including glycine; antioxidants; chelating agents including EDTA or glutathione; adjuvants (e.g., aluminum hydroxide); and preservatives. Compositions of this disclosure are in one aspect formulated for intravenous administration.

Pharmaceutical compositions of this disclosure may be administered in a manner appropriate to the disease to be treated (or prevented). The quantity and frequency of administration is determined by such factors as the condition of the patient, and the type and severity of the patient's disease, although appropriate dosages may be determined by clinical trials.

Suitable pharmaceutically acceptable excipients can include or exclude phosphate buffered saline (e.g. 0.01 M phosphate, 0.138 M NaCl, 0.0027 M KCl, pH 7.4), an aqueous solution containing a mineral acid salt including a hydrochloride, a hydrobromide, a phosphate, or a sulfate, saline, Ringer's solution, a solution of glycol or ethanol, and a salt of an organic acid including an acetate, a propionate, a malonate or a benzoate. In some embodiments, an adjuvant including a wetting agent or an emulsifier, and a pH buffering agent can also be used. In some embodiments, the pharmaceutically acceptable excipients described in Remington's Pharmaceutical Sciences (Mack Pub. Co., N.J. 1991) (herein incorporated herein by reference) is appropriately used. The composition of this disclosure is formulated into a known form suitable for parenteral administration, for example, injection or infusion. In some embodiments, the composition of this disclosure may comprise formulation additives including a suspending agent, a preservative, a stabilizer and/or a dispersant, and a preservation agent for extending a validity term during storage.

Methods of Using Engineered T Cells

In some embodiments, a eukaryotic cell expressing the engineered CAR and further comprising the targeting agent and/or targeting molecule is used as a therapeutic agent to treat a disease. The therapeutic agent comprises the eukaryotic cell expressing the expressing the engineered CAR and further comprising the targeting agent and/or targeting molecule as an active ingredient, and may further comprise a suitable excipient. Examples of the excipient include pharmaceutically acceptable excipients for the composition. The disease against which the eukaryotic cell expressing the expressing the engineered CAR and further comprising the targeting agent and/or targeting molecule is administered is not particularly limited as long as the disease shows sensitivity to the eukaryotic cell. Examples of diseases of the invention include a cancer (blood cancer (leukemia), solid tumor etc.).

In some embodiments, the eukaryotic cells with expressing the engineered CAR and further comprising the targeting agent and/or targeting molecule are characterized prior to administration to the subject. In some embodiments, the eukaryotic cells with expressing the engineered CAR and further comprising the targeting agent and/or targeting molecule are tested to confirm the engineered CAR expression.

In some embodiments, the eukaryotic cells with expressing the engineered CAR and further comprising the targeting agent and/or targeting molecule are exposed to a level of ligand(s) that results in a desired level of CAR polypeptide expression in the eukaryotic cell. In some embodiments, this desired level of CAR polypeptide produces eukaryotic cells with a desired level of anti-target cell activity, and/or a desired level of proliferative activity when placed in a subject.

In some embodiments, the engineered CAR is used with a T-lymphocyte that has aggressive anti-tumor properties, including those described in Pegram et al, CD28z CARs and armored CARs, 2014, Cancer J. 20(2):127-133, herein incorporated by reference. In some embodiments, the T-lymphocyte is cultured in a composition comprising high levels of cytokines. The cytokines can include or exclude: IL-2, GMCSF, IL-6, IL-7, IL-4, and IL-15. In some embodiments, the T-lymphocyte is cultured in a composition comprising high levels of chemokine receptors. The chemokine receptors can include or exclude: CCR1, CCR2, CCR4, CCR5, CCR6, CCR7, CCR8, CCR9, CCR10. The chemokine receptors expression level in T cells are monitored by mRNA expression. In some embodiments, chemokine levels are upregulated by culturing the T cells in growth media comprising a cytokine as described herein.

A composition comprising the eukaryotic cells of this disclosure as an active ingredient is administered for treatment of, for example, a cancer (blood cancer (leukemia), solid tumor etc.). The precise amount of the compositions of this disclosure to be administered can be determined by a physician with consideration of individual differences in age, weight, tumor size, extent of infection or metastasis, and condition of the patient (subject). In some embodiments, a pharmaceutical composition comprising the eukaryotic cells described herein may be administered at a dosage of $10^4$ to $10^9$ cells/kg body weight, in some instances $10^5$ to $10^6$ cells/kg body weight, including all integer values within those ranges. In some embodiments, a eukaryotic cell composition may also be administered multiple times at these dosages. In some embodiments, eukaryotic cells are administered by using infusion techniques.

In some embodiments, the targeting molecule specifically binds to an antigen or epitope of interest expressed on the surface of at least one of a damaged cell, a dysplastic cell, an infected cell, an immunogenic cell, an inflamed cell, a malignant cell, a metaplastic cell, a mutant cell, and combinations thereof.

In some aspects, the engineered T cells further comprise at least one exogenous protein that modulates a biological effect of interest in an adjacent cell, tissue, or organ, or an exogenous nucleic acid encoding said protein.

T Cell Therapy

This disclosure provides methods of enhancing the effectiveness of a T cell therapy by adoptive T cell therapy using an engineered T cell comprising an engineered CAR and a targeting agent and/or targeting molecule. In some embodiments, the adoptive T cell therapy can comprise consisting of tumor-infiltrating lymphocyte (TIL) immunotherapy, autologous cell therapy, engineered autologous cell therapy (eACT), allogeneic T cell transplantation, non-T cell transplantation, and any combination thereof. Adoptive T cell therapy broadly includes any method of selecting, enriching in vitro, and administering to a patient autologous or allogeneic T cells that recognize and are capable of binding tumor cells. TIL immunotherapy is a type of adoptive T cell therapy, wherein lymphocytes capable of infiltrating tumor tissue are isolated, enriched in vitro, and administered to a patient. The TIL cells are either autologous or allogeneic. Autologous cell therapy is an adoptive T cell therapy that involves isolating T cells capable of targeting tumor cells from a patient, enriching the T cells in vitro, and administering the T cells back to the same patient. Allogeneic T cell transplantation can include transplant of naturally occurring T cells expanded ex vivo or genetically engineered T cells. Engineered autologous cell therapy, as described in more detail above, is an adoptive T cell therapy wherein a patient's own lymphocytes are isolated, genetically modified to express a tumor targeting molecule, expanded in vitro, and administered back to the patient. Non-T cell transplantation can include autologous or allogeneic therapies with non-T cells including, but not limited to, natural killer (NK) cells.

In one embodiment, the T cell therapy of this disclosure comprises administering an engineered T cell comprising a targeting agent and/or targeting molecule. According to this embodiment, the method can include collecting blood cells from the patient. The isolated blood cells (e.g., T cells) can then be engineered to express an engineered chimeric antigen receptor ("engineered CAR"). In one embodiment, the T cells comprising the engineered CAR are further contacted with a protein tag comprising a first oligonucleotide connected to said protein tag which forms a covalent bond to the adaptor protein on the engineered CAR. The engineered CAR comprising the first oligonucleotide is then contacted with a targeting agent connected to a second oligonucleotide, where a portion of the sequence of the second oligonucleotide is complementary to a portion of the first oligonucleotide and the first and second oligonucleotides form a hybridization duplex. In some embodiments, the targeting agent further comprises a DNA origami nanostructure comprising a plurality of strand sequences. In some embodiments, a first strand sequence comprises a sequence having complementarity to a portion of the first oligonucleotide sequence to form a hybridization duplex. In some embodiments, the first strand sequence comprises a sequence having complementarity to a portion of a first bridging oligonucleotide. In some embodiments, the first oligonucleotide comprises a portion which is complementary to a separate portion of the first bridging oligonucleotide. The first strand, bridging oligonucleotide, and first oligonucleotide can thus form a linked hybridization duplex. In some embodiments, the DNA origami nanostructure can further comprise a second or plurality of distinct strand sequences. The second or plurality of distinct strand sequences can comprise a portion which is complementary to a third oligonucleotide which is connected to a targeting molecule. In some embodiments, the second or plurality of distinct strand sequences can comprise a portion which is complementary to a second bridging oligonucleotide. The third oligonucleotide which is connected to a targeting molecule can comprise a portion which is complementary to a separate portion of the second bridging oligonucleotide. The second or plurality of distinct strand sequences, second bridging oligonucleotide, and third oligonucleotide can form a hybridization duplex.

In one embodiment, the engineered T cells are engineered to express an engineered chimeric antigen receptor. The chimeric antigen receptor can comprise a targeting molecule to a tumor antigen. In some embodiments, the targeting molecule is selected from an antibody or an antigen binding molecule thereof. In some embodiments, the antigen binding molecule is selected from scFv, Fab, Fab', Fv, F(ab')2, and dAb, and any fragments or combinations thereof.

The engineered T cell therapy included in this disclosure involves the transfer of T cells, after manipulation of said T cells into engineered T cells, to a patient. The engineered T cells are administered at a therapeutically effective amount. In some embodiments, the therapeutically effective amount of engineered T cells are at least about $10^4$ cells, at least about $10^5$ cells, at least about $10^6$ cells, at least about $10^7$ cells, at least about $10^8$ cells, at least about $10^9$, or at least about $10^{10}$ cells. In some embodiments, the therapeutically effective amount of the engineered T cells is about $10^4$ cells, about $10^5$ cells, about $10^6$ cells, about $10^7$ cells, or about $10^8$ cells. In one particular embodiment, the therapeutically effective amount of the engineered T cells is about $1\times10^5$ cells/kg, about $2\times10^5$ cells/kg, about $3\times10^5$ cells/kg, about $4\times10^5$ cells/kg, about $5\times10^5$ cells/kg, about $6\times10^5$ cells/kg, about $7\times10^5$ cells/kg, about $8\times10^5$ cells/kg, about $9\times10^5$ cells/kg, about $1\times10^5$ cells/kg, about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^{46}$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^{47}$ cells/kg, or about $9\times10^7$ cells/kg, or between any of the aforementioned T cell amounts. In some embodiments, the therapeutically effective amount of the engineered T cells is about $1\times10^7$ cells.

In some embodiments, a therapeutically effective amount of engineered T cells, is from about $1.0\times10^5$ cells/kg to about $9\times10^{48}$ cells/kg, or any amount between the aforementioned values.

T Cell Therapy Employing Saturated Targeting Molecules

In some embodiments, this disclosure provides for methods of engineered T cell therapy by first presenting a targeting agent and/or targeting molecule to the target cancer cell, where the targeting agent and/or targeting molecule comprises a second oligonucleotide, forming a complex between said targeting agent and/or targeting molecule with its cognate ligand on the target cancer cell, then contacting the second oligonucleotide with a engineered T cell comprising a first oligonucleotide where a portion of the sequence of the first oligonucleotide is complementary to a portion of the sequence of the second oligonucleotide. In certain embodiments, this disclosure relates to a method of killing a cancer cell comprising the steps of contacting a cancer cell with a DNA nanostructure comprising a plurality of staple strands where a first staple strand is unhybridized and a second staple strand is hybridized to a fourth oligonucleotide which is chemically conjugated to a targeting molecule, and said targeting molecule binds to said cancer cell; then contacting the DNA nanostructure with an engineered T cell comprising a first oligonucleotide which is complementary to the first staple strand on the DNA nanostructure to form a hybridization complex between the first oligonucleotide and the first staple strand to bring the engineered T cell in local proximity to the cancer cell and begin a cytolytic mechanism.

The inventors have recognized that the advantages of employing a split-step method for T cell therapy are only possible using the engineered T cells of this disclosure. The advantages of employing a split-step method for T cell therapy include: the ability to saturate the targeted cancer cell with a targeting molecule which may be more economical than presenting engineered T cells to target cancer cells first, and that the targeting molecules which are smaller than T cells can penetrate deeper into the target cancer cell than an engineered T cell complex alone. In some embodiments, the targeting agent and/or targeting molecule which is first presented to the target cancer cell comprises a long oligonucleotide linker (e.g., greater than 100 nt, 150 nt, 200 nt, 250 nt, or 300 nt in length or any length between the foregoing nucleotide lengths) which reduces the steric hindrance for the engineered T cells.

In some embodiments, this disclosure includes a composition comprising the components of the split-step method of T cell therapy as described herein. In some embodiments, this disclosure includes a composition comprising: an engineered T cell comprising a first oligonucleotide, and a DNA nanostructure comprising a targeting molecule and a second oligonucleotide, where the first oligonucleotide comprises a portion of which is complementary to a portion of the sequence of the second oligonucleotide. In some embodiments, the engineered T cell comprising a first oligonucleotide is administered simultaneously or sequentially with the DNA nanostructure comprising a targeting molecule. In some embodiments, when the engineered T cell comprising a first oligonucleotide is administered sequentially with the DNA nanostructure comprising a targeting molecule, the two species are administered within 1 hour, 1 day, 1 week, 2 weeks, 3 weeks, or 4 weeks within each other. In some embodiments, when the engineered T cell comprising a first oligonucleotide is administered sequentially with the DNA nanostructure comprising a targeting molecule, the two species are administered within 1 minute, 5 minutes, 10 minutes, 15 minutes, 20 minutes, 25 minutes, 30 minutes, 35 minutes, 40 minutes. 45 minutes, 50 minutes, 55, minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, or any time between the aforementioned values within each other. In some embodiments, when the engineered T cell comprising a first oligonucleotide is administered sequentially with the DNA nanostructure comprising a targeting molecule, the DNA nanostructure is administered locally to a solid tumor site, and the engineered T cell is administered systemically. In some embodiments, when the engineered T cell comprising a first oligonucleotide is administered sequentially with the DNA nanostructure comprising a targeting molecule the engineered T cell and DNA nanostructure comprising a targeting molecule are administered at or about at the same location in the subject. In some embodiments, the DNA nanostructure comprising a targeting molecule is administered at a dose of about 0.001 mg/kg to about 5 g/kg to the subject, or any dose level between the aforementioned values.

In some embodiments, the targeted cancer cell is any of the cancer cell types described herein.

Cancer Treatment

This disclosure provides for methods treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In some embodiments, the methods induce a complete response. In some embodiments, the methods induce a partial response.

Cancers that may be treated include tumors that are not vascularized, not yet substantially vascularized, or vascularized. The cancer may also include or exclude solid and non-solid tumors. In some embodiments, the cancer is selected from a tumor derived from bone cancer, lung cancer, brain cancer, breast cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the endometrium, carcinoma of the fallopian tubes, carcinoma of the cervix, carcinoma of the vagina, carcinoma of the vulva, Hodgkin's Disease, T-cell rich B cell lymphoma (TCRBCL), Primary mediastinal large B cell lymphoma (PMBCL), non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, primary CNS lymphoma, neoplasm of the central nervous system (CNS), tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In some embodiments, the methods described here are used to treat a tumor, wherein the tumor is a lymphoma or a leukemia. Lymphoma and leukemia are cancers of the blood that specifically affect lymphocytes. The blood cancers which are treated can include or exclude cancers of T lymphocytes (T cells), B lymphocytes (B cells), natural killer cells, and plasma cells. Leukocytes arising from the lymphoid progenitor cells include megakaryocytes, mast cells, basophils, neutrophils, eosinophils, monocytes, and macrophages. Lymphomas and leukemias can affect one or more of these cell types in a patient.

In some embodiments, the methods described herein are used to treat a lymphoma or a leukemia, wherein the lymphoma or leukemia is a B cell malignancy. In some embodiments, the lymphoma or leukemia is selected from B-cell chronic lymphocytic leukemia/small cell lymphoma, B-cell prolymphocytic leukemia, lymphoplasmacytic lymphoma (e.g., Waldenstram macroglobulinemia), splenic marginal zone lymphoma, hairy cell leukemia, plasma cell neoplasms (e.g., plasma cell myeloma (i.e., multiple myeloma), or plasmacytoma), extranodal marginal zone B cell lymphoma (e.g., MALT lymphoma), nodal marginal zone B cell lymphoma, follicular lymphoma (FL), transformed follicular lymphoma (TFL), primary cutaneous follicle center lymphoma, mantle cell lymphoma, diffuse large B cell lymphoma (DLBCL), Epstein-Barr virus-positive DLBCL, lymphomatoid granulomatosis, primary mediastinal (thymic) large B-cell lymphoma (PMBCL), Intravascular large B-cell lymphoma, ALK+ large B-cell lymphoma, plasmablastic lymphoma, primary effusion lymphoma, large B-cell lymphoma arising in HHV8-associated multicentric Castleman's disease, Burkitt lymphoma/leukemia, T-cell prolymphocytic leukemia, T-cell large granular lymphocyte leukemia, aggressive NK cell leukemia, adult T-cell leukemia/lymphoma, extranodal NK/T-cell lymphoma, enteropathy-associated T-cell lymphoma, Hepatosplenic T-cell lymphoma, blastic NK cell lymphoma, Mycosis fungoides/Sezary syndrome, Primary cutaneous anaplastic large cell lymphoma, Lymphomatoid papulosis, Peripheral T-cell lymphoma, Angioimmunoblastic T cell lymphoma, Anaplastic large cell lymphoma, B-lymphoblastic leukemia/lymphoma, B-lymphoblastic leukemia/lymphoma with recurrent genetic abnormalities, T-lymphoblastic leukemia/lymphoma, and Hodgkin lymphoma. In some embodiments, the cancer is refractory to one or more prior treatments, and/or the cancer has relapsed after one or more prior treatments.

In some embodiments, the cancer is selected from follicular lymphoma, transformed follicular lymphoma, diffuse large B cell lymphoma, and primary mediastinal (thymic) large B-cell lymphoma. In some embodiments, the cancer is diffuse large B cell lymphoma.

In some embodiments, this disclosure includes a method of treating a patient having a lymphoma comprising administering to the patient a therapeutically effective amount of engineered T cells which further comprise a targeting agent and/or targeting molecule, and wherein the targeting molecule binds to CD19 and the engineered T cells further comprises a CAR which expresses a CD28 costimulatory domain and a CD3-zeta signaling region.

When used for immunotherapy applications, T-cells are removed from a patient through leukopheresis and T-cells are preferentially sorted and saved. T cells are subjected to lentiviral or retroviral introduction (or other means of nucleic acid introduction) of the transgene that encodes the engineered CAR as described herein. The engineered T cells with the expressed engineered CAR are then contacted with the targeting first oligonucleotide comprising a protein tag, then contacted with a targeting agent connect to a second oligonucleotide which comprises a portion which is complementary to the sequence of the first oligonucleotide. The engineered T cells comprising the targeting agent are then expanded to target therapeutic cell concentrations and infused into the patient, resulting in an autologous treatment with minimal graft to host complications.

Figure 30A:
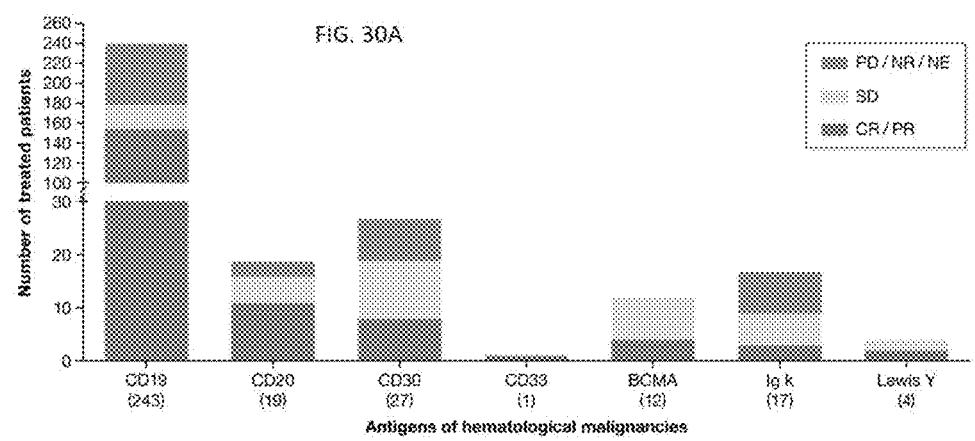
FIGS. 30A-30B. Clinical outcome of published CAR T therapies.
Figure 30B:
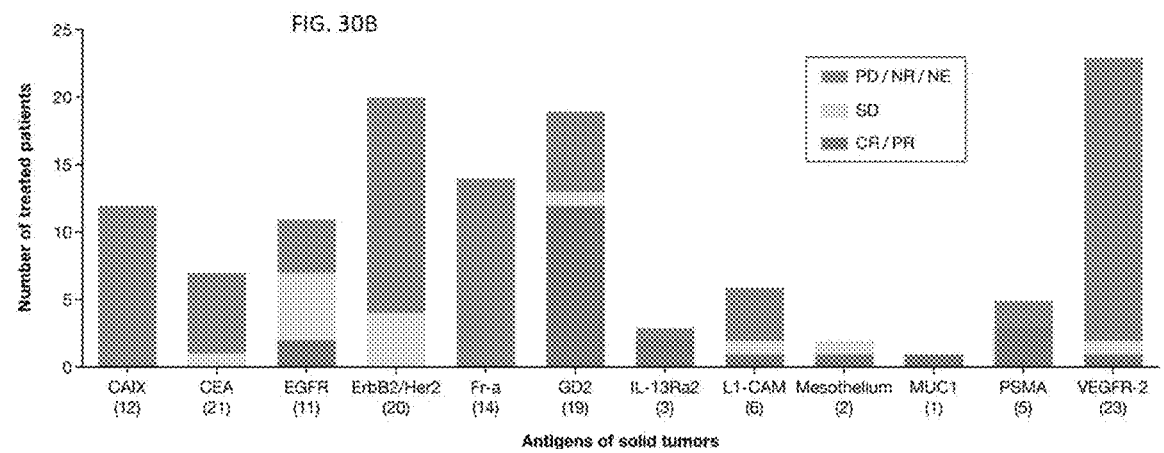
Figure 31:
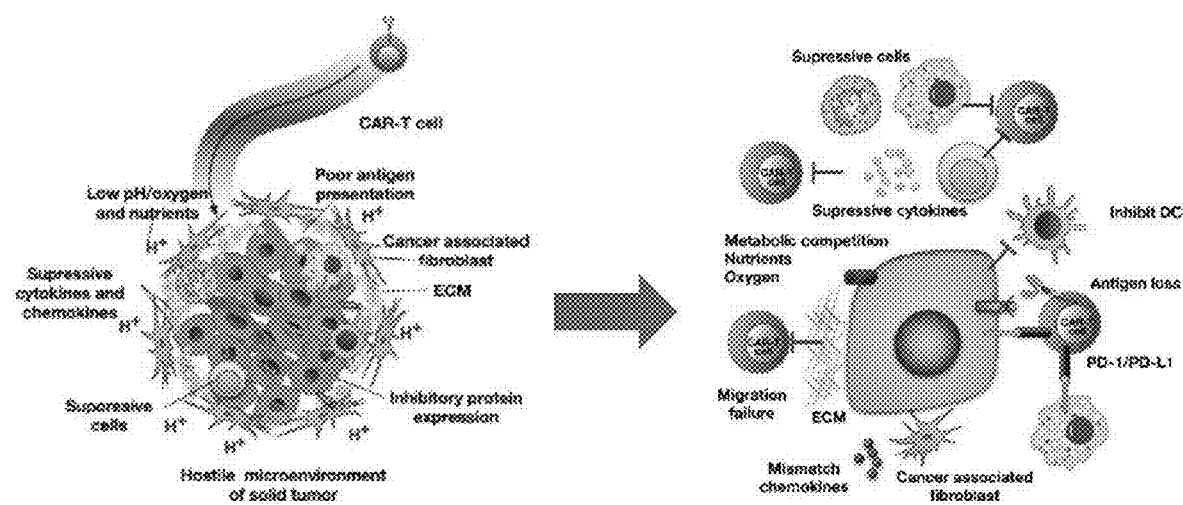
FIG. 31. Summary of challenges of published CAR T cells in solid tumor therapy which demonstrate the difficulties of targeting solid tumor cells with a T cell therapy. The challenges include low pH/oxygen and nutrients, poor antigen presentation, cancer associated fibroblasts, ECM, inhibitory protein expression, suppressive cells, suppressive cytokines and chemokines. Each of the challenges and difficulties are overcome using the novel methods of the present disclosure as shown in FIG. 31B.
Figure 32:
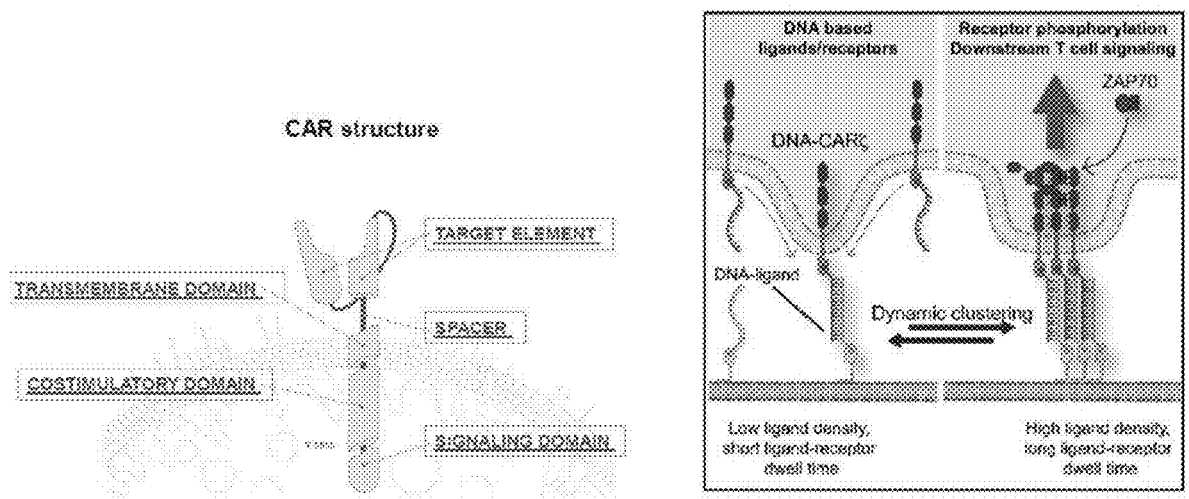
FIG. 32. Depiction one embodiment of a CAR structure which comprises a targeting agent ("targeting element") (e.g. a scFv), a spacer, a transmembrane domain, a costimulatory domain, and a signaling domain. The costimulatory domain and signaling domain are positioned to be intracellular, while the targeting element is extracellular.
Figure 33A:
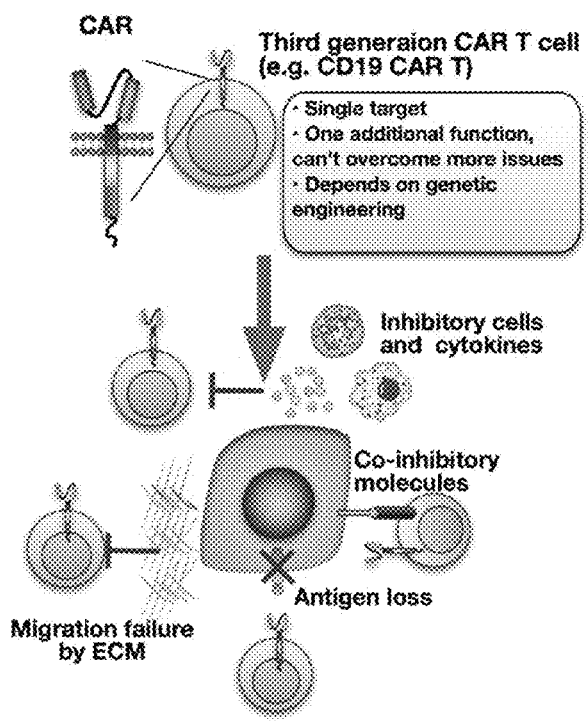
FIGS. 33A-33B.
Figure 33B:
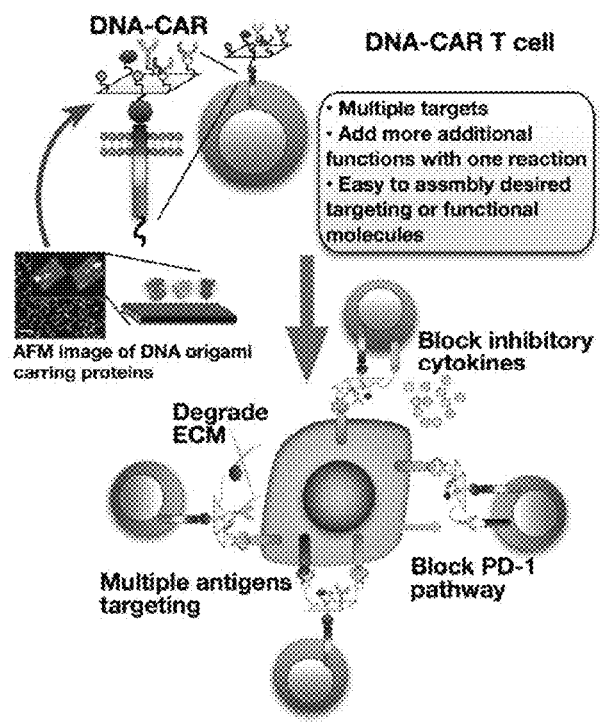
Figure 34:
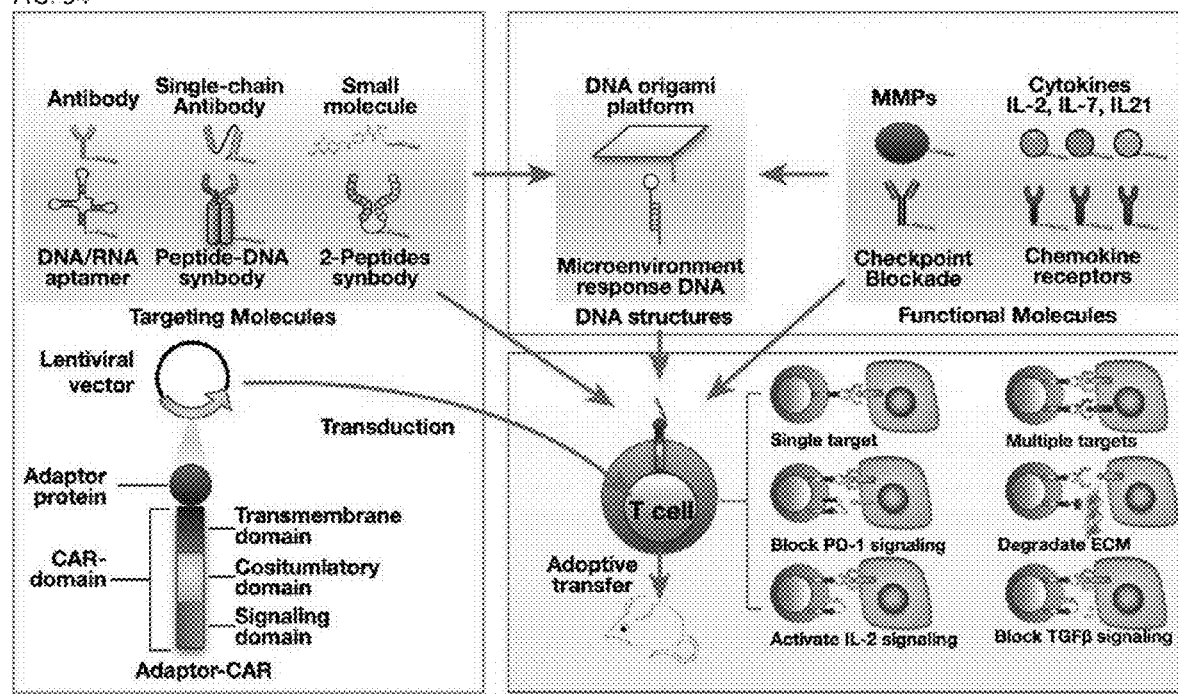
FIG. 34. Depiction of the general adoptive transfer strategy utilizing a variety of engineered T cell types based on a variety of engineered T cells of this disclosure.
Figure 35:
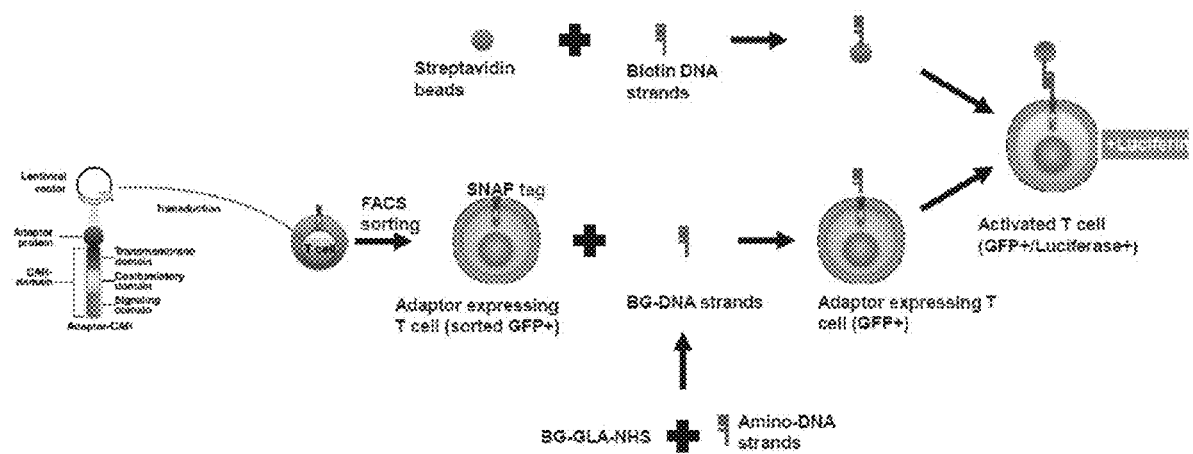
FIG. 35. Depiction of the proof of concept experiments performed in this disclosure to establish the enablement of the methods described herein. Luciferase levels are measured when the T cells are activated upon a stimulus in the model Luc-infected Jurkat cells. In addition, the cells are transfected with a GFP gene for co-location of the cells when performing fluorescent imaging.
Figure 36:
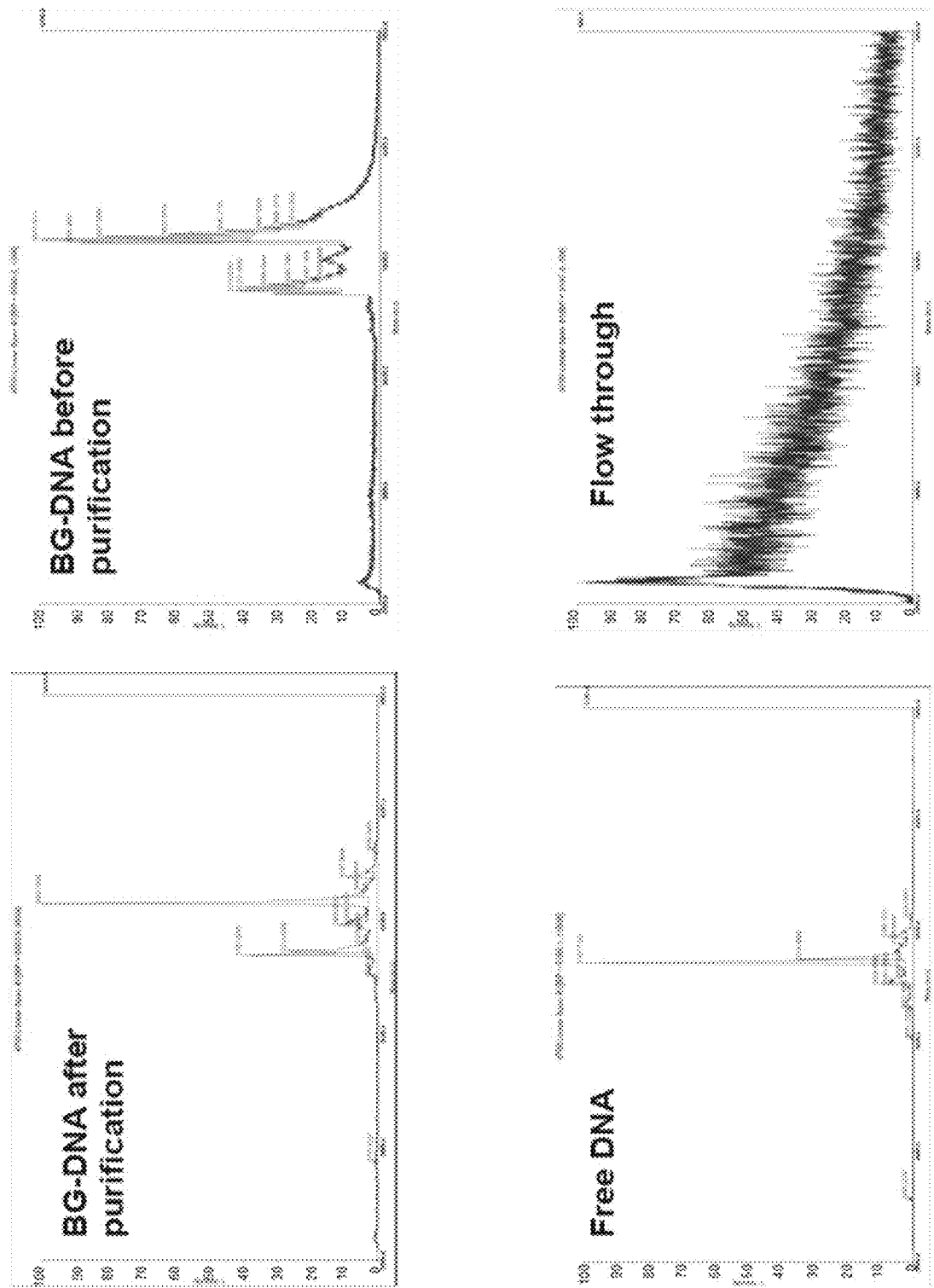
FIG. 36. MALDI-TOF confirmation of the synthesis of one embodiment of an oligonucleotide modified with a protein tag (e.g., benzoguanine, "BG").
Figure 37:
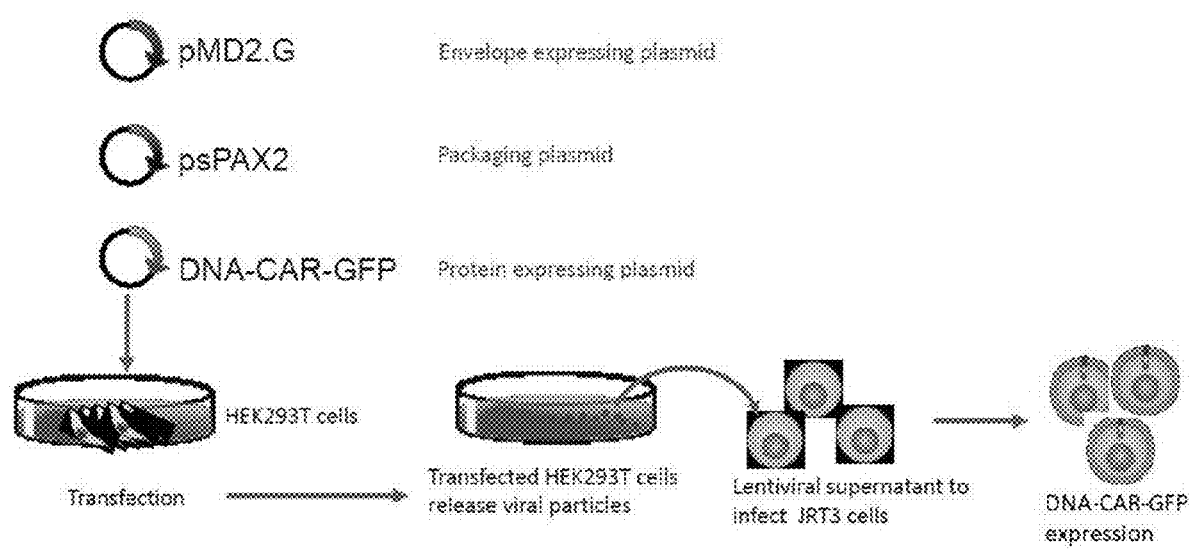
FIG. 37. One embodiment of the transfection strategy for incorporating a vector encoding the engineered CAR into T cells. The first step is to generate a T cell line expressing engineered CAR by lentivirus transduction.
Figure 38:
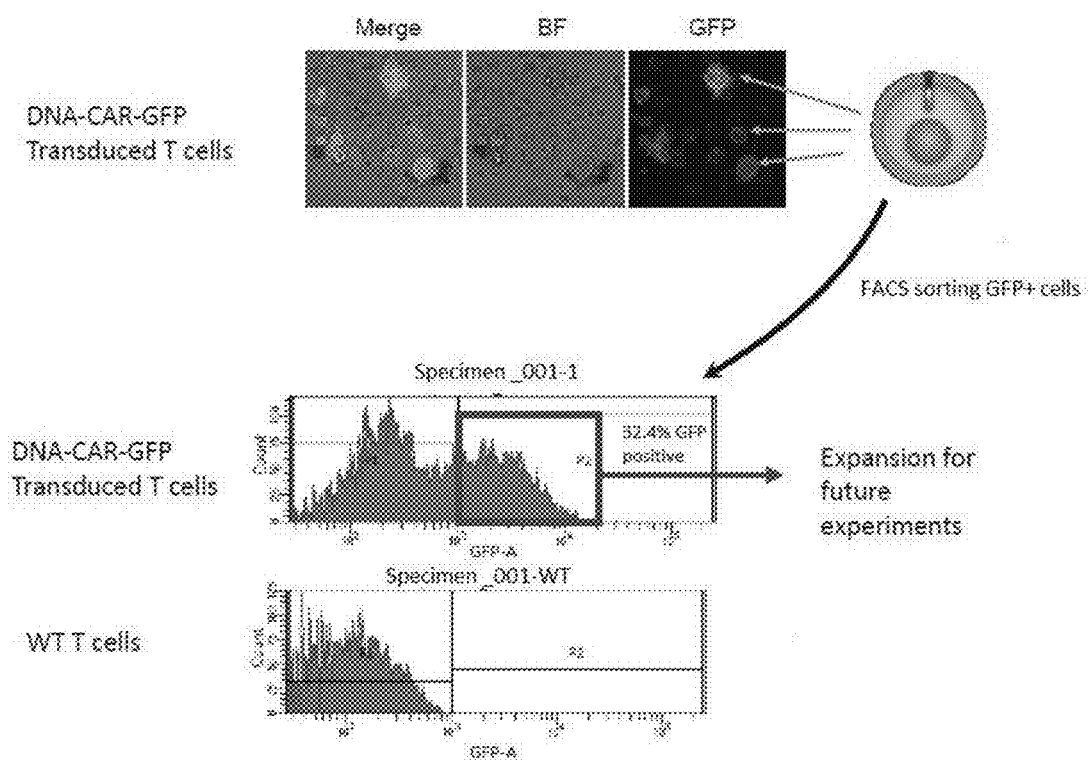
FIG. 38. Engineered CAR-GFP transduced T cells and wildtype (WT) T cells are imaged by fluorescent microscopy demonstrate that the transduced cells express GFP. In some embodiments, the transduced GFP cells are isolated and expanded for future experiments and/or T cell treatment therapy.

In some embodiments, the engineered T cell comprising a targeting molecule and/or agent is engineered to target a particular cancer cell antigen. In some embodiments, the cancer cell antigen is selected from CD19 CD20, ROR1, CD22, carcinoembryonic antigen, alphafetoprotein, CA-125, 5T4, MUC-1, epithelial tumor antigen, prostate-specific antigen, melanoma-associated antigen, mutated p53, mutated Ras, HER2/Neu, folate binding protein, HIV-1 envelope glycoprotein gp120, HIV-1 envelope glycoprotein gp41, GD2, BCMA, IgK, Lewis Y, CD123, CD33, CD138, CD23, CD30, CD56, c-Met, mesothelin, GD3, HERV-K, IL-IlRalpha, kappa chain, lambda chain, CSPG4, ERBB2, EGFRvIII, PSMA, MUC1, L1-CAM, IL13Ra2, Fr-a, CEA, CAIX, VEGFR2, HER2-HER3 in combination, HER1-HER2 in combination, and any combination thereof. In one particular embodiment, the cancer cell antigen is CD19. FIG. 30A shows the present clinical outcomes of published attempts at CAR T cell therapy for hematological malignancies, indicating that T cells targeted to CD19 have the highest rate of complete response or positive response for hematological malignancies. FIG. 30B shows the present clinical outcomes of other attempts at CAR T therapy for solid tumor therapies, indicating that T cells targeting GD2 have the highest complete response or positive response for solid tumor malignancies.

In some embodiments, the engineered T cell comprises a targeting molecule to a testicular, placental, or fetal tumor antigen. In one embodiment, the testicular, placental, or fetal tumor antigen is selected from the group consisting of NY-ESO-1, synovial sarcoma X breakpoint 2 (SSX2), melanoma antigen (MAGE), and combinations thereof.

In some embodiments, the engineered T cell comprises a targeting molecule to a lineage specific antigen. In one particular embodiment, the lineage specific antigen is selected from the group consisting of melanoma antigen recognized by T cells 1 (MART-1), gp100, prostate specific antigen (PSA), prostate specific membrane antigen (PSMA), prostate stem cell antigen (PSCA), and combinations thereof.

In some embodiments, the engineered T cell therapy comprises administering to the patient engineered T cells comprising a targeting molecule and/or agent that binds to CD19, and further comprises a CD28 costimulatory domain and a CD3-zeta signaling region.

Kits

This disclosure includes pharmaceutical kits, comprising engineered T cells for engineered T cell therapy. Kits can include or exclude a label indicating the intended use of the contents of the kit and instructions for use. The term "label" includes any writing, or recorded material supplied on or with the kit, or which otherwise accompanies the kit. Kits can include or exclude a pharmaceutically acceptable carrier as described herein. The pharmaceutically acceptable carrier can include or exclude saline, Ringer's solution, a citrate, a phosphate, PBS, and any other carrier as described herein.

The invention will now be illustrated by the following non-limiting Examples.

EXAMPLES

Within this application, unless otherwise stated, the techniques utilized may be found in any of several well-known references including: Molecular Cloning: A Laboratory Manual (Sambrook, et al., 1989, Cold Spring Harbor Laboratory Press), Current Protocols in Molecular Biology (Ausebel et al., Wiley-Interscience, 1988. New York), and PCR Protocols: A Guide to Methods and Applications (Innis, et al. 1990. Academic Press, San Diego, Calif.), each of which is herein incorporated by reference.

Example 1: Designing Engineered T Cells to Target Solid Tumors

Engineered T cell therapy involves the use of a T cell with an engineered CAR which comprises an adaptor protein which is connected to a protein tag, an oligonucleotide, and a targeting agent, a transmembrane spacer, and an intracellular signaling/activation domain(s). The engineered T cells are transfected into T cells using plasmid transfection, mRNA, or viral vector transduction to direct the cells toward surface-exposed tumor-associated antigens (TAAs). The CAR structure has evolved from an initial composition involving only the CD3ζ signaling domain (dubbed a "first-generation CAR") to more complex forms in which costimulatory endodomains have been added, giving rise to second-generation (e.g., CD3ζ plus 41BB or CD28 signaling domains) and third-generation (e.g., CD3ζ plus 41BB and CD28 signaling domains) CARs that have augmented T cell persistence and proliferation.

The adoptive transfer of T cells to solid tumors presents difficulties including physical barriers that are absent in hematologic malignancies. Discovery of specific tumor antigens that are highly and uniformly expressed has been rare. Unlike hematologic malignancies, tumor cell malignancies require T cells to successfully traffic from the blood into solid tumor sites in spite of potential T cell chemokine receptor-/tumor-derived chemokine mismatches. The T cells must then successfully infiltrate the stromal elements of solid tumors to elicit TAA-specific cytotoxicity, regardless of antigen loss or heterogeneity. Even after successful trafficking and infiltration, T cells become rapidly dysfunctional owing to 1) a hostile tumor microenvironment (TME) characterized by oxidative stress, nutritional depletion, acidic pH, and hypoxia; 2) the presence of inhibitory soluble factors and cytokines; 3) suppressive immune cells, namely regulatory T cells (Tregs), myeloid-derived suppressor cells (MDSCs), and tumor-associated macrophages (TAMs) or neutrophils (TANs); and 4) T cell-intrinsic negative regulatory mechanisms, including upregulation of cytoplasmic and surface inhibitory receptors programmed cell death protein 1 (PD-1) and cytotoxic T-lymphocyte-associated antigen 4 (CTLA4) (FIG. 1).

The clinical results of using T cell therapy in solid tumors have been unsuccessful due to the hostile microenvironment of solid tumors, including physical matrix barriers, antigen loss, co-inhibitory molecules and inhibitory cytokines. The present disclosure includes a novel DNA nanostructure-based strategy to further engineer T cells to: 1) Precisely target tumor cells through dual/multiple-binding specificities to minimize tumor immune escape; 2) Increase cell survival and trafficking to tumor area; and 3) Generate multifunctional engineered T cells rapidly. A novel engineered T cell toolkit is generated using DNA nanotechnology ("engineered T cells"). Engineered T cells are designed to express signaling CAR domains and further comprise an "adaptable receptor" protein (also referred to as an "adaptor protein") that enables the attachment of a targeting agent. In some embodiments, the targeting agent comprises a DNA origami nano-scaffold ("DNA nanostructure"). These DNA nanostructures comprise targeting molecules which can include or exclude peptides, synbodies, aptamers, and small molecules. In some embodiments, the targeting molecules include additional functionality including cytokines and matrix metallopeptidases (MMPs) to enhance T cell survival and their penetration infiltration into the tumor environment of solid tumors. The inventors were the first to recognize that this highly modular and combinatorial approach circumvents the issues with genetic engineering, enabling non-genetically encodable functionality, and enhance engineered T cell activity through multivalent effects. The final engineered T cells significantly improve the application of engineered T cell therapy to treating solid tumors.

This disclosure provides for a solution to tumor cell targeting using engineered T cells without the use of long-term molecular cloning and structure optimizations.

The inventors have surprisingly discovered a novel method to engineer T cells to include a variety of, and population of, targeting agents and/or targeting compounds which enables modulation for optimal cancer cell targeting.

Engineered T cell immunotherapy for solid tumor cancers overcomes problems including low level or loss of tumor antigen expression, poor T cell trafficking and infiltration into the tumor, and an immune response-repressive environment (FIG. 1). Using DNA, RNA and/or peptide nanotechnologies, engineered T cells are provided that target cancer cells (e.g., tumor cells) with remarkable specificity for different levels of expression, have increase survival resistance to the immunosuppressive solid tumor environment, and increase T cell traffic to the tumor area. This method also allows for low-cost and rapid methods of generating multi-functional engineered T cells without further genetic engineering. In some embodiments, the T cell is engineered to comprise a targeting molecule specific for different cancer types, stages and cancer antigen expression of individual patients. In some embodiments, the novel DNA nanotechnology-based strategy to engineer T cells disclosed herein can: 1) allow for precise tumor targeting through dual/multiple-binding specificities to minimize tumor immune escape; 2) increase cell survival and trafficking to tumor area; and/or 3) generate multifunctional engineered T cells rapidly and at low cost. T cells are engineered that express signaling CAR domains and an "adaptable receptor" protein domain (also referred to herein as "adaptor protein") that enables the attachment of a DNA origami nanostructure with high efficiency (FIG. 3B). These DNA nanostructures can carry targeting molecules which can include or exclude peptides, synbodies, aptamers, or small molecules. In some embodiment, the DNA nanostructures can carry and/or present functional molecules to enhance T cell survival and penetration into the solid tumor environment.

Conventional CAR T therapy on solid tumors has not been successful due to the hostile microenvironment of solid tumors, including physical barriers presented by the extracellular matrix (ECM), loss of the targeted antigen, or the presence of co-inhibitory molecules and inhibitory cytokines (FIG. 3A).

In some embodiments, the approach for engineering T cells is presented in FIG. 3B, where one single T cell expressing a CAR domain is engineered with a protein "adaptor" that allows the attachment of a targeting agent comprising DNA origami nano-scaffold to the cell surface using a single, reliable chemistry. In some embodiments, the adaptor protein is a protein which has the ability to form a covalent bond with a small molecule, where the small molecule may be covalently linked to an oligonucleotide. In some embodiments, the adaptor protein is a SNAP-Tag™, CLIP-Tag™, or HALO-Tag™ protein.

This disclosure provides for methods and compositions for overcoming challenges in T cell therapy targeting solid tumors: low T cell infiltration (as shown in FIG. 4, left "Aim 1"), and low T cell activity (as shown in FIG. 4, right, "Aim 2"). By dissecting these challenges, a series of solutions are provided that are unified under a common engineered T cell. The first challenge that allows tumor cells to escape T cell recognition is antigen loss and or heterogeneity. To address this challenge, peptide-based multivalent synbodies, antibodies or aptamers targeting cancer surface biomarkers broadly expressed in different cancer types are screened. The antigens can include or exclude any of the antigens in Table 2. These T cells carry targeting molecules-including peptides, aptamers, and/or proteins-allowing for a highly modular system that can target any desired cancer, without the requirement for genetic surface engineering of the T cell. In some embodiments, the targeting agent is DNA origami (also referred to herein as "DNA nanostructures" or "DNA origami nanostructures") which yields highly programmable structures and can used for attracting and trapping circulating T cells and/or targeted delivery of T cell recruiting chemokines. These DNA nanostructures can comprise targeting molecules for addressing the issues inherent with targeting solid tumors. In some embodiments, the targeting molecule is selected from an extracellular matrix (ECM)-degrading matrix metallopeptidases (MMPs), a blocking repressive pathway, or activating T cell proliferation.

In some embodiments, the engineered T cell is tested in an adoptive transfer mouse model to obtain the best combinations of functional targeting molecules. The inventors have discovered that the use of DNA origami allows for rapid prototyping of ligand combinations with multivalency, control over nanoscale spacing, and incorporation of non-genetically encodable components like imaging agents, small molecules, or peptides with non-canonical amino acid functionality. These modular multifunctional engineered T cells synergistically improve the application of engineered T cell therapy in treating in solid tumors.

TABLE 2

Engineered T cell antigen candidates for solid tumors

| Antigen | Type of cancer |
| --- | --- |
| CD133 | Liver, brain, breast, AML, ALL |
| CEA | Lung, colorectal, gastric, pancreatic Colorectal, adenocarcinoma Liver metastases |
| EGFR | Lung, colorectal, ovary, pancreatic Advanced glioma Malignant glioma, glioblastoma |
| GD2 | Sarcoma, osteosarcoma, neuroblastoma, melanoma, Relapsed/refractory Neuroblastoma Metastatic melanoma |
| GPC3 | Lung squamous cell carcinoma |
| HER2 | Glioblastoma multiforme, Her+ cancers Breast, ovarian, lung, pancreatic, gastric, HCC, endometrial, refractory to chemotherapy and Her2 antibody, Advanced sarcoma |
| Mesothelin | Pancreatic adenocarcinoma, ovarian cancer, malignant epithelial pleural mesothelioma, Malignant mesothelioma, Metastatic Her2- breast, Glioma, colorectal carcinoma, gastric carcinoma |

This disclosure provides for methods of promoting T cell infiltration in solid tumors by DNA nanostructure to demonstrate feasibility of using engineered T cells to kill cancer cells and to activate engineered T cells in the presence of a cancer cell.

Figure 6:
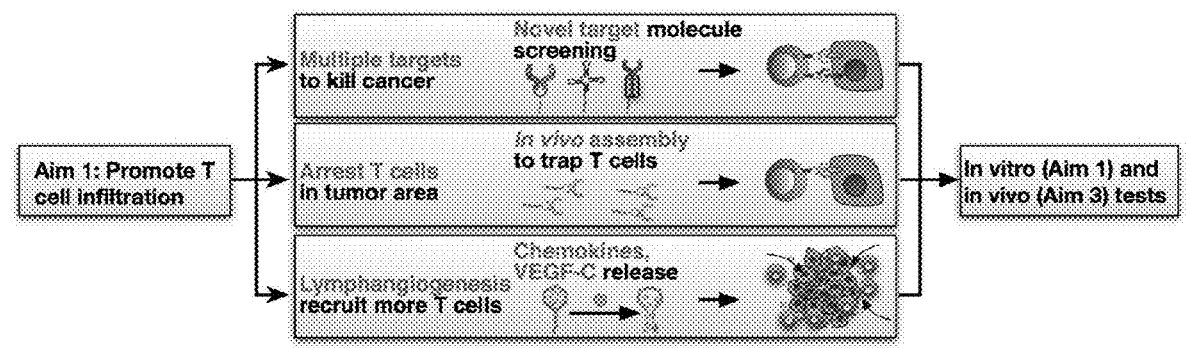
FIG. 6. Strategies of increasing engineered T cell infiltration in solid tumors. T cells expressing adaptor-CAR proteins link different targeting molecules including DNA aptamers, dipeptide synbodies, or single chain antibody to generate engineered T cells. Single or multiple targeting molecules recognize tumor cells and activate engineered T cells. DNA nanostructures are used to capture engineered T cell in tumor microenvironment. Tumor-trigged DNA nanocages open and release chemokines or VEGF-C to recruit engineered T cells to solid tumor area.
Figure 7A:
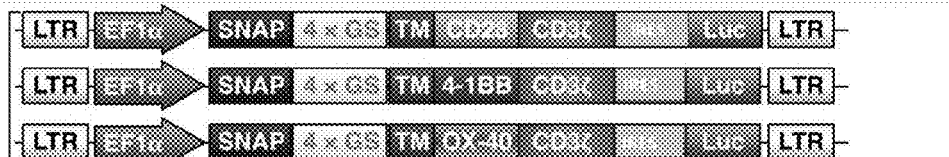
FIG. 7A-FIG. 7D. Design of lentiviral vector encoding adaptor-CAR proteins.
Figure 7B:
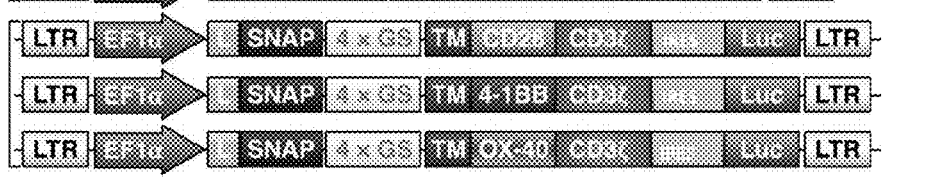
Figure 7C:
Figure 7D:
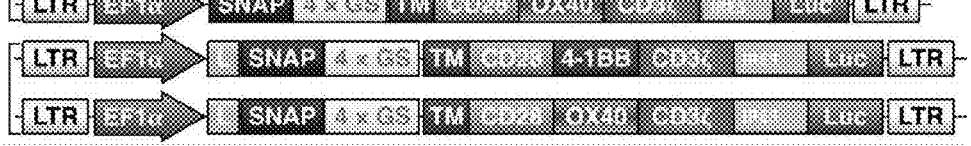
Figure 8:
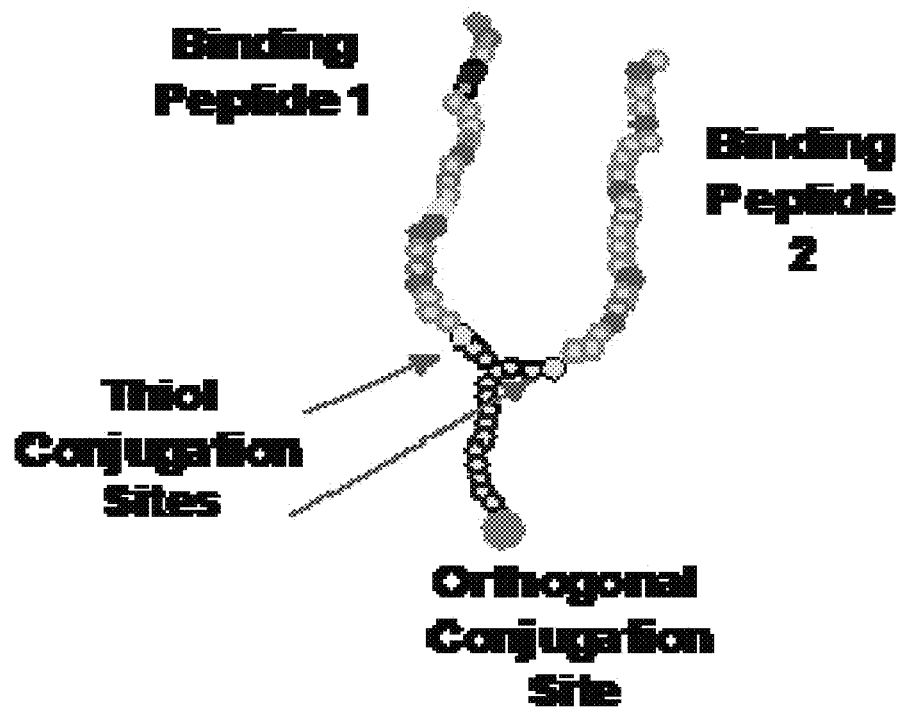
FIG. 8. Illustration of a synbody affinity ligand.

Solid tumors present a unique therapy challenge due to growth and the interaction with cells associated with the tumor cell microenvironment. The competition for nutrients and mismatches in chemokines resist T cell infiltration from circulations. Also, lymphangiogesis blocks T cells from getting into the tumor cell area. High mutation rates that cause antigen loss or heterogeneity also help solid tumor cells escape killing by T cells. The inventors have surprisingly discovered a unique design to address these issues by engineering an T cell comprising one or a plurality of targeting agent comprising a DNA nanostructure which comprises targeting molecules on or about at the T cell surface. By using the adaptor protein connected to a first oligonucleotide which has a portion of the sequence is complementary to a portion of a second oligonucleotide, where the second oligonucleotide is a staple strand in a DNA nanostructure, the adaptor-CAR expressing T cells can add multiple types of targeting molecules to the T cell surface which is presented to the tumor antigen. In some embodiments, the DNA nanostructure is a DNA nanocage. The DNA nanocage can open upon a stimulus to present a biomolecule. In some embodiments, the biomolecule is a chemokine or VEGF-C, which can build lymphic vessels for T cells to increase T cell recruiting, as shown in FIG. 6.

This disclosure provides for methods to trap engineered T cells in solid tumor by DNA nanostructure to demonstrate feasibility of using engineered T cells to kill cancer cells and to activate engineered T cells in the presence of a cancer cell.

In some embodiments, as an alternative to attaching a pre-formed DNA nanostructure comprising targeting ligands to the engineered T cell, and allowing the cells to circulate and bind to the tumor, a two-step process is performed: first, a DNA nanostructure comprising targeting molecules (e.g. synbodies, aptamers) is injected and allowed to circulate, accumulating in the tumor area. This DNA nanostructure comprises additional DNA staple strands, thereby effectively displaying addressable "handles" on the tumor. In a second step, engineered T cells comprising staple strands which comprise complementary DNA handles are injected, allowing them to accumulate in the tumor region through DNA hybridization. This method effectively decouples the nanostructure binding to the tumor from the engineered T cell modification. The method also enables for enhanced multivalency in both the targeting and cell modification steps.

The DNA nanostructures used to trap engineered T cells in solid tumor comprises a plurality of unique staple strands, where each staple strand presents a unique "handle" to trap the engineered T cells comprising a first oligonucleotide which is complementary to the sequence of the "handle" sequence in circulation. The inventors have recognized that a key advantage of DNA origami targeting structures is the facile incorporation of a plurality of DNA handles (staple sequences) to significantly enhance subsequent cell binding; in effect, a single recognition event in the tumor results in the display of many identical DNA handles. In some embodiments, the DNA nanostructures present a dense array of 10-15 nt handles, as shown in FIG. 13. In some embodiments, the DNA nanostructure comprises a dendrimeric architecture, assembled from multiple generations of Y-shaped branched DNA monomers, as shown in FIG. 13A, allowing for a plurality (e.g., 8-16) handles per targeting structure. In some embodiments, the DNA nanostructure further comprises a self-assembled linear repeating nanoribbons, as shown in FIG. 13B, which is modulated to display a plurality of identical ssDNA handles (staple strands). In some embodiments, staple strands for each approach is mixed in equimolar ratios and annealed beginning from about 95° C. down to about 4° C. for several hours (e.g., 1 to 8 hours, in some embodiments, the annealing time is 1 hour, 2 hours, 3, hours, 4 hours, 5 hours, 6 hours, 7 hours, 8 hours, or any time between the aforementioned times) to anneal them, followed by purification using polyacrylamide or agarose gel electrophoresis. In some embodiments, the annealing temperature begins at about 97° C., 96° C., 95° C., 95° C., 93° C., 92° C., 91° C., 90° C., 89° C., 88° C., 87° C., 86° C., 85° C., 84° C., 83° C., 82° C., 81° C., 80° C., or any temperature between the aforementioned temperatures. In some embodiments, the start annealing temperature is set to be above the highest melting temperature ("Tm") of the complementary oligonucleotide sequences in the DNA or RNA nanostructure, but below that of the boiling point of the aqueous solution in which the oligonucleotides are dissolved. In some embodiments, the annealing temperature can end at any temperature below the lowest melting temperature ("Tm") of the complementary oligonucleotide sequences in the DNA or RNA nanostructure, but higher than the freezing temperature of the aqueous solution in which the oligonucleotides are dissolved. In some embodiments, the annealing temperature can end at about 15° C., 14° C., 13° C., 12° C., 11° C., 10° C., 9° C., 8° C., 7° C., 6° C., 5° C., 4° C., 3° C., 2° C., or 1° C. In some embodiments, one side of a DNA origami substrate is modified with a plurality of staple strands (e.g., 10-100) by simply extending staple strands with a constant single-stranded region. In some embodiments, tumor localization is assessed using fluorescently labeled nanostructures (via incorporation of fluorophore-modified oligonucleotides into the annealing protocol).

In some embodiments, the engineered T cells are contacted with an adaptor protein (e.g., SNAP-Tag™) which is connected to an oligonucleotide which is hybridized to a branching DNA structure. In some embodiments, the branching DNA structure is a multivalent structure comprising series of oligonucleotides which comprise a sequence of complementary sequences to other branching oligonucleotides, each of which is connected to a protein tag (e.g. benzylguanine residue). In some embodiments, methods of this disclosure include presenting DNA nanostructures comprising branching DNA structures to tumor cells to decorate both the tumor and the targeting cells with a dense brush of DNA comprising protein tags, akin to Velcro, to significantly enhance engineered T cell binding. A standard trans-well assay measures whether engineered T cells are arrested by tumor cells using the methods described herein. Cell modification strand sequences is labeled with a different fluorescent dye to probe co-localization between the tumor and the cells.

This disclosure provides for smart DNA nanostructures to increase engineered T cells in tumor area to demonstrate feasibility of using engineered T cells to kill cancer cells and to activate engineered T cells in the presence of a cancer cell.

Chemokines are essential coordinators of cellular migration and cell-cell interactions, and therefore have significant impact on tumor development. In the tumor microenvironment (TME), tumor-associated host cells and cancer cells release an array of different chemokines, resulting in the recruitment and activation of different cell types that mediate the balance between antitumor and pro-tumor responses. In addition to their primary role as chemo-attractants, chemokines are also involved in other tumor-related processes, including tumor cell growth, angiogenesis, and metastasis. Chemokines play an important role in leukocyte infiltration into any tissue, including tumors. Hence, they have a critical role shaping the immune cell composition in the TME, which affects tumor development. Immune cells that are responsible for the removal of cancer cells are called "effector cells," which are able to kill or control the growth of tumor cells. Many human tumors produce low levels of chemokines, while others produce chemokines for which effector T cells lack receptors. As a consequence, adoptively transferred T cells may simply fail to "find" the tumors. In some embodiments, methods of this disclosure include enhancing engineered T cell trafficking by increasing the expression of the chemokine receptor CCR2 is performed to reduce the residual chemokine levels.

In some embodiments, the DNA nanostructures are DNA nanocages comprising a therapeutic agent. DNA nanocages are comprised of DNA structures which are shaped to contain a delivery agent. In some embodiments, the delivery agent is a therapeutic agent as described herein. In some embodiments, the therapeutic agent is a targeting molecule.

Figure 15A:
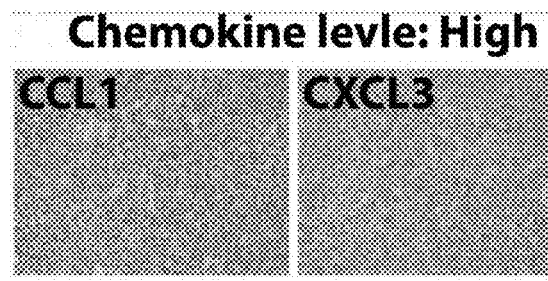
FIGS. 15A-15C. Chemokine expression levels in MDA-MB-231 breast cancer cells. Immunohistochemistry Staining (IHC) staining of chemokines in MDA-MB-231-derived tumor.
Figure 15C:
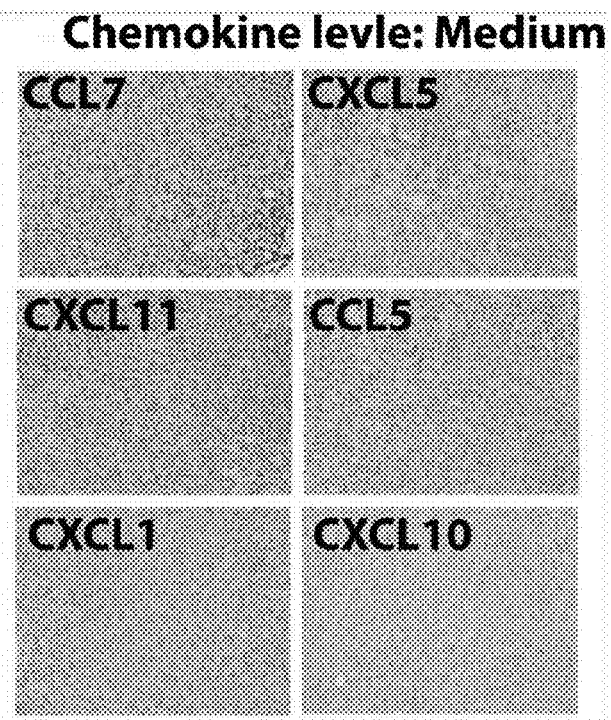
Figure 15:
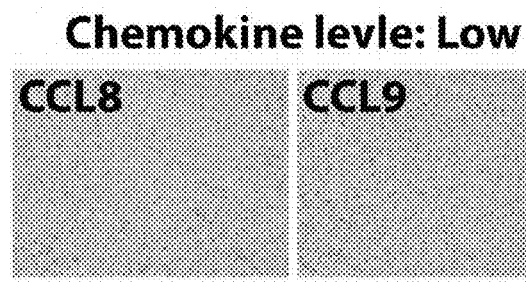

Only a few antigen-specific T cells infiltrate breast cancer tissue. Different chemokines expression levels in MDA-MB-231 breast cancer tumor were measured by immunohistochemistry (IHC) staining, as shown in FIG. 15. CCL1, which is the ligand of CCR8 and CXCL3, which is the ligand of CXCR3 expression, are high in MDA-MB-231 breast cancer tumors; however, the receptor of CCL1, CCR8, is low in antigen-specific T cells. In addition, T cells express high levels of CCR2, which is the receptor of CCL7 and CCL8. CCL7 and CCL8 expression is low in tumor tissue. The mismatch of chemokines from tumor cells and chemokine receptors on antigen specific T cells is one reason for low T cell infiltration.

Design and Demonstration of a Model Nucleolin-Responsive DNA Nanocage Opening to Present Therapeutic Agents in the TME In some embodiments, the DNA nanocage (also referred to as "DNA origami nanocage") comprises thrombin for delivery to tumor-associated blood vessels to block the tumor blood supply. In some embodiments, the DNA nanocage is that described U.S. patent application Ser. No. 16/208,103, herein incorporated by reference. In some embodiments, the DNA origami nanocage comprises two aptamers to nucleolin along opposite sides of the periphery of a DNA nanostructure which is in the form of a flat sheet.

Figure 16A:
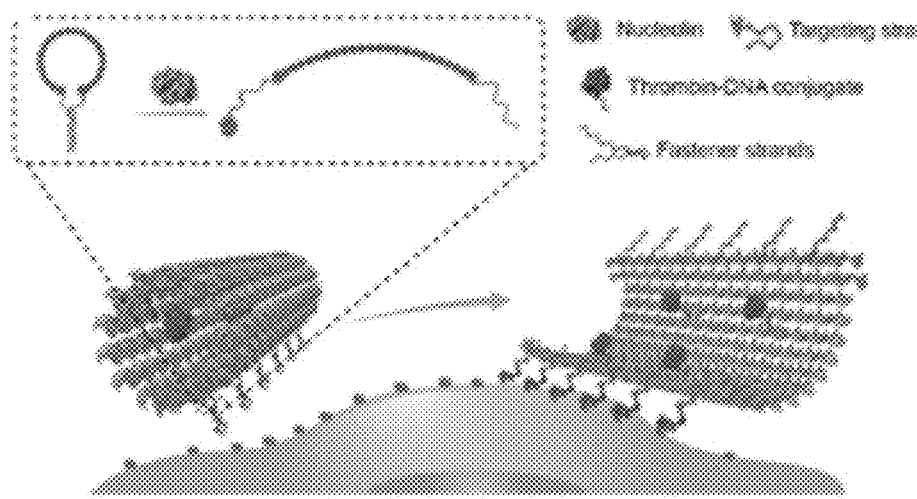
(FIG. 16A) Schematic illustration of the construction of a thrombin-loaded DNA nanocage that opens into a flat sheet in response to nucleolin binding.
Figure 16B:
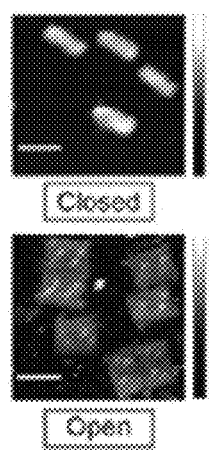
(FIG. 16B) Corresponding AFM images.

In the presence of nucleolin, the aptamers bind to nucleolin bringing the periphery of the DNA nanostructure together to form a tube. The two aptamers bound to the nucleolin form the cage seam. In some embodiments, the therapeutic agent is thrombin. In some embodiments, thrombin molecules is attached at designated positions inside the DNA cage, with the aptamer nucleolin displayed on the outside of said cage. When the aptamers recognize their target nucleolin, a protein highly expressed on the surface of tumor vascular endothelia, the hybridized duplexes of the fastening strands dissociate, and the DNA nanocage undergoes a massive reconfiguration to expose its inside surface and the bound thrombin molecules causing tumor infarction, as shown in FIG. 16.

In some embodiments, the therapeutic agent is selected from chemokines and VEGF-C.

In some embodiments, the structure of the DNA nanocages is designed using the DNA origami method, whereby a long circular scaffold DNA strand folds itself into a prescribed shape with the hybridization of a plurality of short (e.g., 12-25 nt in length) staple DNA strands ("staple strands"). Design parameters, including the inner cage volume and cage lock position and number is tailored to achieve a desired loading capacity and lock/unlocking efficiency. In some embodiments, the constructed DNA nanocages are purified with Amicon columns or gel electrophoresis to remove excess staple strands. Final structures are imaged with transmission electron microscopy (TEM) to validate their 3D structural features. The basic DNA nanocage is functionalized with the following three functional modules. First, the nanocage is modified with a nucleolin aptamer lock. In some embodiments, the aptamer is chemically modified with PS2 or MS2 modifications to achieve better biological stability. In some embodiments, the therapeutic agent is a chemokine molecule which is used to recruit circulating T cells after being released from DNA nanocage. In some embodiments, the therapeutic agent is VEGF to increase lymphatic vessels in solid tumors. In some embodiments, both a plurality of different chemokine molecules is used to synergistically kill tumor cells.

In some embodiments, the DNA nanostructure is functionalized by modifying selected staple strands with polyethylene glycol (PEG) to increase stability during circulation.

This disclosure provides for methods of overcoming the hostile solid tumor microenvironment using engineered T cells to establish the enablement of using engineered T cells to kill cancer cells and to activate engineered T cells in the presence of a cancer cell.

Figure 17:
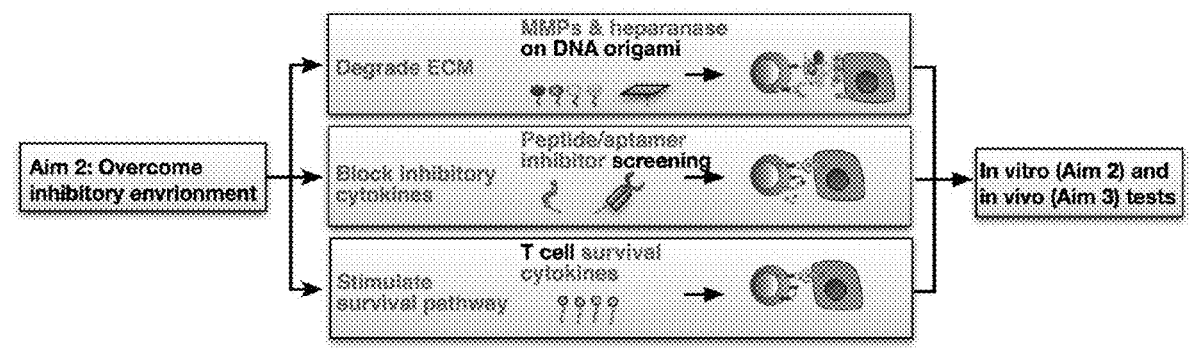
FIG. 17. Depiction of strategies to enhance engineered T cell functions. DNA origami carrying matrix metallopeptidases (MMPs) or heparinase (HSPE) help engineered T cells degrade extracellular matrix (ECM) of cancer. Peptide or aptamer block inhibitory cytokine pathways of engineered T cells. Increased engineered T cell survival rate is achieved by cytokines linked to the engineered T cell surface.

The solid tumor microenvironment blocks killing by T cells with both physical barriers like the extracellular matrix (ECM), high levels of repressive cytokines including IL-10 and TGFbeta, and low levels of the proliferation cytokine IL-2. Furthermore, once T cells have entered the tumor area, they can be repressed by inhibitory ligands including PD-L1. The inventors have discovered that engineered T cells comprising engineered CAR constructs which encode a second adaptor protein (e.g., CLIP-Tag™), allows for conjugation to additional targeting molecules on the engineered T cell surface. Besides expressing more adaptor proteins on the T cell, the use of DNA nanostructures enables conjugation of a plurality of types of proteins, peptides or aptamers to the engineered T cell, as shown in FIG. 17 using the CAR constructs depicted in FIG. 18. In some embodiments, the engineered T cells comprises a targeting molecule which is a matrix metallopeptidases (MMPs) or heparanase, to degrade tumor ECM. In some embodiments, the targeting molecule is a peptide or aptamer to block inhibitory cytokine pathways of T cells. In some embodiments, the targeting molecule links cytokines to the engineered T cell surface to increase the engineered T cell survival rate.

Targeting ECM in Solid Tumors

This disclosure provides for methods of degrading ECM by connecting DNA conjugated functional molecules to establish enablement of using engineered T cells to kill cancer cells and to activate engineered T cells in the presence of a cancer cell.

Tumor fibroblasts and myeloid cells are responsible for the development of a fibrotic extracellular matrix (ECM), which may impede T cell penetration. The enzyme heparinase (HPSE) can disintegrate heparan sulphate proteoglycans, which largely constitutes the ECM. However, in vitro-cultured non-modified T cells do not express HPSE. In some embodiments, the engineered T cells comprise an engineered CAR which expresses HPSE to degrade the ECM resulting in improved engineered T-cell infiltration and antitumor activity.

In some embodiments, the targeting molecule is hybridized to the DNA nanostructure by chemically conjugating the targeting molecule with an oligonucleotide which comprises a sequence of which a portion is complementary to a portion of the staple strand on the DNA nanostructure. In some embodiments, the targeting molecule is chemically conjugated to the oligonucleotide using a heterobifunctional linker (e.g. bis-NHS esters).

The inventors have discovered a strategy to synthesize targeting molecule-DNA conjugates so as to not occlude the functional regions—the catalytic site responsible for matrix degradation for MMPs, and the receptor binding face of cytokines like IL-2, which need to bind to hetero-trimeric receptors on the engineered T cell surface—of said targeting molecules. Where the targeting molecule is selected from a MMP or proliferative cytokines, a strategy to not occlude the functional regions of these proteins is employed, as show in FIG. 21D. In some embodiments, a unique reactive surface amino acid including cysteine in the protein (for expression in E. coli), is introduced for modification with a maleimide-modified DNA, as shown in FIG. 21E. In other embodiments, the peptide sequence LPETG (SEQ ID NO: 12) is introduced into a terminus or loop of the targeting molecule proteins, which is then modified after expression using the enzyme sortase, with a DNA-(G)5 conjugate, as shown in FIG. 21F.

TABLE 3

Molecule candidates for bioconjugation

| Molecules | Functions | Name |
| --- | --- | --- |
| Proteins | ECM degrade | MMP2 |
| | | MMP9 |
| | | heparanase |
| | T cell recruiting | CCL7 |
| | | CCL8 |
| | | VEGF-C |
| | T cell survival | IL-2 |
| | | IL-7 |
| | | IL-15 |
| | | IL-21 |

TABLE 3-continued

Molecule candidates for bioconjugation

| Molecules | Functions | Name |
| --- | --- | --- |
| Peptide | Targeting synbody | CD133 |
| | | CEA |
| | | EGFR |
| | | GD2 |
| | | GPC3 |
| | | HER2 |
| | | Mesothelin |
| | Inhibitory synbody | PD-1 |
| | | PD-L1 |
| | | TGFβ |
| | | TGFβR |
| | | CTLA4 |

In some embodiments, the targeting molecule is a protein or peptide listed in Table 2.

In some embodiments, the protein/peptide-DNA conjugates are purified by anion-exchange and/or size-exclusion chromatography and optionally characterized by polyacrylamide gel electrophoresis. In some embodiments, the functionality of the DNA handle is probed by hybridization to its complementary oligonucleotide strand and analyzed by mobility gel shift assay. The protein/peptide-DNA conjugates are immobilized on DNA nanostructures by hybridization with their cognate staple strand sequences. In some embodiments, the functionality of MMPs on the DNA nanostructures is confirmed via a matrix degradation assay. In some embodiments, the functionality of cytokines is confirmed using receptor binding studies.

In some embodiments, the engineered T cells comprise a targeting molecule which is an attached matrix metallopeptidases (MMPs) to the DNA region of the T cell CAR to degrade tumor extracellular matrix (ECM), where the targeting molecule is immobilized to the DNA nanostructure ("MMP-DNA-CAR-T cell"). In some embodiments, the engineered T cells comprise a targeting molecule which is an attached heparinase (HPSE) to the DNA region of the T cell CAR to degrade tumor extracellular matrix (ECM), where the targeting molecule is immobilized to the DNA nanostructure ("HPSE-DNA-CAR-T cell"). The capacity of each type of engineered T cell subset to degrade ECM is examined in vitro using the BioCoat Matrigel Invasion assay (Becton Dickinson Biosciences). Data is expressed as the percentage of invasion through the Matrigel and the membrane relative to the migration through the control membrane (8 μm polyethylene terephthalate membrane pores). The percentage of invasion is calculated as follows: (mean of cells invading through the Matrigel chamber membrane/mean of cells migrating through the control insert membrane)×100. The invasion and antitumor activity of MMP-DNA-CAR-T cell or HPSE-DNA-CAR T cells is determined using the BioCoat Matrigel Invasion assay by plating MMP-DNA-CAR-T cells (1.4×10^5) in the bottom of a 24-well plate with MMP-DNA-CAR-T cell and H-DNA-CAR T cells. 2.5×10^6 cells are placed in the upper chamber/insert. Chambers and inserts are removed 24 h later. After 3 d of culture cells are then collected from the lower chamber and quantified by flow cytometry to identify tumor cells and T cells, respectively. Multiplex analysis for matrix metalloproteases (MMPs) analysis is performed using Milliplex Map kit panel 1 and 2 (Millipore) according to the manufacturer's instructions. In particular, FI-T cells is activated with OKT3 and anti-CD28 mAbs in presence of IL-2 (50 U/ml or 2000 U/ml) or IL-7 and IL-15 (10 ng/ml and 5 ng/ml, respectively). The engineered T cells are fed twice a week. At days 3, 7 and 10 of culture, supernatants and T cells are collected and 60 μg of sample is tested per well. The protein-DNA conjugates which bind to DNA nanostructures are optimized to retain the function of the ECM-degrading protein.

Blocking T Cell Inhibitory Pathways to Target Solid Tumors

In some embodiments, this disclosure provides methods of blocking T cell inhibitory pathways in solid tumors by synbodies or DNA aptamers to show enablement of using engineered T cells to kill cancer cells and to activate engineered T cells in the presence of a cancer cell.

Checkpoint inhibitory proteins are often upregulated on tumors, including PD-L1 with the normal function of modulating immune response. Once PD-L1 binds to its inhibitory receptor PD-1 on T cells, the function of T cells is inhibited; in other words, T lymphocytes can become hypofunctional.

The tumor microenvironment (TME) comprises numerous types of suppressive immune cells and molecular factors which inhibit T cells anti-tumor immune function within the TME. Thus, T lymphocytes must overcome tremendous challenges to exert effective antitumor activity, including immune suppressor cells including Tregs, myeloid-derived suppressor cells (MDSCs), and tumor-associated macrophages (TAMs); cytokines and soluble factors associated with immunosuppression, including TGF-β and IL-10; and checkpoint inhibitory proteins, including PD-L1 and/or CTLA4. The inventors have recognized that alteration of the immunosuppressive TME may make engineered T cells restore anti-tumor effect and pave the way for improving engineered T cell function.

Transforming growth factor β (TGF-β) is one of the most important inhibitory tumor cytokines. The TGF-β impairs anti-tumor responses through negative regulation of cytotoxic cell function and promotion of T-regulatory cell maturation. In some embodiments, the engineered T cells comprise targeting molecules which neutralize TGF-β to enhance CD8+ T-cell-mediated anti-tumor immune responses.

Figure 11A:
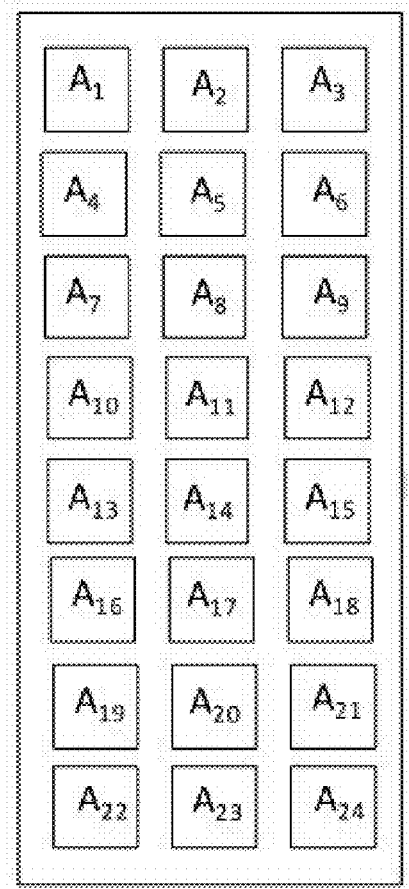
FIGS. 11A-11C. Protein screening against in situ synthesized peptide microarrays.
Figure 11B:
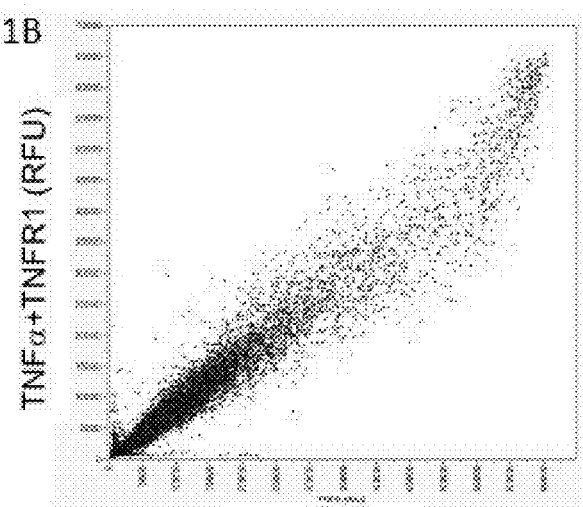
Figure 11C:
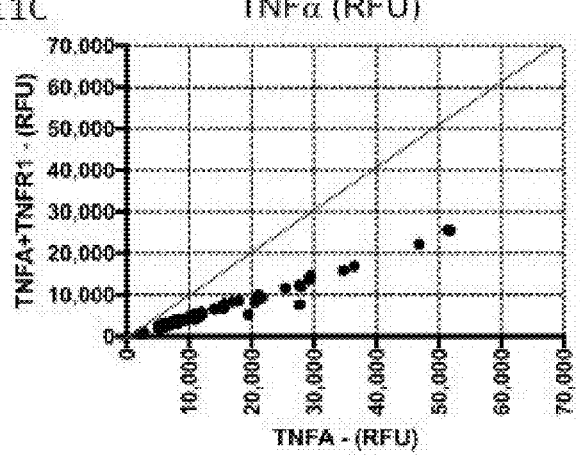
Figure 19:
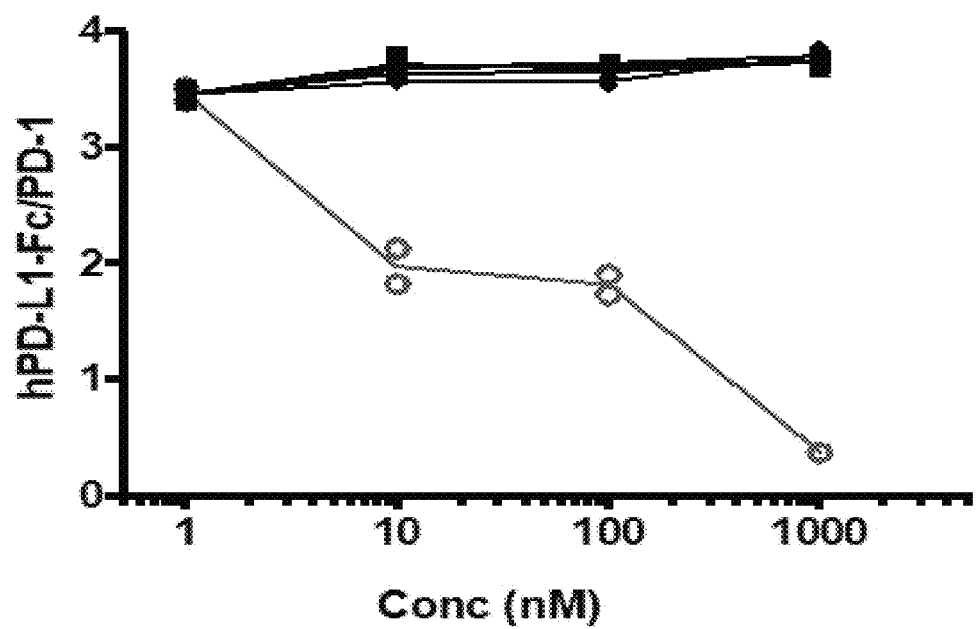
FIG. 19. Inhibition ELISA to screen inhibitors for PD-1/PD-L1 inhibition. PD-1 is immobilized in the wells of a 96-well plate and 1.25 ug/mL PD-L1-Fc is incubated with and without inhibitors. Non-inhibiting synbodies (squares) and a known PD-L1 inhibitor (round circles) were screened.

This disclosure includes methods to develop synbodies that block T cell inhibitory pathways. Synbody development for inhibitors of T cell inhibitory pathways proceeds as described herein. In addition, each target is screened alone and in complex with its receptor, similar to TNFα/TNFR1 in FIG. 11. The parallel screening enables identification of peptides that target the PPI (protein-peptide interaction) interface which is necessary to produce synbodies that inhibit the targeted PPI. Furthermore, the synbody libraries are screened by inhibition assays to identify synbodies that block the desired PPI. In some embodiments, an ELISA based assay is used to screen for PPI inhibition similar to that shown in FIG. 11. In the ELISA based assay, the receptor PD-1 is coated in the wells of a 96-well plate, and the responsive is measured as a function of aptamer, as shown in FIG. 19. The coated wells are incubated with the target protein produced as an Fc fusion, (e.g., PD-L1). Target binding is detected by an anti-Fc-HRP conjugated secondary antibody as in a standard ELISA assay. With this basic assay format, multiple candidates incubated with the target protein and then screened for inhibition to identify selected synbodies of this disclosure.

Each target protein of the PPI is commercially available and screened on high volume (e.g., 125,000) D,L-peptide microarrays. In one embodiments, the screening assay includes where TGF-B is fluorescently labeled and screened alone and in complex with its un-labeled receptor, TGFBR. In parallel, TGFBR is labeled and screened alone and in complex with un-labeled TGFB. This general format is repeated with PD-1/PD-L1 and CTLA4/B7. Peptides can be obtained from commercial peptide synthesis vendors (e.g., Polypeptides, San Diego, CA). Synbody libraries are prepared for each target as described herein. In some embodiments, synbody libraries are screened in parallel by SPR and by inhibition ELISA. In this manner, synbodies that have high affinity, KD<10 nM, and inhibitory activity, $IC_{50}$<50 nM for each target are selected to be chemically conjugated to oligonucleotides for later immobilization to the staple strands of the DNA nanostructure that comprises a sequence which has a portion which is complementary to a portion of the oligonucleotide which is chemically conjugated to the synbodies.

In some embodiments, this disclosure provides for a method to develop aptamers that block T cell inhibitory pathways. Aptamers act as inhibitors by binding and inhibiting enzyme activities or protein-protein interactions. High aptamer binding affinity and specificity allows for effective inhibition. In some embodiments, T cell inhibitory pathways are blocked by blocking the related ligand and receptor interactions including TGFβ/TGFβ receptor, PD1/PDL-1, and CTLA4/B7. In some embodiments, the blocking occurs from the targeting molecule. In some embodiments, the targeting molecule is an scFv, aptamer, antibody, or fragment thereof to TGFβ/TGFβ receptor, PD1/PDL-1, and/or CTLA4/B7. This disclosure provides for a method of identifying and synthesizing distinct aptamers for a single target separately and then linking the aptamers to facilitate the coordinate between different aptamers and linker.

In some embodiments, this disclosure provides for a method to perform an in vitro assay of engineered T cell resistance to inhibitory pathways to confirm the ability of engineered T cells to penetrate the TME and kill cancer cells. In some embodiments, the engineered T cells comprise a targeting molecule which comprises an anti-TGFβ peptide. The cytotoxic specificity of the engineered T cells with or without anti-TGFβ peptide in the presence of TGF-1, is measured using an LDH release assay. In some embodiments, expanded engineered T cells in cell medium supplemented with 3,000 IU/ml IL-2 is washed to remove excess cytokines. In the cytotoxity assays, $1\times10^4$ engineered T cells and $5\times10^4$ or $1\times10^5$ 4T1 cells are added per well in a u-bottom 96-well plate culture for 4 hours, and LHD release is measured with CytoTox 96 Non-Radioactive Cytotoxicity Assay kit (Promega). The mean percentage of specific lysis of triplicate wells is calculated as follows: [(test counts spontaneous counts)/(maximum counts spontaneous counts)]100%. In ELISA assays, $5\times10^4$ T cells with engineered CAR is co-cultured with $1\times10^4$ 4T1 cells or MDA-MB-231 cells for 12 hours, IFN γ, GM-CSF, IL-2, IL-10 is measured with specific primary and secondary antibodies.

This disclosure provides for methods of boosting T cell proliferation by associating a cytokine to the engineered T cell surface to establish enablement of using engineered T cells to kill cancer cells and to activate engineered T cells in the presence of a cancer cell.

Numerous cytokines profoundly affect T-cell development, differentiation, and homeostasis. IL-2, IL-7, IL-15, and IL-21 are members of a cytokine family whose heteromeric receptors share the common chain (c). Each cytokine is a T-cell growth factor and each can augment the T-cell antitumor immune response. In preferred embodiments, the selected cytokine is IL-2.

Figure 20A:
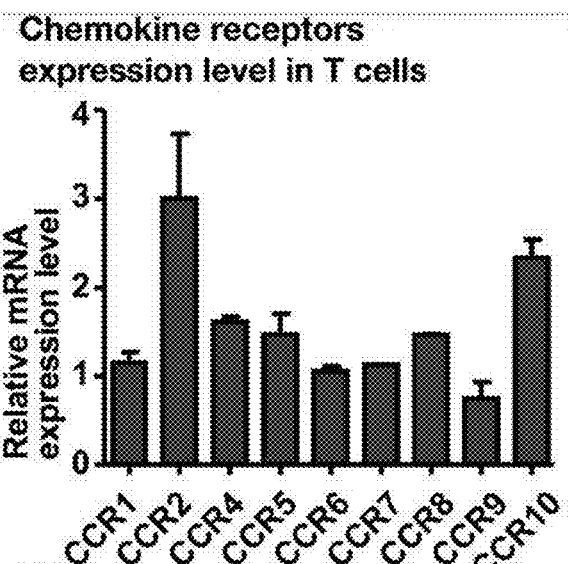
FIGS. 20A-20C. Cytokines increase T cell proliferation and CCR8 mRNA expression.
Figure 20B:
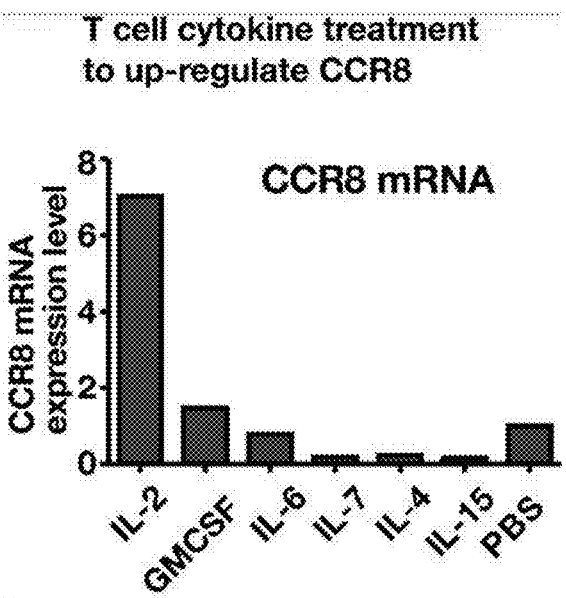
Figure 20C:
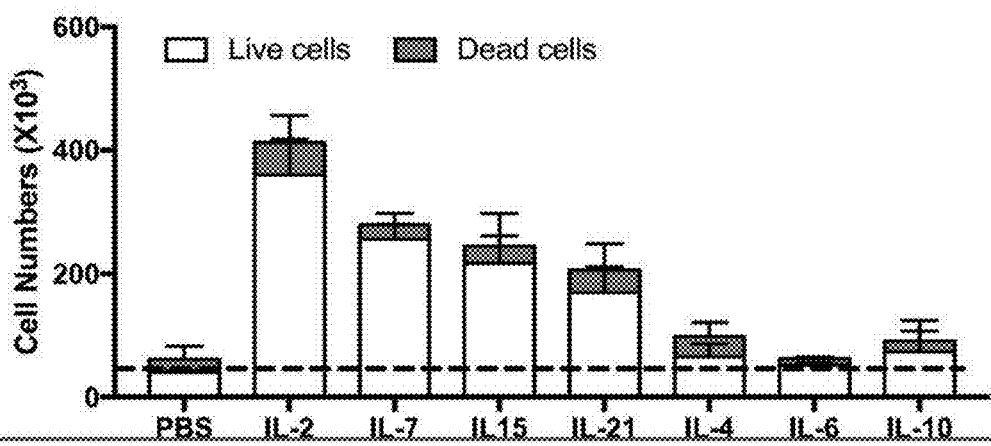

This disclosure provides a method to confirm the effects of cytokines for T cell survival and proliferation. Human T cells are isolated from peripheral blood and cultured with different cytokines. The inventors surprisingly discovered that T cell proliferation significantly increased after IL-2, IL-7, IL-15 or IL-21 treatment, as shown in FIG. 20. In addition, IL-2 also can elevate mRNA levels of chemokine receptor CCR8 (as shown in FIG. 20 A, and FIG. 20B), which is the receptor of chemokine CCL1 but expression level is low without cytokine treatment. FIG. 20C depicts the cytokine increased T cell proliferation as a function of enriched culturing medium.

This disclosure provides a method for performing cytokine conjugation and linkage methods. After performing the chemical conjugation methods described herein, an in vitro assay of cytokine carrying engineered T cell proliferation and activities is performed where transduced engineered T cells are co-incubated in triplicate at $5\times10^4$ cells/well with irradiated autologous EBV-LCLs at a 4:1 stimulator-to-responder ratio titrated concentrations of TGF-1 up to 20 ng/mL. After a 72-hour co-incubation period, wells are pulsed with 0.037 MBq (1 Ci)/well of [3H]thymidine (Amersham Pharmacia Biotech) for 18 hours, and the samples are harvested onto glass fiber filter paper for—scintillation counting (TriCarb 2500 TR; Packard BioScience).

Example 2: Using Engineered T Cell Subcomponents on Mouse Model to Demonstrate Enablement of the Engineered T Cell Ensemble This disclosure provides for methods of the in vivo analysis of therapeutic effects of engineered T cells to demonstrate enablement of using engineered T cells to kill cancer cells and to activate engineered T cells in the presence of a cancer cell.

In some embodiments, this disclosure provides for methods of evaluating antigen specific engineered T cell infiltration using iRFP-expressing tumor model. The NOD-SCID-IL2-receptor common gamma chain knockout (NSG) mouse can grow tumor-grafts from patients. After irradiation, this fluorophore is a classic model for confirming T cell adoptive transfer. For cancer models, all cell lines are first transduced with iRFP, which is a near-infrared fluorescence protein. In some embodiments, the iRFP is derived from the organism *Rhodopseudomonas palustris* and comprises the peptide sequence: AEGSVARQPDLLTCDDEPIHIPGAIQPHGLL-LALAADMTIVAGSDNLPELTGLAIG ALIGRSAAD-VFDSETHNRLTIALAEPGAAVGAPITVGFTMRKDAG-FIGSWHRHDQ LIFLELEPPQRDVAEPQAFFRRTNSAIRRLQAAETLE-SACAAAAQEVRKITGFDRV MIYRFASDFSGEVIAE-DRCAEVESKLGLHYPASTVPAQARRLYT-INPVRIIPDINYR PVPVTPDLNPVTGRPIDLS-FAILRSVSPVHLEFMRNIGMHGTMSISILRGERLWGLI VCHHRTPYYVDLDGRQACELVAQVLAWQIGVMEE (SEQ ID NO: 13). The iRFP allows for monitoring tumor growth and antitumor activities of engineered T cells in real-time. In some embodiments, the engineered CAR comprises a luciferase domain which enables tracking adoptive transferred engineered T cell in mouse and co-localization with sup-Q injected iRFP-expressing tumor cells.

Figure 24:
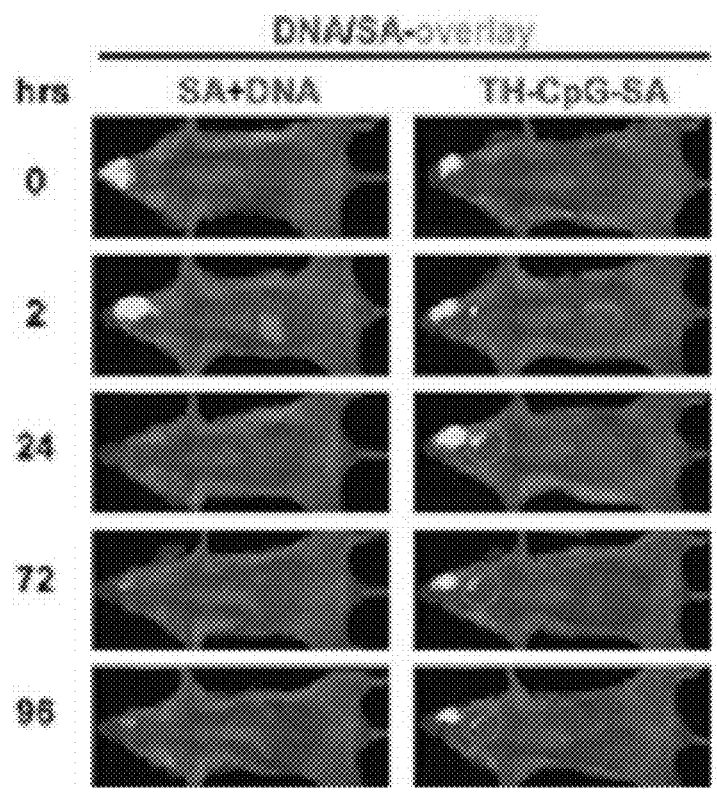
FIG. 24. In vivo stability and delivery of dual labeled DNA (red) and SA (green) to the neck lymph nodes (highlighted in circles) at various times after injections of either the mixture of DNA and SA or DNA-TH assembled SA.

In some embodiments, the engineered T cell circulation is tracked using simultaneous bioluminescence of the iRFP and luciferase fluorescent stains. Engineered T cells that transduced with luciferase expressing lentivirus are tracked using small animal live image equipment up to seven days, as shown in FIG. 24.

Figure 14A:
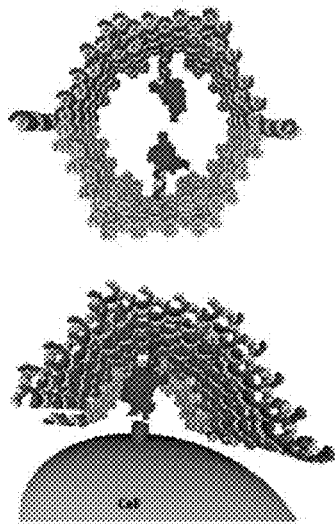
FIGS. 14A-14C. Some embodiments of a DNA nanocage of this disclosure.
Figure 14B:
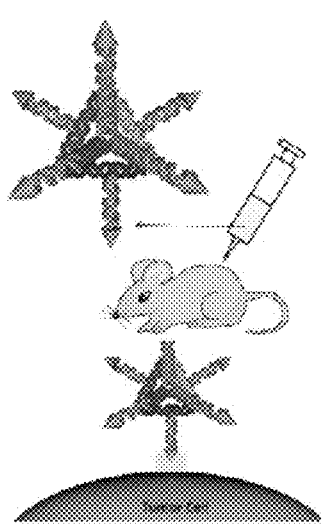
Figure 14C:
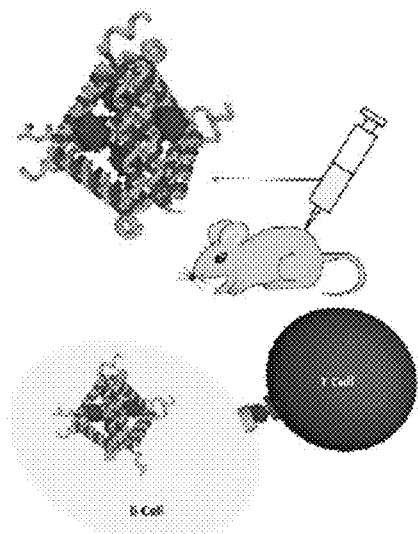

In some embodiments, this disclosure provides for method of testing the in vivo stability of DNA-nanostructures. The function of a tetrahedral DNA nanostructure ("DNA-TH") as a delivery vehicle has been demonstrated in vivo, as shown in FIG. 14B and FIG. 24. Two near-infrared fluorescence probes are used to label DNA and streptavidin (SA). The stability and co-delivery of labeled DNA and SA protein is measured, in the form of mixtures, or assembled as complexes, to the draining lymph nodes. While the labeled DNA strands in the mixture were detectable 2 hrs post the injection, they were cleared out within 24 hrs, leaving only the labeled SA remaining at the delivery site (green). In contrast, even 96 hrs after the administration of the DNA-TH nanostructure assembled DNA-SA complex, both labeled DNA and SA were still present in the administration site and draining lymph nodes (yellow), indicating stable retention of both DNA and SA. This result confirms the structural stability of DNA nanostructures and their feasibility for in vivo applications.

In some embodiments, tumor models are monitored by transducing iRFP, a near-infrared fluorescence protein, into cancer cell lines. MDA-MB-231, which is a CD133 and mesothelin positive breast cancer cell line; BT-474 Her2+ A549 which is GD2+, EGFR+, Raji CD19+ lymphoma cell to monitor tumor growth and assess anti-tumor immunity of adoptive transfer of engineered T cells with function modules in vivo. In addition, fluorophore labeled engineered CAR structure on luciferase expressing cells tracks T-cell circulation in mouse models.

This disclosure provides for a method of monitoring the tumor killing activities of the engineered T cells described herein. The MDA-MB-231-iRFP cell line is the tumor model to monitor tumor growth in vivo. To determine whether the engineered T cell target and kill tumor cells, adoptive transfer luciferase expressing engineered T cells are constructed with an IRDye800-labeled targeting molecule (e.g. CD133-synbody ("CD133 engineered T")) or MSLN-synbody ("MSLN engineered T"), so that the engineered T cell and tumor mass volumes are followed in real time. In some embodiments, tumor tissue is collected after adoptive engineered T cell transfer and total T cell infiltration is monitored using IHC staining using an anti-CD3 antibody. Engineered T cell infiltration is monitored using an anti-SNAP-Tag™ antibody. Total tumor killing is monitored using an anti-Ki67 antibody. Target tumor killing efficiency is monitored using an anti-CD133 or anti-MSLN antibody. In some embodiments, peripheral blood is collected from engineered T cell adoptive transferred mice. T cells are isolated by Dynabeads Untouched Human T Cells Kit, using flow cytometry. Engineered T cell activation efficiency is analyzed by INF-γ or exhausting by PD-1 staining. Serum is used to quantify different cytokine release by activated T cells by ELISA. Furthermore, since MDA-MB-231 is a CD133 and MSLN double positive breast cancer cell line, engineered T cell infiltration and trafficking is measured between single targeting molecule (CD133 or MSLN) or multiple targeting molecules (CD133-MSLN) using the engineered T cells generated by the methods described herein. In some embodiments, single positive (e.g. shRNA knockdown MSLN to generate CD133 single positive or shRNA knockdown CD133 to generate MSLN single positive MDA-MB-231-iRFP cells) models are used as a tumor model to compare single or multiple targeting molecule engineered T cells.

This disclosure provides for methods of evaluating engineered T cell trafficking in a mouse model to establish enablement of using engineered T cells to kill cancer cells and to activate engineered T cells in the presence of a cancer cell. In some embodiments, an engineered T cell comprising a therapeutic agent comprising a DNA nanocage as described herein can achieve on-target tumor infarction by tunable thrombin release.

In some embodiments, DNA nanocages are used to transport molecular payloads (e.g., thrombin protein) in vivo for targeted cancer therapeutics through on-site tumor infarction. The DNA nanocage is functionalized with tumor endothelium-specific DNA aptamers displayed on its external surface and the blood coagulation protease thrombin within its inner cavity, as shown in FIG. 24. The thrombin-comprising DNA nanocage initiates tumor vessel occlusion and induces tumor necrosis, as shown in FIG. 25 A. Overexpression of nucleolin on the surface of tumor endothelial cells enables nucleolin-targeting aptamers to serve as triggering molecules for mechanical opening of the DNA nanocage to release thrombin molecules which activate coagulation at the tumor sites. The DNA nanocage migrates to the tumor site as early as 4 hours after injection, as reflected by the tumor fluorescence intensity, which peaked 8 hours after injection. Minimal fluorescence was detected anywhere in the body, including the tumor site, at 24 hours after injection, as shown in FIG. 25B and FIG. 25C, demonstrating the site-specific activation of the DNA nanocage. Tumor-comprising mouse models of breast cancer are used to demonstrate that i.v. injected DNA nanocage delivers thrombin specifically to the tumor-associated vessels and induces intravascular thrombosis, resulting in inhibition of tumor growth and necrosis, as shown in FIG. 25E, FIG. 25F, FIG. 25G, and FIG. 25H. The efficacy of DNA nanocages in site-specific tumor targeting indicates the enablement of an engineered T cell comprising a targeting agent comprising a DNA nanocage for the site-specific tumor targeting to kill cancer cells and/or activate T cells in the presence of a cancer cell.

This disclosure provides for methods of testing engineered T cell recruitment in vivo with DNA-nanocage carrying chemokine or VEGF-C to establish enablement of using engineered T cells to kill cancer cells and to activate engineered T cells in the presence of a cancer cell. In some embodiments, the anti-tumor activities and immunities of the DNA nanocages are associated with the presence of the anti-nucleolin aptamer on the DNA nanocage. A combination of chemokines and cytokines is used. 4T1-OVA-iRFP breast cancer cells and OT-II transgenic mice are used as the T cell immunotherapy model. To further examine the interplay between CD4 and CD8 in coordinating antigen-specific immunity, TCR-transgenic mice (O-II) are used, wherein DO.11 CD4 T cells recognize the OVA323-339 peptide in the context of MHC-II (I-Ad of B6 background). Specifically, after 4T1-OVA-iRFP-tumors reach 4-6 mm in diameter, DNA nanocages are intra-tumorally injected. CD4 T cells isolated from OT-II transgenic mice are adoptively transferred into the aforementioned recipients at different times. Without being bound by theory, it is believed that the transferred CD4 cells are programmed in the recipients to become potent effector cells (IFNg+Foxp3−PD1−), facilitating the generation of cytotoxic CD8 cells, or to function as Treg cells, promoting the production of exhausted/immunosuppressive cells, thereby inhibiting tumor-specific CD8 cells. The antigen-specific T cell infiltration of tumor tissue is measured by the IHC staining of the useful parameters that could be used to optimize the DNA nanostructures for better and more effective anti-tumor immunity for any given tumor sample.

This disclosure provides for methods of using a combination of anti-PD-1 antibody and DNA nanocages for cancer immunotherapy to establish one embodiment of using engineered T cells to kill cancer cells and to activate engineered T cells in the presence of a cancer cell. T cell functions are related to the initiation of the PD1-PDL1 checkpoint circuit. Potent tumor regression is also applicable by applying cytokines or chemokines. Thus, the inventors have recognized that the incorporation of cytokines or chemokines into a DNA-nanocage can further enhance anti-tumor immunity by increase T cell proliferation and trafficking.

This disclosure provides for method of evaluating how multifunctional engineered T cells overcome the hostile tumor microenvironment to show that using engineered T cells kill cancer cells and to activate engineered T cells in the presence of a cancer cell. The invasion of tumor cells is a complex, multistage process, which starts with proteases including MMP degrading the basement membrane and the ECM surrounding the original tumor. In a model mouse, subcutaneous injection helps tumor cells form ECM. Since NGS is an immune deficient mouse strain, exogenous immune repressive cytokines including IL-10, IL-6 or TGF-beta are injected to sub-Q injected tumors to mimic tumor microenvironment. The tumor inhibition induced by the DNA nanocage without overt in vivo pro-inflammatory activity or toxicity is established.

Using a syngeneic melanoma model (F10-B16), the inventors demonstrated that the transiently delivered thrombin-loaded DNA nanocage, but not free thrombin or DNA nanocage, induced significant reduction of tumor loads at both the primary inoculation site and the metastatic liver (FIG. 26A and FIG. 26B). However, the injected thrombin-containing DNA nanostructures caused no elevation of pro-inflammatory cytokines in the serum (FIG. 26C). Thrombin has been shown to initiate a coagulation cascade, leading to thrombosis formation within blood vessels. To determine whether thrombin-loaded DNA nanocages also inflict this side effect, a cerebral microthrombi formation assay was used to assess possible leakage of enwrapped thrombin from the DNA nanocage. As shown in FIG. 27D, no microthrombi were detected in MDA-MB-231-comprising mice treated with thrombin-loaded DNA-nanocages, although free thrombin did induce microthrombi formation. Thus, the DNA nanocage designed to induce tumor infarction demonstrates a good safety profile. These findings are in line with the lack of a sequence motif in the DNA nanostructures because this motif was implicated in the DNA-mediated signaling pathway for inflammation and autoimmunity This disclosure provides for methods to evaluate engineered T cell survival in vivo to establish feasibility of using engineered T cells to kill cancer cells and to activate engineered T cells in the presence of a cancer cell.

The NSG mouse model is used to assess the in vivo antitumor effect of control and transduced engineered T cells checkpoint inhibitor modulators. 8-10-week-old male and female NSG mice are injected i.p. with either MDA-MB-231 breast cancer cells (CD133+ and MSLN+) or A549 lung cancer cells (GD2+ and EGFR+) resuspended in Matrigel (BD Biosciences). Tumors are induced by subcutaneous injection of 2×10^6 tumor cells, and mice are treated by IV injection of T cells as indicated. For re-challenge experiments, mice are injected subcutaneously with 0.5×10^5 cells in the flank opposite to the site of the previously rejected tumor. All experiments are randomized and blinded. Tumor growth and condition of mice are monitored every other day. For antitumor efficacy, six to eight mice per group are used. To further assess the potency of PD-L1 or CTLA4 engineered T cells, mice are treated with a mixture comprising subcutaneous MDA-MB-231 tumors with PD-L1 or CTLA4 engineered T cells. PD-L1 or CTLA4 engineered T cells induced superior antitumor immunity as compared with mice receiving engineered T cells without PD-L1 or CTLA4 peptide. PD-L1 or CTLA4 engineered T cells is either stimulated with anti-CD3 antibody, anti-CD3 plus anti-CD28 antibodies or with anti-CD3 antibody plus recombinant PD-L1 and resulting IFN-γ release is measured by ELISA. PD-L1 or CTLA4 engineered T cells are either left unstimulated or stimulated with anti-CD3 antibody or with anti-CD3 antibody plus recombinant PD-L1 and phosphorylation of AKT is measured by flow cytometry or Western blotting. Tumor samples are collected after adoptive transfer (from day 1 to day 10) to check T cell infiltration into the tumor by CD3 staining. Peripheral blood samples are collected to analyze T cell activities by flow cytometry and IFNγ, IL-2 and PD-1 staining.

This disclosure provides for methods of the characterization of immune cells in tumor draining lymph nodes (TDLNs) to demonstrate feasibility of using engineered T cells to kill cancer cells and to activate engineered T cells in the presence of a cancer cell.

The TDLN microenvironment has a significant modulatory influence on host immune responses for tumor rejection or tumor tolerance and metastasis. To determine whether DNA nanostructure module 1 can induce ICD and break tumor tolerance, the TDLN environment is examined by analyzing various cell types in the lymph nodes, including DCs (CD11c/CD80, CD86), activated T cells (CD8/CD69 and CD4/CD69), Treg or suppressive/exhausted T cells (CD4/CD8/CD25/KLRG1/PD1/Foxp1), and MDSC (CD11b/Gr1/Lyc6). Lymph nodes are removed 2 to 7 days after intra-tumoral injection to examine the presence of A20 tumor cells and characterize various types of immune cells and their functional status. Fluorescence microscopy is performed on frozen tissues or flow cytometry-based cell phenotyping of suspension cells for these analyses.

Figure 27:
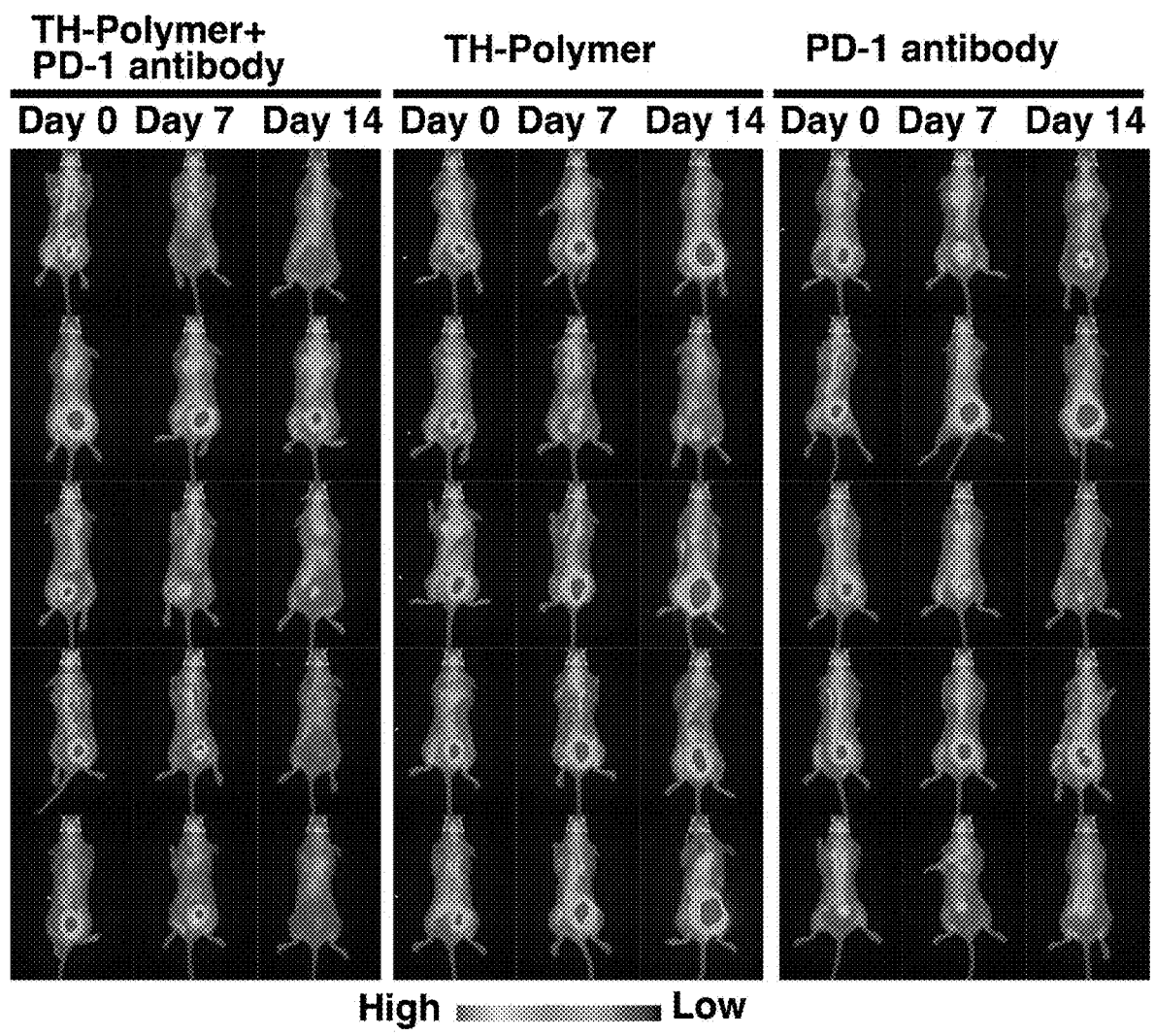
FIG. 27. Combinatory effect of DNA-TH-CpG and anti-PD1 antibody on tumor suppression. A tumor was formed 10 days post sub-Q injection of A20-iRFP cells. Different groups of tumor-comprising mice were treated with intratumor injection of 1) DNA-TH-CpG followed by anti-PD1 antibodies on both day 2 and day 4; 2); DNA-TH-CpG (Day 0) and 3) anti-PD1 antibodies. Tumor growth was monitored with LI-COR Pearl Small Animal Imaging system, and the images were linked and quantified with ImageStudio software.
Figure 28:
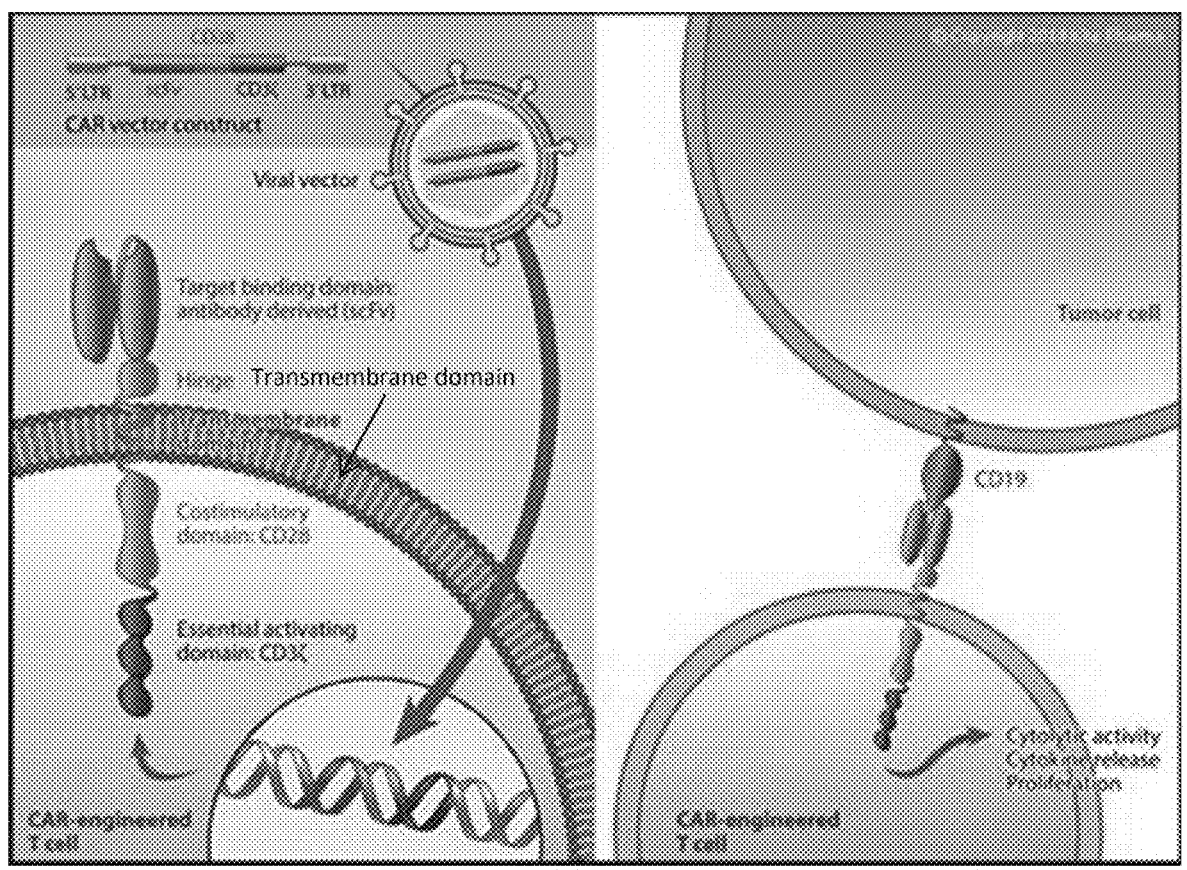
FIG. 28. The strategy for CAR T cell therapy. A viral vector is transfected into a T cell to produce a CAR construct expressed on or about the surface of a T cell. The scFv of the CAR binds to its cognate ligand (e.g., CD19), bringing the T cell into local proximity with the tumor cell and activating the T cell to release cytolytic activity including cytokine release and T cell proliferation. In some embodiments, the engineered T cells of this disclosure can comprise a targeting molecule and/or agent which binds to a cognate ligand resulting cytolytic activity including cytokine release and T cell proliferation.
Figure 29:
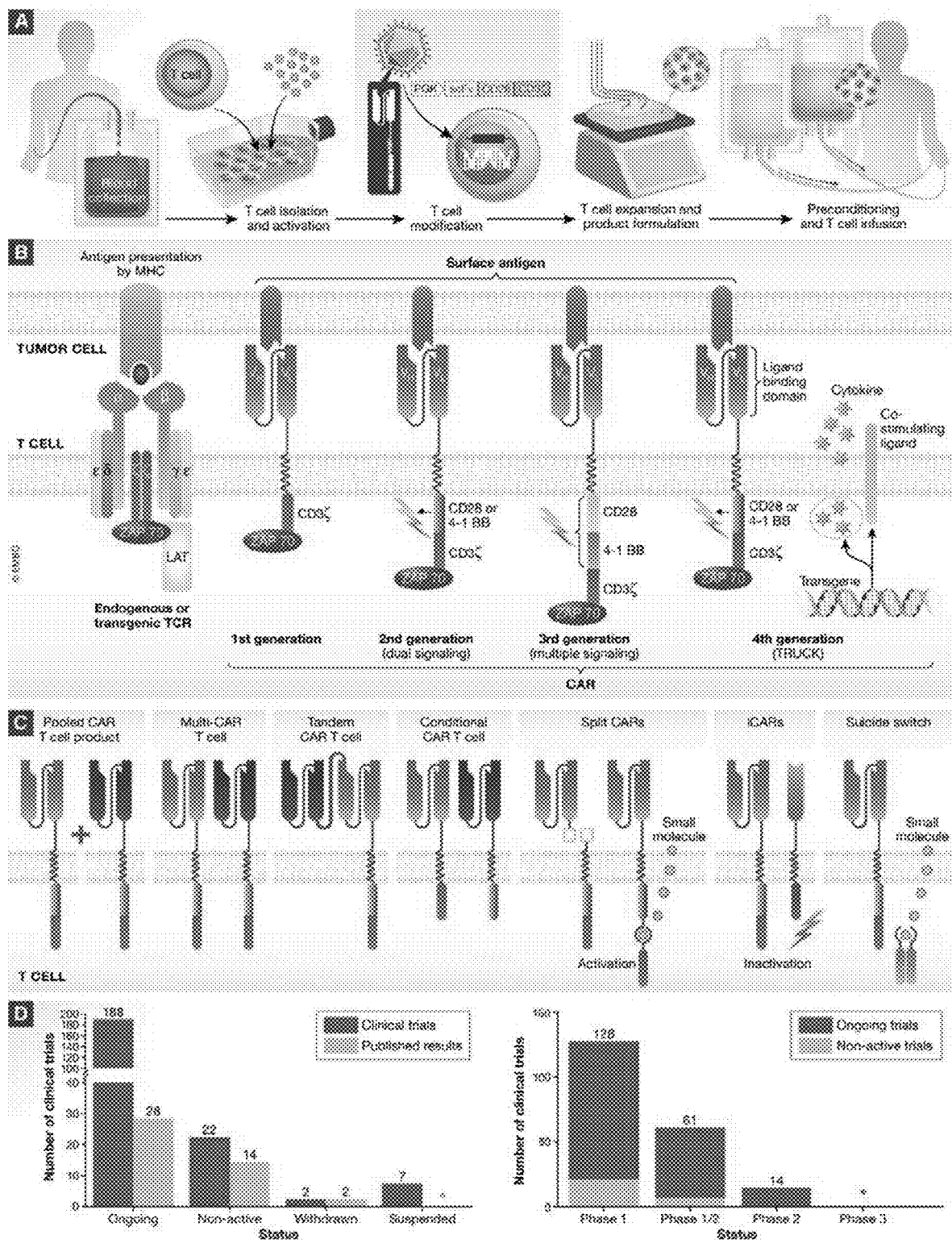
FIG. 29A depicts the autologous T cell isolation and activation strategy of T cells from a subject, engineering said T cells, and administering the engineered T cells into the subject.
FIG. 29B shows optional CAR constructs of this disclosure.
FIG. 29C shows optional targeting agent constructs of this disclosure.
FIG. 29D shows a summary of the number and status of Clinical Trials using DNA-CAR T cells in cancer immunotherapy.

This disclosure provides for the combination of DNA-TH and anti-PD1 for elicitation of anti-tumor immunity to demonstrate feasibility of using engineered T cells to kill cancer cells and to activate engineered T cells in the presence of a cancer cell. The DNA-TH nanostructure assembled with CpG was demonstrated to show anti-tumor immunity. An iRFP expressing A20 line was created, in which iRFP is a near infrared (NIR) protein, which allows assessment of tumor growth in real-time. Here, 15 mice injected with A20-iRFP tumor cells subcutaneously in the back developed palpable and imaginable tumor lump (3-6 mm in diameter) within 8 days. Since PD-L1 is highly expressed in A20 cells, these mice were randomly grouped and given with intra-tumor injection of 1) DNA-TH-CpG followed by anti-PD1 antibodies. 2); DNA-TH-CpG and 3) anti-PD1 antibodies. As shown in FIG. 27, the combination of DNA-TH-CpG with anti-PD1 antibody resulted in a significant reduction in tumor size whereas in the other groups many mice showed enlarged tumors post the treatment. Furthermore, the mice with tumor regression observed in the combination treatment group were also resistant to the lymphoma re-challenge at a different site 30 days later, indicating their development of systemic anti-tumor immunity.

This disclosure provides for methods to evaluate the resistance to immune repression of engineered T cell with peptide inhibitor to demonstrate enablement of using engineered T cells to kill cancer cells and to activate engineered T cells in the presence of a cancer cell.

Immunodeficient NSG mice are subcutaneously inoculated with 1×10^6 MDA-MB-231 cells. When tumors are approximately 200 m3, mice are given 10^7 CAR-expressing engineered T cells via intravenous administration. Tumor volume is monitored by caliper measurements twice weekly, and at different time points, tumor-comprising mice are sacrificed for mechanistic studies using immunoblotting and/or flow cytometry. All experiments had a minimum of 5 mice per group and were performed at least three times. The phosphorylation status of various proximal T-cell signaling entities was assessed by immunoblotting (pERK, pAkt, pLek) using engineered T cells and plate-bound CD3/CD28 antibodies. Engineered T cells were also exposed to mesothelin-coated beads as described and harvested after 20 minutes. For ex vivo T-cell analysis, tumors were harvested from mice, microdissected, digested, and used in ex vivo tumor assays as described previously.

To confirm engineered T cells can elevate endogenous immune response, in vivo CTL proliferation of leukocytes is measured by 5-bromo-2-deoxyuridine (BrdU) incorporation according to the manufacturer's specifications. BrdU is added to the drinking water and provided throughout the duration of the study. Four mice per group is killed, and spleens and livers is harvested 20 days after engineered T cell injection.

To evaluate whether engineered T cells with overcome Treg repression in vivo, Tregs are isolated from spleens of naive wild-type (WT) mice by MACs column selection to more than 90% purity. CD8 T cells from WT mice are isolated by MACs column selection and transduced with and labeled with 1M carboxyfluorescein succinimidyl ester (CFSE). T and NK cell-depleted splenocytes from WT mice are used as APCs. A total of 5×10^4 CFSE-labeled CD8 T responder cells is stimulated with 1.5×10^5 APCs in RPMI-c and 1 g/mL purified anti-CD3. Where indicated, 1×10^5 Tregs from WT mice and/or anti-TGFβ or control IgG at 0.5 g/mL is added to the culture. Four days later, cells are harvested and proliferation is determined by CFSE dilution. Cell supernatant is harvested for IFN-γ levels as determined by IFN-γ ELISA.

To assess in vivo suppression, 10^6 Tregs isolated from breast cancer-comprising mice (25 days after MDA-MB-231 injection) is transferred into WT mice that had been injected with 1×10^4 engineered T cells 7 days before the adoptive transfer. Anti-TGFβ or control rat IgG (200 g/dose) is given every other day from day 3 to day 14 after engineered T cell injection. Thirteen days after the engineered T cell injection, spleens and livers are harvested. Leukocytes from livers are isolated with discontinuous Percoll gradient centrifugation. Cells are stimulated for 5 hours in vitro with CD3 (1 μg/ml) and CD28 (1 μg/ml), and labeled with CD8-FITC, IFN-PerCP, and CD45.1-allophycocyanin, and 100 000 live events is gated to determine the percentage of IFN-producing CD8 CTLs.

In vivo CTL proliferation of leukocytes is measured by 5-bromo-2-deoxyuridine (BrdU) incorporation according to the manufacturer's specifications. BrdU is added to the drinking water and provided throughout the duration of the study. Four mice per group is killed, and spleens and livers are harvested 20 days after engineered T cell injection.

This disclosure provided for a method for an in vivo ECM degrading T cell invasion assay to demonstrate feasibility of using engineered T cells to kill cancer cells and to activate engineered T cells in the presence of a cancer cell.

Figure 54:
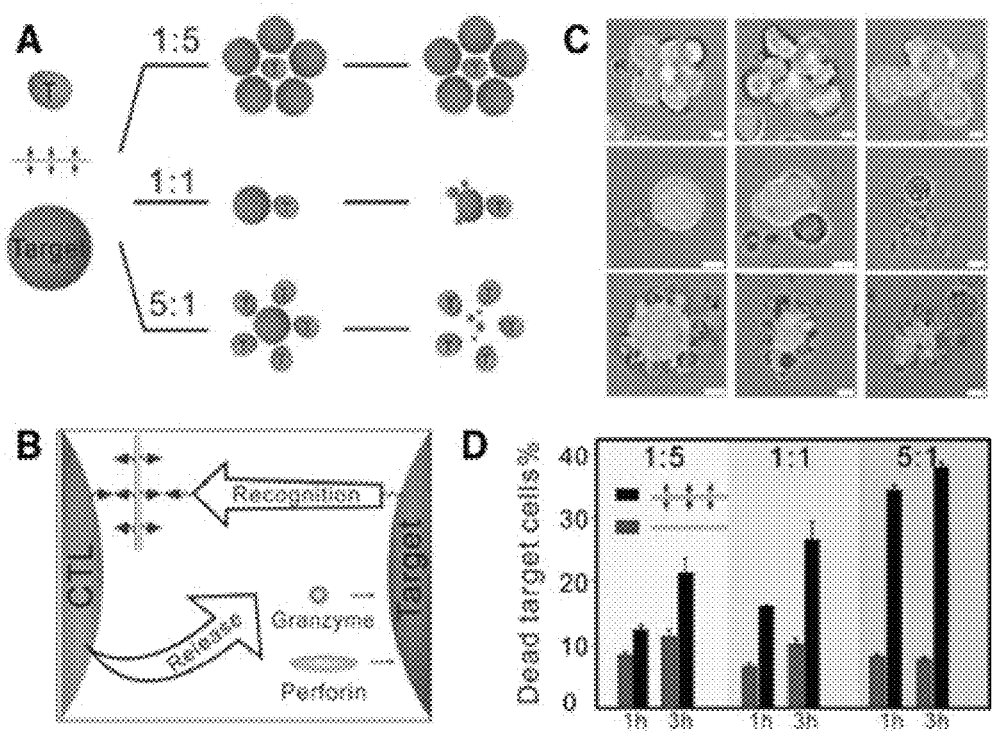
FIG. 54A: DNA origami-assisted CD8+ T cells targeting and killing of leukemia cells.
FIG. 54B: Scheme and principle of cell-killing assay at different effector to target ratios.
FIG. 54C: Fluorescence image overlays of primary CD8+ T cells and their interaction with L1210 cells. Scale bars: 10 nm.
FIG. 54D: Cell survival of target cell at different effector to target (E:T) ratio.

In some embodiments, this disclosure provides for a method of using DNA origami assisted lymphocytes to kill tumor cells. CD8+ cytotoxic T lymphocyte (CTL) cells were first activated by CD3 and CD28 signal pathways resulting in perforin granule release from the CTL. The perforin/granzyme cell pathway requires direct contact between target cancer cells ("T") and effector cells ("E"), as shown in FIG. 54. CTL without an antigen in target cell (L1210) surfaces therefore cannot recognize target cells. However, when assisted by a DNA origami nanostructure comprising CD8+, different mixtures of cell patterns were observed in a dose-dependent manner (FIG. 54), which demonstrated that the DNA origami facilitated interactions between effector and target cells. Thus, the DNA origami nanostructure can interact with a T cell surface to kill tumor cells. In some embodiments, the DNA origami nanostructure is that described in U.S. Pat. No. 8,440,811, herein incorporated by reference.

Example 3: Adaptor T Cell (SNAP_GS4_TM_41BB_CD3z_GFP) Production

A. Preparation of Lentivirus Supernatant.

Slitted 293T cells cultured on 10% FCS/DMEM/PS medium were trypsinized 10-15 seconds overnight. Next, 9 to 10 million overnight culture of 293 T cells were plated onto each 10-cm poly-lysine coated plate using 10 ml of 10% FCS/DMEM medium. The cells were allowed to let sit in a lamellar hood for 10 to 20 minutes to allow the cells to evenly distribute on the plate surface. The cells were then carefully transferred to the C02 incubator. The cells were allowed to grow for 4 to 6 hours to 80% confluence. The growth medium was removed by aspiration. The cells were then quickly overlayed with pre-warmed 5 ml of OPTI-MEM medium and quickly put back into the incubator.

DNA/Lipofectamine 2000 complexes were prepared from the following: 1.5 ml OPTI medium, pLenti-EF1a_SNAP_GS4_TM_41BB_CD3z_GFP 13 μg, pMD2.G 6 μg, and psPAX2 9 μg.

In a separate tube was added 60 μl of Lipofectamine was added in 1.5 ml OPTI medium.

The two tubes were combined and mixed and incubated in a hood for 20 minutes. Next was added the DNA/Lipofectamine mixture to the Cells dropwise. The plate was gently swirled to distribute the mixture throughout the plate. After 6 hours of transfection, the DNA mixture was removed and add 5 ml of pre-warmed 5% FCS/DMEM/5 mM sodium butyrate viral production medium was added to collect the virus particles. On the second day, another 5 ml of medium was added. A total of 10 to 12 ml of medium was added per plate. The supernatant was harvested after 48 hours of culturing. Care was taken to ensure that the medium did not turn yellow because the half-life of the virus is less than 10 minutes at pH 6.0 or 8.0

The supernatant was centrifuged at 1500 rpm for 5 minutes to remove debris and filter the supernatant through a 0.45 μM filter. The supernatant was centrifuged at 25,000 rpm for 2 hr at 4° C. The supernatant was then gently aspirated. The tubes were inverted on a paper towel for 4-5 minutes to remove most of the remaining liquid that inhibits infection efficiency and T cell proliferation. Next, was added 100 μl of 1% FCS/PBS (Ca2+/Mg2+ free PBS) on the tube and the tube was then sealed and vortexed at the lowest speed on a table-top vortexer for at least 2 hr at 4° C. The resuspended virus was centrifuged at 5000×g for 5 min at 4° C. to remove debris. Next, the supernatant was flash frozen on dry ice and stored at −80° C.

B. Infection of Engineered T Cells.

One day before infection, engineered Jurkat T cells were seeded at a concentration of 1×10^6/ml. Virus was added in 0.5 ml of 5% FCS/RPMI medium/(8 µg/ml polybrene) to Jurkat T cells in a 24-well plate and centrifuged for 1 hr at 1800×g at room temperature. After at least 4 to 5 hours of incubation in the incubator, 2 ml of T cell medium was added. The infection was checked every 24 hours, with repeated infections as necessary until infection was confirmed.

Example 4: NFAT-Luc Jurkat Activation Assay

This protocol was used for end-point readings using a luminometer with an injector. This protocol can be adapted for use with kinetic measurements or a luminometer with a manual set-up.

Cells were centrifuged at 1000-1500 rpm (RC 200-300 g) for 5 min. Supernatant was removed and the Jurkat-Lucia NFAT cells at 2×10^6 cells/mL were resuspended in fresh, pre-warmed growth medium. Next, was added 20 µL of sample/well including PMA (50 ng/mL) with ionomycin (3 µg/mL) or concanavalin A (10 µg/mL) as positive control and endotoxin free water as negative control (use new tips between). Next, was added 180 µL cell suspension (~400,000 cells)/well of 96 well plate. Cell suspension was in RPMI or IMDM. Next, the plate was incubated at 37° C. in C02 incubator for 18-24 hours. The luminometer was set with the following parameters: 50 µL injection, end-point measurement w/ 4 second start time, and 0.1 second reading time. Samples were pipetted (10-20 µL/well) into 96 well white (opaque) OR black plate, OR a luminometer tube.

Example 5: BG and DNA Oligonucleotide Conjugation

The DNA oligonucleotide was dissolved in HEPES buffer to prepare 1 mM stock solution.

Fresh 50 mM TCEP was prepared in 10 mM pH 7.4 sodium HEPES buffer and adjusted pH to ~7.0 using NaOH. Next, 10-fold pH 7.0 TCEP (50 mM stock) 10 µL was added into 1 mM DNA stock 50 µL, shaken at room temperature for 2-3 hours, and store in a 4° C. refrigerator. Next was added 5 fold BG-maleimide (dissolved in DMF, 50 mM) 5 µL into deprotected thiol-modified DNA (In HEPES buffer, 1 mM) 50 µL. Then, a defined volume of PBS buffer was added to reach final DNA concentration of 200 µM. The reaction was allowed to proceed overnight at room temperature. The reaction was washed with PBS buffer (using 3 kD Amicon centrifugal dialysis filters) at 13000 rpm for 20 min for 3 times. The products were quantified by adsorption of 260 nm. BG-DNA was stored in −20° C. freezer.

Example 6: BG-DNA and Jurkat T Cell Conjugation

Adaptor T cells expressing the engineered CAR with a SNAP-Tag™ adaptor protein were washed two times with PBS buffer, then resuspended 2 million cells in 50 µL DPBS buffer of defined concentration of BG-DNA. The reaction was allowed to proceed for 30 min at room temp. The reacted cells were washed 2 times with DPBS buffer, then resuspended in 1 µM BG-T 20 (or A20) 50 µL. The reaction was allowed to proceed for 30 min, then washed 2 times again. The conjugated T cells were imaged in confocal microscope or flow cytometry.

Example 7: Conjugating the Targeting Molecule, Anti-PD-L1 Antibody ("aPD-L1") with a DNA Oligonucleotide Thiol-modified DNA oligo deprotection (TCEP cleavage, purification and storage)

DNA oligonucleotide was dissolved in water to prepare a 10 mM stock. Next, fresh buffer was prepared: 50 mM TCEP in 10 mM pH 7.4 sodium HEPES buffer and adjusted pH to ~7.0 using NaOH. Next, 250 µM, 2 mL DNA deprotection mix was prepared from a solution of 10 mM DNA stock 50 µL, 20-fold excess of pH 7.0 TCEP (50 mM stock) 200 µL was added. Next, 10 mM sodium HEPES buffer was added to reach the final volume and shook at room temperature for 2-3 hours. The mixtures was then washed with water using a centrifugal dialysis membrane (3 kD Ultracel 4 mL Amicon) at 4000 rpm for 45 min for 3 times. (at a temperature of 4-10° C.). The deprotected thiol-DNA oligos were able to be stored in −20° C. freezer for up to one month.

II. Protein Preparation and Protein-DNA Conjugation

The SH-T20 was reacted with the crosslinker SPDP (ThermoFisher). A solution of SPDP (50 mM in DMSO), 10 µL, was added into 100 µL 1 mM DNA. The reaction was performed 37° C. for 30 min Excess SPDP crosslinker was removed by centrifuge 130000 rpm 20 min 3 times with 3 k filter tubes, as described above. The antibody solution was prepared by in pH 7.4, 10 mM sodium PBS buffer at a concentration ~50 µM for storage. The NHS-DNA was mixed with aPD-L1 at a ratio of 50:1, and the reaction allowed to proceed overnight at room temperature. The excess DNA oligonucleotides were removed by centrifugation 3000 g 10 min 3 times with a 100 KDa filtration dialysis tube (Amicon).

Example 8: Test Killing Efficiency of Engineered T Cell to Target Cells

Engineered T cells were conjugated with BG-A20/BG-T20 as described above before. The reaction solution was centrifuged at 1500 rpm 2 min 2 times, the pellet isolated, and the supernatant removed by pipette to remove unreacted DNA. Next, complementary DNA (T20 or A20) covalently conjugated to the modified antibody was added. In some embodiments, aptamers are used instead of the antibody. The complex was hybridized at room temp for 30 min. The engineered T cells were then centrifuged at 1500 rpm 2 min 2 times, the pellet isolated, and the supernatant removed by pipette to remove unreacted targeting molecules. Next, target cancer cells were conjugated with the engineered T cells at a ratio of 1:5 in RPMI 1640 medium (serum inactivated). The complex was incubated in a cell incubator with 5% C02 for 24 h. The luciferase level was then monitored to test the engineered T cell activation level in the presence of the cancer cell.

Example 9: Lenitviral Transfer of Plasmid Encoding an Engineered CAR

All reference to "Jurkat cells" indicate Jurkat-Lucia™ NFAT cells (Invivogen, San Diego, CA).

As shown in FIG. 42A-C, lentiviral transfer plasmid encoding one embodiment of an engineered CAR was achieved using an expression cassette comprising long terminal repeat (LTR), human elongation factor 1 alpha promoter (EF1α), human CD8-leader sequence (L), benzylguanine binding protein SNAP-Tag™ (SNAP), 4 repeats of the peptide linker GGGS-GGGS-GGGS-GGGS (4×GS) (SEQ ID NO: 14), human CD8 transmembrane Domain™, human 4-1BB, human CD3ζ and GFP. As shown in FIG. 42B, the procedure of transferring lentiviral vector into Jurkat T cells was as follows: NFAT-Luc Reporter T lymphocytes were used as a model to study T cell activation. Jurkat-Lucia™ NFAT cells were derived from the human T lymphocyte-based Jurkat cell line by stable integration of an NFAT-inducible Lucia reporter construct. The Lucia gene, which encodes a secreted coelenterazine-utilizing luciferase, was driven by an ISG54 minimal promoter fused to six copies of the NFAT consensus transcriptional response element. Jurkat-Lucia™ NFAT cells were used for the study of NFAT activation following stimuli treatments by monitoring Lucia luciferase activity. Levels of Lucia luciferase were readily measurable in the cell culture supernatant when using QUANTI-Luc™, a Lucia luciferase detection reagent. As shown in FIG. 42C, flow cytometry results show that GFP positive Jurkat cells transduced with lentivirus encoding engineered CAR (FIG. 42C) were isolated and sorted by flow cytometry.

Example 10: Conjugating Functional Agents to Engineered T Cells Comprising an Engineered CAR Domain Engineered T cells comprising an engineered CAR which further comprises an adaptor protein were able to conjugate a protein tag which was covalently conjugated to a first oligonucleotiode, and then hybridize a second oligonucleotide comprising a functional agent to the first oligonucleotide. In some embodiments, the functional agent is a targeting agent. In some embodiments, the functional agent is a fluorophore.

As shown in FIG. 43A-D, adaptor Jurkat T cells conjugate BG (benzoguanine)-modified ssDNA (polyT) and hybridize with ssDNA (Alexa647-labelled polyA). The first oligonucleotide comprises the sequence of a polyT strand (15 nt). The second oligonucleotide comprises the sequence of a polyA strand (15 nt). The Alexa647-labelled polyA was obtained from commercial vendors (IDT). The BG-modified oligo was prepared as described above. As shown in FIG. 43B, confocal imaging of adaptor Jurkat T cells were linked with a functional molecule (e.g., Alexa647 fluorophore) through immobilization of a DNA strands (e.g., a first oligonucleotide and a second oligonucleotide). The GFP signal represents the starting material, the Alexa647 signal represents the location of the product. The merged image identifies that the fluorophore-labelled oligonucleotide selectively hybridizes to the first oligonucleotide on the adaptor T cells (engineered T cells) which were conjugated with BG-polyT. Alexa 647 and GFP double positive cells indicate DNA strands have successfully conjugated on Jurkat cells. BG-Alexa 647 was used as a positive control.

FIG. 43C shows the fluorescence intensity of Alexa 647 on Adaptor Jurkat T cells (engineered T cells). Alexa647-polyA intensity of Jurkat T cells were analyzed by flow cytometry. Alexa647 intensity of Jurkat with adaptor was higher than Jurkat T cells without adaptor structures, indicating that the second oligonucleotide comprising a functional agent was immobilized to the engineered T cell. As shown in FIG. 43D, the ratio of Alexa 647 positive Adaptor Jurkat T cell to that of GFP is displayed for control (adaptor Jurkat+polyT-Alexa647) cells to the hybridized cells (Adaptor Jurkat+BG-polyA+poltT-Alexa). The ratio increased when higher concentration BG-polyA was add to conjugate DNA, demonstrating that the functional agent was associated to the adaptor T cells (engineered T cells) via hybridization of the first oligonucleotide to the second oligonucleotide.

Example 11: Engineered T Cells are Activated in the Presence of a Target

Figure 44A:
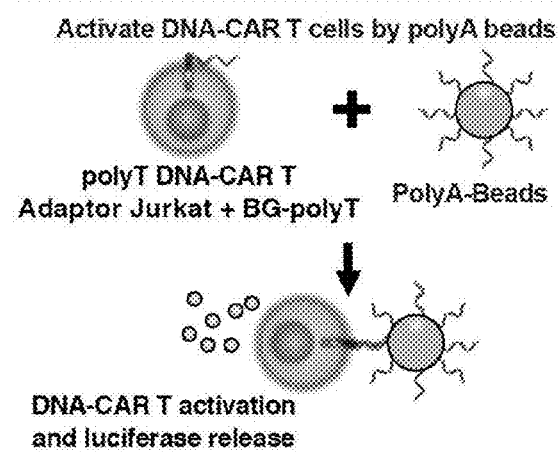
FIG. 44A: Adaptor Jurkat T cell conjugation to BG-polyT to generate polyT engineered T cells.
Figure 44B:
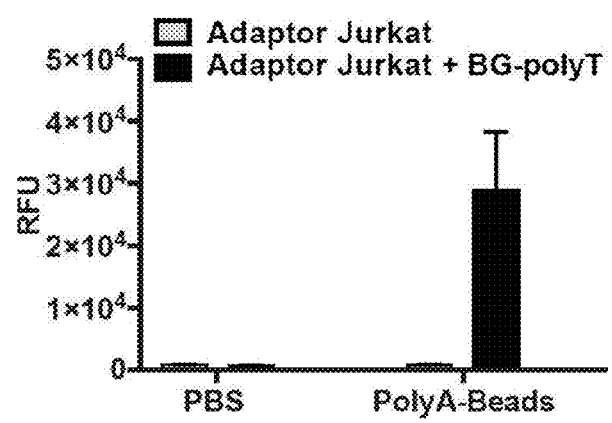
FIG. 44B: Monitoring T cell activation of released luciferase in the presence of polyA-coated agarose beads shows the T cells are activated in the presence of a model target.

As shown in (new FIG. 44A-B), the engineered T cells were activated upon hybridization to a target. The model target was a polyA-coated agarose bead (15 microns in diameter). The polyA-coated agarose beads were prepared by standard methods to create a model cancer cell target. NHS-activated agarose beads conjugated with $NH_2$-polyA ("polyA beads") (polyA sequence was 15 nt long) and engineered T cells were incubated for 12 hours. T cell activation levels were monitored by relative luminescence units (RLU) (also referred to herein as relative fluorescence units (RFU)) of released luciferase in the cell medium, as per the manufacturer's instructions for measuring RLU. As shown in FIG. 44B, engineered T cells were activated by DNA strands on agarose beads surface only when the engineered T cell comprises a first oligonucleotide which was connected to the adaptor protein. In addition, T cell activation did not occur in PBS control solution, indicating that the engineered T cells were activated in the presence of a model target for a cancer cell.

Figure 45A:
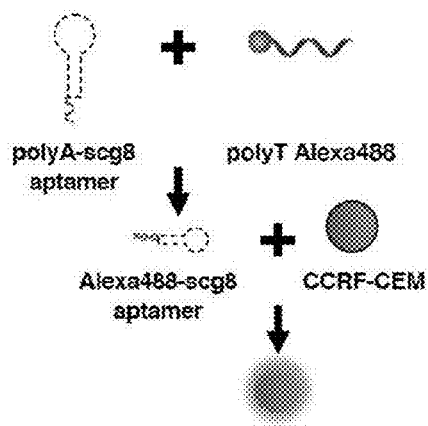
FIG. 45A: Procedure of conjugating fluorescent aptamers to engineered T cells.
Figure 45B:
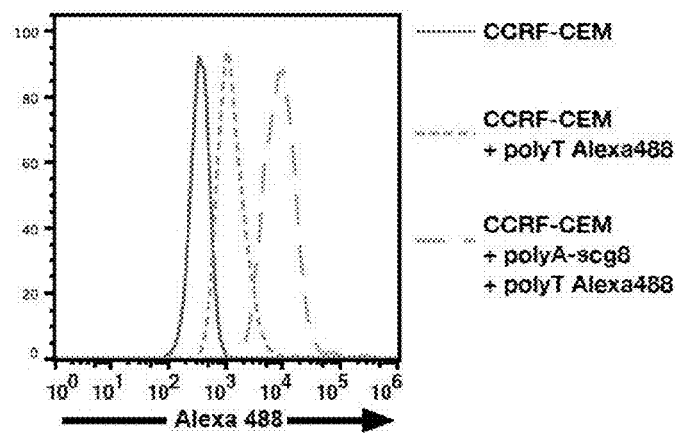
FIG. 45B: Fluorescence intensity of Alexa488-labelled scg8 aptamers in the presence of CCRF-CEM cancer cells showing that the dye labelled aptamer can recognize the CCRF-CEM successfully.
Figure 47:
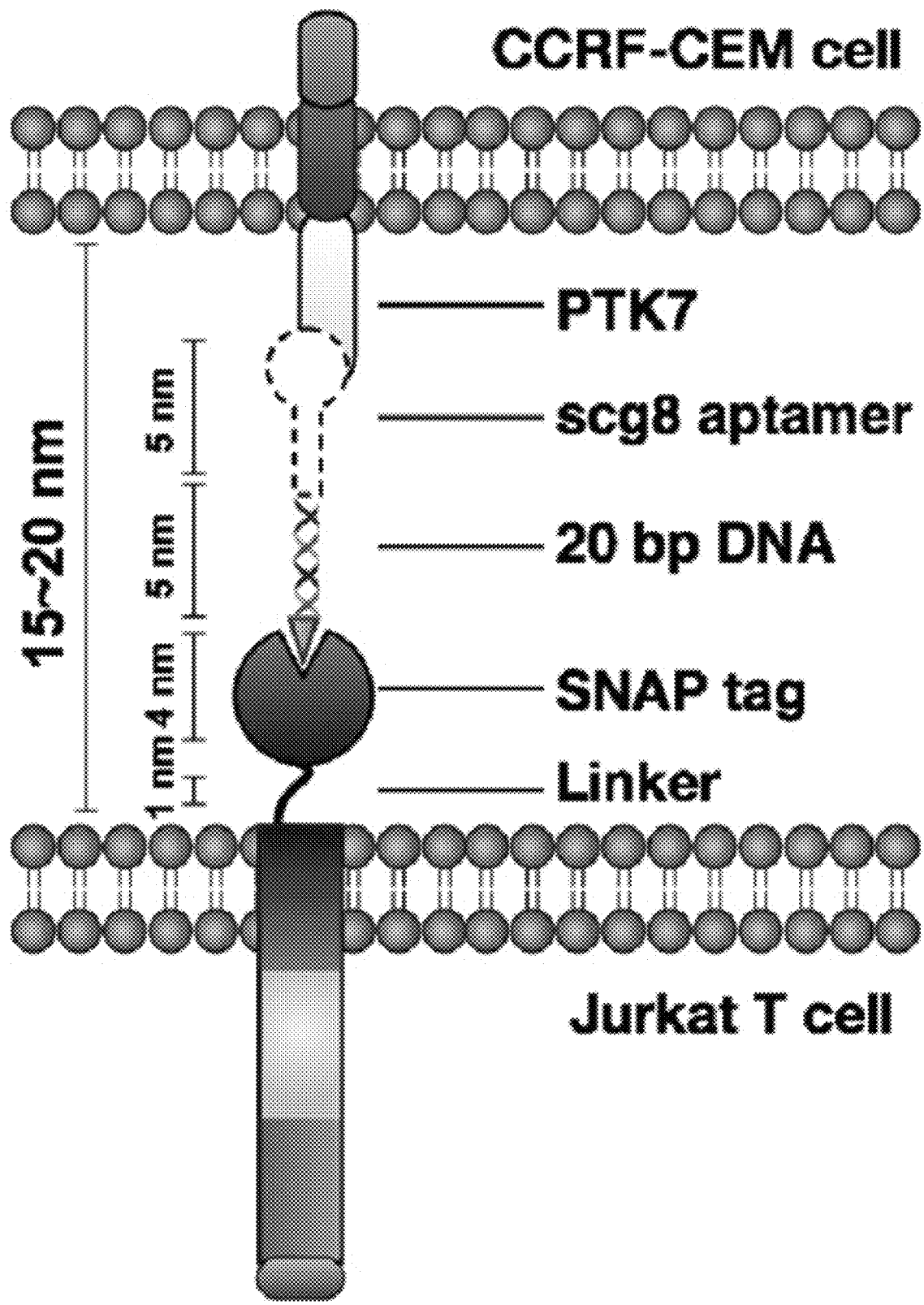
FIG. 47: Relative dimensions of engineered T cell to CCRF-CEM cancer cell depicting the involved components of the cell-cell interaction.

Example 12: Engineered T Cells were Activated in the Presence of a Target Cancer Cell As shown in FIG. 45A and FIG. 45B, engineered T cells comprising cancer cell-specific aptamers were activated in the presence of a cancer cell. The engineered T cells comprising ssDNA of polyT were prepared as described above. A polyA-scg8 aptamer was prepared using the methods described herein. The target cancer cell was CCRF-CEM cells. CCRF-CEM is a T lymphoblastoid line obtained from the peripheral blood of a 4 year old Caucasian female with acute lymphoblastoid leukemia which targets protein tyrosine kinase 7 (PTK7) on CCRF-CEM cell membrane. The construct for the engineered T cell is depicted in FIG. 47, which depicts the relative spacing differences between the linker domain, the SNAP-Tag™ protein, the first and second oligonucleotides hybridized, the aptamer, and the total cell-cell separation. The distances were approximately 1 nm for GS-linker, 4 nm for SNAP-Tag™, 5 nm for 20 double-stranded DNA, and 5 nm for scg8 aptamer, with the total cell-cell distance about 15 nm to about 20 nm separation. The inventors have recognized and designed constructs for, in some embodiments, the GS spacer and/or the first and second oligonucleotide lengths can be modulated to increase or decrease the total cell-cell distance to enhance the potency of the engineered T cell in the presence of a cancer cell.

PolyA-scg8 aptamers hybridized with polyT-Adaptor488 to produce Alexa488-scg8. The binding efficacy of scg8 was analyzed by flow cytometry. As shown in FIG. 56B, the fluorescence intensity of Alexa488-scg8 labeled CCRF-CEM demonstrates that Alexa488-scg8 recognized the target cancer cell CCRF-CEM. Thus, engineered T cells comprising targeting molecules (e.g., the scg8 aptamer) bind to target cancer cells.

Figure 46A:
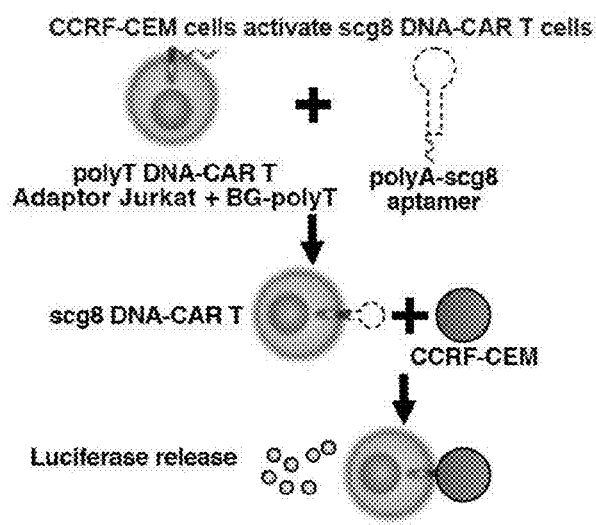
FIG. 46A-FIG. 46B: Activation of scg8 aptamer-comprising T cells by CCRF-CEM cancer cells.
Figure 46B:
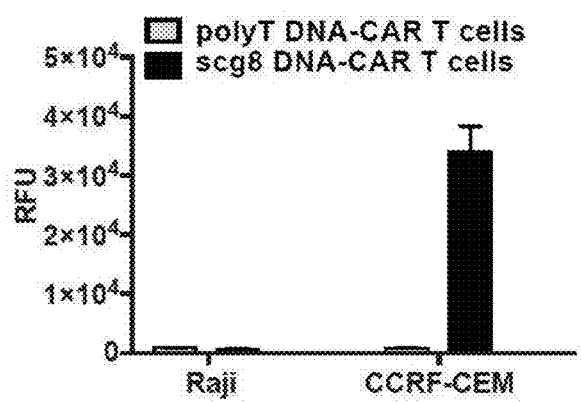

As shown in FIG. 46A-B, CCRF-CEM cancer cells activated engineered T cells. As shown in FIG. 46A, adaptor Jurkat T cell (engineered T cell) conjugated with BG-polyT generated polyT engineered T cells. CCRF-CEM cells and scg8 DNA-CAR T cells were incubated for 12 hours, after which T cell activation levels as measured by luciferase activity were measured by relative luminescence units (RLU). As shown in FIG. 46B, engineered T cells were activated by cancer cells, whereas the engineered T cells were not activated in the presence of non-cancerous cells ("Raji").

Example 13: Engineered T Cells are Activated in the Presence of a Target Tumor Cancer Cell As shown in FIG. 39, engineered T cells comprising targeting molecules which also comprised a tumor cell-specific aptamer were activated in the presence of said tumor cell. The cancer tumor cells were MDA-MB-231, which was a Programmed death-ligand 1 (PD-L1) positive human breast cancer cell line; A549, which was an epidermal growth factor receptor (EGFR) positive lung cancer cell line; and MCF7, which was a Mucin 1 (MUC1) positive breast cancer cell line.

Figure 39A:
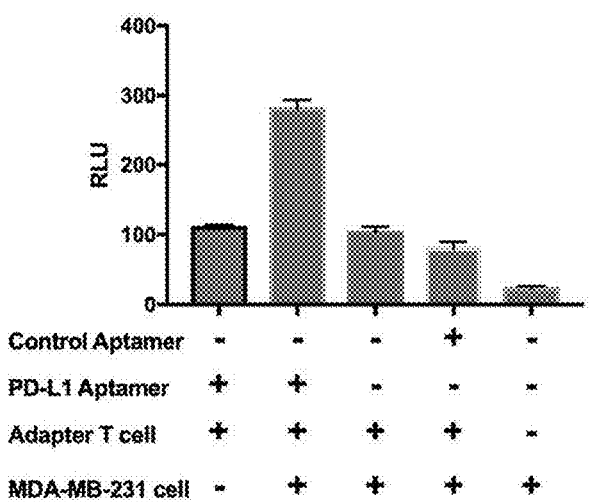
FIG. 39A: Luciferase activity levels (indicating T cell activation levels) of MDA-MB-231 breast cells and anti-PD-L1 engineered T cells incubated for 12 hours showing that anti-PD-L1 engineered T cells can be activated by MDA-MB-231 cells.

Engineered T cells comprising aptamers were prepared as described herein. The aptamer sequences used were those described herein, including those in Table 1 and FIG. 40. MDA-MB-231 breast cells and anti-PD-L1 comprising engineered T cells were incubated for 12 hours, after which T cell activation levels as measured by luciferase activity were measured by relative luminescence units (RLU). The "+" indicates the species was present, and "−" indicates the species was absent for each column on the bar graphs. The second column in FIG. 39A shows that anti-PD-L1 engineered T cells were activated by MDA-MB-231 cells. Only low levels of luciferase release were observed in T cell alone, tumor cell alone, T cells without aptamer or with T cells with a control aptamer group. The results demonstrate that engineered T cells were activated in the presence of a solid tumor cell.

Figure 39B:
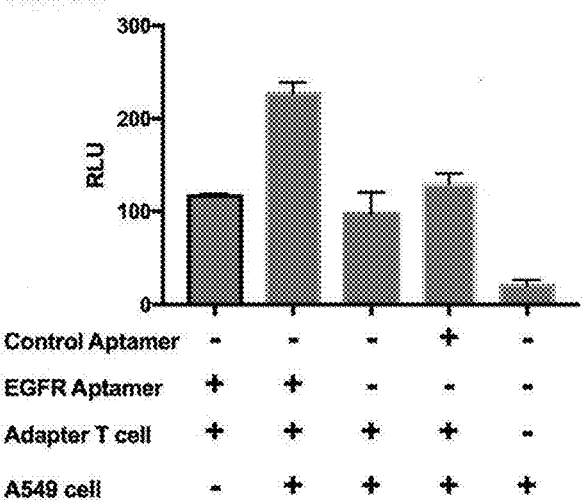
FIG. 39B: Luciferase activity levels (indicating T cell activation levels) of A549 lung cancer cells and anti-EGFR engineered T cells incubated for 12 hours showing that anti-EGFR engineered T cells can be activated by A549 tumor cells.

A549 lung cancer cells and anti-EGFR engineered T cells were incubated for 12 hours after which T cell activation levels as measured by luciferase activity were measured by relative luminescence units (RLU). As shown in FIG. 39B, the second column shows that anti-EGFR engineered T cells were activated by A549 cells. Low levels of luciferase release were observed in T cell alone, tumor cell alone, without aptamer or with control aptamer group. The results demonstrate that engineered T cells were activated in the presence of a solid tumor cell.

Figure 39C:
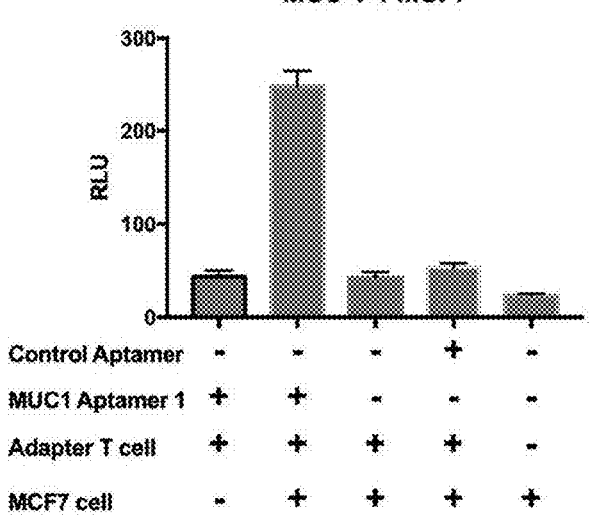
FIG. 39C: Luciferase activity levels (indicating T cell activation levels) of MUC1-1 engineered T cells incubated with MCF7 tumor cells showing that anti-MUC1-1 engineered T cells can be activated by MCF7 tumor cells.
Figure 39D:
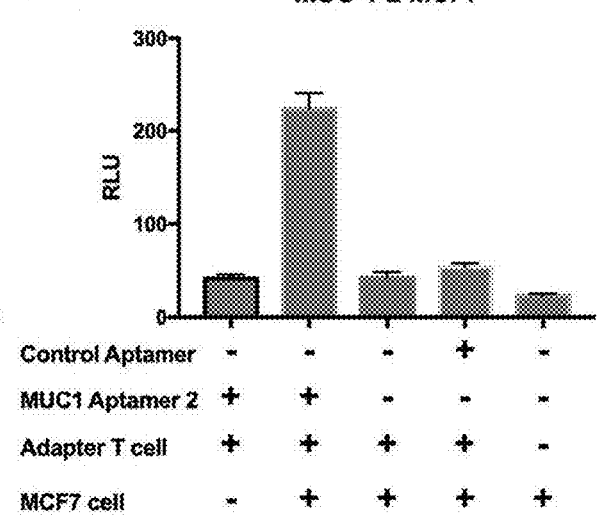
FIG. 39D: Luciferase activity levels (indicating T cell activation levels) of MUC1-2 engineered T cells incubated with MCF7 tumor cells showing that anti-MUC1-2 engineered T cells can be activated by MCF7 tumor cells.
Figure 39E:
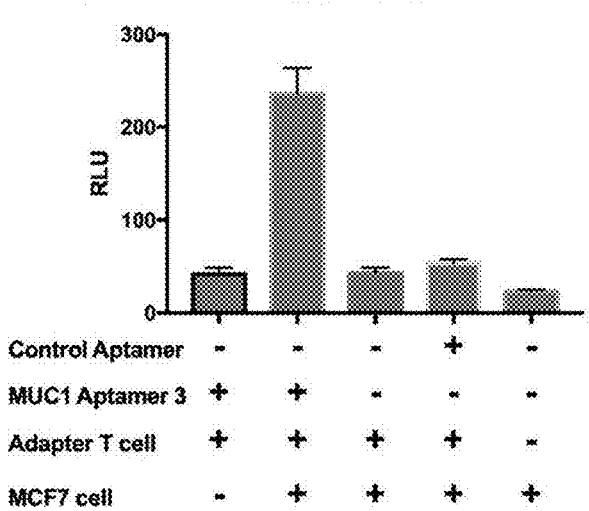
FIG. 39E: Luciferase activity levels (indicating T cell activation levels) of MUC1-3 engineered T cells incubated with MCF7 tumor cells showing that anti-MUC1-2 engineered T cells can be activated by MCF7 tumor cells.

As shown in their respective figures FIG. 39C, FIG. 39D, and FIG. 39E, the second columns show that three different anti-MUC1 engineered T cells were activated by MCF7 cells. Low levels of luciferase release were observed in T cell alone, tumor cell alone, without aptamer or with control aptamer group. The results demonstrate that engineered T cells prepared by the methods described herein were activated in the presence of a variety of different solid tumor cell types.

Engineered T cell activation further results in tumor cell death in the presence of said tumor cell.

Figure 49:
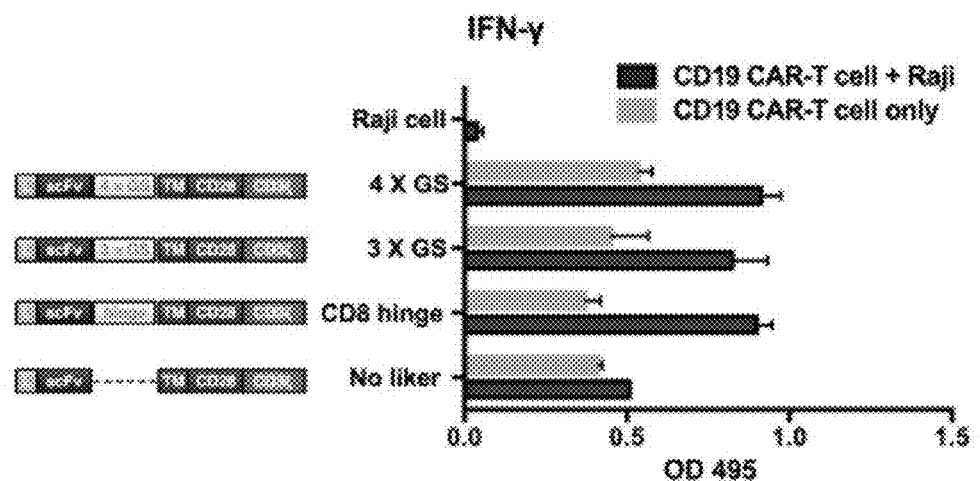
FIG. 49: CD19 CAR with linkers help T cell release more IFN-gamma when cosulcutre with Raji cells. The length of the linker affects the T cell activity.

Example 14. Engineered T Cells Comprising a scFv with Different Linker Morphologies are Activated Under a Selected Stimulus In some embodiments, the linker is selected from a (Gly-Gly-Gly-Gly-Ser)$_n$ sequence where n is from 1 to 8 (SEQ ID NO: 1), or a human C8 hinge sequence. It was found that a spacer was required to position the targeting molecule from the transmembrane domain. Engineered T cells comprising a CD19 CAR with linkers (4×GS linker (n=4), 3×GS (n=3) linker, or CD8 hinge) help engineered T cells release more IFN-γ when cocultured with Raji cells compared to engineered T cells with no linker. Moreover, it was surprisingly discovered that the linker length of the 4×GS (which consists of 20 amino acids) resulted in about the same effect as the CD8 hinge (which consists of about 43 amino acids), but both linkers exhibited slightly higher IFN-γ release compared to the 3×GS (which consisted of 15 amino acids), suggesting a plateau in the linker length on the IFN-γ release levels. As shown in FIG. 49, the engineered CD19 CAR vector comprised a leader sequence (L), CD19 single-chain variable fragment (scFv), linker, CD8 transmembrane Domain™, CD28 intracellular domain (CD28) and CD3ζ signaling domain. The vectors encoding the four types of engineered CARs were transduced into human T cells to generate engineered T cells. CD19 positive human Raji cell lines were cocultured with engineered T cells. IFN-γ release of CAR-T cells was measured by ELISA. The results also confirm that, inter alia, engineered T cells comprising a scFv as the targeting molecule was activated in the presence of a target cell.

Example 15. Engineered T Cells Comprising an Antibody are Activated in the Presence of a Target Tumor Cell As shown in FIG. 50, engineered T cells comprising an antibody as the targeting molecule were chemically connected to a second oligonucleotide linked which was immobilized to a first oligonucleotide which was chemically connected to the adaptor protein of the engineered CAR.

Figure 50A:
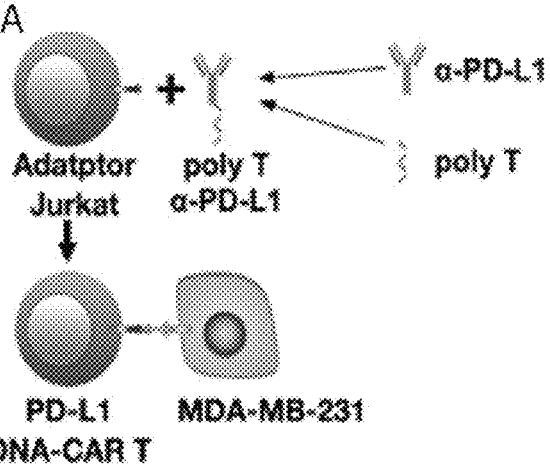
FIG. 50A: Production of PD-L1 engineered T cells.
Figure 50B:
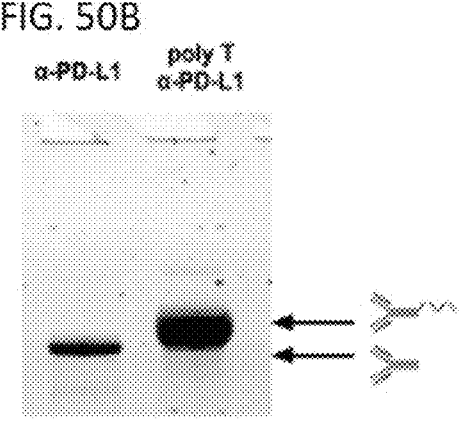
FIG. 50B: SDS-PAGE of PD-L1 antibody (α-PD-L1) and PD-L1 antibody conjugated with polyT (Poly T α-PD-L1)

MDA-MB-231 was a Programmed death-ligand 1 (PD-L1) positive human breast cancer cell line. FIG. 50A shows the strategy for the production of aPD-L1 engineered T cells. The aPD-L1 antibody was obtained from commercial vendors, and the aPD-L1 engineered T cells were generated by the methods described herein. As shown in FIG. 50B, the PD-L1 antibody (alpha-PD-L1) and PD-L1 antibody conjugated with polyT (Poly T alpha-PD-L1) exhibited different mobilities in SDS-PAGE. The mobility difference demonstrates that the engineered T cell comprising an antibody was generated. PD-L1 positive MDA-MB-231 cells activated PD-L1 DNA-CAR T cells.

Figure 50C:
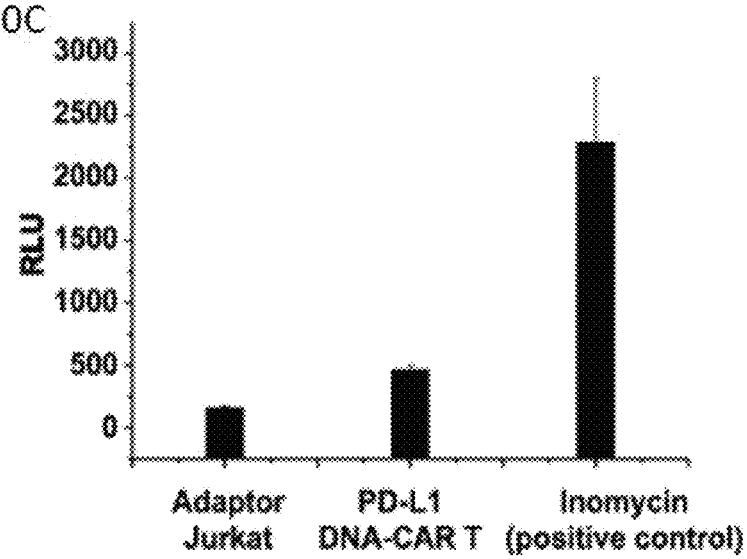
FIG. 50C: Luciferase assay results showing PD-L1 positive MDA-MB-231 cells activate PD-L1 DNA-CAR T cells.
Figure 51:
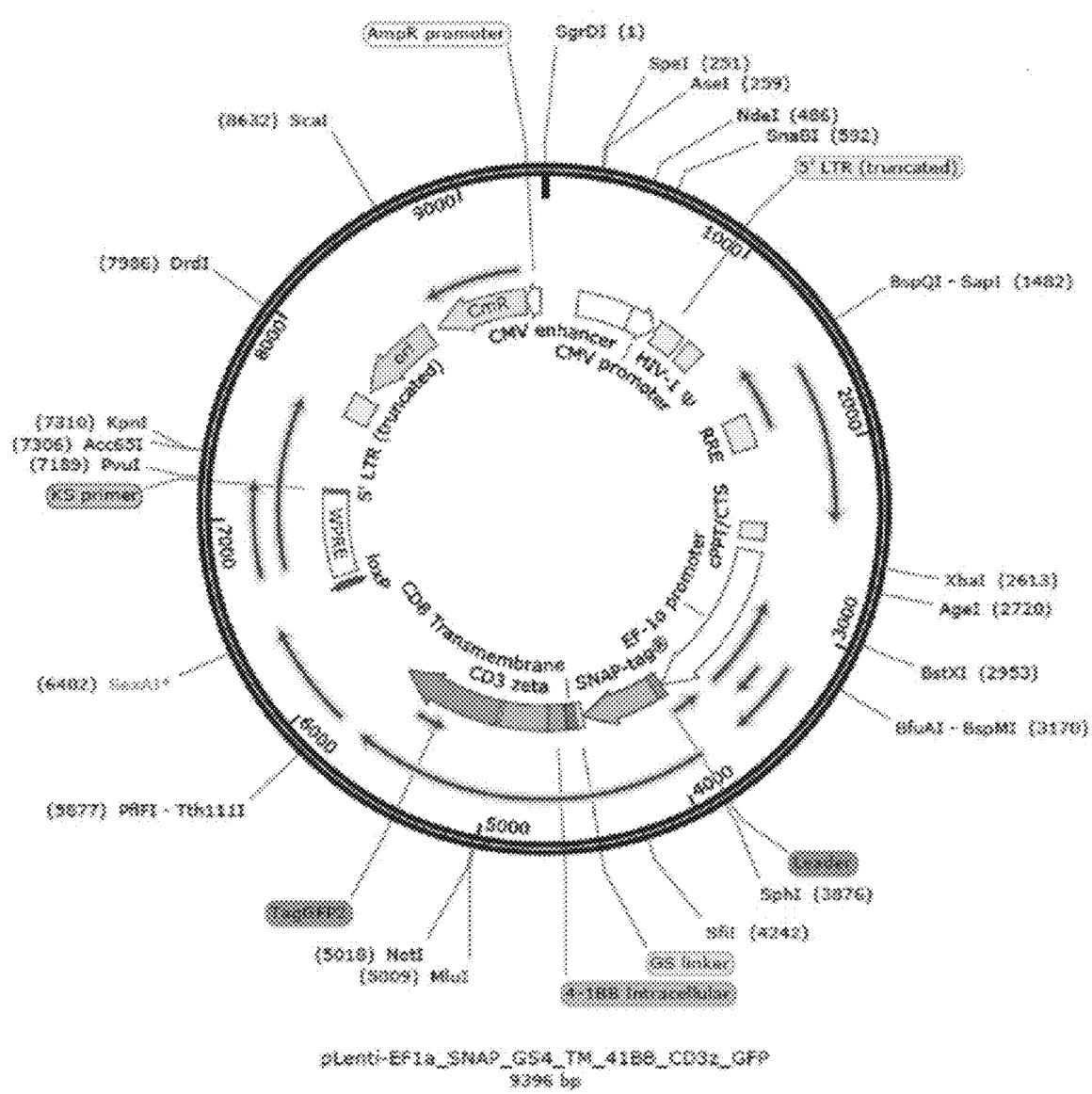
FIG. 51 The plasmid construct of a lentivirus encoding one embodiment of an engineered CAR of this disclosure.

MDA-MB-231 breast cells and anti-PD-L1 engineered T cells were incubated for 12 hours, after which T cell activation levels of luciferase was measured by relative luminescence units (RLU). In FIG. 50C, the second column shows that PD-L1 engineered T cells were activated by tumor cancer MDA-MB-231 cells. Only low levels of luciferase release were observed in Adaptor Jurkat T cell alone, indicating that the engineered T cells comprising an antibody as the targeting molecule were specifically activated in the presence of the cancer tumor cell. Combined with the experiment described above demonstrating that an engineered T cell comprising an aptamer bound to a cancer cell target, these data demonstrate that engineered T cells comprising a genus of targeting molecules bind to their cognate ligands on cancer cells to activate said engineered T cells.

Example 16. Engineered T Cells in a Mouse Model Kill Cancer Cells

The NSG mouse model is used assess the in vivo antitumor effect of control and transduced engineered Jurkat T cells. The CCRF-CEM cell line was used, which expresses the PT7 tumor marker, to monitor tumor growth in vivo.

Figure 48:
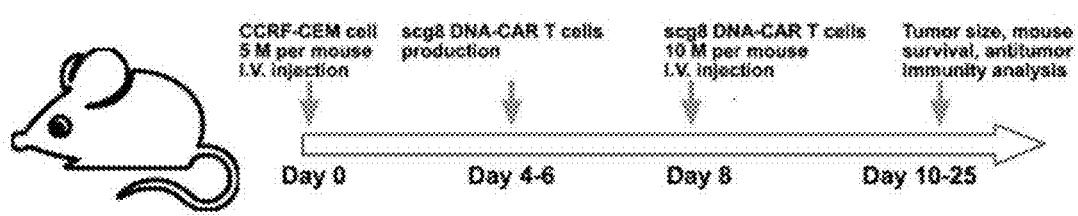
FIG. 48: Mice model dosing and monitoring regimen.

8-10-week-old male and female NSG mice are injected intraperitoneally with CCRF-CEM cancer cells resuspended in Matrigel (BD Biosciences). Tumors are induced by subcutaneous injection of $5\times10^{\wedge}6$ tumor cells, and mice are treated by IV injection of $\times10^{\wedge}7$ T cells as indicated in FIG. 48. For re-challenge experiments, mice are injected subcutaneously with $0.5\times10^{\wedge}6$ cells in the flank opposite to the site of the previously rejected tumor. All experiments are randomized and blinded. Tumor growth and condition of mice are monitored every other day. For antitumoral efficacy 6-8 mice per group are used.

An engineered T cell comprising scg8 aptamers is generated using the methods described herein. The scg8 engineered T cells are used to eliminate CCFR-CEM cells in a NSG humanized mouse model. Before injected tumor cells, NSG mice are irradiated and injected with 100 million (M) human PBMC to create a human T cell friendly immune system. Before injecting tumor cells, NSG mice are irradiated and injected with 100 million (M) human PBMC to create a human T cell friendly immune system. After PBMC transplantation 30 days, mice are injected with PTK7 positive CCRF-CEM cells (Day 0). About 100 million engineered T cells comprising scg8 aptamers is injected at Day 8 to the cohort test mice. T cell survival and CCRF-CEM cells is analyzed by flow cytometry at day 10.

In addition, peripheral blood from engineered T cell adoptive transferred mice is collected for analysis. Engineered T cells are isolated by Dynabeads Untouched Human T Cells Isolation Kit. Using flow cytometry, T cell activation efficiency by INF-γ or exhausting by PD-1 staining is measured. Serum is used to quantify different cytokine release by activated T cells by ELISA.

The mouse tumor model is also used for evaluating DNA-CAR T cell function in vitro proliferation. Tumor samples are collected after adoptive transfer (from day 1 to day 10) to check T cell infiltration into the tumor by CD3 staining. Peripheral blood samples are also collected to analyze T cell activities by flow cytometry and IFNγ, IL-2 and PD-1 staining.

The expected results show that engineered T cells conjugated with targeting molecules traffic to solid tumor area and successfully reduce tumor volume and prolong survival mouse life. Mouse survival of each cohort is also measured which shows that the mice cohort treated with the engineered T cells exhibit a longer survival time than the control cohorts. The results confirm that engineered T cells are both activated and can kill cancer cells in the presence of a cancer cell. Targeting efficiency or engineered T cell trafficking may lower than expected, peptides and DNA nanostructures including aptamers and origami are further optimized to get better outcomes. Furthermore, since the engineered T cell is easy to customize, different combinations of targeting molecules, spacers domains, and/or targeting agents are tested to obtain higher T cell potency. In some embodiments, three or four targeting molecules can simultaneously be added to the engineered T cells, or multiple targeting molecules plus cytokines are added to the engineered T cells, or multiple targeting molecules plus checkpoint blockade are added to the engineered T cells.

All DNA and RNA sequences presented herein are oriented 5'→3', unless noted otherwise.

Although the foregoing specification and examples fully disclose and enable this disclosure, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "including") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. An engineered T cell comprising:
   (a) an expressed engineered chimeric antigen receptor (CAR) which comprises an extracellular adaptor protein selected from $O^2$-alkylcytosine DNA alkyltransferase which reacts with $O^2$-benzylcytosine moiety, or $O^6$-alkylguanine DNA alkyltransferase which reacts with $O^2$-benzylcytosine moiety;
   (b) a protein tag bound to said adaptor protein;
   (c) a first oligonucleotide connected to said protein tag;
   (d) a second oligonucleotide wherein a portion of the second oligonucleotide sequence is complementary to a portion of the first oligonucleotide sequence; and
   (e) a targeting agent connected to the second oligonucleotide, wherein the targeting agent comprises one or a plurality of targeting molecules,
wherein the targeting agent comprises
   (i) a DNA origami nanostructure comprising a central polynucleotide strand and a first staple strand which comprises the second oligonucleotide sequence and a plurality of second staple strands which comprises one or a plurality of third distinct oligonucleotide sequences; and
   (ii) one or more targeting molecules connected to one or a plurality of fourth distinct oligonucleotide sequence(s),
wherein a portion of the third distinct oligonucleotide sequence is complementary to a portion of the fourth oligonucleotide sequence.

2. The engineered T cell of claim 1, wherein the expressed engineered chimeric antigen receptor comprises:
   (i) a signaling polypeptide domain;
   (ii) a transmembrane polypeptide domain;
   (iii) a spacer polypeptide domain configured to be between the transmembrane polypeptide domain and the adaptor protein tag domain;
   (iv) a costimulatory polypeptide domain; and
   (v) an adaptor protein tag domain.

3. The engineered T cell of claim 1, further comprising a fluorescent protein domain.

4. The engineered T cell of claim 3, wherein the fluorescent protein domain is green fluorescent protein (GFP).

5. The engineered T cell of claim 2, further comprising an antibiotic resistant gene.

6. The engineered T cell of claim 2, wherein the signaling polypeptide domain is CD3ζ, the transmembrane polypeptide domain is CD8, the costimulatory domain is 4-1BB, the spacer polypeptide domain is (Gly-Gly-Gly-Gly-Ser)$_4$ (SEQ ID NO: 2), and the adaptor protein tag domain is O$^6$-alkylguanine-DNA alkyltransferase which reacts with O$^6$-benzylguanine moiety.

7. The engineered T cell of claim 1, wherein the targeting agent comprises one or a plurality of targeting molecules selected from a group of targeting molecules consisting of: an aptamer, a synbody, an antibody, and a fragment of an antibody thereof.

8. The engineered T cell of claim 7, wherein the targeting agent is a fragment of an antibody fragment, and further wherein the fragment of an antibody is a ScFv.

9. The engineered T cell of claim 1, wherein one of the one or a plurality of targeting molecules comprises a matrix metalloproteinase.

10. The engineered T cell of claim 1, wherein one of the one or a plurality of targeting molecules comprises a cytokine or chemokine.

11. The engineered T cell of claim 1, wherein one of the one or a plurality of targeting molecules comprises an inhibitory pathway overcoming agent which is an anti-PD-1L aptamer.

12. The engineered T cell of claim 7, wherein the aptamer is scg8 having SEQ ID NO: 10.

13. The engineered T cell of claim 1, wherein the T cell is selected from a group of T cells consisting of: a natural killer T cell, a regulatory T cell, a helper T cell, a cytotoxic T cell, a memory T cell, a gamma delta T cell and a mucosal invariant T cell.

14. A method of preparing the engineered T cell of claim 1 comprising:

(a) inserting a DNA sequence which encodes for the CAR polypeptide into a virus;
(b) contacting the virus with a T cell to form a viral-infused T cell;
(c) growing the viral-infused T cells to produce an adaptor T cell expressing the CAR polypeptide comprising an extracellular adaptor protein;
(d) isolating the adaptor T cell;
(e) contacting the isolated adaptor T cells with a first oligonucleotide functionalized with a cognate protein tag;
(f) forming a complex between the extracellular adaptor protein of the adaptor T cells with the cognate protein tag to form a first oligonucleotide-functionalized adaptor T cell; and
(g) contacting the first oligonucleotide-functionalized adaptor T cell with a second oligonucleotide comprising a targeting agent under appropriate conditions to form a hybridization complex between a portion of the first linker oligonucleotide and a portion of the second linker oligonucleotide, wherein said virus is selected from a lentivirus, retrovirus or adeno-associated virus.

15. A method of activating an engineered T cell, the method comprising contacting a cancer cell with the engineered T cell of claim 1.

16. The engineered T cell of claim 11, wherein the anti-PDL1 aptamer comprises a sequence having SEQ ID NO: 5.

* * * * *